US007273928B2

(12) United States Patent
Markl et al.

(10) Patent No.: US 7,273,928 B2
(45) Date of Patent: Sep. 25, 2007

(54) NUCLEIC ACID MOLECULE COMPRISING A NUCLEIC ACID SEQUENCE CODING FOR A HAEMOCYANIN

(75) Inventors: Jürgen Markl, Gau-Bischofsheim (DE); Benjamin Altenhein, Wiesbaden (DE); Bernard Lieb, Mainz (DE); Thomas Stiefel, Stuttgart (DE)

(73) Assignee: Biosyn Arzneimittel GmbH, Fellbach (DE)

( * ) Notice: Subject to any disclaimer, the term of this patent is extended or adjusted under 35 U.S.C. 154(b) by 0 days.

(21) Appl. No.: 11/512,044

(22) Filed: Aug. 29, 2006

(65) Prior Publication Data

US 2007/0154486 A1    Jul. 5, 2007

Related U.S. Application Data

(62) Division of application No. 10/049,988, filed on Jul. 15, 2002, which is a division of application No. PCT/EP00/08129, filed on Aug. 21, 2000, now Pat. No. 7,125,557.

(30) Foreign Application Priority Data

Aug. 20, 1999 (DE) ................................ 199 39 578

(51) Int. Cl.
   C07H 21/00    (2006.01)
(52) U.S. Cl. ..................................... 536/23.1
(58) Field of Classification Search .............. 530/350, 530/857; 424/278.1; 536/23.1
   See application file for complete search history.

(56) References Cited

U.S. PATENT DOCUMENTS

| 5,021,560 A | 6/1991 | Montreuil et al. |
| 5,831,033 A | 11/1998 | Zetter et al. |
| 5,888,775 A | 3/1999 | Tai et al. |

FOREIGN PATENT DOCUMENTS

| EP | 0244295 A1 | 11/1987 |
| EP | 0621039 A1 | 10/1994 |
| EP | 0252829 A1 | 1/1999 |
| WO | WO 94/11019 | 5/1994 |
| WO | WO 00/55192 | 9/2000 |

OTHER PUBLICATIONS

Geyer et al., "Identification and Characterization of Keyhole Limpet Hemocyanin N-Glycans Mediating Cross-reactivity with *Schistosoma mansoni*", *J. of Biol. Chem.*, 280(49):40731-40748 (2005).
Kurokawa et al., "Hemocyanin from the keyhole dlimpet *Metgathura crenulata* (KLH) carries a novel type of N-glycans with Gal(β1-6)Man-motifs", *Eur. J. Biochem*, 269:5459-5473 (2002).
J. V. Hamilton, et al., "Periodate-Sensitive Immunological Cross-Reactivity Between Keyhole Limpet Haemocyanin (KLH) and Serodiagnostic *Schistosoma mansoni* Egg Antigens," *Parasitology*, 118:83-89 (Jan. 1, 1999).
Karen I. Miller, et al., "Sequence of the *Octopus dofleini* Hemocyanin Subunit: Structural and Evolutionary Implications," *J. Mol. Biol.* 278:827-842 (May 15, 1998).
Stanka Stoeva, et al., "Primary Structure and Unusual Carbohydrate Moiety of Functional Unit 2-c of Keyhole Limpet Hemocyanin (KLH)," *Bioclinica et Biophysica Acta.*, 1435: 94-109 (Nov. 16, 1999).
Wolfgang Gebauer, et al., Keyhole Limpet Hemocyanin Type 2 (KLH2): Detection and Immunolocalization of a Labile Functional Unit h, *Journal of Structural Biology* 128: 280-286 (Dec. 30, 1999).
J. Robin Harris, et al., "Immunoelectron Microscopy of Hemocyanin from the Keyhole Limpet (*Megathura crenulata* ): A Parallel Subunit Model," *Journal of Structural Biology*, 111:96-104 (1993).
M. Rocia A. Carrera, et al., "Cocaine Vaccines: Antibody Protection Against Relapse in a Rat Model," *PNAS*, 97(11)6202-6206 (May 23, 2000).
Sabine M. Söhngen, et al., "Mass Determination, Subunit Organization and Control of Obligomerization States of Keyhole Limpet Hemocyanin (KLH)," *Eur. J. Biochem.*, 248: 602-624 (1997).
M. Rocio A. Carrera, et al., "Suppression of Psychoactive Effects of Cocaine by Active Immunization," *NATURE*, 378: 727-730 (Dec. 14, 1995).
Bernhard Lieb, et al., The Sequence of a Gastropod Hemocyanin (HtH1 from *Haliotis tuberculata*), *The Jorunal of Biological Chemistry*, 275(8) 5675-5681 (Feb. 25, 2000).
Bernhard Lieb, et al., "Subunit Organization of the Abalone *Haliotis tuberculata* Hemocyanin Type 2 (HtH2), and the cDNA Sequence Encoding its Functional Units d, e, f, g and h," *Eur. J. Biochem.* 265: 134-144 (Oct. 1999).
Richard D. Swerdlow, et al., "Keyhole Limpet Hemocyanin: Structural and Functinoal Characterization of Two Different Subunits and Multimers," *Comp. Biochem. Physiol.*, 113B (3) 537-548 (1996).

(Continued)

*Primary Examiner*—Karen Cochrane Carlson
*Assistant Examiner*—Suzanne M. Noakes
(74) *Attorney, Agent, or Firm*—Welsh & Katz, Ltd.

(57) ABSTRACT

A nucleic acid molecule or construct alone or with a promoter suitable for expression control is contemplated that codes for a HLH2 haemocyanin polypeptide and comprises at least one intron sequence, as well as haemocyanin fusion proteins. The construct further can comprise a nucleic acid sequence that codes for an antigen. Host cells are also contemplated that contain the nucleic acid molecules or construct and recombinant expression product thereof. The invention further relates to a pharmaceutical composition that comprises the expression product of that nucleic acid and antibodies obtainable by immunization of an animal therewith, as well as use of the antibodies in screening methods for the identification of tumors.

21 Claims, 43 Drawing Sheets

OTHER PUBLICATIONS

Henning Keller, et al., "Abalone (*Haliotis tuberculata*) Hemocyanin Type 1 (HtH1) Organization of the ≈400 kDa Subunit, and Amino Acid Sequence of its Functional Units f, g and h," *Eur. J. Biochem.* 264: 27-39 (Aug. 1999).

Keller et al., *European Journal of Biochemistry*, 264:27-38 (1999).

J. Robin Harris, et al., "Keyhole Limpet Haemocyanin (KLH): Purification of Intact KLH1 Through Selective Dissociation of KLH2," *Micron,* 26(3) 201-212 (1995).

Wolfgang Gebauer, et al., "Quaternary Structure, Subunits and Domain Patterns of Two Discrete Forms of Keyhole Limpet Hemocyanin: KLH1 and KLH2," *Zoology* 98: 51-68 (1994.

Lieb et al., "Structures of two molluscan hemocyanin genes: Significance for gene evolution", *PNAS* 98(8):4546-4551 (Apr. 2001).

Drexel et al., "Complete Amino-Acid Sequence of a Functional Unit from a Molluscan Hemocyanin (*Helix pomatia*)", *Biol. Chem. Hoppe-Seyler* 386:617-635 (Jun. 1987.

The 1995 Sigma Product Catalog, p. 520, product # H 7017.

International Search Report from PCT/EP00/02410, dated Jul. 3, 1999.

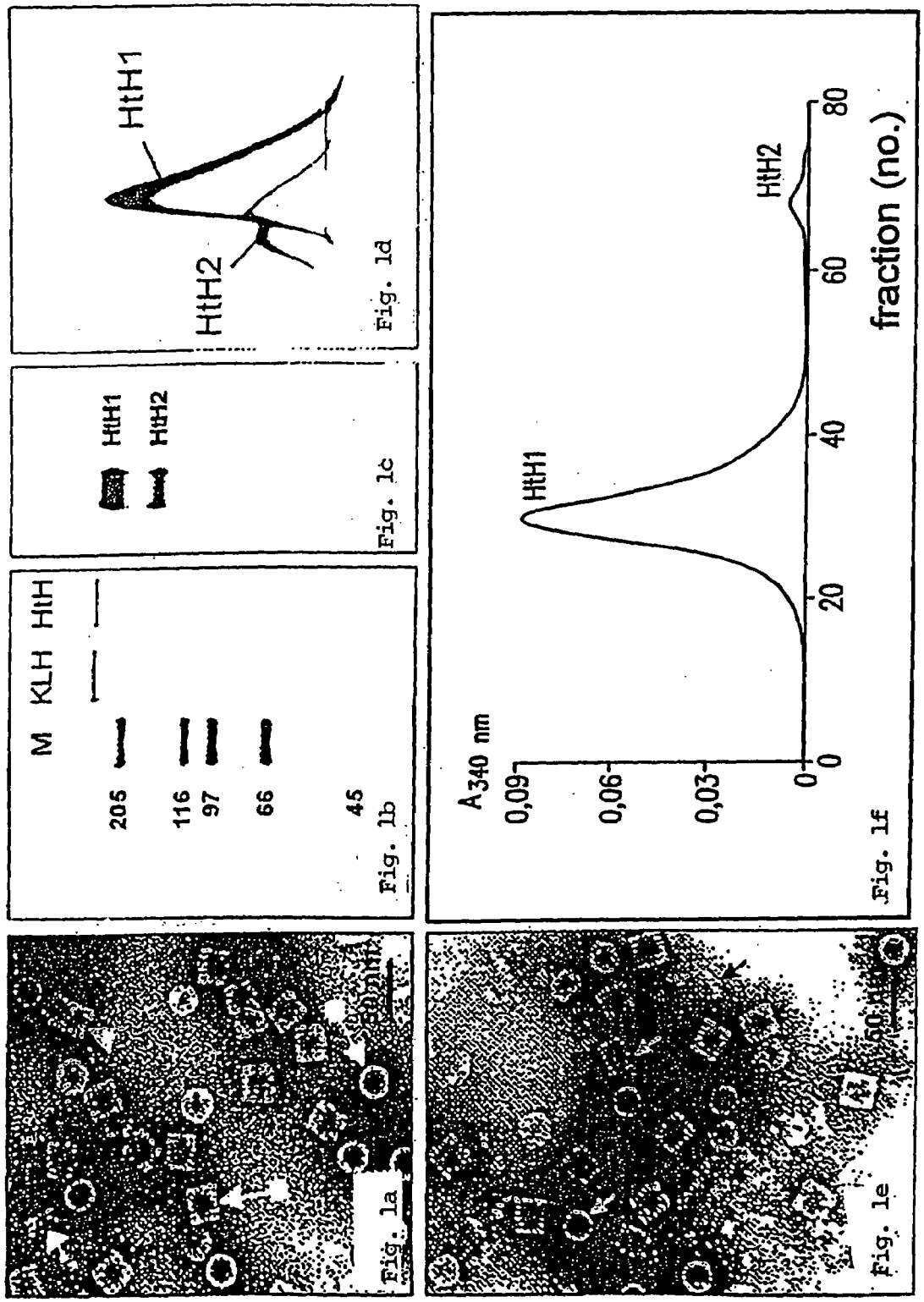

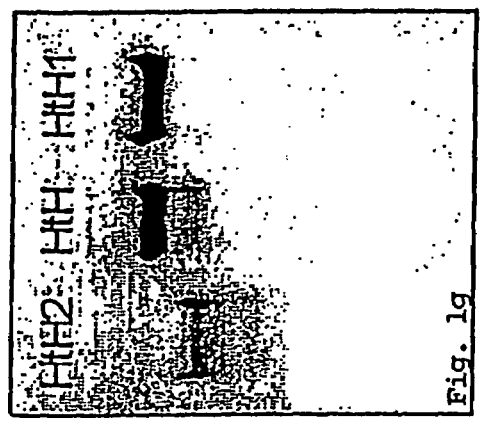
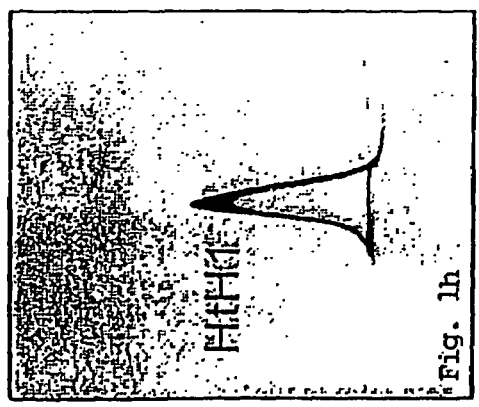
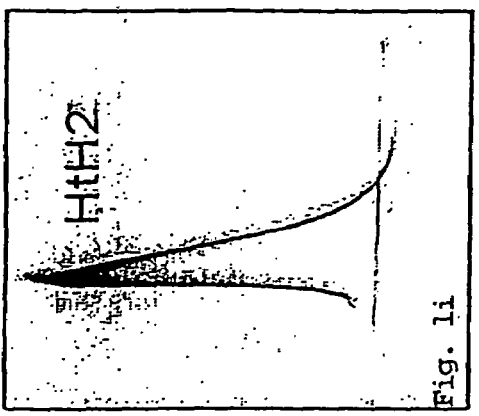
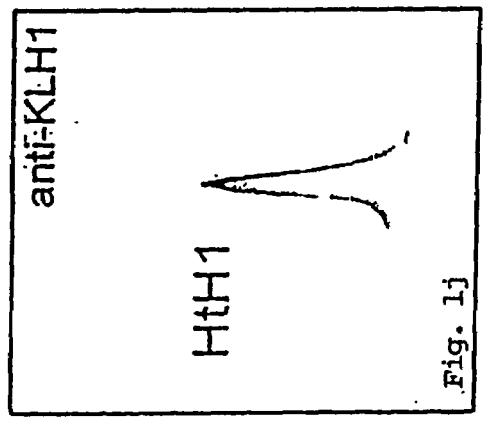
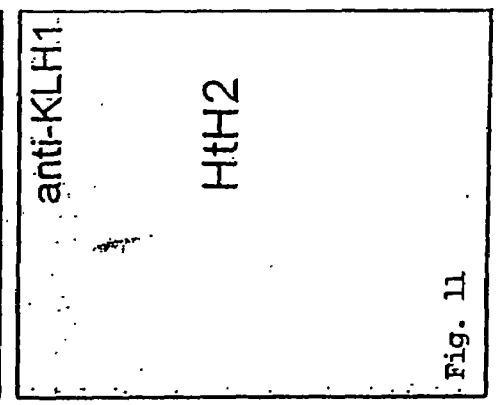
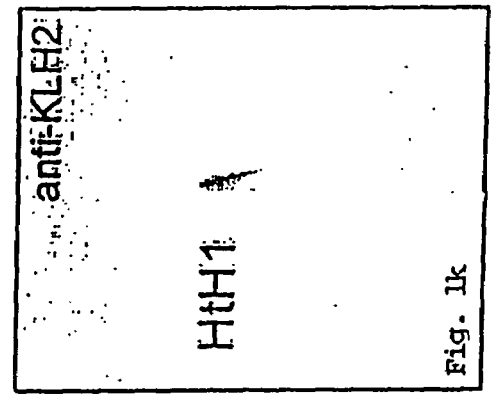
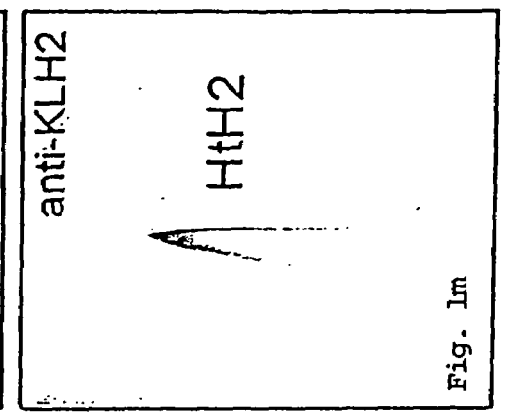

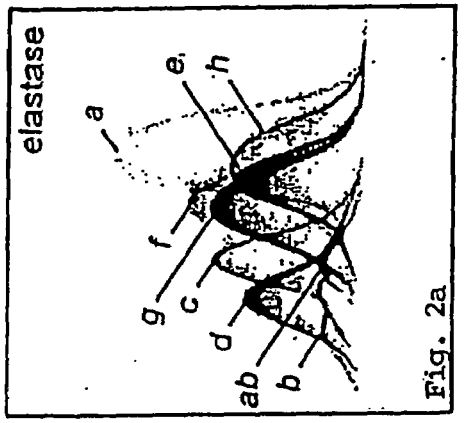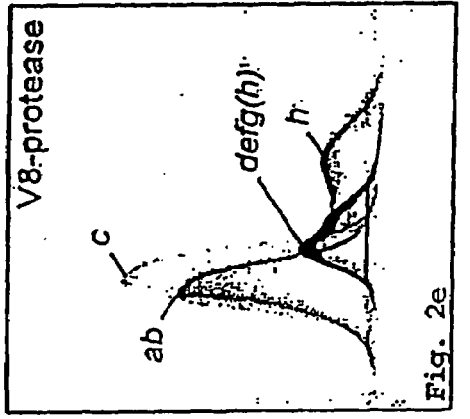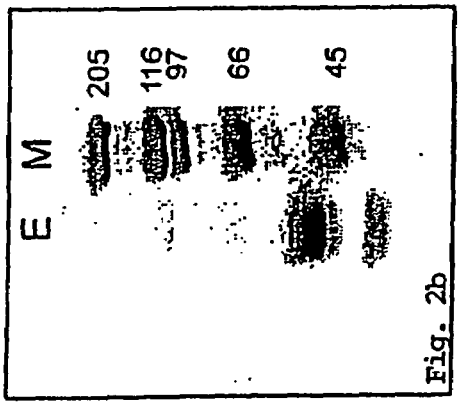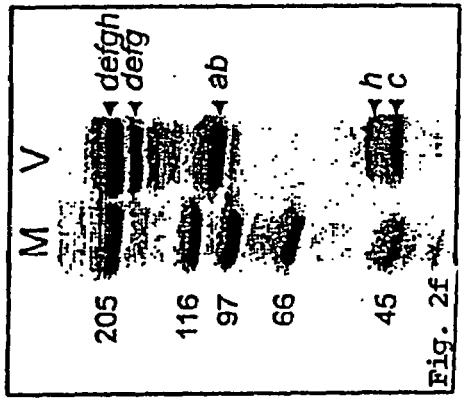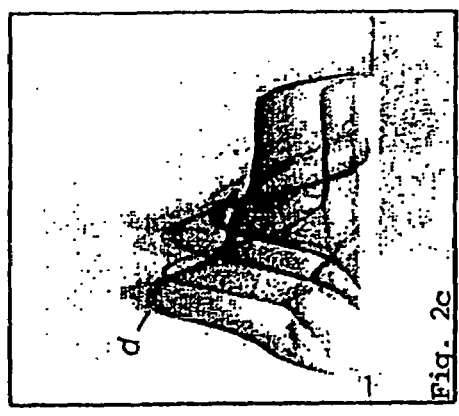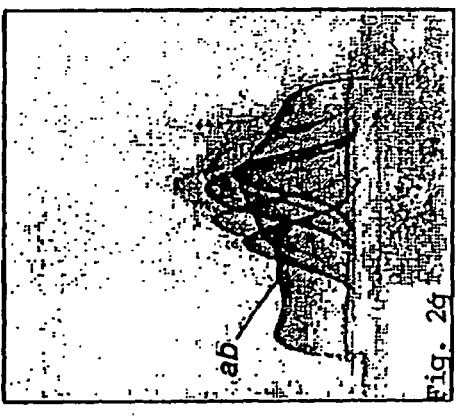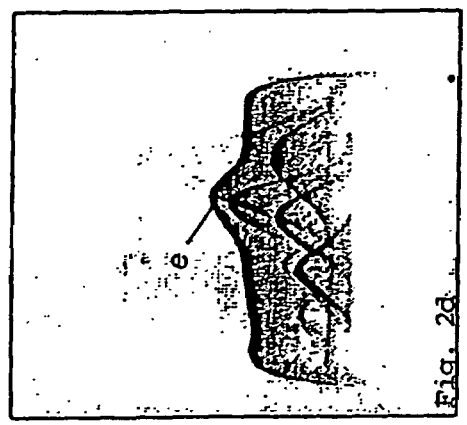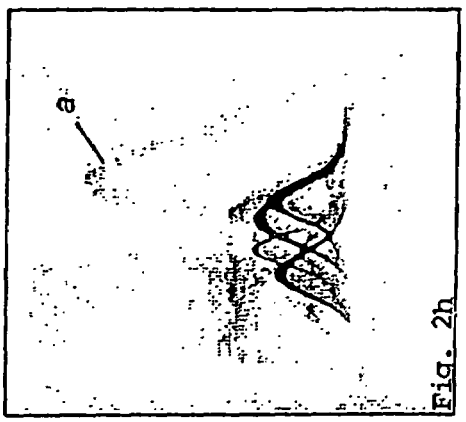

papain chymotrypsin trypsin

Fig. 4a

Genomic sequence of the HtH1 gene

SIGNAL PEPTIDE SEQUENCE 1S-1 (1st part)

GGCTTGTTCAGTTTCTACTCGTCGCCCTTGTG

INTRON 1S-1/1S-2 (SEQ ID NO:109)

GTAAGTCAACGTCTTTGTTTAAGTTTGATGCATATCTATCATTGCGTTTTAAAATACCA
TTACAACCAACGTGTCTCTATTGGTCTTCACCTGTTTAACGTATATATTGTTTTTAATGT
GAAAATCTGAGATTATTTTCATTTCCGTCAATATTCGTAAAATACTATACAAATAAAATT
GCTTCAGCCTATTGCATTGGCAGTTTTCGCAGAATAACGAGGGAAGGCGTACATAAAATA
TAAACCAGTGTATATTCAAGCATGTTTATAATTTCTTTATAGATTATAACATCATATCAA
AACACCAATCTGGATTTAAACCCGTGAATCCAAAGTATACCAATTAACGGAACTTTATCA
TGTTTTATCAAAGGTTTTAGATGAGGGTAAAGAAGTCCGAGCTATATTTGCGATATCAG
CAAAGCCTTCTATCACGTCTTGCACACAGGGCTGGTATCTAAACTCGAATCCACAGGAAT
AAATATTTCAGCCGATAGAGAACAGTCGGTGGCTATCATTGGTCACAAAACAAGTCCAAA
ATCTGCATTAGCCGGTGTTCCCCAAGGCTCTGTCTTGGGGCCACTATTATTTCTCACCTA
TATAAACGATTCAACTAATGGAATATAAAGCAACGTAAACCTCACCGCAGATGAAACACT
AAGTTATAGACAATCCGTTTAAAACCCAGCCACTGCTTAATAATGACTTAGGCCGTCTTT
CAGACTGGGCTAGTAAGCGGCAGGTTAAATTTCACCTTGAAAAGACAGAAACCATGGTAT
ATTTCAAAAACACGAATGCAAGTCCTAAACTTCAACTACTACTTGATGATACTGGGATTT
CTAAAGTGTGTGAACAAAAACACATTGGCCTGATCCTACAAGATAACCAGACAGAAACCA
TGTTTTTTTTCAATAACACGAATGCAAGTCCTAAACTTCAACTACTACTTGATGATACTG
GGATTTCTAAAGTGTGTGGTGAACACAAACACCTTGGCCTGATTCTGCAAGATAATGGAA
AATGTCAGAAACATAAGCAAGTTGATGTGGGGTTTTCTGGGGGTTGTGACAACACCGAAA
GACCCTGCAACTAATGTTAGCTCAAAGGGTTTTACACCCGGTCACAAGTGGGGATCGACC
CAGGCACCTTTTGCCTTTGACAGCTCGCCTTTCAAAAAATCTCAATTCGAAAACGAAATC
TAATAATTTCATGAGCGATACAACCGTTTTTCATAATGCTGTGGTACCGCATACTGTGGA
AACATCTGTCTACCCATTTGGTAGTCCCCCATAAAATGTATTTATGTTTATAAACACAAT
GTTTATAGGGTTACAGTTAGAAGAAGCATTTCTATTGGCTAATGTACATTGCTTGTTTTT
ACTATTGTGCAAAGGCATATTACAGGTCTTTTAGGAAATTAAATACTGTTTAAATCACAT
ACACTACCGGTAATCCTATTATGCTTATCCTGCCAACATTCTGCCCAAGCAAACGCATGA
AAGTTAAAGCTGAGTGTAAAATACTGATTGCTGTGTTACTTCACAACCAGTGGACTGAAT
ACAACCATGTTTTTTCTTGAAAGTCACAAACATCCAGTCGGTTTCTAATGTGTTAAGTTT
CTAGTTTCATAAAGAGCATGACGTAATGGTGAATAGGAGTTATCAATGTTTCTATCTAAT
GACTCCTAGTTCGTTACTTTTTAATAAAACATCCATGTGTTTAATGTTTGGCCACAGAT
ATAACAAGAAAGAAATCGGATAAAATCTACATTTTGACCAATCGGAAGGCTGCCCCCTCC
CTAATCCTAATCATTTTGTGCCTCAAAACATACTCAACCAGACATTTGAACTATGTATA
TATCAGAATGAAATGGTAACAATAAACTTGTATGTTGACCAGACAGAATTAGGGTGAATC
TGAATACCAACTATTGTCACATATGAATATGGATAAGCTCTGCGCGTGCGTGCGGGCGGT
GTAGTGCGTGTGTGTCTGTGTGTGTGTGTGTGTGCGTTTGTGTGTGTGTCTGCGTGCGTG
TGTGTGCGCGTGTGTGCGTGTGTGTGTGTGCAGTGTGCCGAGTGTGTGTGTGTGTG
TGCACAGACATGTGGTTGAGACACACTTGATTCAGTGCAGGATTATGTCCTTCAACCGAG
TGTAGTCTTTAAGTGTGCCTGGAAACAAAAAACTGCGTTGGGTTGCATCGCCTCTGTAGC
AAGCTTGGACGCGTCACGCAGCTCTGATACCACGTATTGGCACCATGTTTCATCGGTCTC
ACGCGAATATTATGCTATGTGTGGCGTATCATACCATAGGTTGGGAACGTTTCAATACTG
TACCGAGCTTGGGCGTGTCACAAAGCTATGATAAGATGACAACACGTCTTGGCATCTTGT
TTCCTCGGTATCACGCGCTGTTATGCTATGTGTGGCTATCACACCTTAGGTTGGGAAAGT

Fig. 4b

TTCCACATTTTCCAGCCTCGTACATGTTTCCTTTTGTTTTTTCCTTAGTTATCAGCATAC
CGTATATTCTATATTTAATGAGCATTTGTATTTTTCTACAG

SIGNAL PEPTIDE SEQUENCE 1S-2(2nd part)

GTGGGGGCTGGAGCAG

INTRON 1S-2/1A-1 (SEQ ID NO:110)

GTGAGTTTCTTAACATTGTCATGGTACATGGATATACGCTCAGTGGGAAAGCAGGATATC
CCCTTGGTTCAAGTATTCACTTGTCACGCCAAGTGTTCGATTCCCAACATGGAATACTGT
CATATAGTAAATTGATACACTACTTACATTTAATTCTCCACTAAACGTCAACGTCCTTTA
CTTCATGGCCCACATGGTCCGTATTAGTGAGTGAGTGAGTCAGGGCATAAGTATTTAACG
TCAAATCAGCAATATTTCAGCCATATTGTGACAAGAATTGAATATAAATAATTATACTTA
TAATGCTTATAAATATAAATTATATAAATACCTATAACTATAAATTAGTTATACTAGTAT
TTATCAAAACATATTTGCCACGACACTGCACGCCGATACTTCAAGTGTCTTCACCTCAAG
CGTGTAACTCCTCATACTCTGTAATAAGTATGTACACTAAGTGAGTGCTATCATCTCCAT
GCTTCATTAGTTTCGTCAGATGCGTGTATCCATACGAGTACATTCAGATTATGGATCCA
GAGCTTTCTTATCTCAAGTATTTCCGATTGTAAAGCCATACTACTTCCCCAATGACTGAC
GAGACAGATGGCAACCGTTCTTTCCTCCTGACTAGGTGAGTGCCACTGATAAATCATTAT
GCCTTTAACATTAGGAATGTTAGCAGTGCACATGTTTCAGAATTGCGACCTTATGGTTGT
AAAGATTACAAACTTTACAACTTACTTGAGACAGGTTCCATATGTCGTATCTGAAATAGT
GTGAAGGTATCTGATTCGATGCAATACACAGACATATAAACATATTGTCGCCCTGCTATT
CCGGAAAGGTCATTTTGTATGTAACGTTCCTTAATGGACACAAACGGAATTATTAGTTAA
ACATACTCAACAAAACTATGTTATTTTGCAATGGGTAGCACCGAAATCTACCGACAGTGG
TTCGTAAAAGTAGAACATTCTGACATAAAGAAAAATCATTGGCTTTAAATATATGCAAGT
TACTTGTCTCTAACAACCAGTTTTATACACATTTCAGAGAACGGGGAATCCGCGATGACA
ATATCAACGAGTATATACAGAATATATAATTAAAAACGATGAGTGCCTGGCAAGGGAAAG
AGCGAGATTTGCCAAACAGGGGGTGGTGTTGAGCTTGAATCGTGGAGAAACGTAGATTG
AAAGACAAGATGACATCTAATGATCCGAAAATCAAACACAGGATTAACTGGGATGCAGAA
GAATGAATATCTCAAGCATACATGCAACACTTCATGAATGCATCTCAAACATTTTCGTCA
GATCGGATGCATGAAGATTTGTAAAGCAATGGTTTAAATTGTCCCTAAACGTTTAGTTGG
AGATGTATGAGGCTAGGCTGTATGTTGAACGAAACCATTTAACATTGTTGTTCATGATTA
TTTAATATTTTTTCATTTTATAGATGTACAATAAAATTGGAAACTAAACATTTCCCTTTA
TTGTTTTGTATTTACCTGTTCATGGGTATGTTTTGAAAGATCGTGATATTTAGTTGGCAT
TCACAAGTTGGAAAAAGGTCACTCAGTTTGATTTCAAGTTTATGTAACCTCTTTATCTGA
CGCTCCAAAATATGTATAGCCTTGTTCATCTGTCGGTATGTGGATATTCCTACTTCAGGG
TAGGGTAGCATTAATACTTACAAAACATAACGTGTACCAGATTTCAGTCACCTCAGAGAT
GATAATGCATGTCGATATGATAGGTCAAAACTTTCGATATCAATCACAATGAACCTATGG
ACCCTGAATCGGAATGATACGTTACACTTTAGAAACAATTCACAAATATGACTGTCACCC
TTTCAGGTAATAATGTTTGACGGACTACGATAGTGCTGAACAGCAGGAGAGGCAACATGG
TTCGATTGTGAGACAGGTTTAGTGTATTTGTTTGCGAATTTAAGGTTCTGAATCACAATA
GACACGGTTCAGTTAATGGATAAACCAATCATTAGATAGATAGAGATTAGTCGCGATATT
GCTGGGATAAAGCTTAGTGGGACGTTAAGTCCCATCTCAATCTCTCTCATTTTTTCCAAA
ACAGTTTTAATTCAGGCTCATGACAAGGTCGTACTGTTGCAAAGGATTCTACTTCAAGCA
GAGATGTCTCATGAATACAGTACAGGGTTTTTGAAGTTTATCCAGTGCAGCGCTGGCACC
ATCTCTGCATGCGAATTATACCATCCATGCCGCTCTAGGCTATTTGTATTAAGTCTGTAG
AATTAAATTCGCGAGTTGCAAATACTGCTCACCATTATCTGCCTCAACCCAGTTTGGGTA
CATGCGATTTACACAATATTATGTATAATGTTCGCTTTTCGAAAACAAAACACCTAAATT
CATCCAAAGTTTTGGGAGATTTTATTCGAGAAATCAACCTGAGATGTTGAATCGGGAGCT
GCGCTTATTCAATGGTGGACTCGGAAGGGAAGTAACCGCTGATGAGGCAAAACAATAACG

Fig. 4c

CAAACATATGGAAGTGGAACTCTTTGAACCAGTATTATGTTTGTGTGGACATGTATGTGT
TAATTTGACCATTCGAACAACTTTACTATTCTATTCATAATGTGTTTAGATTTACATTTG
AATTAAAAGAGATGAGTTTAAGATATTAATATTTTCCTTTTATAGTCTGTCGTGATTGTA
GGGCAATATTTATGTATGTTCGTTCATTTTTCATTTATCATTTGGAAAGGTATATCATAA
GATTATTATTATCATTCTTGAAGTAATGTATACATATATATGTCTTGAGTAGCTTATT
TTCAATTTATTATCATCCGTCATCCAATTTTATTTCACGAAAGTATAAGAAATAACGAGA
GAGAGAGAGAGAGAGAGAGAAAAGACAGAAATGAAGTTAGGAGATATNAGTTATCAAGAA
AACAACAGTTTGAATTTTTTGTTTAGACAAGATATCATATCAATAACCTCGCACTATTAC
GGGAATAGGCGGGCGTTCCATATGCACAATGAATCGTCAGTTAAAATCAACATTAAACTT
AAAATACTCCTCATATTTAAAGTTGATCTACCTCTTGTATTATTGTAGACTATTAGACAG
AAGTCGACAGTGACACCAGCAACCAGATATCATACCCAGACTTAAAAAGCTGTTTCCTTG
ATGTTTCAATTTATTTCCATTTCCATTATTTCCCTTTATTGGTTTCCATTTATCAAACTT
ACCATCTGCACCAGTGGGAGATTGATATGTTGTATTTATTTATATTTCTTGTACTACAAT
ATCAAGAATGTATAGGAGCTATTCCTTGTTCCTAAAACCGGATAGATCCATAATTTCCAT
TTTGGGATAAATGGAAACTAAACACAACTTTTACAGTAAACACGAGTGAGCAAGTTGAGT
TTTACGCCGTTTTTAGTAGTATTCCAGCAATATCGCGGCGGGGGACACCAGAAATGGGCT
TCACACAGTGAATGCATGTGGGGATTCGAACCCGGGTCTTCGGCGTGACGAGTGAACGCT
TTAGCCACTAGGCTACCCCACCGCCTATTTATAGTTAAGACGAATACTTTTCTCAAGCCT
CAAATATGTCCATTCTAGAGAGACTGAATCTGATCCTGAATCTGCGGACCGGTCTTGAAT
ATCATCCCACTAACTCATTGTACAAAGTACCTGTAGATTGTCAGTTCAAAGACAGATTTC
ACAACCCTATTATATTTTGTCCTGCTCATTAAGATATTCAGACTCACTCAAACTGCTAAA
TGATTTTAATCCTACTTTGAGATGTTTTAACTTTTATTCGATGCATTTTTGCGTTCTGCG
TCCTGTATAAAGGTAAAGCAGGTAAACTAACCTAACCTGTTGATTTATTTCATAGTTTTG
CGATCAGATTGAAACCGGAATGCACAGTGAAGTGTGGCATACATCTTTCCACAGAGATAC
TGGATACTAGGTGGTACAACCGCATTGGCTTTGTGAAAGGATATTAGTGTTTTATGAGAC
TGACTCATGTTTCAATGCTTAGAGCGGAATGATCTCGGTCTTCATGAAAAATATTGTGTT
GAAGTAACCCCCCAGTCCCTAACAGAACGTGGGGAAAGCAGATGGATATGCCAAGACATC
TTCGCATGGTGTGAAGATGATCGTTACAACATCTGCAGAAAAAGTTATTTCTGTGAAGAA
TATGCCAAAGCATCACTGTGAGTGTTTTGAAGATGTGATATGGCAACACGCAGCGTGTAA
TTATGCTTTGTGTGTATTTCTGAAGATCCGTATGAGCATGGCGCCAAACTATCAGTTAAA
TGGCTATGCGAAGATCTTCCCGAGATGGTAAACACATATTTTGGCCATTTTCTTTGTAAG
TGGGCGACACAGAAGATCCCCCTGATTGTGTGGATGAGGACACAAAAACGGGTCCCCCTT
CCTTTGCTGATGCTAATGACGCCCTGGAAACATTGAAAGACTTCTTCTCCAGCAAGCAAG
CCACCAACCACAAGTTGTATAAATCGCTTGCGGACTTGAATACGGCAGTTGGACAGATAC
ATACAGCCAGAGAGGGCCGAACTAAAACATCTAAACATGGAAAAACTGTAAAGACAGGCT
TTGTTGTACGACGTACGTAAATTCATTGAATGTTTGAAAAGGTAGAAAATTATTAAATCT
TTGAAACCTCGCTCTGTTTGTTTGTTATTGTCCCCCACATTTGCAAATGGTATCCAAAAA
GGGCAGACACATTTGTTTTAATCTTAGCCAGGTTCAATTTAGCCTTGCGCCCAGACTCAT
TGTATCTGGTGAAGGCTATAGGTGGCCACGTCTTCTAAGATGCTATGCTATTCTTACCAG
AATCCAATGTAAAGAGTTCAAACGCATGGTTCGCTTTGATTGTGATTCTTTCTTAGCACC
TCTCTCCTACCCAGAGTTCACCTGCACTGCTCCTGACTCACAATAAGCTGACGTGCTGTC
ATATATGTGCAACATTGTATACGTTGGCGTTAAGCCCAACTCACTTCCGCTGTCTTTTGG
CAG

DOMAIN 1A-1 (1st part of domain a)

ACAACGTCGTCAGAAAGGACGTGAGTCACCTCACAGTTGACGAGGTGCAAGCTCTTCACG
GCGCCCTCCATGACGTCACTGCATCTACAGGGCCTCTGAGTTTCGAAGACATAACATCTT
ACCATGCCGCACCAGCGTCGTGTGACTACAAGGGACGGAAGATCGCCTGCTGTGTCCACG
GTATGCCCAGTTTCCCCTTCTGGCACAGGGCATATGTCGTCCAAGCCGAGCGGGCACTGT

Fig. 4d

TGTCCAAACGGAAGACTGTCGGAATGCCTTACTGGGACTGGACGCAAACGCTGACTCACT
TACCATCTCTTGTGACTGAACCCATCTACATTGACAGTAAAGGTGGAAAG

INTRON 1A-1/1A-2 (SEQ ID NO:111)

GTAACTACAAACGTCGTCCCATTCATACAGGAGAAATATACAATTGTGTTGTAAGAGCGG
TATACTGTTTGCCAACTGTGTAATTGAAACGTTGATGATGGTGTCTTTGTATTTCAATTT
GTATGCACTTAGACATGATCAATGTTTCTGATGTGTCAAGGATGTTCGGTGTGTCACTTT
CAAAAGATCAAATTCATATGACGTACACAGAGCAAGAACCAACAGTAAGAAGTCTGTATG
ACTTCGCTCTTAAAAGCAATGGAAAAATATTTTCACTTAACACCTAGCCCATAATCACGC
ATATTAGATTATTCAAGCGATGTCAACATGTTTTAATATCAATCTCATGGTTCTGATAT
TACCGGAGACATGCAACAGGCTGCCATTATAGCCAGGAAATCTTATGAATATGTGCATAT
TTTTTCTTTGATTCTGTATGACGAGAAATATTCGGAGGCAAAGATTGTGTTTTCAGAACA
GAATCAGGGTATCAGTGACATCGTCACTGCATGGCTACAATATTGCTGATGTGACTGTTT
CTCCAAGGATTTTCATCTCACTGTCTGTACTTTGAATCTACAAATTCGTATTAAAGTTAT
GACAATTTTACCCCTGCCTATTTGTAAACGAAATATAACATGAGTGTTTATGCTGACAG

DOMAIN 1A-2 (2nd part of domain a)

GCTCAAACCAACTACTGGTACCGCGGCGAGATAGCGTTCATCAATAAGAAGACTGCGCGA
GCTGTAGATGATCGCCTATTCGAGAAGGTGGAGCCTGGTCACTACACACATCTTATGGAG
ACTGTCCTCGACGCTCTCGAACAGGACGAATTCTGTAAATTTGAAATCCAGTTCGAGTTG
GCTCATAATGCTATCCATTACTTGGTTGGCGGTAAATTTGA

INTRON 1A-2/1A-3 (SEQ ID NO:112)

GTAAGTTTGGTTTACAGTTTCATTATAAAAACATAGCAGTTTTAAGTTTAGGGGCAGATT
CTAATCTCTAATATTCCTTTCAACTCACTTTATTGGTGCCTTCTTGGAGTGACATTTAGA
AACTAAGACAAGAGGAAGATGAACAATGTTTGTAGGGATAGACAGCTTGGATGCAATTTC
GGACCAGATTCTAACAGCGTCATGAAGCAAGTGATACACAACGTTATCAATAACGAGAAT
ATACACATAGATGGTTTGAGTTTATAAATGAACTATTAACGGCATTGTGGTTATAGACAG
TGAGGAAGACGCCAGATAGACAAAGGGTAGGGGCCTTGGTTAGATAATGAGAAGTTGAAG
AGGTGTAATAACTTAAATCTCTCTTGACTATTGATTGTGTCTAAGAGTTTTCTTATCTTA
CAGTCGGCCAGTTGGGTCAAAGATGGTGTGATTCGGATGTGCTTTGTGTGTTCTGCGATG
GCTGATTTAGAGTCAGTTTACTTCAGATGAATGAAGTTCCCCGATTCTTATGTTTAAGTT
TGTTTCACCTACGCATGAAGACATCACCAGCAGGGTCGTCTTTATTTCTAGTAGCTTATT
TACAGCAAGCTTGTAACGTATGCTGAATTGCTGTGCCTCTGTAGAACACAGCATCTATGT
TTGCTTGCTTCTTTAGTAGACTGCGGATGTGATGGTTGGTTACCTGGTATGCTGACGAAA
GAATTGTTGACGTGGTGGTTTGCCTTGATGGGTTCGTTGACTTGGTTTGTTGGATACTGA
TTAAGGTGACTCTGCTGGGAGGCTTGGATTCTGGGCCGGTGTTCTTTGCTCTCCTGTCT
AGGGTGGCGATTATTTCCCAACCCACTTGTTCCATTACACTCAAAACCTGCTATCAATTT
ACAG

DOMAIN 1A-3 (3rd part of domain a)

ATATTCAATGTCAAACTTGGAATACACCTCCTACGACCCCATCTTCTTCCTCCACCACTC
CAACGTTGACCGCCTCTTCGCCATCTGGCAGCGTCTTCAGGAACTGCGAGGAAAGAATCC
CAATGCAATGGACTGTGCACATGAACTCGCTCACCAGCAACTCCAACCCTTCAACAGGGA
CAGCAATCCAGTCCAGCTCACAAAGGACCACTCGACACCTGCTGACCTCTTTGATTACAA
ACAACTTGGATACAG

Fig. 4e

INTRON 1A-3/1A-4 (SEQ ID NO:113)

GTGAGACATTATTACACTTCTATTTAGTAGTGGGGGCGGGATAGCTCAGGTGGTAGAGCG
TCGGCCTTCAGCTTCTAGTCTCGCCCACAAGAGCGCGCTGGCTAAAGGGCCGGAGTTAGA
TTCCCGCGGGCGGCAGGCAATATCTCCGAAGGGGAGAACAGTTCTCCAGTCGGTGAAATT
GGGGTGCAATGTTGTACCACTGAAATGCGTGCAGCACCAACCATCCAAATACCAGCCTTG
CCGCGCTGGTCTGACTACATAGTACCACCCGGATTCAACCGGGCTATATAGGTTCTCCTC
CAGCAGTAAATCTGACAGTCGCCATATAGCTGGGATATTGCTGAGTGCGACGTTAAGCCC
CAACTCACTCACTTTATATTTAGTATTCTATTTAGTATCGACGCATGACCATGTGTGGTG
GTCTACTCATCTCAACACGACCGATTAACGTTAAGAGCTGCCAACATGATTCTCTTTCTC
TCTTTAGCCTCTTTATGCCAAAAGCTATATATTAATGTAGGACCCTACATATATTATTTC
CAG

DOMAIN 1A-4 (4th part of domain a)

CTACGACAGCTTAAACCTGAATGGAATGACGCCAGAACAGCTGAAAACAGAACTAGACGA
ACGCCACTCCAAAGAACGTGCGTTTGCAAGCTTCCGACTCAGTGGCTTTGGGGGTTCTGC
CAACGTTGTTGTCTATGCATGTGTCCCTGATGATGATCCACGCAGTGATGACTACTGCGA
GAAAGCAGGCGACTTCTTCATTCTTGGGGGTCAAAGCGAAATGCCGTGGAGATTCTACAG
ACCCTTCTTCTATGATGTAACTGAAGCGGTACATCACCTTGGAGTCCCGCTAAGTGGCCA
CTACTATGTGAAAACAGAACTCTTCAGCGTGAATGGCACAGCACTTTCACCTGATCTTCT
TCCTCAACCAACTGTTGCCTACCGACCTGGGAAAGGTCACCTTGACC

INTRON 1A-4/1B (SEQ ID NO:114)

GTAAGTTGATTGTCTTAATATTGTTTTAATTTTTGCAGAAATTTGATTTTAAATTGTGTA
ATAACAGTACACATTTTTACGCAACAGCAGTCATTATTGTGTGTGAAGATGTCAAACCAG
AAAGGTTTCAATCGTGAAAACAAAAACAATTCTCTATCTGTATACCCCTCAATACCAGTA
TGATCACAAATCTAGGAAATATTACAATACTGCTTCATAGAGTAACTGCTGTTTGTGGCA
GAGCTGGATACGAAGTTTCTGATAGTTCACAGCTACATGATAGTAAATGAACCTGTACAC
ATCAACGGTTGATCATGAAAATTTTGTATGTGTGAAAGTGCTACCTGTATTAGTGAACGT
GCTACCTGTATAACTGAAAGTGCTACCTGTATGACTGAAAGTGCTACCTGTATGCTGAAA
GTGCTACCTGTATTAGTGAACGTGCTACCTGTATAACTGAAAGTGCTACCTGTATGACTG
AAAGTGCTACCTGTATTAGTGAAAGTGCTACCTGTATGAGTGAACGTGCTACCTGTATAA
CTGAAAGTGCTACCTGTATGACTGAAAGTGCTACCTGTATTAGTGAAAGTGCTGCCTGTA
TTAGTGAAAGTGCTACCTGTATGACTGAGCGTGTTACCTGTATGACTGAACGTGCTACCT
GTATTAGTGAAAGTGTAATCTGTATGAGTGAAAGTGCTACCTGTATTAGTGAAAGTGCTA
CTTGTATTAGTGAAAGTGCTACATGTATGACTGAAAGTGCTACATGTATGAATGAGAGTG
CTACCTGTGTGACTGAAAGTGCTACCTGTATTAGTGAAAGTGCTACCTGTATGACTGAAC
GTGCTACCTGTATTAGTGATAGTGTCACTGGTACCAACTGGATGTTCTCACTTCTTTGGC
GAATATCTGGGCTCAAAACAGTTTTTCAGTATCATAGTCGTATCAGTTTGATTTGTATGT
GCAGTGGAATCATTTTCGTCAAATAATCAAAACTGGTGTTGAACTGGCGTTCACGTTTTA
TGGTTGTAAAACAAATTCTGTAAGTAAAGATATTTAGGGATATCTGTATGACATGAACT
GAATTGCTTAAGGTTAGCATGCCATGACAAATTGCTGAATGTCTGAGGATTGGTGGAGCA
ATAAATCATTATTAAGACAAAAATCAGAAACGTCCATTTTCACTTTTAACAGTGTATCTG
TCTGAATGCCCCCTACTTTTTGGAAGAGTATATATGAATTATCGGCAATATAAAACGTTA
AATGGCAAATGTCGGGCATATGTCAGGACATTATTACCGCAGTTTATAGTCATATTTACC
GGGTCTAGGACAATTGTCACCCGACAATTGCCACCCGGACAATTGCCACCCAAAAATAA
AATATACGTAAACAGAAAACAAATATTGCTTTCAGCCTTTATTGAGTTAGATAATGACAT
TTATGTTGATAAATATGTCGTTTGATAATAATAATAACAATAATATAATATTACAATACT
GCAATAGTACTATCAGTACTTATCATTTTATCACAGATTATATATAGATTCTAGAGTCCG

Fig. 4f

ATGTTGTAGGCAACACTTCGTCGGTAGGCCGTTAGGTAGTTATCATTAGGGCTGAGTATT
GCGCCAAATTTCGTATTGCTATATACTGCGATACACGGTTACCTGTTTTGCAATACGTAA
ACTTAGGCAAATATGACAGTTTTTCCATGATTATTTTCACGTTTCAATGCTTAAAATGGT
CTTATCTGTTATCTCCTTGAAGGTTTAATAAAATAACAATAAACATAAATCATTATTGAA
AATTAATGAACAAAAGTAAAGCGCTTCTCAGTTACCTTAACCTAACTTATTTATGAATGG
GATTACTATCCAAGAATGTGAAATTCACAAACACCTTGGGATAACACTGCAAAACGACTG
TTCATGGGACGGACATGAAAAAGGTGAGTCCCATGTTAAACTGTTGAGAAAGTTTCCTAT
ACTGTTTGTCCCGAAAAAGGCTAAAGACCATGTACTAATCAATTATTCTATCTATTTTCG
ATTACTGTTCTCATATTTGGGACAACTGTGCAGATCGGTAGCATCCAAGCTCGTCTAAAT
CGGTTTGATAAACCTTGTCAAATAACATGTTGTCTCAACATCCAAGCTCACCTAAACCTT
GTCAATACCTGCATCTGAACAAATGTATATTTAAGACGATAGCATCCAAGCTCATCTTTA
AAATGAATATTTTCTCTTTTTCTACCAAAACATTATTTGGTTGACAGTTGTCCTCCCTAT
TATAGTAAAAGAACTGGGTGGCAATTGTCCTAGGTGGCAATTGTCCGGATGGCAATTGT
CCGGGTGGCAATTGTCCGGGTGGCAGTTGTCCAGGTGGCTATTGTCCTGTTCCCATATTT
ACGTATCCCATTTTCTGCTCTGTAATTTTAAATAAACTCACCTGCCTAAGGTAAGACGAC
ATGTGTCACGTGAACATCGTTTGGGGGCAAGGGCGGAATCCCTTCGTTGAAAGTAAATGA
ATACTGTACATAGAGATGCGTATCTTGAACTCTTTATTAGCTTTGATATTGTGCTTAATA
TTACATGAATGTATTTCAATATGTAATTATGTGTTCAAATGAATGGTTGACTTGAATGGT
TTTATTGCTTTATATGCTACATCAACATGTGTGTTTCTTTTCATTTCAG

DOMAIN 1B

CACCTGTGCATCATCGCCACGATGACGATCTTATTGTTCGAAAAAATATAGATCATTTGA
CTCGTGAAGAGGAATACGAGCTAAGGATGGCTCTGGAGAGATTCCAGGCCGACACATCCG
TTGATGGGTACCAGGCTACAGTAGAGTACCATGGCCTTCCTGCTCGTTGTCCACGACCAG
ATGCAAAAGTCAGGTTCGCCTGTTGTATGCATGGCATGGCATCCTTCCCTCACTGGCACC
GGCTGTTCGTTACCCAGGTGGAAGATGCTCTTGTACGGCGTGGATCGCCTATCGGTGTTC
CTTATTGGGACTGGACAAAACCTATGACTCACCTTCCAGACTTGGCATCAAATGAGACGT
ACGTAGACCCGTATGGACATACACATCATAATCCATTCTTCAATGCAAATATATCTTTTG
AGGAGGGACACCATCACACGAGCAGGATGATAGATTCGAAACTGTTTGCCCCAGTCGCTT
TTGGGGAGCATTCCCATCTGTTTGATGGAATCCTGTACGCATTTGAGCAGGAAGATTTCT
GCGACTTTGAGATTCAGTTTGAGTTAGTCCATAATTCTATTCATGCGTGGATAGGCGGTT
CCGAAGATTACTCCATGGCCACCCTGCATTACACAGCCTTTGACCCCATTTTCTACCTTC
ATCATTCCAATGTCGATCGTCTATGGGCAATCTGGCAAGCTCTTCAAATCAGGAGACACA
AGCCATATCAAGCCCACTGTGCACAGTCTGTGGAACAGTTGCCAATGAAGCCATTTGCTT
TCCCATCACCTCTTAACAACAACGAGAAGACACATAGTCATTCAGTCCCGACTGACATTT
ATGACTACGAGGAAGTGCTGCACTACAGCTACGATGATCTAACGTTTGGTGGGATGAACC
TTGAAGAAATAGAAGAAGCTATACATCTCAGACAACAGCATGAACGAGTCTTCGCGGGAT
TTCTCCTTGCTGGAATAGGAACATCTGCACTTGTTGACATTTTCATAAATAAACCGGGGA
ACCAACCACTCAAAGCTGGAGATATTGCCATTCTTGGTGGTGCCAAGGAAATGCCTTGGG
CGTTTGACCGCTTGTATAAGGTCGAAATAACTGACTCATTGAAGACACTTTCTCTCGATG
TCGATGGAGATTATGAAGTCACTTTTAAAATTCATGATATGCACGGAAACGCTCTTGATA
CGGACCTGATTCCACACGCAGCAGTTGTTTCTGAGCCAGCTCACC

INTRON 1B/1C (SEQ ID NO:115)

GTAAGTAAATTTACAAAATTTGGTGTTCTCTAACTATCCTAAGTATTCAATCGTTAGCGT
GTACCTATCTGCATAATGCAATACCCTGACTCCATATAAGTATAGTATATTTACTCTGGT
CGAAAACAAACAAATTGAAAACAAGAGTGGACGTGCTGTTATGATTTCTTTTTCATTCTT
GGTTCGTTGTGTAATGCCACAGCCAGCAATTCCAGATATATAGCGACGGTCTATGAATAC
TCCAGTCTGGACCAGACAATCGTGTGGAATGGTTTAGGCACATTATATCAAATTCATTGT

Fig. 4g

TGAAGATATGAGTTATGAGGTCACAATGTTGTCTTGTTACCCCGTGTCAGTAGTGACGTC
ATTTCATGACTGAAATCTCTTCAACGCCGTTTAGCAATAATAGGCTCAGTAGTATTCAAC
CAATTACAATCAGTAGAAAATTCTCTATACTATTCTTATGTTGCATCCTGATATCCCTAT
GCAAAAATTAGTCATCTAATATAATCATTTTCGATAAATACTTTGGGCAAACAAATCAAT
GTAACATCTATTTTCTTTCAG

DOMAIN 1C

CTACCTTTGAGGATGAAAAGCACAGCTTACGAATCAGAAAAAATGTCGACAGCTTGACTC
CTGAAGAAACAAATGAACTGCGTAAAGCCCTGGAGCTTCTTGAAAATGATCATACTGCAG
GTGGATTCAATCAGCTTGGCGCCTTCCATGGAGAGCCTAAATGGTGCCCTAATCCTGAAG
CGGAGCACAAGGTTGCATGCTGTGTTCATGGCATGGCTGTTTCCCTCATTGGCACAGGC
TTCTTGCTCTCCAGGCGGAGAATGCTCTTAGAAAGCATGGGTACAGTGGTGCTCTACCAT
ACTGGGATTGGACTCGCCCCCTTTCCCAACTTCCTGATCTGGTTAGTCATGAGCAGTATA
CAGATCCTTCCGACCATCACGTGAAGCATAACCCGTGGTTCAATGGCCACATCGATACAG
TAAATCAGGATACCACCAGAAGCGTACGGGAGGATCTTTATCAACAACCTGAATTTGGAC
ATTTCACGGATATTGCTCAACAAGTCCTCTTAGCATTAGAACAAGATGACTTCTGTTCGT
TTGAAGTGCAGTATGAGATTTCCCATAATTTTATCCATGCACTTGTAGGAGGAACCGACG
CTTATGGCATGGCATCGCTGAGATATACAGCATACGATCCAATCTTTTTCTTGCATCATT
CAAACACCGACAGGATCTGGGCTATTTGGCAATCCCTGCAAAAATACAGAGGCAAACCGT
ACAACACTGCCAACTGCGCCATAGAATCTATGAGAAGGCCCCTGCAACCATTTGGACTAA
GCAGTGCCATTAACCCTGACAGAATCACCAGAGAGCATGCTATCCCGTTTGATGTCTTCA
ACTATAGAGATAACCTTCATTACGTATATGATACCCTGGAATTTAATGGTTTGTCGATTT
CACAACTTGATAGAGAGCTGGAAAAAATCAAGAGTCACGAAAGAGTATTTGCTGGATTCT
TGCTGTCGGGGATTAAAAAATCTGCTCTTGTGAAATTCGAAGTTTGTACTCCACCTGATA
ATTGTCATAAAGCAGGGGAGTTTTATCTACTCGGGGACGAAAACGAGATGGCTTGGGCCT
ATGACCGACTTTTCAAGTATGATATTACTCAGGTTCTGGAAGCAAACCATCTACACTTCT
ATGATCATCTCTTCATTCGCTACGAAGTCTTTGATCTTAAAGGAGTGAGTTTGGGAACTG
ACCTGTTCCACACTGCAAATGTGGTACATGATTCCGGCACAG

INTRON 1C/1D (SEQ ID NO:116)

GTACGTGGATTTGATTACATAGCAATGCTATATGATTTCAGTAATTACAACCTCAAGTCA
TGTAGCCGTTTTAGATTGCATTACATCAAACAGCATTGGATTAAATTGGGGGATTGTCCA
GGCCGCATTATGTTGCATTCCGAAAATAGTTTGTGTCCAGTGTCCACGTTTAAAATTAAA
CCATTTTAATCATATTAGGGATAATTTTAATAGATGTTATAGTGCTTTATTTCATATTGT
TACAGTGGACAGTCACCAAGGACATATTTTACTCTATAGATACACAAACACCAATTAAAA
CCCTGCTTTGGAAAGTCTAACTTTTTCCCCACAG

DOMAIN 1D

GCACCCGTGATCGTGATAACTACGTTGAAGAAGTTACTGGGGCCAGTCATATCAGGAAGA
ATTTGAACGACCTCAATACCGGAGAAATGGAAAGCCTTAGAGCTGCTTTCCTGCATATTC
AGGACGACGGAACATATGAATCTATTGCCCAGTACCATGGCAAACCAGGCAAATGTCAAT
TGAATGATCATAATATTGCGTGTTGTGTCCATGGTATGCCTACCTTCCCCCAGTGGCACA
GACTGTATGTGGTTCAGGTGGAGAATGCTCTCCTAAACAGGGGATCTGGTGTGGCTGTTC
CTTACTGGGAGTGGACTGCTCCCATAGACCATCTACCTCATTTCATTGATGATGCAACAT
ACTTCAATTCCCGACAACAGCGGTACGACCCTAACCCTTTCTTCAGGGGAAAGGTTACTT
TTGAAAACGCAGTCACAACAAGGGACCCACAAGCCGGGCTCTTCAACTCAGATTATATGT
ATGAGAATGTTTTACTTGCACTGGAGCAGGAAAATTATTGTGACTTTGAAATTCAGTTTG
AGCTTGTTCATAACGCACTTCATTCCATGCTGGGAGGTAAAGGGCAGTACTCCATGTCCT

Fig. 4h

CCCTGGACTATTCTGCGTTTGATCCCGTCTTCTTCCTACATCATGCCAACACGGACAGAC
TGTGGGCAATCTGGCAGGAACTACAAAGATTCCGAGAACTGCCTTATGAAGAAGCGAACT
GTGCAATCAACCTCATGCATCAACCACTGAAGCCGTTCAGTGATCCACATGAGAATCACG
ACAATGTCACTTTGAAATACTCAAAACCACAGGACGGATTCGACTACCAGAACCACTTCG
GATACAAGTATGACAACCTTGAGTTCCATCACTTATCTATCCCAAGTCTTGATGCTACCC
TGAAGCAAAGGAGAAATCACGACAGAGTGTTTGCGGGCTTCCTTCTTCATAACATAGGAA
CTTCTGCTGACATAACTATCTACATATGTCTGCCTGACGGACGGCGTGGCAATGACTGCA
GTCATGAGGCGGGAACATTCTATATCCTCGGAGGCGAAACAGAGATGCCTTTTATCTTTG
ACCGTTTGTATAAATTTGAAATCACCAAACCACTGCAACAGTTAGGAGTCAAGCTGCATG
GTGGAGTTTTCGAACTGGAGCTTGAGATCAAGGCATACAACGGTTCCTATCTGGATCCCC
ATACCTTTGATCCAACTATCATCTTTGAACCTGGAACAG

INTRON 1D/1E (SEQ ID NO:117)

GTAATGCCATCTTAATACAGTTCGTTCGTTAAATTATATATGTTCGTTTACAACACCATA
CCTTGAATTGAGGTAATACATCACTTGATATTGATAATGTAATGGTAATTGTTCTTGTTT
GTAAAACCGTTTCTGGGGTGTTTATTCACTATCCACCTGGTGGATAGTGAGTAAACACAT
TCGGTTTAATATGGGTATCTAATGGACAGTGAAGTGTGCTGGCTAGGCAGATACCTTGGT
TTCTGTGAATGGAGGTAGTAGAAAGGGGTTTTGATGATTGCAG

DOMAIN 1E

ATACCCATATCTTGGACCACGACCATGAGGAAGAGATACTTGTCAGGAAGAATATAATTG
ATTTGAGCCCAAGGGAGAGGGTTTCTCTAGTCAAAGCTTTGCAAAGAATGAAGAATGATC
GCTCCGCTGATGGGTACCAAGCCATTGCCTCTTTCCATGCCCTGCCACCACTCTGTCCCA
ATCCATCTGCAGCTCACCGTTATGCTTGCTGTGTCCATGGCATGGCTACATTTCCCCAGT
GGCACAGACTGTACACTGTTCAGGTTCAGGATGCCCTGAGGAGACATGGTTCACTTGTTG
GTATTCCTTACTGGGACTGGACAAAACCAGTCAACGAGTTACCCGAGCTTCTTTCTTCAG
CAACATTTTATCATCCAATCCGGAATATTAATATTTCAAATCCATTCCTCGGGGCTGACA
TAGAATTTGAAGGACCGGGCGTTCATACAGAGAGGCACATAAATACTGAGCGCCTGTTTC
ACAGTGGGGATCATGACGGATACCACAACTGGTTCTTCGAAACTGTTCTCTTTGCTTTGG
AACAGGAAGATTACTGCGATTTTGAAATACAATTTGAGATAGCCCATAATGGCATCCACA
CATGGATTGGTGGAAGCGCAGTATATGGCATGGACACCTTCACTATGCATCATATGATC
CAATTTTCTACATCCACCATTCACAGACGGACAGAATATGGGCTATTTGGCAAGAGCTGC
AGAAGTACAGGGGTCTATCTGGTTCGGAAGCAAACTGTGCCATTGAACATATGAGAACAC
CCTTGAAGCCTTTCAGCTTTGGGCCACCCTACAATTTGAATAGTCATACGCAAGAATATT
CAAAGCCTGAGGACACGTTTGACTATAAGAAGTTTGGATACAGATATGATAGTCTGGAAT
TGGAGGGGCGATCAATTTCTCGCATTGATGAACTTATCCAGCAGAGACAGGAGAAAGACA
GAACTTTTGCAGGGTTCCTCCTTAAAGGTTTTGGTACATCCGCATCTGTGTCATTGCAAG
TTTGCAGAGTTGATCACACCTGTAAAGATGCGGGCTATTTCACTATTCTGGGAGGATCAG
CCGAAATGCCATGGGCATTCGACAGGCTTTATAAGTATGACATTACTAAAACTCTTCACG
ACATGAACCTGAGGCACGAGGACACTTTCTCTATAGACGTAACTATCACGTCTTACAATG
GAACAGTACTCTCGGGAGACCTCATTCAGACGCCCTCCATTATATTTGTACCTGGACGCC

INTRON 1E/1F-1 (SEQ ID NO:118)

GTGAGTACCTGTTTGCACTAAGACTTCTGTAGGCTAAAAGTGTAAGAAATATCAATTAAT
TTCAATTCACCCAAACTTGAAAACGGTACCTATATAGGTTAACTTTTTGTCTACAGTAAA
CTGAACATACCTACACATTTCATGAAATGATCTCTCAATATTTTCCACCAACAG

Fig. 4i

DOMAIN 1F-1 (1st part of domain f)

ATAAACTCAACTCACGGAAACATACACCTAACAGAGTCCGCCATGAGCTAAGTAGCCTTA
GTTCCCGTGACATAGCAAGCTTGAAGGCAGCTTTGACAAGCCTTCAACATGATAATGGGA
CTGATGGTTATCAAGCTATTGCTGCCTTCCATGGCGTTCCTGCGCAGTGCCACGAGCCAT
CTGGACGTGAG

INTRON 1F-1/1F-2 (SEQ ID NO:119)

GTAAATTTACAGAGCTTTATGAAGTGTGTTCAGAGTGAAGAGACCAAGATATACTTATAC
CCAAAACTAGCTAGCAACAGACGATTTCACTTGTTTCGGACACTTTGTATTATACGTTGG
ATCCCAAGGTAAACGGAAACGTAACCGAGAATCAGTCCGTAAAGTGAGTGAGTGAGTTTG
GGGCTTAACGTCGCACTCAGCAATACCCCAGCTATGTGGCGACTCTCAGATTTACTGCTG
GAGGAGAACCTACATAGCCCGGTTTAACCCGTGTGGTATGTAGTAAGACCAGCGCGGCAT
GGCTGGTATCTGACGGACGAAGGGTGGCGCTGCACGTATTCCAGTGGTACAACACTGCAC
CCCAATTTCACCGACCGGAGAACTGATCTCCCCTTCGGAGATATCGCCTGCCTTCCACGG
GATTCGAACTCGGTGACCTTCAAGCCAGCGCGCTTCTAGCGGGGGCGATTAGAGGTTNAA
GGCCGACGGCTCTACCACCTTAACTATCCCCCGGCCCCACTCCTGACGGAAATGTTTATA
ATTCAGCCTTTGTTTTCTTATTAAACACTCTTGGCAGATTTTCTATAGATAATGGATTCA
CATGTAGACAGTCTCCCATTGTTGTAACTGGTAGTCAAGAGTTAGAATCTGAATACATTC
TCCAAGATGGATCAAGGAAAACAATAATTACTTGATGTTGCAG

DOMAIN 1F-2 (2nd part of domain f)

ATCGCCTGTTGCATCCACGGCATGGCGACGTTTCCTCACTGGCACCGGTTGTACACTCTG
CAGTTGGAGCAAGCGCTGCGCAGACACGGGTCCAGTGTTGCTGTTCCATACTGGGACTGG
ACCAAGCCAATCACCGAACTGCCACACATTCTGACAGACGGAGAATATTATGACGTTTGG
CAAAATGCCGTCTTGGCCAATCCGTTTGCAAGAGGTTATGTGAAAATTAAAGATGCATTT
ACGGTGAGAAATGTCCAGGAAAGTCTGTTCAAAATGTCAAGTTTTGGAAAGCACTCGCTT
CTGTTTGACCAGGCTTTGTTGGCTCTTGAACAAACTGACTACTGTGACTTCGAAGTTCAG
TTTGAAGTGATGCATAACACGATCCATTATCTCGTAGGAGGGCGTCAAACGTACGCCTTC
TCCTCTCTCGAGTATTCCTCATACGATCCAATCTTCTTTATTCACCACTCGTTTGTTGAC
AAAATATGGGCTGTATGGCAAGAACTGCAAAGCAGGAGACATCTACAGTTTAGAACAGCT
GATTGTGCTGTGGGCCTCATGGGTCAGGCAATGAGGCCTTTCAACAAGGATTTCAACCAC
AACTCGTTCACCAAGAAGCACGCAGTCCCTAATACAGTATTTGATTATGAAGATCTTGGC
TATAACTATGACAACCTTGAAATCAGTGGTTTAAACTTAAATGAGATCGAGGCGTTAATA
GCAAAACGCAAGTCACATGCTAGAGTCTTTGCTGGGTTCCTGTTGTTTGGATTAGGAACT
TCGGCTGATATACATCTGGAAATTTGCAAGACATCGGAAAACTGCCATGATGCTGGTGTG
ATTTTCATCCTTGGAGGTTCTGCAGAGATGCATTGGGCATACAACCGCCTCTACAAGTAT
GACATTACAGAAGCATTGCAGGAATTTGACATCAACCCTGAAGATGTTTTCCATGCTGAT
GAACCATTTTTCCTGAGGCTGTCGGTTGTTGCTGTGAATGGAACTGTCATTCCATCGTCT
CATCTTCACCAGCCAACGATAATCTATGAACCAGGCGAAG

INTRON 1F-2/1G-1 (SEQ ID NO:120)

GTGAGATATATGCAAATTGAATGTTGTCCAGATGCGTTGTTTACATTTATATGCTTGGAA
TTGTCCTGAACGAATACAGTGGAATAACCAAAAGCTGAAAAATAAAAAGATATATACTTC
ATTCTGAATTTGTCAGTATTGCTGACCCAAAAACACGTTATCCATGTCGACACTATATTT
GCCTTTCTGAATCTGAGACTGCGTTATGTTTCTAATAATCACGAAATATGGTATACAGGT
TGTGTATCTGTAGAATACCCAAGGCAGAATTTAAAGGGTCACACCCTGTTTAATACAG

Fig. 4j

DOMAIN 1G-1 (1st part of domain g)

ATCACCATGACGACCATCAGTCGGGAAGCATAGCAGGATCCGGGGTCCGCAAGGACGTGA
ACACCTTGACTAAGGCTGAGACCGACAACCTGAGGGAGGCGCTGTGGGGTGTCATGGCAG
ACCACGGTCCCAATGGCTTTCAAGCTATTGCTGCTTTCCATGGAAAACCAGCTTTGTGTC
CCATGCCTGATGGCCACAACTACTCATGTTGTACTCACG

INTRON 1G-1/1G-2 (SEQ ID NO:121)

GTAAGTTTGTGTTGGTTAGTGTTGGTTGCATGTTTTGCCATATCGATAGTATCAGTGTGG
TAACATCTGGTTTCTAGTTCATTCAGTTCACCTTATCAGAAGCTGTTTGCTCTCGTCTAC
AATAGTGACGTCTTTCAGTTTTAGAACCGTGTACATCCGGGTTATATTGGTCTCCAGCAA
CCCGTGCTTGTCGTGGGAGGCCACTGATGGGAACGGGTGGTCAGACTCGCTCACTTAGTT
GACACATGTCAATTGCGAAGATCGATGCTGAGGTTGTTAAACATTGGATTGTCTGGTCCA
GACTCGATTATTTACAGACAGCCGCCATGTACCTGGAATATTGCTGAGTGCGGCGTTAAA
CAACAAACTAGTCAGACTAATCTTTCACTGTTTATAATGATGGCTCGAACCTAGCACTCA
TGTCCCAAGTTGGCGAACATCTGGAAGGGAATTTCAAATGAAAAGAACAATCTTTCACGT
CTATTGGTATCACGCTCCTGGAGAAGAACATGATGTTCACGGCGTTACTTCCTCTTACCT
GTTTTACTTGTTCCCACGTTTCTTCATATTTAAAGAGTATTTGGGTATTAGAGCTTTGGT
GCTGTTACAATGCTACTCAACTGTTCAGTGCGGGCGACCGCGCTTGTTTACACATTAAGT
TTTGTTTGTTGGTTGGTTTGTGTGTGTGTGTGTATGTGTGTGTGTGTGTGTGTGTGTGTA
TGTGTGTGTGTGTATCTATGTCTATGTGTCTGTGTCTGTGTGTCTGTCTATGTGTGTG
TGTGTCTGTGTCTATGTGTGTGTCTGCGTGTGTGTCTGTGTCCGTATGTGGCTGTGTCTA
TGTGTGTGTGTCTGTGTTTATGTGTGTATATGCGTGTGTGTCTGTGTCCGTATGTGGC
TGTGTCTATGTGTGTGACATGCAATACATGCTGTGATACTCACTAGCTGCGTCTATCGAC
CAG

DOMAIN 1G-2 (2nd part of domain g)

GCATGGCTACCTTCCCACACTGGCATCGCCTCTACACCAAGCAGATGGAGGATGCAATGA
GGGCGCATGGGTCTCATGTCGGCCTGCCCTACTGGGACTGGACTGCTGCCTTCACCCACC
TGCCAACACTGGTCACCGACACGGACAACAACCCCTTCCAACAT

INTRON 1G-2/1G-3 (SEQ ID NO:122)

GTAAGAGCGGGGTAGGGATGGGGTGGTAGGGGGTGGGTTGTTCTATTACTTCCCGCTTCA
CTTGTATGAAATGGATAACCTTGGCTGCATCCCAATTGCGTGATCGATTCTCTTTCGATT
CACTCGTGCGATTAGACTGCCTTATTTACTATAGTAGTTAGAATGTTGCTCAGTGCGCCG
TTAAACAACTAATACACAAAACCGCATTTGTTTTATATGGTCACTCTACTGTTTATCACG
TATATGTATGTTCCGACTCACTGGTTGGTGCGTACCATTCTACTGTCACACTGAGAGCCA
ATGTTCTCAGATGTGTGAAATGTTTGAAAGCCGTTTCTACATAATATTGCAGGAATACCA
TTGTAGAATGTAGTCAAACAGGTAACAATCTGTTAGTGAGCCCAGTTCGAGGTTGCGTTG
TAGGGTGTAGTCCAACAGGTAGGCAGTCCATAAGCATAGTTTTTAAGCATTTTAGATCAT
CTATAATTAACCACATGGTTAGCCGCTATGTTTAGTTTAATCCAGTATAAGTTAGAACTG
TTATATTTCGAAGGGAAGTGAGTAAATCCTTATTCCTTGACTACCATTTAATAGATTTCC
CAATGACTCCATTCAACTCCTAACTTTCACATCACTGCTCTCTTCAACAG

DOMAIN 1G-3 (3rd part of domain g)

GGACACATTGATTATCTCAATGTCAGCACAACTCGATCTCCCCGAGACATGCTGTTCAAC
GACCCCGAGCATGGATCAGAGTCGTTCTTCTACAGACAAGTCCTCTTAGCTCTGGAACAA

Fig. 4k

ACTGATTTCTGCAAATTCGAAGTTCAGTTTGAGATAACCCACAATGCCATCCATTCCTGG
ACAGGTGGCCACAGCCCCTACGGAATGTCCACTCTCGACTTCACTGCCTACGATCCTCTC
TTCTGGCTTCACCACTCCAACACCGACAGAATCTGGGCTGTCTGGCAAGCTTTGCAAGAA
TACAGAGGACTTCCATACAACCATGCCAATTGTGAGATCCAGGCAATGAAAACGCCCCTG
AGGCCTTTCAGTGACGATATCAACCACAACCCAGTCACAAAGGCTAACGCGAAGCCATTA
GATGTGTTCGAGTATAATCGGTTGAGCTTCCAGTACGACAACCTCATCTTCCATGGATAC
AGTATTCCGGAACTTGATCGCGTGCTTGAAGAAAGAAAGGAGGAGGACAGAATATTTGCT
GCCTTCCTTCTCAGTGGAATCAAGCGTAGTGCTGATGTAGTGTTCGACATATGCCAGCCA
GAACACGAATGTGTGTTCGCAGGGACTTTTGCGATTTTGGGAGGGGAGCTAGAAATGCCC
TGGTCCTTCGACAGACTGTTCCGCTATGATATCACCAAGGTGATGAAGCAGCTACACCTG
AGGCATGACTCTGACTTTACCTTCAGGGTGAAGATTGTCGGCACCGACGACCACGAGCTT
CCTTCAGACAGTGTCAAAGCACCAACTATTGAATTTGAACCGGGCG

INTRON 1G-3/1H (SEQ ID NO:123)

GTGAGTACGACAGGCATTTCTAGTAAAAACCTACTTTTGGTAAAAGGTTCGAGAAATCAC
TTGAAGCAACAACATGATTTGTAACGCCTATTACACGTGAACATGTCACACCCGGTGAT
GCCGTTTAATGGACATGCCTCTGTTAATGAAAGGGGTAAGTACATGTGTATGGGGATGGG
ATGGGAGCCACCTGTCCCAATTTCATAGGTCCCTAGGATCCCAGTTGCGTAGGAATCCCC
TGATTAATGCCTTGTGAATTCCTCCTGGAATTGTCCTGGCCCAAATTTTTACAAACCCGC
CCCGATATACCTTGGAAATAATTGGGCCTAAGGGTGGGGCTTTTAAGGACCAAGAACCCA
ACCTAAACCCCAACCCATTTTTTCCCACCCATTCCAGGTTTTGTTTTACCAAATAAAAAG
GTTTCCACTTTGAGGAAACCCTTTAAGGGGTTCTTTTCAGGGCTTTTTTTCTTTTCTGGGA
ATTCCAATTCCGGGGGAACAAAATACATATATTTCACAGACCTTTGGTCAAATTTATATA
ATTTCCGACTTCATGTCATAGGTTTGTCTTTCTTCCTACACAG

DOMAIN 1H

TGCACAGAGGCGGAAACCACGAAGATGAACACCATGATGACAGACTCGCAGATGTCCTGA
TCAGGAAAGAAGTTGACTTCCTCTCCCTGCAAGAGGCCAACGCAATTAAGGATGCACTGT
ACAAGCTCCAGAATGACGACAGTAAAGGGGGCTTTGAGGCCATAGCTGGCTATCACGGGT
ATCCTAATATGTGTCCAGAAAGAGGTACCGACAAGTATCCCTGCTGTGTCCACGGAATGC
CCGTGTTCCCCCACTGGCACCGCCTGCATACCATTCAGATGGAGAGAGCTCTGAAAAACC
ATGGCTCTCCAATGGGCATTCCTTACTGGGATTGGACAAAGAAGATGTCGAGTCTTCCAT
CTTTCTTTGGAGATTCCAGCAACAACAACCCTTTCTACAAATATTACATCCGGGGCGTGC
AGCACGAAACAACCAGGGACATTAATCAGAGACTCTTTAATCAAACCAAGTTTGGTGAAT
TTGATTACCTATATTACCTAACTCTGCAAGTCCTGGAGGAAAACTCGTACTGTGACTTTG
AAGTTCAGTATGAGATCCTCCATAACGCCGTCCACTCCTGGCTTGGAGGAACTGGAAAGT
ATTCCATGTCTACCCTGGAGCATTCGGCCTTTGACCCTGTCTTCATGATTCACCACTCGA
GTTTGGATAGAATCTGGATCCTTTGGCAGAAGTTGCAAAAGATAAGAATGAAGCCTTACT
ACGCATTGGATTGTGCTGGCGACAGACTTATGAAAGACCCCCTGCATCCCTTCAACTACG
AAACCGTTAATGAAGATGAATTCACCCGCATCAACTCTTTCCCAAGCATACTGTTTGACC
ACTACAGGTTCAACTATGAATACGATAACATGAGAATCAGGGGTCAGGACATACATGAAC
TTGAAGAGGTAATTCAGGAATTAAGAAACAAAGATCGCATATTTGCTGGTTTTGTTTGT
CGGGCTTACGGATATCAGCTACAGTGAAAGTATTCATTCATTCGAAAAACGATACAAGTC
ACGAAGAATATGCAGGAGAATTTGCAGTTTTGGGAGGTGAGAAGGAGATGCCGTGGGCAT
ATGAAAGAATGCTGAAATTGGACATCTCCGATGCTGTACACAAGCTTCACGTGAAAGATG
AAGACATCCGTTTTAGAGTGGTTGTTACTGCCTACAACGGTGACGTTGTTACCACCAGGC
TGTCTCAGCCATTCATCGTCCACCGTCCAGCCCATGTGGCTCACGACATCTTGGTAATCC
CAGTAGGTGCGGGCCATGACCTTCCGCCTAAAGTCGTAGTAAAGAGCGGCACCAAAGTCG

Fig. 4I

AGTTTACACCAATAGATTCGTCGGTGAACAAAGCAATGGTGGAGCTGGGCAGCTATACTG
CTATGGCTAAATGCATCGTTCCCCCTTTCTCTTACCACGGCTTTGAACTGGACAAAGTCT
ACAGCGTCGATCACGGAGACTACTACATTGCTGCAGGTACCCACGCGTTGTGTGAGCAGA
ACCTCAGGCTCCACATCCACGTGGAACACGAGTAG

3´UTR

TTCACAG

INTRON 3´UTR (SEQ ID NO:124)

GTGAGGAGAAGGCCCCAGGCTAGCAGGGCAATGGATGAAGGAAATAGGGGCAAAGGGAAT
AGCAGTTACACCATCGACATTTCCAACCTCCTCAGAAACTAATATATAGCCTTAATACAA
CCAGCCAAGACTCAACGGGCAGCCGGGGTGGGGGGATTTGGTGGTCGCTGTTTCAGACCA
GGGTGCAAAATATCAGTGCGCAAATCAACATGTTGCGTGTCAGACACTGACACAGCAGTC
ATTGAACCTGCAGACCCATAACAGGAAAATGGGGCAGATACGATCAAAGACAGTGTAAAA
TAGGGATAAGTAGGCATATGCAACCACCTGATGGAAATGAAAAGGGGTAAGTTTAAACCC
CGGCTACCAAAGGTCCAATGGTTCCTTAACCCAGCTTACGCTATCCCTCTAATTTCAGTA
TTGAGCTGATTTCTGTCGAGTTCATGTAAACTGTATACTTTCTGTATTATTACAG

3´UTR

GTTGCTATGCCGACTGCGCTATATTGGTGAACGAGACGATGAGGACATCTCTGAAAGAGT
TCGCCAAGTGATGTGTAGGTCACGGAAGTATTGTTGAGCTAACAATATGATGATTTCAAA
ATGACTTGGCGCTCTAGGACAAAGACATAATTCATCAGCACCCTGTGCACCAACTCTTTG
TTTGCTGCAAACGTCTGACAAGCGACACGTCAATCAACAAGCTGTTCAAACTCAAGTGGA
TGTAACTAGAATCGTTGGGCCATCGTTCACAAAGTATTGACAGATGTCACACATGATGGC
GAGAAACACTTTAGAACTTTTAATGACCTAGAGTGACTTGTAAATATGTAAATATATTCT
TCAAAGACTCAGCTGAACTATTGTTGGATAACACATCAATTCCCTCAACAAAATGCTTTA
TCTTCACATGGATGTATGTAATGTGGCCGGCAATAAAGTATATATATGTAT

Fig. 5a

Primary structure of the HtH1 protein

SIGNAL PEPTIDE

LVQFLLVALVVGAGA

DOMAIN A

DNVVRKDVSHLTVDEVQALHGALHDVTASTGPLSFEDITSYHAAPASCDYKGRKIACCVHGMPSFP
FWHRAYVVQAERALLSKRKTVGMPYWDWTQTLTHLPSLVTEPIYIDSKGGKAQTNYWYRGEIAFIN
KKTARAVDDRLFEKVEPGHYTHLMETVLDALEQDEFCKFEIQFELAHNAIHYLVGGKFEYSMSNLE
YTSYDPIFFLHHSNVDRLFAIWQRLQELRGKNPNAMDCAHELAHQQLQPFNRDSNPVQLTKDHSTP
ADLFDYKQLGYSYDSLNLNGMTPEQLKTELDERHSKERAFASFRLSGFGGSANVVVYACVPDDDPR
SDDYCEKAGDFFILGGQSEMPWRFYRPFFYDVTEAVHHLGVPLSGHYYVKTELFSVNGTALSPDLL
PQPTVAYRPGK

DOMAIN B

GHLDPPVHHRHDDDLIVRKNIDHLTREEEYELRMALERFQADTSVDGYQATVEYHGLPARCPRPDA
KVRFACCMHGMASFPHWHRLFVTQVEDALVRRGSPIGVPYWDWTKPMTHLPDLASNETYVDPYGHT
HHNPFFNANISFEEGHHHTSRMIDSKLFAPVAFGEHSHLFDGILYAFEQEDFCDFEIQFELVHNSI
HAWIGGSEDYSMATLHYTAFDPIFYLHHSNVDRLWAIWQALQIRRHKPYQAHCAQSVEQLPMKPFA
FPSPLNNNEKTHSHSVPTDIYDYEEVLHYSYDDLTFGGMNLEEIEEAIHLRQQHERVFAGFLLAGI
GTSALVDIFINKPGNQPLKAGDIAILGGAKEMPWAFDRLYKVEITDSLKTLSLDVDGDYEVTFKIH
DMHGNALDTDLIPHAAVVSEPAH

DOMAIN C

PTFEDEKHSLRIRKNVDSLTPEETNELRKALELLENDHTAGGFNQLGAFHGEPKWCPNPEAEHKVA
CCVHGMAVFPHWHRLLALQAENALRKHGYSGALPYWDWTRPLSQLPDLVSHEQYTDPSDHHVKHNP
WFNGHIDTVNQDTTRSVREDLYQQPEFGHFTDIAQQVLLALEQDDFCSFEVQYEISHNFIHALVGG
TDAYGMASLRYTAYDPIFFLHHSNTDRIWAIWQSLQKYRGKPYNTANCAIESMRRPLQPFGLSSAI
NPDRITREHAIPFDVFNYRDNLHYVYDTLEFNGLSISQLDRELEKIKSHERVFAGFLLSGIKKSAL
VKFEVCTPPDNCHKAGEFYLLGDENEMAWAYDRLFKYDITQVLEANHLHFYDHLFIRYEVFDLKGV
SLGTDLFHTANVVHDSGT

DOMAIN D

GTRDRDNYVEEVTGASHIRKNLNDLNTGEMESLRAAFLHIQDDGTYESIAQYHGKPGKCQLNDHNI
ACCVHGMPTFPQWHRLYVVQVENALLNRGSGVAVPYWEWTAPIDHLPHFIDDATYFNSRQQRYDPN
PFFRGKVTFENAVTTRDPQAGLFNSDYMYENVLLALEQENYCDFEIQFELVHNALHSMLGGKGQYS
MSSLDYSAFDPVFFLHHANTDRLWAIWQELQRFRELPYEEANCAINLMHQPLKPFSDPHENHDNVT
LKYSKPQDGFDYQNHFGYKYDNLEFHHLSIPSLDATLKQRRNHDRVFAGFLLHNIGTSADITIYIC
LPDGRRGNDCSHEAGTFYILGGETEMPFIFDRLYKFEITKPLQQLGVKLHGGVFELELEIKAYNGS
YLDPHTFDPTIIFEPGT

DOMAIN E

DTHILDHDHEEEILVRKNIIDLSPRERVSLVKALQRMKNDRSADGYQAIASFHALPPLCPNPSAAH
RYACCVHGMATFPQWHRLYTVQVQDALRRHGSLVGIPYWDWTKPVNELPELLSSATFYHPIRNINI
SNPFLGADIEFEGPGVHTERHINTERLFHSGDHDGYHNWFFETVLFALEQEDYCDFEIQFEIAHNG

Fig. 5b

IHTWIGGSAVYGMGHLHYASYDPIFYIHHSQTDRIWAIWQELQKYRGLSGSEANCAIEHMRTPLKP
FSFGPPYNLNSHTQEYSKPEDTFDYKKFGYRYDSLELEGRSISRIDELIQQRQEKDRTFAGFLLKG
FGTSASVSLQVCRVDHTCKDAGYFTILGGSAEMPWAFDRLYKYDITKTLHDMNLRHEDTFSIDVTI
TSYNGTVLSGDLIQTPSIIFVPGR

DOMAIN F

HKLNSRKHTPNRVRHELSSLSSRDIASLKAALTSLQHDNGTDGYQAIAAFHGVPAQCHEPSGREIA
CCIHGMATFPHWHRLYTLQLEQALRRHGSSVAVPYWDWTKPITELPHILTDGEYYDVWQNAVLANP
FARGYVKIKDAFTVRNVQESLFKMSSFGKHSLLFDQALLALEQTDYCDFEVQFEVMHNTIHYLVGG
RQTYAFSSLEYSSYDPIFFIHHSFVDKIWAVWQELQSRRHLQFRTADCAVGLMGQAMRPFNKDFNH
NSFTKKHAVPNTVFDYEDLGYNYDNLEISGLNLNEIEALIAKRKSHARVFAGFLLFGLGTSADIHL
EICKTSENCHDAGVIFILGGSAEMHWAYNRLYKYDITEALQEFDINPEDVFHADEPFFLRLSVVAV
NGTVIPSSHLHQPTIIYEPGE

DOMAIN G

DHHDDHQSGSIAGSGVRKDVNTLTKAETDNLREALWGVMADHGPNGFQAIAAFHGKPALCPMPDGH
NYSCCTHGMATFPHWHRLYTKQMEDAMRAHGSHVGLPYWDWTAAFTHLPTLVTDTDNNPFQHGHID
YLNVSTTRSPRDMLFNDPEHGSESFFYRQVLLALEQTDFCKFEVQFEITHNAIHSWTGGHSPYGMS
TLDFTAYDPLFWLHHSNTDRIWAVWQALQEYRGLPYNHANCEIQAMKTPLRPFSDDINHNPVTKAN
AKPLDVFEYNRLSFQYDNLIFHGYSIPELDRVLEERKEEDRIFAAFLLSGIKRSADVVFDICQPEH
ECVFAGTFAILGGELEMPWSFDRLFRYDITKVMKQLHLRHDSDFTFRVKIVGTDDHELPSDSVKAP
TIEFEPG

DOMAIN H

VHRGGNHEDEHHDDRLADVLIRKEVDFLSLQEANAIKDALYKLQNDDSKGGFEAIAGYHGYPNMCP
ERGTDKYPCCVHGMPVFPHWHRLHTIQMERALKNHGSPMGIPYWDWTKKMSSLPSFFGDSSNNNPF
YKYYIRGVQHETTRDINQRLFNQTKFGEFDYLYYLTLQVLEENSYCDFEVQYEILHNAVHSWLGGT
GKYSMSTLEHSAFDPVFMIHHSSLDRIWILWQKLQKIRMKPYYALDCAGDRLMKDPLHPFNYETVN
EDEFTRINSFPSILFDHYRFNYEYDNMRIRGQDIHELEEVIQELRNKDRIFAGFVLSGLRISATVK
VFIHSKNDTSHEEYAGEFAVLGGEKEMPWAYERMLKLDISDAVHKLHVKDEDIRFRVVVTAYNGDV
VTTRLSQPFIVHRPAHVAHDILVIPVGAGHDLPPKVVVKSGTKVEFTPIDSSVNKAMVELGSYTAM
AKCIVPPFSYHGFELDKVYSVDHGDYYIAAGTHALCEQNLRLHIHVEHE

Fig. 6a

Genomic sequence of the HtH2 gene

DOMAIN 2A-1 (1st part of domain a)
[domain a, parts 1-4: SEQ ID NO:156]

GGTCTTCCGTACTGGGACTGGACGCAGCATCTGACTCAACTCCCAGATCTGGTGTCAGACCCCTTG
TTTGTCGACCCGGAAGGAGGAAAG

INTRON 2A-1/2A-2 (SEQ ID NO:125)

GTAAGGGATCTCAGATCCGTCAGAGTGAGTGAGTGAGTGAGTGAGTGCCCAGCAACTGAAGCTAGG
CCGCCCTACTGGGGATCACAGGGAATGTATGTCAATGGTTGAAGAAAGGAGCAGTGGGTTACAACG
CCGCGTTCAAAGTCATGGCAGTTTCATAGCGCATTGTGCGCGCGTGTGTATCTGTGTGCGCGCGTG
TGTGCTTGCGTGCGTGTGAGTGAGTCCGCTTGTGCATTTGTACTAGCACAGACTAATGCTGGTTCT
AGAGAGCCTACTGATAAATGTTTACATTAAGATCTTTACAGTATACTGAGATTCGAGCCCAGACCA
GCGGAACACCAGGCAGGGTAACAACAAATAACGCCTTTCCACACAACCGACGCAGCCTAAAGTGGC
TCTGATAGGCTGATACCGGTGTATTCTTAGAACTTGTAATTTGTGCTTTGCCATAATACATGTACT
TCAGTTAACTGTAATACAGCATAAGACTGGACCGGTGTTTACGACGCAATGAGCAATAATTACTCT
ACGAAAAGATTTGGTTAGACATATTCAATAATTGTAACATTCATTAACAATGAACACCACGTGCAC
TCTCGTTTGTGTCAACGTATTCATAATCATTCTCATGCATCTGTTAGCTCAGATATTTGATGTTT
CAAGAGATTTGTACGAACGTATGGGCTGGTGCCCCATGAAATTACATACAATGAATTCAGGTGAAA
TACCTGGCGAGACAATAAGATCTTACTAGTGCTGCCACTTCAGTATGGTGTCCCCGATGGTGTCTG
GTGTATGGGTGTGTTTGGCGTCAGTTGTTACTGGAAAAGTCAGCTCTAATTATGTCTTTATGTGGT
TAAAGACCCCATAACCTAGATGTCTGGGTTTAACTTAACATGATAGTAACAGTCGGCTGTATAGCC
TGACGCTTAAACGTTAGATGAATAAGGACTATATTGTGTTGTATAACATTTCTATAACCTCCTTTC
TATATCATTTAG

DOMAIN 2A-2 (2nd part of domain a)

GCCCATGACAACGCATGGTATCGTGGAAACATCAAGTTTGAGAATAAGAAGACTGCAAGAGCTGTT
GACGATCGCCTTTTCGAGAAGGTTGGACCAGGAGAGAATACCCGACTCTTTGAAGGAATTCTCGAT
GCTCTTGAACAGGATGAATTCTGCAACTTCGAGATCCAGTTTGAGTTGGCTCACAACGCTATCCAC
TACCTGGTTGGCGGCCGTCACAC

INTRON 2A-2/2A-3 (SEQ ID NO:126)

GTGAGTCACGTTCTCTGATGGTCACGAGTCACGTTCTCTGATGGTCACGAGTCACGTTCTCTGATG
GTCACGAGTCACGTTCTCTGATGGTCACGAGTCACATTCTCTGATGGTCACGAGTCACATTCTCTG
TTGAGTGAAGTCTCAGTACCATTTATTTCTCTTACCTTCTTCTAACCAGGGGTTTCAGCGTGGATC
GTCTGAGAAGTTAGCGCAAATCTATATTGAAGTCATTTTTCTATCATATAACCATCGTTATATCCA
CGTGCGAAAGTGTTCATTAATTATTTTTATTTTCATTTATGAAGGTCTAAAAGAAAATATGTATTG
TTGGAAACTATATTCGAAGGTGAAGGCAACACGAGTGTATTAATATTCTCAATATCAATGTACGCT
CTGTCAGCACCTGTTTCACCAGGAACTACACCTTTAGCGTACCAAAATATCAGCTGATGATTTCGA
AGCGGACTATACCCTCACCACTTGTTTTGTGTGTGTATTTATGTGTGCATGTGTGTGCGTGCGTGC
GTGTGTGTGTGTCCTACGTATGTTGATATTTTGTTCTGACTGTATATGTTCGTGCTTACCATTG
AAG

Fig. 6b

DOMAIN 2A-3 (3rd part of domain a)

GTACTCCATGTCTCATCTCGAGTACACCTCCTACGACCCCCTCTTCTTCCTCCATCACTCCAACAC
CGACCGCATCTTCGCCATCTGGCAACGTCTTCAGGTACTCAGAGGAAAGGACCCCAACACCGCCGA
CTGCGCACACAACCTCATCCATGAGCCCATGGAACCGTTCCGTCGGGACTCGAACCCTCTTGACCT
CACCAGGGAAAACTCCAAACCAATTGACAGCTTTGATTATGCCCACCTTGGCTACCA

INTRON 2A-3/2A-4 (SEQ ID NO:127)

GTATGTATGATTCTAATAATGAATGTTTTTACCTCCGGTTTAAACAATATTTTAGTATTACGAAAG
GAGAAGTACCTCGAGAGGTCTAGGTCTCAGATGTTTAGAAACCCATGAAGACAGGTATGCTTCTGA
AAAACAAAGTAACATCATGAGGCTAAAGTTCAGATTCAAACCATCGTAGTTCGAATCCAGCATGCA
AAGGGCCCTAACCCTGTAGATGGCGCTGCTTGAAACAGAGTAGTCTGTTCAGGGTCAGTACTGTCC
CCACAAACATCATAGTCAGGGTCAGTACTGTCCCCACAAACATCATAGTCAGGGTCAGTACTGTCC
CCACAAACATCACAGTCAGGGTTAATTTTGGATTCGGTTTCGAATGCGAAGAAGACAGTCACGCCC
TGACACTGGACCGAGGTTGCCGAGAAAGCTCGTGATATTGCTGGAATACTGCCCAGTAAAACCATC
ATTTATTTTAGGCTATTTATTACGAAAAATAATAATATGTATAGAAATGCATATGATCGCTGTTTG
AATGTAAAATTTAGAATGGGTTTGGGAGTGTTCACTATTTTTTCATCAAAATTTCATGTATTTTAA
CCGATCGACGCTGAAGACAAACTACCGTTAATCAGGCAGTTCATTCATATCTGATAGGGAATATTG
GTTGTTAACCAACGCTACATTGTGTCCAG

DOMAIN 2A-4 (4th part of domain a)

GTATGATGACTTGACCCTGAACGGTATGACCCCAGAGGAATTGAACTCATATCTGCATGAACGGTC
AGGCAAGGAGGGGGTGTTCGCAAGCTTCCGACTCTCAGGTTTTGGCGGCTCTGCTAACGTTGTTGT
CTACGCATGCCGTCCTGCCCACGATGAAATGGCTGTCGATCAGTGCGACAAAGCCGGCGACTTCTT
TGTGTTGGGCGGACCCACCGAGATGCCCTGGAGGTTTTACAGAGCATTCCACTTCGACGTCACCGA
CAGCATCGACAACATCGACAAGGACCGCCACGGCCACTATTATGTAAAGGCGGAATTATTCAGTGT
AAATGGAAGTGCGCTACCGAATGATCTCCTGCCTCAACCCACCATCTCACACAGGCCAGCCCGCGG
ACACGTTGATG

INTRON 2A-4/2B (SEQ ID NO:128)

GTAAATGGCCATTGTATACATGCATTCATTTGGACTTTGAGTGAGTGAGTGGATGCGTATTCAGTA
AGTGAGAGTGTGAGTGGGTATTAGGTCTGTGAGTGGGTTGGTGAGTGGATGGGTGAGTAAGAGTGG
GTTGGTGAGAAAGTGAGTGAGTCACTTGGTGGGTGCGTTAGTGGAAGCGTGATTGAGTGGATGGGA
GGTAGGTGAGTGAGTGAATTGGTGGGGGGTGAGTGAGGTTAACGCTGTTCTGCTGTTCAATCACA
CCACATGTTGCCAGCTTACTGTGCAGGACGAATCCAGGGTTGTGTTAAATTTTATATGTTTATATA
TAACGATGGACGTGTCTGGATGTGGCGAATGTGTCAAGAGAATTATGCGGCTTTGTGCTGCTCCGC
GTATTTATTGCACGCGCGTTGGTACGCGGTTGATAAAGTAGTTCAAAACATTTCCCAGCCATCTTT
GTCTGTTGTGAAAACCTACTCCAGGACCATCCATTTCAATATGTGTCTGCGTTCATGGAGTTATAC
ATGTTAAACTGTAGAGCGCAGATGAGCACACTTGAGCATTTCTTCAGTAAATCAGAATGTGTATAT
TTCAAAATTTACCAAATGCAATATCATCAAGCAAATTATGCAGCTCTATAGTAACATCGGAGTCAA
TGGTCCAGTGTGCCCTCGGCTGCCATTCCGACCTCCCTGGCCAGAATACACCCCGGTCAGGATCAG
TTATCCGTCAGAAGGCACGGTGCGGAATGAAAACATAAACACATAGTCGCTTAGTAGTATGCTGAT
TTAGGCACGCAAAATCCGAATGTGAATTACTGTGAATTGCATTACCTGTTACAG

Fig. 6c

DOMAIN 2B

AGGCCCCAGCTCCCTCCTCGGATGCTCACCTCGCCGTCAGGAAGGATATCAACCATCTGACACGCG
AGGAGGTGTACGAGCTGCGCAGAGCTATGGAGAGATTCCAGGCCGACACATCCGTTGATGGGTACC
AGGCTACGGTTGAGTATCACGGCTTACCTGCTCGATGTCCATTCCCCGAGGCCACAAATAGGTTCG
CCTGTTGCATCCACGGCATGGCGACATTCCCTCATTGGCACAGACTGTTCGTTACCCAGGTGGAAG
ATGCACTGATCAGGCGAGGATCCCCTATAGGGGTCCCCTACTGGGACTGGACTCAGCCTATGGCAC
ATCTCCCAGGACTTGCAGACAACGCCACCTATAGAGATCCCATCAGCGGAGACAGCAGACACAACC
CGTTCCACGATGTTGAAGTTGCCTTTGAAAATGGGCGTACAGAACGTCACCCAGATAGTAGATTGT
TTGAACAACCTCTATTTGGCAAACATACGCGTCTCTTCGACAGTATAGTCTATGCTTTTGAGCAGG
AGGACTTCTGCGATTTTGAAGTTCAATTTGAGATGACCCATAATAATATTCACGCCTGGATTGGTG
GCGGCGGGAAGTATTCCATGTCTTCTCTACACTACACAGCCTTCGACCCTATCTCCTACCTTCATC
ACTCCAACACTGACCGTCTCTGGGCAATTTGGCAAGCGTTGCAGATACGAAGAAACAAACCGTATA
AGGCTCATTGTGCTTGGTCTGAGGAACGCCAGCCTCTCAAACCTTTCGCCTTCAGTTCCCCACTGA
ACAACAACGAAAAAACCTACGAAAACTCGGTGCCCACCAACGTTTACGACTACGAAGGAGTCCTTG
GCTATACTTATGATGACCTCAACTTCGGGGGCATGGACCTGGGTCAGCTTGAGGAATACATCCAGA
GGCAGAGACAGAGAGACAGGACCTTTGCTGGCTTCTTTCTGTCACATATTGGTACATCAGCGAATG
TTGAAATCATTATAGACCATGGGACTCTTCATACCTCCGTGGGCACGTTTGCTGTTCTTGGCGGAG
AGAAGGAGATGAAATGGGGATTTGACCGTTTGTACAAATATGAGATTACAGATGAACTGAGGCAAC
TTAATCTCCGTGCTGATGATGGTTTCAGCATCTCTGTTAAAGTAACTGATGTTGATGGCAGTGAGC
TGTCCTCTGAACTCATCCCATCTGCTGCTATCATCTTCGAACGAAGCCATA

INTRON 2B/2C (SEQ ID NO:129)

GTAAGTAGCTACCTGTTTATTCAATTTTTTCGCTTTGCCAATCAATTCATTCAGCTTGAAATTCAA
TAATTGTGTTTTGCATGGCTGAAAACCAATTTGAACTCTTTTCTTTTCTCAGGTCGAACTCAAATA
AATAATCACTAATTGTTATGCACGCGGGTAGGGCATACATACTATATCCACATCGGTCATCTCAAA
ATGCAAACAAATTGTCTTATTTCCGTTGGGACAAGCAAACCCCCTTTCCTGTAATCTTGCCTTTGG
CATCCACTGGAATTAATGTTGACTGGTAATTGATACTGGCTCTCTTCTTGCATAGAGTTAATATCT
ATAGTTTGTAAATCTTTATGATTTTGCTATTTATATTTCGACAGCATGCTATAGACACCCTAGACT
ATTGTATAGCCACTTGTATTGTTTTTCCATTTATTATTTATAACAGAACATGGCTTGTAATTTTTA
TTTACCTTCCAG

DOMAIN 2C

TTGACCATCAGGACCCTCATCAGGACACAATCATCAGGAAAAATGTTGATAATCTTACACCCGAGG
AAATTAATTCTCTGAGGAGGGCAATGGCAGACCTTCAATCAGACAAAACCGCCGGTGGATTCCAGC
AAATTGCTGCTTTTCACGGGGAACCCAAATGGTGCCCAAGTCCCGATGCTGAGAAGAAGTTCTCCT
GCTGTGTCCATGGAATGGCTGTCTTCCCTCACTGGCACAGACTCCTGACCGTGCAAGGCGAGAATG
CCCTGAGAAAGCATGGATGTCTCGGAGCTCTCCCCTACTGGGACTGGACTCGGCCCCTGTCTCACC
TACCTGATTTGGTAAGTCAGCAGAACTACACCGATGCCATATCCACCGTGGAAGCCCGAAACCCCT
GGTACAGCGGCCATATTGATACAGTTGGTGTTGACACAACAAGAAGCGTCCGTCAAGAACTGTATG
AAGCTCCCGGATTTGGTCATTATACTGGGGTCGCTAAGCAAGTGCTTCTGGCTTTGGAGCAGGATG
ACTTCTGTGATTTTGAAGTCCAGTTTGAGATAGCTCACAATTTCATCCACGCTCTTGTCGGCGGAA
GCGAGCCATATGGTATGGCGTCACTCCGTTACACTACTTATGATCCAATTTTCTACCTCCATCATT
CTAACACTGACAGACTCTGGGCTATATGGCAGGCTCTACAAAAGTACAGGGGCAAACCTTACAATT
CCGCCAACTGTGCCATTGCTTCTATGAGAAAACCCCTACAGCCCTTTGGTCTGACTGATGAGATCA
ACCCGGATGATGAGACAAGACAGCATGCTGTTCCTTTCAGTGTCTTTGATTACAAGAACAACTTCA
ATTATGAATATGACACCCTTGACTTCAACGGACTATCAATCTCCCAGCTGGACCGTGAACTGTCAC
GGAGAAAGTCTCATGACAGAGTATTTGCCGGATTTTTGCTGCATGGTATTCAGCAGTCTGCACTAG

Fig. 6d

TTAAATTCTTTGTCTGCAAATCAGATGATGACTGTGACCACTATGCTGGTGAATTCTACATCCTTG
GTGATGAAGCTGAAATGCCATGGGGCTATGATCGTCTTTACAAATATGAGATCACTGAGCAGCTCA
ATGCCCTGGATCTACACATCGGAGATAGATTCTTCATCAGATACGAAGCGTTTGATCTTCATGGTA
CAAGTCTTGGAAGCAACATCTTCCCCAAACCTTCTGTCATACATGACGAAGGGGCAG

INTRON 2C/2D (SEQ ID NO:130)

GTGAGAACATTGATAATAGTTCAAATGAAGTATATCCGATTCAAGCTGTCGATACAAGATGAGATA
CATAATCACAATGTTTGTATTAGATATCTCTCTTAATTTAATGCCGCTTTTATCAATATTCGAGCA
ATCCTTCAGCAACATACACCAGCAAATGTTTCATCAACAGACTATATTATTTAATATTTTAAAAAT
CCTTCTCTGTTGTTATAAATACTTAAAGTATCGAATTCCTTGAATGCGTCTTCTCTGCAGCATATA
GTTAAGTTGTTGTGTTTCTCTGTCAG

DOMAIN 2D

GTCACCATCAGGCTGACGAGTACGACGAAGTTGTAACTGCTGCAAGCCACATCAGAAAGAATTTAA
AAGATCTGTCAAAGGGAGAAGTAGAGAGCCTAAGGTCTGCCTTCCTGCAACTTCAGAACGACGGAG
TCTATGAGAATATTGCCAAATTCCACGGCAAGCCTGGGTTGTGTGATGATAACGGTCGCAAGGTTG
CCTGTTGTGTCCATGGAATGCCCACCTTCCCCAGTGGCACAGACTCTATGTCCTCCAGGTGGAGA
ATGCTTTGCTGGAGAGAGGATCTGCCGTCTCTGTGCCATACTGGGACTGGACTGAAACATTTACAG
AGCTGCCATCTTTGATTGCTGAGGCTACCTATTTCAATTCCCGTCAACAAACGTTTGACCCTAATC
CTTTCTTCAGAGGTAAAATCAGTTTTGAGAATGCTGTTACAACACGTGATCCCCAGCCTGAGCTGT
ACGTTAACAGGTACTACTACCAAAACGTCATGTTGGCTTTTGAACAGGACAACTACTGCGACTTCG
AGATACAGTTTGAGATGGTTCACAATGTTCTCCATGCTTGGCTTGGTGGAAGAGCTACTTATTCTA
TTTCTTCTCTTGATTATTCTGCATTCGACCCTGTGTTTTTCCTTCACCATGCGAACACAGATAGAT
TGTGGGCCATCTGGCAGGAGCTGCAGAGGTACAGGAAGAAGCCATACAATGAAGCGGATTGTGCCA
TTAACCTAATGCGCAAACCTCTACATCCCTTCGACAACAGTGATCTCAATCATGATCCTGTAACCT
TTAAATACTCAAAACCCACTGATGGCTTTGACTACCAGAACAACTTTGGATACAAGTATGACAACC
TTGAGTTCAATCATTTCAGTATTCCCAGGCTTGAAGAAATCATTCGTATTAGACAACGTCAAGATC
GTGTGTTTGCAGGATTCCTCCTTCACAACATTGGGACATCCGCAACTGTTGAGATATTCGTCTGTG
TCCCTACCACCAGCGGTGAGCAAAACTGTGAAAACAAAGCCGGAACATTTGCCGTACTCGGAGGAG
AAACAGAGATGGCGTTTCATTTTGACAGACTCTACAGGTTTGACATCAGTGAAACACTGAGGGACC
TCGGCATACAGCTGGACAGCCATGACTTTGACCTCAGCATCAAGATTCAAGGAGTAAATGGATCCT
ACCTTGATCCACACATCCTGCCAGAGCCATCCTTGATTTTTGTGCCTGGTTCAA

INTRON 2D/2E (SEQ ID NO:131)

GTAAGAAAGTTTCACTGTCTAAATCTTTTTTTATGATAGAGGGTAGAGAAGTGGAGACAATGTGAC
AATATATTGAATAAAGTTGTTTAAAATTTATAACTCTCATAAGTTCATATTATGCTGAAGCTGTAG
CCATCTATAACTGTGTAACATGAAATGTTAAGACATTAACCTAAATACTTCAGCTGATAACAAAAC
AATGTTAATACATACGTCAATGTAACATTTTCTTATCTTTAGGTTATAGCATAAACACTTCAGAGA
TACAGTGACGAAAACCTCTATTTAAATATTTCAG

DOMAIN 2E

GTTCTTTCCTGCGTCCTGATGGGCATTCAGATGACATCCTTGTGAGAAAAGAAGTGAACAGCCTGA
CAACCAGGGAGACTGCATCTCTGATCCATGCTCTGAAAAGTATGCAGGAAGACCATTCACCTGATG
GGTTCCAAGCCATTGCCTCTTTCCATGCCCTGCCACCACTCTGCCCTTCACCATCTGCAACTCACC
GTTATGCTTGCTGTGTCCACGGCATGGCTACATTTCCCCAGTGGCACAGACTGTACACTGTACAGT

Fig. 6e

TCCAGGATGCACTGAGGAGACATGGAGCTGCAGTAGGTGTACCGTATTGGGATTGGCTGCGACCGC
AGTCTCACCTACCAGAGCTTGTCACCATGGAGACATACCATGATATTTGGAGTAACAGAGATTTCC
CCAATCCTTTCTACCAAGCCAATATTGAGTTTGAAGGAGAAAACATTACAACAGAGAGAGAAGTCA
TTGCAGACAAACTTTTTGTCAAAGGTGGACACGTTTTTGATAACTGGTTCTTCAAACAAGCCATCC
TAGCGCTTGAGCAGGAAAACTACTGTGACTTTGAGATTCAGTTTGAAATTCTTCACAACGGCGTTC
ACACGTGGGTCGGAGGCAGTCGTACCCACTCTATCGGACATCTCCATTACGCATCCTACGACCCTC
TTTTCTACCTCCACCATTCCCAGACAGACCGTATTTGGGCAATCTGGCAAGAACTCCAGGAACAGA
GAGGGCTCTCAGGTGATGAGGCTCACTGTGCTCTCGAGCAAATGAGAGAACCATTGAAGCCTTTCA
GCTTCGGCGCTCCTTATAACTTGAATCAGCTAACACAGGATTTCTCCCGACCCGAGGACACCTTCG
ACTACAGGAAGTTTGGTTATGAATATGACAATTTAGAATTCCTAGGAATGTCAGTTGCTGAACTGG
ATCAATACATTATTGAACATCAAGAAAATGATAGAGTATTCGCTGGGTTCCTGTTGAGTGGATTCG
GAGGTTCCGCATCAGTTAATTTCCAGGTTTGTAGAGCTGATTCCACATGTCAGGATGCTGGGTACT
TCACCGTTCTTGGTGGCAGTGCTGAGATGGCGTGGGCATTTGACAGGCTATACAAATATGACATTA
CTGAAACTCTGGAGAAAATGCACCTTCGATATGATGATGACTTCACAATCTCTGTCAGTCTGACCG
CCAACAACGGAACTGTCCTGAGCAGCAGTCTAATCCCAACACCGAGTGTCATATTCCAGCGGGGAC
ATC

INTRON 2E/2F-1 (SEQ ID NO:132)

GTAAGTAGTAAACTGCTCAGATTGTTTTCATAATTACTCCACTATTAAGTAAAAAGTACTAGTAAT
TCAATAGTACTGTTCACAGAGAAATGTAACACAATAGACCACAGAGTCCATTTGTTAAACGCCTTT
GGCTTGGTAAGTCTGAGATTTTGGTGACTGATGGAAAGCTAAAATATATTTTGACAG

DOMAIN 2F-1 (1st part of domain f)

GTGACATAAATACCAAGAGCATGTCAGCGAACCGTGTTCGCCGTGAGCTGAGCGATCTGTCTGCGA
GGGACCCGTCTAGTCTCAAGTCTGCTCTGCGAGACCTACAGGAGGATGATGGCCCCAACGGATACC
AGGCTCTTGCAGCCTTCCATGGGCTACCAGCAGGCTGCCATGATAGCCAGGGAAATGAG

INTRON 2F-1/2F-2 (SEQ ID NO:133)

GTATATTTAAGTATTTTATCTTACGCATGACCCTGACCCTATTTATTTTTTTTAATCCTCGGATT
TGTTTAATCCTGTTACCAGCGAAGGTCCGGGTTAGAATTGATCTTCAGTCAACTATTCTTGTCGTA
GGACTAACGAGTTGTCTGGCTTGCTTACTCGGTTGACACGTGTCAACGGATCCCAATTGCAATTAG
ATCGATGCTCATGCTGTTGATCCCTGGATTGCCTGGTCCGGACTCCACATACCGCCGCCATATTGC
TGGTATATTGTCGAATGCGACGCTAAACAGCAAGCCAACCAACAATACTGAGACCTGGTGGTACAT
GTCAGTTCTCTATTGCTGGGGTTCCAAACATAGCCATCAGTTGAAATATTTCATACATAGAAGAAT
ACCTCTGAATATGATGATGAAACATTTACTTAGACTTGCCTGTGAGCCCCAGGCAAAATGCACTGT
AAAAATACACTGACAGAGGATTAGGCATTCTTGGGAGTACTGTATAGTTAGTTGCATACATATTAG
CGTTCCCTCACTAAAACGAATCTCTGAATGCTATCAATTAAAGATCATGATGCTTTGATTGTGTCT
ACTGTATTTAAAATGGTGTTAAGATTTGCAATTACAATATACACAAACACGTTTCCTGCATCTCGG
AGAATGCAATCTTTCGTTGTACGCGTCTGTTTTCATATTTTTATGCATGTAGTTTGCACTACTTAG
CGTCCAATAAATCCATTCACAAAATCACACAAACAAACGATTTTAGGAATGTGACTGTAGCTGCAA
CGAATATACCTGATCCTTTCTTGTTCCAG

DOMAIN 2F-2 (2nd part of domain f)

ATCGCATGTTGCATTCACGGTATGCCGACCTTCCCCCAGTGGCACAGACTGTACACCCTGCAGTTG
GAGATGGCTCTGAGGAGACATGGATCATCTGTCGCCATCCCCTACTGGGACTGGACAAAGCCTATC

Fig. 6f

TCCGAACTCCCCTCGCTCTTCACCAGCCCTGAGTATTATGACCCATGGCATGATGCTGTGGTAAAC
AACCCATTCTCCAAAGGTTTTGTCAAATTTGCAAATACCTACACAGTAAGAGACCCACAGGAGATG
CTGTTCCAGCTTTGTGAACATGGAGAGTCAATCCTCTATGAGCAAACTCTTCTTGCTCTAGAGCAA
ACCGACTACTGTGATTTTGAGGTACAGTTTGAGGTCCTCCATAACGTGATCCACTACCTTGTTGGC
GGACGTCAGACCTACGCATTGTCTTCTGCATTATGCATCCTACGACCCATTCTTCTTTATACAC
CATTCCTTTGTGGATAAGATGTGGGTAGTATGGCAAGCTCTTCAAAAGAGGAGGAAACTTCCATAC
AAGCGAGCTGACTGTGCTGTCAACCTAATGACTAAACCAATGAGGCCATTTGACTCCGATATGAAT
CAGAACCCATTCACAAAGATGCACGCAGTTCCCAACACACTCTATGACTACGAGACACTGTACTAC
AGCTACGATAATCTCGAAATAGGTGGCAGGAATCTCGACCAGCTTCAGGCTGAAATTGACAGAAGC
AGAAGCCACGATCGCGTTTTTGCTGGATTCTTGCTTCGTGGAATCGGAACTTCTGCTGATGTCAGG
TTTTGGATTTGTAGAAATGAAAATGACTGCCACAGGGGTGGAATAATTTTCATCTTAGGTGGAGCC
AAGGAAATGCCATGGTCATTTGACAGAAACTTCAAGTTTGATATCACCCATGTACTCGAGAAAGCT
GGCATTAGCCCAGAGGACGTGTTTGATGCTGAGGAGCCATTTTATATCAAGGTTGAGATCCATGCT
GTTAACAAGACCATGATACCATCGTCTGTGATCCCAGCCCCAACTATCATCTATTCTCCTGGGGAA
G

INTRON 2F-2/2G-1 (SEQ ID NO:134)

GTGAGAGAACCAGTAATAGCTACTGTCTACAAAGAATGTGTTCATTTAAAGACCTGACTGTAGGCC
GATGGCTGCTGTCATCTCCTCCGCCTCCTCCTCCTGTTCCTCCTCCGAAGGGGTCAGCTTCAGGTT
CTCTTGCCAATATGCCAAGCAGACCTCCTGAGCAGGCAGTATATATACGTAAGGGAAGCAAGTATG
GACCATCGCGCGGCATGTAGAGATACAATGATCAGCTGTCTGCTGTTCCACTCCTGTCAGACAATG
AGATAAACATGAATACAGTATTACTCAGCAGCGTTCCAATTTTCAACCCTCGTATTTATTAAAAAA
AGGAATTTTTAATATATTTTTCTCCTTGTTGAAATATTTTAGTAACTGTTAATCGATATAGAGTGG
AGTAGTGACGCTTTATTTCGGTTCATTCTCGAAACAAAAATATAATAGTCCACTGAACTCTCTTAA
ATTGTTTTTACAACCTTCAACTGCCACAGACGTAATCCCTCACGTTATTTGAGCTGACAACGTGT
TGAATTGAGTGTGTTCCGAATTCTAAATAAGCATGTATATATTTACGTCTCATGCAAGTAATATAT
GTTTAACTGATGACGTCACTTGGTGACCACTGATTTAGTTCCTTTGTCATAATTGCAGTTTCTGTT
GTCACGGGGACGGTGGGGAAGCCAGGTTCCTCCTGTCACGCTGAATATCCCGTTCGAATCCCCCAC
ATGGGTACAAAGTGTGATGCCTATTTCTGGTGTCCCCCACCGTGATATTGCTGGAATAAGTGGCTT
AATACCATATACACTCACTCTATTGTCACACTACTGCCACCGGCTCACACCTCTGATGCTTCTGTT
CTATCCAG

DOMAIN 2G-1 (1st part of domain g)

GTCGCGCTGCTGACAGTGCACACTCAGCCAACATTGCTGGCTCTGGGGTGAGGAAGGACGTCACGA
CCCTCACTGTGTCTGAGACCGAGAACCTAAGACAGGCTCTTCAAGGTGTCATCGATGATACTGGTC
CCAATGGTTACCAAGCAATAGCATCCTTCCACGGAAGTCCTCCAATGTGCGAGATGAACGGCCGCA
AGGTTGCCTGTTGTGCTCACG

INTRON 2G-1/2G-2 (SEQ ID NO:135)

GTAATTAATGGATGTGAAGTCAATGTCCGAGGGTATAATAAGGATTTAAATACTTCAGTCGTGTAA
TACTGTATGACATGTGTATTGGATGGTGTAGGTATTACAGGTTATAAGGCCAGTGTGTGTTGGGAC
GGTTACTTTCCTGCACTAGTAATAAGCATTGTATTTAGCTAGCTTTTATCATATAACTTTAGTTTC
ATGGTTTGTGGCAATTGAAATCGAAATTTTCTTTCATTTCAAGGTTATCGCACTCGTGTGTTAGAA
TAGTTACTATGCTGCATTGAGAATAACACTATAGTAATAAAGCATATCATACAGTAAGAATAACAC
TATAGTAATAAAGTATATCATACAGTAAGAATGTCATTGTATGATAAATAGGTTATCACACTCGTG
TGTTTTAGAATGGTTACTATCCCAGGAATAACCACTATGTATTACATGTATATTGGGCAGTGTAAG
TAGTAGCATTGTATATTAAATCAGTATATCGTGCTTCAAAACACCAGGATATATGGGGTATACAGT

Fig. 6g

```
GGGCAGTGTAAGTAGCAACATTGTATATTAAATCAGTATATCGTACTTCAAAACACCAGGATTATG
GGGTATACAGTGGGCAGTGTAAGTAGTAGCATTGTATATTAAATCAGTATATCGTACTTCAAAACA
CCAGGATATAATTCAGTATATCGTGCTTCAAAACACCAGGATATAATTCAGTATATCGTGCTTCAA
AACACCAGGATATATGGGATATACAGTGCGGGTTTGCATACAACCTCCACCCTTTACAG
```

DOMAIN 2G-2 (2nd part of domain g)

```
GTATGGCCTCCTTCCCACACTGGCACAGACTGTATGTGAAGCAGATGGAAGACGCCCTGGCTGACC
ACGGATCACATATCGGCATCCCTTACTGGGACTGGACAACTGCCTTCACAGAGTTACCCGCCCTTG
TCACAGACTCCGAGAACAATCCCTTCCATGAG
```

INTRON 2G-2/2G-3 (SEQ ID NO:136)

```
GTCAGTTTAGTCTCCTGTCTGAGCTAACGATACCAATTTCCTATTTTCGAGAACCACGATGACGAG
AAAACAAGCAATATAGATATAGATGCAGTATAGATCAAGTTAATGAATTCATTGCTATATGTTTGC
TTGTAATAAACTTTAAGAAAACGAGAGCATGCACACAAATGAAACAAACAATTATGTGTTTGATAG
GAATATGATATATGTATTTGGGGGCTGACGTGAGCAGGGTTGAAGGGACAGTTTACATTGTCAGTA
ACACTGGGAGTATTCTTTGATCCACAATATATAGTTTCATTGTGTTCAGCAGTTACAACTAACATT
ATATCATACATTACGTCGTAACATGCTTCTTTTGTCCTCTTCTGCCAG
```

DOMAIN G-3 (3rd part of domain g)

```
GGTCGCATTGATCATCTCGGTGTAACCACGTCACGTTCCCCCAGAGACATGCTGTTTAACGACCCA
GAGCAAGGATCAGAGTCGTTCTTCTATAGACAAGTCCTCCTGGCTTTGGAGCAGACTGACTACTGC
CAGTTCGAAGTCCAGTTTGAGCTGACCCACAACGCCATTCACTCCTGGACAGGTGGACGTAGCCCT
TACGGAATGTCGACCCTCGAGTTCACAGCCTACGATCCTCTCTTCTGGCTTCACCACTCCAACACC
GACAGAATCTGGGCTGTCTGGCAAGCACTGCAGAAATACCGAGGACTCCCATACAACGAAGCACAC
TGTGAAATCCAGGTTCTGAAACAGCCCTTGAGGCCATTCAACGATGACATCAACCACAATCCAATC
ACCAAGACTAATGCCAGGCCTATCGATTCATTTGATTATGAGAGGTTTAACTATCAGTATGACACC
CTTAGCTTCCATGGTAAGAGCATCCCTGAACTGAATGACCTGCTCGAGGAAAGAAAAAGAGAAGAG
AGAACATTTGCTGCCTTCCTTCTTCGTGGAATCGGTTGCAGTGCTGATGTCGTCTTTGACATCTGC
CGCCCCAATGGTGACTGTGTCTTTGCAGGAACCTTTGCTGTGCTGGGAGGGGAGCTAGAAATGCCT
TGGTCCTTCGACAGACTGTTCCGCTATGACATCACCAGAGTCATGAATCAGCTCCATCTCCAGTAT
GATTCAGATTTCAGTTTCAGGGTGAAGCTTGTTGCAACCAATGGCACTGAGCTTTCATCAGACCTC
CTCAAGTCACCAACAATTGAACATGAACTTGGAG
```

INTRON 2G-3/2H (SEQ ID NO:137)

```
GTATGTTATCTTATTATCAAATGTGTAATCAGATACTGGAGACGTTTTCATATTAACTTGGTCAGC
ATTAGTTGATGATTTTGGTGCGATATTGACGACAAGGAGTTAAGCATTAACACGTTCAACACATCT
TTAATCTGATATGAGAAGGGAATAAATTGATCCAGTATTGATGATTGAAGTTAGATTAACAGTGAA
AGATATACCAGTTTTGATAATCGTATAAAACAGTAGCAGAATTGTATCGTGAAAACTAAATGTGGG
AAGGCGAACGCCAAGCAGATTTTAGATTACGATCGTGTGCTAGAATAATTCACAATAACCCAGACG
TCGGAAATGTGGTTGTCTATGGCAATAGTTACGATTAATTGCTAACATGCACGATTTACCTATTTC
AG
```

DOMAIN 2H

```
CCCACAGAGGACCAGTTGAAGAAACAGAAGTCACTCACCAAAATACTGACGGCAATGCACACTTCC
ATCGTAAGGAAGTTGATTCGCTGTCCCTGGATGAAGCAAACAACTTGAAGAATGCCCTTTACAAGC
```

Fig. 6h

```
TACAGAACGACCACAGTCTAACAGGATACGAAGCAATCTCTGGTTACCATGGATACCCGAATCTGT
GTCCGGAAGAAGGCGATGACAAATACCCCTGCTGCGTCCACGGAATGGCCATCTTCCCCCACTGGC
ACAGACTCTTGACCATCCAACTGGAAAGAGCTCTCGAGCACAATGGTGCACTGCTTGGTGTTCCTT
ACTGGGACTGGACCAAGGACCTGTCGTCACTGCCGGCGTTCTTCTCCGACTCCAGCAACAACAATC
CCTACTTCAAGTACCACATCGCAGGTGTTGGTCACGACACCGTCAGAGAGCCAACTAGTCTTATAT
ATAACCAGCCCCAAATCCATGGTTATGATTATCTCTATTACCTAGCATTGACCACGCTTGAAGAAA
ACAATTACTGTGACTTTGAGGTTCAGTATGAGATCCTCCACAACGCCGTCCACTCCTGGCTTGGAG
GATCCCAGAAGTATTCCATGTCTACCCTGGAGTATTCGGCCTTTGACCCTGTCTTTATGATCCTTC
ACTCGGGTCTAGACAGACTTTGGATCATCTGGCAAGAACTTCAGAAGATCAGGAGAAAGCCCTACA
ACTTCGCTAAATGTGCTTATCATATGATGGAAGAGCCACTGGCGCCCTTCAGCTATCCATCTATCA
ACCAGGACGAGTTCACCCGTGCCAACTCCAAGCCTTCTACAGTTTTTGACAGCCATAAGTTCGGCT
ACCATTACGATAACCTGAATGTTAGAGGTCACAGCATCCAAGAACTCAACACAATCATCAATGACT
TGAGAAACACAGACAGAATCTACGCAGGATTTGTTTTGTCAGGCATCGGTACGTCTGCTAGTGTCA
AGATCTATCTCCAACAGATGACAATGACGAAGAAGTTGGAACTTTCACTGTCCTGGGAGGAGAGA
GGGAAATGCCATGGGCCTACGAGCGAGTTTTCAAGTATGACATCACAGAGGTTGCAGATAGACTTA
AACTAAGTTATGGGGACACCTTTAACTTCCGACTAGAGATCACATCCTACGATGGATCGGTGGTAA
ACAAGAGCCTACCCAATCCTTTCATCATCTACAGACCTGCCAATCATGACTACGATGTTCTTGTTA
TCCCAGTAGGAAGAAACCTTCACATCCCTCCCAAAGTTGTCGTCAAGAGAGGCACCCGCATCGAGT
TCCACCCAGTCGATGATTCAGTTACGAGACCAGTTGTTGATCTTGGAAGCTACACTGCACTCTTCA
ACTGTGTGGTACCACCGTTCACATACCGCGGATTCGAACTGAACCACGTCTATTCTGTCAAGCCTG
GTGACTACTATGTTACCGGACCAACGAGAGACCTTTGCCAGAATGCAGATGTCAGGATTCATATCC
ATGTTGAGGATGAGTAA
```

3´UTR

```
CGCAACAG
```

INTRON 3´UTR (SEQ ID NO:138)

```
GTGAGATAAGAAACCCTTCTAACAGTAATACGACACCACATTACAGCTTAAACATGATTGCCATCG
ATGTTTTCATGTGTAGTATACGCTTTTCAGTTCTACATAATTTTGTTTTTCAAATCAAGTTTAGCA
AATGAATCTATCACTGGAAAATAGGGTAGGGTAGCCAAGTGGTTAAAGCGGTCACTGATCACGCCA
AAGACGAGTGTCCTAACCTGCATGGGTACAAAAGTGAAGACCATTGCTGGTGTCTACCGCCGTAAT
ATTGTTTTTAGTATTGCTAAAACTTATACTCACCCATGCGCTGTAAAAGTGGAATAATAATCATAT
TTCAACAAAAGCACAAAACCATTTCATTTTCATGAAAGCCTCTTGTTCACCTGAAAGACGCAAGAG
AACAATAGTTCCTAACATTATTTTCAGACATTGGAAATGTCCTGCACGTGTAAACCATATATCCTT
TGAAATTTTTACGACTGCATCGTATACAATTTATGATATAAATTTAAAACTTTATTTCAG
```

3´UTR

```
GTTTCTTGGTCTCCACATATTCACACATCAGCACCAAACGGTTTCGAAGGACATTGGCGTTCTTCT
CTGGCAATGCATTTCAATACAACATTGAAAATGACTTCAGCATATCAGTGTGCTTCGAACGTGTTC
CGGAAGTACTCAAATGTGCTATGACTGAATTATTGTACATACATAACTTATTGATGTTCAATAAAT
AAATGTTGAAACG
```

Fig. 7a

Primary structure of the HtH2 protein

DOMAIN A (SEQ ID NO:156)

GLPYWDWTQHLTQLPDLVSDPLFVDPEGGKAHDNAWYRGNIKFENKKTARAVDDRLFEKVGPGENT
RLFEGILDALEQDEFCNFEIQFELAHNAIHYLVGGRHTYSMSHLEYTSYDPLFFLHHSNTDRIFAI
WQRLQVLRGKDPNTADCAHNLIHEPMEPFRRDSNPLDLTRENSKPIDSFDYAHLGYQYDDLTLNGM
TPEELNSYLHERSGKEGVFASFRLSGFGGSANVVVYACRPAHDEMAVDQCDKAGDFFVLGGPTEMP
WRFYRAFHFDVTDSIDNIDKDRHGHYYVKAELFSVNGSALPNDLLPQPTISHRPARGHVDEAPAPS
SDAHLAVRKDINHLTREEVYELRRAMERFQADTSVDGYQATVEYHGLPARCPFPEATNRFACCIHG
MATFPHW

DOMAIN B

HRLFVTQVEDALIRRGSPIGVPYWDWTQPMAHLPGLADNATYRDPISGDSRHNPFHDVEVAFENGR
TERHPDSRLFEQPLFGKHTRLFDSIVYAFEQEDFCDFEVQFEMTHNNIHAWIGGGGKYSMSSLHYT
AFDPISYLHHSNTDRLWAIWQALQIRRNKPYKAHCAWSEERQPLKPFAFSSPLNNNEKTYENSVPT
NVYDYEGVLGYTYDDLNFGGMDLGQLEEYIQRQRQRDRTFAGFFLSHIGTSANVEIIIDHGTLHTS
VGTFAVLGGEKEMKWGFDRLYKYEITDELRQLNLRADDGFSISVKVTDVDGSELSSELIPSAAIIF
ERSH

DOMAIN C

IDHQDPHQDTIIRKNVDNLTPEEINSLRRAMADLQSDKTAGGFQQIAAFHGEPKWCPSPDAEKKFS
CCVHGMAVFPHWHRLLTVQGENALRKHGCLGALPYWDWTRPLSHLPDLVSQQNYTDAISTVEARNP
WYSGHIDTVGVDTTRSVRQELYEAPGFGHYTGVAKQVLLALEQDDFCDFEVQFEIAHNFIHALVGG
SEPYGMASLRYTTYDPIFYLHHSNTDRLWAIWQALQKYRGKPYNSANCAIASMRKPLQPFGLTDEI
NPDDETRQHAVPFSVFDYKNNFNYEYDTLDFNGLSISQLDRELSRRKSHDRVFAGFLLHGIQQSAL
VKFFVCKSDDDCDHYAGEFYILGDEAEMPWGYDRLYKYEITEQLNALDLHIGDRFFIRYEAFDLHG
TSLGSNIFPKPSVIHDEGA

DOMAIN D

GHHQADEYDEVVTAASHIRKNLKDLSKGEVESLRSAFLQLQNDGVYENIAKFHGKPGLCDDNGRKV
ACCVHGMPTFPQWHRLYVLQVENALLERGSAVSVPYWDWTETFTELPSLIAEATYFNSRQQTFDPN
PFFRGKISFENAVTTRDPQPELYVNRYYYQNVMLAFEQDNYCDFEIQFEMVHNVLHAWLGGRATYS
ISSLDYSAFDPVFFLHHANTDRLWAIWQELQRYRKKPYNEADCAINLMRKPLHPFDNSDLNHDPVT
FKYSKPTDGFDYQNNFGYKYDNLEFNHFSIPRLEEIIRIRQRQDRVFAGFLLHNIGTSATVEIFVC
VPTTSGEQNCENKAGTFAVLGGETEMAFHFDRLYRFDISETLRDLGIQLDSHDFDLSIKIQGVNGS
YLDPHILPEPSLIFVPGSS

DOMAIN E

SFLRPDGHSDDILVRKEVNSLTTRETASLIHALKSMQEDHSPDGFQAIASFHALPPLCPSPSATHR
YACCVHGMATFPQWHRLYTVQFQDALRRHGAAVGVPYWDWLRPQSHLPELVTMETYHDIWSNRDFP
NPFYQANIEFEGENITTEREVIADKLFVKGGHVFDNWFFKQAILALEQENYCDFEIQFEILHNGVH
TWVGGSRTHSIGHLHYASYDPLFYLHHSQTDRIWAIWQELQEQRGLSGDEAHCALEQMREPLKPFS
FGAPYNLNQLTQDFSRPEDTFDYRKFGYEYDNLEFLGMSVAELDQYIIEHQENDRVFAGFLLSGFG
GSASVNFQVCRADSTCQDAGYFTVLGGSAEMAWAFDRLYKYDITETLEKMHLRYDDDFTISVSLTA
NNGTVLSSSLIPTPSVIFQRGH

Fig. 7b

DOMAIN F

RDINTKSMSANRVRRELSDLSARDPSSLKSALRDLQEDDGPNGYQALAAFHGLPAGCHDSQGNEIA
CCIHGMPTFPQWHRLYTLQLEMALRRHGSSVAIPYWDWTKPISELPSLFTSPEYYDPWHDAVVNNP
FSKGFVKFANTYTVRDPQEMLFQLCEHGESILYEQTLLALEQTDYCDFEVQFEVLHNVIHYLVGGR
QTYALSSLHYASYDPFFFIHHSFVDKMWVVWQALQKRRKLPYKRADCAVNLMTKPMRPFDSDMNQN
PFTKMHAVPNTLYDYETLYYSYDNLEIGGRNLDQLQAEIDRSRSHDRVFAGFLLRGIGTSADVRFW
ICRNENDCHRGGIIFILGGAKEMPWSFDRNFKFDITHVLEKAGISPEDVFDAEEPFYIKVEIHAVN
KTMIPSSVIPAPTIIYSPGE

DOMAIN G

GRAADSAHSANIAGSGVRKDVTTLTVSETENLRQALQGVIDDTGPNGYQAIASFHGSPPMCEMNGR
KVACCAHGMASFPHWHRLYVKQMEDALADHGSHIGIPYWDWTTAFTELPALVTDSENNPFHEGRID
HLGVTTSRSPRDMLFNDPEQGSESFFYRQVLLALEQTDYCQFEVQFELTHNAIHSWTGGRSPYGMS
TLEFTAYDPLFWLHHSNTDRIWAVWQALQKYRGLPYNEAHCEIQVLKQPLRPFNDDINHNPITKTN
ARPIDSFDYERFNYQYDTLSFHGKSIPELNDLLEERKREERTFAAFLLRGIGCSADVVFDICRPNG
DCVFAGTFAVLGGELEMPWSFDRLFRYDITRVMNQLHLQYDSDFSFRVKLVATNGTELSSDLLKSP
TIEHEL

DOMAIN H

GAHRGPVEETEVTHQNTDGNAHFHRKEVDSLSLDEANNLKNALYKLQNDHSLTGYEAISGYHGYPN
LCPEEGDDKYPCCVHGMAIFPHWHRLLTIQLERALEHNGALLGVPYWDWTKDLSSLPAFFSDSSNN
NPYFKYHIAGVGHDTVREPTSLIYNQPQIHGYDYLYYLALTTLEENNYCDFEVQYEILHNAVHSWL
GGSQKYSMSTLEYSAFDPVFMILHSGLDRLWIIWQELQKIRRKPYNFAKCAYHMMEEPLAPFSYPS
INQDEFTRANSKPSTVFDSHKFGYHYDNLNVRGHSIQELNTIINDLRNTDRIYAGFVLSGIGTSAS
VKIYLRTDDNDEEVGTFTVLGGEREMPWAYERVFKYDITEVADRLKLSYGDTFNFRLEITSYDGSV
VNKSLPNPFIIYRPANHDYDVLVIPVGRNLHIPPKVVVKRGTRIEFHPVDDSVTRPVVDLGSYTAL
FNCVVPPFTYRGFELNHVYSVKPGDYYVTGPTRDLCQNADVRIHIHVEDE

Fig 8a

Genomic sequence of the KLH1 gene

DOMAIN 1B

GGCCTACCGTACTGGGACTGGACTGAACCCATGACACACATTCCGGGTCTGGCAGGAAACAAAACT
TATGTGGATTCTCATGGTGCATCCCACACAAATCCTTTTCATAGTTCAGTGATTGCATTTGAAGAA
AATGCTCCCCACACCAAAAGACAAATAGATCAAAGACTCTTTAAACCCGCTACCTTTGGACACCAC
ACAGACCTGTTCAACCAGATTTTGTATGCCTTTGAACAAGAAGATTACTGTGACTTTGAAGTCCAA
TTTGAGATTACCCATAACACGATTCACGCTTGGACAGGAGGAAGCGAACATTTCTCAATGTCGTCC
CTACATTACACAGCTTTCGATCCTTTGTTTTACTTTCACCATTCTAACGTTGATCGTCTTTGGGCC
GTTTGGCAAGCCTTACAGATGAGACGGCATAAACCCTACAGGGCCCACTGCGCCATATCTCTGGAA
CATATGCATCTGAAACCATTCGCCTTTTCATCTCCCCTTAACAATAACGAAAAGACTCATGCCAAT
GCCATGCCAAACAAGATCTACGACTATGAAAATGTCCTCCATTACACATACGAAGATTTAACATTT
GGAGGCATCTCTCTGGAAAACATAGAAAAGATGATCCACGAAAACCAGCAAGAAGACAGAATATAT
GCCGGTTTTCTCCTGGCTGGCATACGTACTTCAGCAAATGTTGATATCTTCATTAAAACTACCGAT
TCCGTGCAACATAAGGCTGGAACATTTGCAGTGCTCGGTGGAAGCAAGGAAATGAAGTGGGGATTT
GATCGCGTTTTCAAGTTTGACATCACGCACGTTTTGAAAGATCTCGATCTCACTGCTGATGGCGAT
TTCGAAGTTACTGTTGACATCACTGAAGTCGATGGAACTAAACTTGCATCCAGTCTTATTCCACAT
GCTTCTGTCATTCGTGAGCATGCACGTGGTAAGCTGAATAGAG

INTRON 1B/1C (SEQ ID NO:139)

GTTTTGTAATAATTATGTAGAATTCTTTACCTCAGAATAAGATGAGGTCACATGGGTTTTGCAAAA
CTATTACGTTCGAATTAATATTAATAATACCGGACCCTCCACTGGTACATATTTATCTTTATAACG
ATAATAGCGATGATGATGATGATGATGATGATGATGATGATGATGATAATGATGATGCCGGTATTG
CACGTAATCCAGCCGACTTAGATGACACCCTAAGGGTGCAGAAAGTATAACAATTAGATTGCGTTT
GCATCTGTGTATGCGTGTGCTTTAACCAAAAGTCAAAATAAAAGTGCAAACCCTTAGTTTATTCAT
TTGATAGAGCCTTTTACGATAAGAACAATGTAATAAATTAGAACATAACTGAAACCTCCGAAAGAA
GGCCTGTTTGTCAAGAGAGGTATCGACATGATTGACTTATAAACCTGTGCTTCTATATTTGGAAC
TGTCCACTTTCTTGTTGTGTGTACTGTAATCACATCGCACTATGGCTGCAAGACGTGTACGAGTAC
ACTATATACTTACCTAATGACCAACCACAAGGCTGGCTTTGTTAATATTGTTATTTCACAGAAATA
AACACAGAATTCCAGCATTTGGCTGGTGTATTTAGCAAAACACCGATATGACACTCATGTTTTATT
ACATTTTTTCAG

DOMAIN 1C

TTAAATTTGACAAAGTGCCAAGGAGTCGTCTTATTCGAAAAAATGTAGACCGTTTGAGCCCCGAGG
AGATGAATGAACTTCGTAAAGCCCTAGCCTTACTGAAAGAGGACAAAAGTGCCGGTGGATTTCAGC
AGCTTGGTGCATTCCATGGGGAGCCAAAATGGTGTCCTAGTCCCGAAGCATCTAAAAAATTTGCCT
GCTGTGTTCACGGCATGTCTGTGTTCCCTCACTGGCATCGACTGTTGACGGTTCAGAGTGAAAATG
CTTTGAGACGACATGGCTACGATGGAGCTTTGCCGTACTGGGATTGGACCTCTCCTCTTAATCACC
TTCCCGAACTGGCAGATCATGAGAAGTACGTCGACCCTGAAGATGGGGTAGAGAAGCATAACCCTT
GGTTCGATGGTCATATAGATACAGTCGACAAAACAACAACAAGAAGTGTTCAGAATAAACTCTTCG
AACAGCCTGAGTTTGGTCATTATACAAGCATTGCCAAACAAGTACTGCTAGCGTTGGAACAGGACA
ATTTCTGTGACTTTGAAATCCAATATGAGATTGCCCATAACTACATCCATGCACTTGTAGGAGGCG
CTCAGCCTTATGGTATGGCATCGCTTCGCTACACTGCTTTTGATCCACTATTCTACTTGCATCACT
CTAATACAGATCGTATATGGGCAATATGGCAGGCTTTACAGAAGTACAGAGGAAAACCGTACAACG
TTGCTAACTGTGCTGTTACATCGATGAGAGAACCTTTGCAACCATTTGGCCTCTCTGCCAATATCA
ACACAGACCATGTAACCAAGGAGCATTCAGTGCCATTCAACGTTTTTGATTACAAGACCAATTTCA
ATTATGAATATGACACTTTGGAATTTAACGGTCTCTCAATCTCTCAGTTGAATAAAAAGCTCGAAG

Fig. 8b

CGATAAAGAGCCAAGACAGGTTCTTTGCAGGCTTCCTGTTATCTGGTTTCAAGAAATCATCTCTTG
TTAAATTCAATATTTGCACCGATAGCAGCAACTGTCACCCCGCTGGAGAGTTTTACCTTCTGGGTG
ATGAAAACGAGATGCCATGGGCATACGATAGAGTCTTCAAATATGACATAACCGAAAAACTCCACG
ATCTAAAGCTGCATGCAGAAGACCACTTCTACATTGACTATGAAGTATTTGACCTTAAACCAGCAA
GCCTGGGAAAGATTTGTTCAAGCAGCCTTCAGTCATTCATGAACCAAGAATAG

INTRON 1C/1D (SEQ ID NO:140)

GTACTTGTTATATGTTTCGAATATTGCCGATACCTTCAATATATATACTTTATCAAAGTAATTGAT
TAATCTGAAGTAATTTTCCTTTCCAGTAGAGATTCAGTTGATACAACAAGAATTCGCCCTGTTGTA
TGTCACTTTATTTTCATCAAACGATTCGAAGTGAGCTGTCCATGCCACAATGGGGTCTCTGTAACT
TTCTCGTATGGGGTATAGATTATATAGACGTGGCAGACCTTACGTATAACTAATATTTGTGTAATG
TCGTTTCAG

DOMAIN 1D

GTCACCATGAAGGCGAAGTATATCAAGCTGAAGTAACTTCTGCCAACCGTATTCGAAAAAACATTG
AAAATCTGAGCCTTGGTGAACTCGAAAGTCTGAGAGCTGCCTTCCTGGAAATTGAAAACGATGGAA
CTTACGAATCAATAGCTAAATTCCATGGTAGCCCTGGTTTGTGCCAGTTAAATGGTAACCCCATCT
CTTGTTGTGTCCATGGCATGCCAACTTTCCCTCACTGGCACAGACTGTACGTGGTTGTCGTTGAGA
ATGCCCTCCTGAAAAAGGATCATCTGTAGCTGTTCCCTATTGGGACTGGACAAAACGAATCGAAC
ATTTACCTCACCTGATTTCAGACGCCACTTACTACAATTCCAGGCAACATCACTATGAGACAAACC
CATTCCATCATGGCAAAATCACACACGAGAATGAAATCACTACTAGGGATCCCAAGGACAGCCTCT
TCCATTCAGACTACTTTTACGAGCAGGTCCTTTACGCCTTGGAGCAGGATAACTTCTGTGATTTCG
AGATTCAGTTGGAGATATTACACAATGCATTGCATTCTTTACTTGGTGGCAAAGGTAAATATTCCA
TGTCAAACCTTGATTACGCTGCTTTTGATCCTGTGTTCTTCCTTCATCACGCAACGACTGACAGAA
TCTGGGCAATCTGGCAAGACCTTCAGAGGTTCCGAAAACGGCCATACCGAGAAGCGAATTGCGCTA
TCCAATTGATGCACACGCCACTCCAGCCGTTTGATAAGAGCGACAACAATGACGAGGCAACGAAAA
CGCATGCCACTCCACATGATGGTTTTGAATATCAAAACAGCTTTGGTTATGCTTACGATAATCTGG
AACTGAATCACTACTCGATTCCTCAGCTTGATCACATGCTGCAAGAAAGAAAAAGGCATGACAGAG
TATTCGCTGGCTTCCTCCTTCACAATATTGGAACATCTGCCGATGGCCATGTATTTGTATGTCTCC
CAACTGGGGAACACACGAAGGACTGCAGTCATGAGGCTGGTATGTTCTCCATCTTAGGCGGTCAAA
CGGAGATGTCCTTTGTATTTGACAGACTTTACAAACTTGACATAACTAAAGCCTTGAAAAAGAACG
GTGTGCACCTGCAAGGGGATTTCGATCTGGAAATTGAGATTACGGCTGTGAATGGATCTCATCTAG
ACAGTCATGTCATCCACTCTCCCACTATACTGTTTGAGGCCGGAACAG

INTRON 1D/1E (SEQ ID NO:141)

GTAACTATTTTGTCACTGTAACCAACAACTGCAGTCTATTTTGCAATTACGATAATAACAATTTTT
GAAATATATCTTTATTAAAGCAAAGGTTTCTAGAGACAAACAGCCGGCTCTAATTATTTTTTCGAA
CTTACGCTTGAGTAAAGATCTGCAAATGGCAACCCTACCTATACTATTAAAAATATAATGTTACAT
TCGTATCTGAATGTTTAATAAATCACTTCATATTCTGTTGCAG

DOMAIN 1E

ATTCTGCCCACACAGATGATGGACACACTGAACCAGTGATGATTCGCAAAGATATCACACAATTGG
ACAAGCGTCAACAACTGTCACTGGTGAAAGCCCTCGAGTCCATGAAAGCCGACCATTCATCTGATG
GGTTCCAGGCAATCGCTTCCTTCCATGCTCTTCCTCCTCTTTGTCCATCACCAGCTGCTTCAAAGA
GGTTTGCGTGCTGCGTCCATGGCATGGCAACGTTCCCACAATGGCACCGTCTGTACACAGTCCAAT
TCCAAGATTCTCTCAGAAAACATGGTGCAGTCGTTGGACTTCCGTACTGGGACTGGACCCTACCTC

Fig. 8c

```
GTTCTGAATTACCAGAGCTCCTGACCGTCTCAACTATTCATGACCCGGAGACAGGCAGAGATATAC
CAAATCCATTTATTGGTTCTAAAATAGAGTTTGAAGGAGAAAACGTACATACTAAAAGAGATATCA
ATAGGGATCGTCTCTTCCAGGGATCAACAAAAACACATCATAACTGGTTTATTGAGCAAGCACTGC
TTGCTCTTGAACAAACCAACTACTGCGACTTCGAGGTTCAGTTTGAAATTATGCATAATGGTGTTC
ATACCTGGGTTGGAGGCAAGGAGCCCTATGGAATTGGCCATCTGCATTATGCTTCCTATGATCCAC
TTTTCTACATCCATCACTCCCAAACTGATCGTATTTGGGCTATATGGCAATCGTTGCAGCGTTTCA
GAGGACTTTCTGGATCTGAGGCTAACTGTGCTGTAAATCTCATGAAAACTCCTCTGAAGCCTTTCA
GCTTTGGAGCACCATATAATCTTAATGATCACACGCATGATTTCTCAAAGCCTGAAGATACATTCG
ACTACCAAAAGTTTGGATACATATATGACACTCTGGAATTTGCAGGGTGGTCAATTCGTGGCATTG
ACCATATTGTCCGTAACAGGCAGGAACATTCAAGGGTCTTTGCCGGATTCTTGCTTGAAGGATTTG
GCACCTCTGCCACTGTCGATTTCCAGGTCTGTCGCACAGCGGGAGACTGTGAAGATGCAGGGTACT
TCACCGTGTTGGGAGGTGAAAAAGAAATGCCTTGGGCCTTTGATCGGCTTTACAAGTACGACATAA
CAGAAACCTTAGACAAGATGAACCTTCGACATGACGAAATCTTCCAGATTGAAGTAACCATTACAT
CCTACGATGGAACTGTACTCGATAGTGGCCTTATTCCCACACCGTCAATCATCTATGATCCTGCTC
ATC
```

INTRON 1E/1F (SEQ ID NO:142)

```
GTAAGTATACACACATTATTTCTCTTCTGCTATATCAGATGAAGAGAACGTTGTATCACTAACCTA
GTCTTGTTTGATTTGTGGTTTCGTTTGCTTCCTGAACAGTAGGGTTGATTTAACTTCTCTGTTTCG
TCTGTACCAATGAAAGACTATGATGCTTGTGTGAAGATGCTTTGTTCATGAGTCAGTCTGTTCTTG
TAATGCTTTGATCTTTGCCATCAACATTCTTGAAATTAATTATGGTTTCCCTTAAATACTTACATA
TTACATTTAAACGTCGCTGCTTGTCTGATTGCATATTCTTTCAAAAATAACTATATATTCCAG
```

DOMAIN 1F-1 (1st part of domain f)

```
ATGATATTAGTTCGCACCACCTGTCGCTCAACAAGGTTCGTCATGATCTGAGTACACTGAGTGAGC
GAGATATTGGAAGCCTTAAATATGCTTTGAGCAGCTTGCAGGCAGATACCTCAGCAGATGGTTTTG
CTGCCATTGCATCCTTCCATGGTCTGCCTGCCAAATGTAATGACAGCCACAATAACGAG
```

INTRON 1F-1/1F-2 (SEQ ID NO:143)

```
GTAAATATACAGTGAAATCCGGATAAGTAAAATCCAGATAAGAAAAAAAACATTTTCTGTGGTCCC
GGCATGTTTCTTCTTCATCTATCATTATTTTGATACGGATAAGTAAAAATCGGCTGAGTAAAACAT
CCGGGTAAGTAAAATGATTTTCGAGGTCTCTTCATCGGATAAGTAAGATACACAAGTGATCATTCC
AATAAACACTAACTGATGCAACACAATACCAGCGCACAGTGTTTTCACTACGTTTGTTTGTATTGT
AATTAACAATTAACACTTAAGTGTTTCCCAATGTGTCCGTGTGCAAACTGATTGGGACAAAGCTTG
CAACAAGCCCGGCAATTCCATGTCGTTTATGTCTACGTTTGTTATTCTGACTGCTTGGAGGGGTTC
GGAAAAAAATAAAAAACGGGTAAATATTATAAAAAATTCACGGTGCCTTGAAATTTTAGGTGTCCG
GATTTCACTGTAGATGATTAATTTCTCACTTGTAAACAAAAGGACCCCAGTACCCTCATTCGTGAC
GTACGTTATAAAATGTAATTATAAAAAGCCCATTATCATGTTATACGTGATCTTGNCTTGCAATTA
TNCTACCGCTTTCTTGATTTTTTAAAGCAATTTCTCCCTCTATGAACTTATTAACATAGCACTCCT
GCAAAAGAAAACAGTCACTGCATGGATCCATATTGAATGTTGCTGCTTATTTCTCATTTTATTACT
CACAGATATTTCAAGAACATCGTACTCTCTAACCAGGCTAAAGCAAAGAGGGTTACATTTTAGCCG
ACAAGTTCACTAGCTGAGTGGAACACGTATATATTAATGGAGATGACTCTGGTCATGATGATTAGG
ACAATTATCATGACGTTATCATTGATCATGACCATGTCAGTATAATAGATAGCTAACAAATAATGT
AATTACTAATTATGAAGCAATGGTGCATTTGCAG
```

DOMAIN 1F-2 (2nd part of domain f)

Fig. 8d

GTGGCATGCTGTATCCATGGAATGCCTACATTCCCCACTGGCACAGACTCTACACCCTCCAATTT
GAGCAAGCTCTAAGAAGACATGGCTCTAGTGTAGCAGTACCCTACTGGGACTGGACAAAGCCAATA
CATAATATTCCACATCTGTTCACAGACAAAGAATACTACGATGTCTGGAGAAATAAAGTAATGCCA
AATCCATTTGCCCGAGGGTATGTCCCCTCACACGATACATACACGGTAAGAGACGTCCAAGAAGGC
CTGTTCCACCTGACATCAACGGGTGAACACTCAGCGCTTCTGAATCAAGCTCTTTTGGCGCTGGAA
CAGCACGACTACTGCGATTTTGCAGTCCAGTTTGAAGTCATGCACAACACAATCCATTACCTAGTG
GGAGGACCTCAAGTCTATTCTTTGTCATCCCTTCATTATGCTTCATATGATCCGATCTTCTTCATA
CACCACTCCTTTGTAGACAAGGTTTGGGCTGTCTGGCAGGCTCTTCAAGAAAAGAGAGGCCTTCCA
TCAGACCGTGCTGACTGCGCTGTTAGTCTGATGACTCAGAACATGAGGCCTTTCCATTACGAAATT
AACCATAACCAGTTCACCAAGAAACATGCAGTTCCAAATGATGTTTTCAAGTACGAACTCCTGGGT
TACAGATACGACAATCTGGAAATCGGTGGCATGAATTTGCATGAAATTGAAAAGGAAATCAAAGAC
AAACAGCACCATGTGAGAGTGTTTGCAGGGTTCCTCCTTCACGGAATTAGAACCTCAGCTGATGTC
CAATTCCAGATTTGTAAAACATCAGAAGATTGTCACCATGGAGGCCAAATCTTCGTTCTTGGGGGG
ACTAAAGAGATGGCCTGGGCTTATAACCGTTTATTCAAGTACGATATTACCCATGCTCTTCATGAC
GCACACATCACTCCAGAAGACGTATTCCATCCCTCTGAACCATTCTTCATCAAGGTGTCAGTGACA
GCCGTCAACGGAACAGTTCTTCCGGCTTCAATCCTGCATGCACCAACCATTATCTATGAACCTGGT
CTCGGTG

INTRON 1F-2/1G-1 (SEQ ID NO:144)

GTCTCGGTGAGTTATTAAAAGAAACAAAATATTTACCATTACCATTGTTAACTACAAAAATGAGTG
AGATATCTTATATCACTGGTACACTACTGATATTTTATGCAATGAAATTACTATTTTTCCAGGTAC
GCTTCAACCCCTCCCCCCCCCCCCCCCCCCCCCCCCCCCCCCCCCCCCCATCATGCTTTTCTGT
AAAACATAAAACACCAATTAACAATGTTCTTAGTGTGTTTGTTGACTCCCTTCCACTGCAACGCCT
ACATAATCAAAGTGTTCGTTTTTTTCCAAACTTTCCAGTTAGTGTTGAAGACTAAAAAGTTAAATA
AGCATTCACATAACTTCTAAGAGCAACTGGGACCATGCAGTTACGTATTGATATTTCTGTGAGAGT
GAAGCAAAACACTGTTTTTCAAGCTTAGGTTTATCAATCAAAATGTCCAATAGTTCATGTTATCGA
AAAGGCAGCGAAGGATAAGAGGCTCCGAGACATCTTGTCTATTCTCGTGTTCATATGATATCAACT
GAGGAGCTTCCATTACATTTTTGACCTTATCATTTAAAGACATACATGGAACATTTTCATTTTACA
GTTAAAGTGAACCACTTCAGGTTCAACTTCAACTTCGAATTCAACTTCTGTTGTGTGTTTATGAG
CCGACTGAAATAGAGTGCCTTACTTTCACTTCTAGTTTCGTTCTGTCTCGTCATCGTTGTTTCTTT
CAGTGTGCATAGTACACGCCTAGTATAGAACACACGAACTTGTCCTTACTTAATAGATTCTGAAAC
TATTATGTGGAAAGTTGGCAGGCTATAGTAACATCCTGGCAAAATTATCATGTATCCTCTTGTTTG
TCATAATTAG

DOMAIN 1G-1 (1st part of domain g)

ACCATCACGAAGATCATCATTCTTCTTCTATGGCTGGACATGGTGTCAGAAAGGAAATCAACACAC
TTACCACTGCAGAGGTGGACAATCTCAAAGATGCCATGAGAGCCGTCATGGCAGACCACGGTCCAA
ATGGATACCAGGCTATAGCAGCGTTCCATGGAAACCCACCAATGTGCCCTATGCCAGATGGAAAGA
ATTACTCGTGTTGTACACATG

INTRON G1-1/1G-2 (SEQ ID NO:145)

GTATGTATTTCCCACTGGTGGTCGCTGACTGCCAACACATACTTGTAATTTATTCATGAAAGTATA
ATAGTTTGTTTGAAAGTATATTTATAACCATCTTGCACAAGCGTCACGAATTTTCACCACAAAGCT
TCAAAACGCCCAAAACATTCTAATAGCGATATATTTGTTAAAAGACCAAAATATAGCCTTACAACA
ATAGATTATTTTAATAAGACCAGTCAGTGCATGCAAATCGATTGGAAACTTTGAAATAAAATATTC
TATGTACTAACTGCCAATCTCATAATACTTGCCTTGGATGTGCTTCTTTTTCACATTCGCGTCGAG
CTTCAACTCCAATGCATAAGCTTAAAAATAATCATAAACACAAACAAATAGCCACAGAGGCGACGA
TCCCTCCAGGCCAGGCTTTATTTGTCTCTTATAGAATATATCGCTATTAGAATGTTTTTGACGTTT

Fig. 8e

TGAAGCTTTGTGGGTGAAAATTCGTGATGTTTATGCGTGGTATTTATGTAAGATGAAAATAAATAT
ATCTTTTCAAACAAGATTTTAGTATTTTGAAGACTTCTATGAATAAATTACACTTATGTGTTAGGT
TATTGGTCACTGAGCGCTTGTGGTATTTTCCCTTCTTCAATTTGTTTGTTCTTTGTTCAATTTCGA
ATAGTTATCCTACTGTGGATAGTCTATATGAGAATCGTTGAAAGAATAATACAATTCTAATGGATT
GCAACTTCTTTAACTTTTATTTGCAACTGCCACGTTTCGGTATACGTTCTTATGCCGTCATCAAGC
ATACGAGTGTACATGTATGCCAAAACGCTGCAAATAAAAATTAAAGAAGTTGCAATCCATAAGAAT
TTCAATGTTCTTTCATCATCACATCAACTTCTAAAAATGCCTATAAAACAATCAACAAACGTACAA
TAGTACATTACCGGATCTCGCAGCATGACCACGTCGATATCTAAACAATATCACTATCCATTAATA
GGATCAAGAGTAGGTACAGACATGTTCAGTTATAAATACTCTTCAAAAAAGTAGGGGAACTTGGAA
TTTCAAGGTCAATAACAAACTAATGATAATAACAATTGGTCCCAAATAATAACAATTGGTCCCAAA
CTAATTGTATCTTTACAAAGAAGAAATTGAGTGAACAATTCACCCGGTATTTTATTACCTAAACCG
TTTCTCTTGCTGTTATGGTGCGTGAAAGAAGAAATGGGTAAGAAACGGAAATTGACATTTTGCGT
CAGTGGTGCGTAATGCCCCCATTGTTGGCCAAACACTGATTGATTCGCTGAGGCATCGTGCATACG
CGTCTACCTATGGTAATTTGATGCAGTCTGTCCCATTCTTCCACCAACGCCTGGACAAGTTCATCT
AGCGTGGCTGGTGGCCTTTCACGTTGACGCACACGTCGGCCCAAGATGTCCCAGACATTTTCAATG
GCCAGGGCTCATTGCTGGTCAGGGCATCCTATGGATATTGTGCCGTTGAAGGTGGTTATGTTGTTC
ACATTGAAATTCCAAGTTCTCCTACTCTTTTAAGAGGAGGTTCACAAAGTACGTTCTTTCATGTT
GGTGAAGAGAATATCAAGGTCTTCTAAGGGATTGTGTCTTATAATATTTGATTTTAAGAAGTTTGA
TATTATCTGCATCCTTCCCAAGAAATTGCAAATGTTCACACACTATTGCGTTTGATAATGTTTTTG
GGGAAATAAACTGTCCAGGACTGCTAAATAGTAATTATTGCTACTTTTAG

DOMAIN 1G-2 (2nd part of domain g)

GCATGGCTACTTTCCCCCACTGGCACAGACTGTACACAAAACAGATGGAAGATGCCTTGACCGCCC
ATGGTGCCAGAGTCGGCCTTCCTTACTGGGACGGGACAACTGCCTTTACAGCTTTGCCAACTTTTG
TCACAGATGAAGAGGACAATCCTTTCCATCAT

INTRON 1G-2/1G-3 (SEQ ID NO:146)

*GTGAGTTCACGTAAGCCTACGAGATCAACATTACTCCTTAACAGCCACGGCATCATGTACCGATAT*
*ATCACAAACAAAAGTATTCAAAGCTTTAAACACGATATGTATGGTTCAAGAATGACATCATTAAAC*
*AAGGACATGAGTCTGAAATAAACATGACTTGACACCGTTGTGGTCACAGTTTTGTTTCTCATTGGT*
*GAACCTGTGAAACAACCTTTCAAACCAAAAGATGCCTATTAATATTGTTAATTCCCATGAATTAGG*
*AGATACACACATTCTACTGTCATTT.........................AATAACCGCTTC*
*CAGCATGAAAACACAATATGATTATCTCAATTCTACCATTACTAATTATAATTTTGACTGGCATTA*
*TTTGACGACGCGTAAAACATCGCTGCTTTACAGACTGCACTGCGGTAACTGTGACGTTTTCATGAC*
*GTCACTACATTCTATTCAAAACATTTCCACAGAAGAGCGAGACCACGGCCGTGATGGGTTCTGGGC*
*AGATGATTACCCAAGTATATATTTATAATAACTTGACTGCTTGCCTGAATAATGTTGACACATGAC*
*AACGAATTTGTGATAGCGTAAGAAGCGTGAATACTGTGAATAGTGTGAGGGGTGTTTGCTGAGAGT*
*TAACCACCGTTAATTGCAAAATTCCCGAATACTTGCATTTGCAGTCGAAGAAGAATTGCATTCTTA*
*CTCCTGTGAATGGACTCATTGTTATTTAGCAGCGGTTATTGAGGTTTTGATCACCTCTAAATAGAC*
*AATCAGGATGCGGCAAACCGGAAAATTATAGCAGAATCTGTAATTCAAGATGGGCTTGCCTGTGAA*
*AATATGCTGCGAGTTCAGTAACACTTTTCCCTTTCGATCATGGCCTGTTTTGCTCTGAATCTGGTC*
*TTTCAGAGGATCCCTGCTTTTTTAAAACTAAAGTCCTCCCAACTCACTTATATTTATGTTTTTTAA*
*TTATTTATAGTTTTAATATGAACAACAAATCATATTTATTTACACATTATATTTTTCAG*

DOMAIN 1G-3 (3rd part of domain g)

GGTCACATAGACTATTTGGGAGTGGATACAACTCGGTCGCCCCGAGACAAGTTGTTCAATGATCCA
GAGCGAGGATCAGAATCGTTCTTCTACAGGCAGGTTCTCTTGGCTTTGGAGCAGACAGAT

Fig. 9a

Primary structure of the KLH1 protein

DOMAIN B

GLPYWDWTEPMTHIPGLAGNKTYVDSHGASHTNPFHSSVIAFEENAPHTKRQIDQRLFKPATFGHH
TDLFNQILYAFEQEDYCDFEVQFEITHNTIHAWTGGSEHFSMSSLHYTAFDPLFYFHHSNVDRLWA
VWQALQMRRHKPYRAHCAISLEHMHLKPFAFSSPLNNNEKTHANAMPNKIYDYENVLHYTYEDLTF
GGISLENIEKMIHENQQEDRIYAGFLLAGIRTSANVDIFIKTTDSVQHKAGTFAVLGGSKEMKWGF
DRVFKFDITHVLKDLDLTADGDFEVTVDITEVDGTKLASSLIPHASVIREHARGKLNR

DOMAIN C

VKFDKVPRSRLIRKNVDRLSPEEMNELRKALALLKEDKSAGGFQQLGAFHGEPKWCPSPEASKKFA
CCVHGMSVFPHWHRLLTVQSENALRRHGYDGALPYWDWTSPLNHLPELADHEKYVDPEDGVEKHNP
WFDGHIDTVDKTTTRSVQNKLFEQPEFGHYTSIAKQVLLALEQDNFCDFEIQYEIAHNYIHALVGG
AQPYGMASLRYTAFDPLFYLHHSNTDRIWAIWQALQKYRGKPYNVANCAVTSMREPLQPFGLSANI
NTDHVTKEHSVPFNVFDYKTNFNYEYDTLEFNGLSISQLNKKLEAIKSQDRFFAGFLLSGFKKSSL
VKFNICTDSSNCHPAGEFYLLGDENEMPWAYDRVFKYDITEKLHDLKLHAEDHFYIDYEVFDLKPA
SLGKDLFKQPSVIHEPRI

DOMAIN D

GHHEGEVYQAEVTSANRIRKNIENLSLGELESLRAAFLEIENDGTYESIAKFHGSPGLCQLNGNPI
SCCVHGMPTFPHWHRLYVVVVENALLKKGSSVAVPYWDWTKRIEHLPHLISDATYYNSRQHHYETN
PFHHGKITHENEITTRDPKDSLFHSDYFYEQVLYALEQDNFCDFEIQLEILHNALHSLLGGKGKYS
MSNLDYAAFDPVFFLHHATTDRIWAIWQDLQRFRKRPYREANCAIQLMHTPLQPFDKSDNNDEATK
THATPHDGFEYQNSFGYAYDNLELNHYSIPQLDHMLQERKRHDRVFAGFLLHNIGTSADGHVFVCL
PTGEHTKDCSHEAGMFSILGGQTEMSFVFDRLYKLDITKALKKNGVHLQGDFDLEIEITAVNGSHL
DSHVIHSPTILFEAG

DOMAIN E

TDSAHTDDGHTEPVMIRKDITQLDKRQQLSLVKALESMKADHSSDGFQAIASFHALPPLCPSPAAS
KRFACCVHGMATFPQWHRLYTVQFQDSLRKHGAVVGLPYWDWTLPRSELPELLTVSTIHDPETGRD
IPNPFIGSKIEFEGENVHTKRDINRDRLFQGSTKTHHNWFIEQALLALEQTNYCDFEVQFEIMHNG
VHTWVGGKEPYGIGHLHYASYDPLFYIHHSQTDRIWAIWQSLQRFRGLSGSEANCAVNLMKTPLKP
FSFGAPYNLNDHTHDFSKPEDTFDYQKFGYIYDTLEFAGWSIRGIDHIVRNRQEHSRVFAGFLLEG
FGTSATVDFQVCRTAGDCEDAGYFTVLGGEKEMPWAFDRLYKYDITETLDKMNLRHDEIFQIEVTI
TSYDGTVLDSGLIPTPSIIYDPAH

DOMAIN F

HDISSHHLSLNKVRHDLSTLSERDIGSLKYALSSLQADTSADGFAAIASFHGLPAKCNDSHNNEVA
CCIHGMPTFPHWHRLYTLQFEQALRRHGSSVAVPYWDWTKPIHNIPHLFTDKEYYDVWRNKVMPNP
FARGYVPSHDTYTVRDVQEGLFHLTSTGEHSALLNQALLALEQHDYCDFAVQFEVMHNTIHYLVGG
PQVYSLSSLHYASYDPIFFIHHSFVDKVWAVWQALQEKRGLPSDRADCAVSLMTQNMRPFHYEINH
NQFTKKHAVPNDVFKYELLGYRYDNLEIGGMNLHEIEKEIKDKQHHVRVFAGFLLHGIRTSADVQF
QICKTSEDCHHGGQIFVLGGTKEMAWAYNRLFKYDITHALHDAHITPEDVFHPSEPFFIKVSVTAV
NGTVLPASILHAPTIIYEPGLG

Fig. 9b

DOMAIN G

```
DHHEDHHSSSMAGHGVRKEINTLTTAEVDNLKDAMRAVMADHGPNGYQAIAAFHGNPPMCPMPDGK
NYSCCTHGMATFPHWHRLYTKQMEDALTAHGARVGLPYWDGTTAFTALPTFVTDEEDNPFHHGHID
YLGVDTTRSPRDKLFNDPERGSESFFYRQVLLALEQTD
```

Fig. 10a

Genomic sequence of the KLH2 gene

DOMAIN 2B

GGCCTGCCCTACTGGGATTGGACCATGCCAATGAGTCATTTGCCAGAACTGGCTACAAGTGAGACC
TACCTCGATCCAGTTACTGGGGAAACTAAAAACAACCCTTTCCATCACGCCCAAGTGGCGTTTGAA
AATGGTGTAACAAGCAGGAATCCTGATGCCAAACTTTTTATGAAACCAACTTACGGAGACCACACT
TACCTCTTCGACAGCATGATCTACGCATTTGAGCAGGAAGACTTCTGCGACTTTGAAGTCCAATAT
GAGCTCACGCATAATGCAATACATGCATGGGTTGGAGGCAGTGAAAAGTATTCAATGTCTTCTCTT
CACTACACTGCTTTTGATCCTATATTTTACCTCCATCACTCAAATGTTGATCGTCTCTGGGCCATT
TGGCAAGCTCTTCAAATCAGGAGAGGCAAGTCTTACAAGGCCCACTGCGCCTCGTCTCAAGAAAGA
GAACCATTAAAGCCTTTTGCATTCAGTTCCCCACTGAACAACAACGAGAAAACGTACCACAACTCT
GTCCCCACTAACGTTTATGACTATGTGGGAGTTTTGCACTATCGATATGATGACCTTCAGTTTGGC
GGTATGACCATGTCAGAACTTGAGGAATATATTCACAAGCAGACACAACATGATAGAACCTTTGCA
GGATTCTTCCTTTCATATATTGGAACATCAGCAAGCGTAGATATCTTCATCAATCGAGAAGGTCAT
GATAAATACAAAGTGGGAAGTTTTGTAGTACTTGGTGGATCCAAAGAAATGAAATGGGGCTTTGAT
AGAATGTACAAGTATGAGATCACTGAGGCTCTGAAGACGCTGAATGTTGCAGTGGATGATGGGTTC
AGCATTACTGTTGAGATCACCGATGTTGATGGATCTCCCCATCTGCAGATCTCATTCCACCTCCT
GCTATAATCTTTGACGTGGTCAGAG

INTRON 2B/2C (SEQ ID NO:147)

GTATTTAAAAAAGTAATAAAACCATATTTTCGAATGCGCTTTATGAAATATCGTGTGACTGGTTCT
TTAGTTTACATGGAGTGTAACAACATGCTCCATCAGTTGACATATACTGCTCACACAAAGTAAGGG
ATATTTGATAATGATAACAAATATAATCAAAGCGGTTATACTATCAAGACTTATTCACATAATTAC
AGGTGAAGGGAGGTGTGATCGTGTTCACTGATCAGGTTGAGGCCAGAGAAGTCCCAGTTTGAGTCT
TGCAGAAGATGATGTTTAGGCATGGGGTCGAATCACCAAAATCACATGACTTCAATAACGGGTTGG
ACCACCTCGAGCGACGATGCAAGCAGTAGAGCGTCTACGCATGCTCCTGATAAGGCGACCAATCTG
TTCCTGGGGAATCAGTCGCCACTCCTCTTGTAGTGCCACGCTCATTTCTGCTACGGTCCTGGGTAC
CTGCTATCGGGTCTTGATCCGTATCCCAAGGATGTCCCACACATGTTCAAGGTGAGAGGTCGGGGA
ACATCGCTGGCCACGGTAAGGTCTGAATTTGATGCCGTTGAAAGTGAGCTCTGACAACCTGAGCAT
GGTGAGCTCTGACGTTGTCGTCCTGAAAGATGAATCCAGCTCCATGACAGCGAGCAAAGGGCAGGA
CGTGTTGGTCAATGCAGTTGTCTCTGCAGTACACACCTGTCACTCGCCACTCACAAGCGTGTAGAT
CTGTACGACCAGTCATGGAGATCCCAGCCCACATCATAACGGACCCCTATCCATACCGATCATGAG
CCACCATAGCAGCGTCTTGATGACGTTCTCCCTGTCGCCTCGACATCCTCACACGGCCAAAAGGAA
CGTGGACTCGTCACTGAACATGACATTAGCCAACCTGGCACTTGTCCACCGCTGATGTTGGCGAGA
CCATTCCAGTCGAGCTCTTCGGTGTCTGGCTTTCATCGATAACACGACGTAAGGTCTGCGGGCGTG
CAAGACGGCTCTATGCAGGCGATTTCGGATTGTCTGGGTGCTAACTCTGATCCCAGGTGCCTGCTG
AAGTTGATGCTGGATCTGTGTGGCATTGAGATGGCGATTCCTTAGGACTGTGGAGATGATGAATCG
ATCTTGACTTATGGTGGTGACATTAGGACGTCGGGTTCGTGTCCTATCCTGCACTCTTCCAGTTGT
TCGGTGACGCTCTGGTACCCGGCTGATTACTGACTGAGAATATCCATCTGCCGTGCGACATGAGCC
TGTGTTGGCCCAGCCTGAAGCATTGCAATCGCCAGAGACGCTCTTCAAAAGTCATTCGACGCATGG
TTTTCTGTTCACAAATGACAGCGTAAAACAGTTTTGGTGCTTTTATGCTTCCCAAGAGCATGAAA
AACACGTTCTATGGTCGTGCACACCTTACATGACAAGTGTGAAAAGTGACTTGCACCCCCTTGTG
TGTTCGGATGCACACTCTGTTTACGTACTGATGCGATTTGGCGTCTAAACATGTTTTGGCGTCTAA
ACATGTTTTCCTGCATGATTCATATACTATTTTGTCATATTCCTGGCATCAAACCAAACTACAGTG
AAATATATTTCAATATCCCCTACTTTGTGTGAGTAGTATAGATCACTGCAGACAACATATAGACAA
TGCAGTTACACCGTCAACAATCCCAGTCATTAATTATGATGACACTTCCACACATAGTGTCAGTGA
TTGTAATTCAACTGTACACACTTTTCCCGTGAACATTCAGGATCTATATGACTAAATATATAACAT
TAGTATACGTGCAGTTTTGTATCGCTACGACATTGTTGTAACTCTTTGTTTAATCATTTAACAG

Fig. 10b

DOMAIN 2C

CTGATGCCAAAGACTTTGGCCATAGCAGAAAAATCAGGAAAGCCGTTGATTCTCTGACAGTCGAAG
AACAAACTTCGTTGAGGCGAGCTATGGCAGATCTACAGGACGACAAAACATCAGGGGGTTTCCAGC
AGATTGCAGCATTCCACGGAGAACCAAAATGGTGTCCAAGCCCCGAAGCGGAGAAAAAATTTGCAT
GCTGTGTTCATGGAATGGCTGTTTTCCCTCACTGGCACAGATTGCTGACAGTTCAAGGAGAAAATG
CTCTGAGGAAACATGGATTTACTGGTGGATTGCCCTATTGGGACTGGACTCGGCCAATGAGCGCCC
TTCCACATTTTGTTGCTGATCCTACTTACAATGATTCTGTTTCCAGCCTCGAAGAAGATAACCCAT
GGTATCATGGTCACATAGATTCTGTTGGGCATGATACTACAAGAGCTGTGCGTGATGATCTTTATC
AATCTCCTGGTTTCGGTCACTACACAGATATTGCAAAACAAGTCCTTCTGGCCTTTGAGCAGGACG
ATTTCTGTGATTTTGAGGTACAATTTGAAATTGCCCATAATTTCATACATGCTCTGGTTGGTGGTA
ACGAACCATACAGTATGTCATCTTTGAGGTATACTACATACGATCCAATCTTCTTCTTGCACCGCT
CCAATACAGACCGACTTTGGGCCATTTGGCAAGCTTTGCAAAAATACCGGGGGAAACCATACAACA
CTGCAAACTGTGCCATTGCATCCATGAGAAAACCACTTCAGCCATTTGGTCTTGATAGTGTCATAA
ATCCAGATGACGAAACTCGTGAACATTCGGTTCCTTTCCGAGTCTTCGACTACAAGAACAACTTCG
ACTATGAGTATGAGAGCCTGGCATTTAATGGTCTGTCTATTGCCCAACTGGACCGAGAGTTGCAGA
GAAGAAAGTCACATGACAGAGTCTTTGCAGGATTCCTTCTTCATGAAATTGGACAGTCTGCACTCG
TGAAATTCTACGTTTGCAAACACAATGTATCTGACTGTGACCATTATGCTGGAGAATTCTACATTT
TGGGAGATGAAGCTGAGATGCCTTGGAGGTATGACCGTGTGTACAAGTACGAGATAACACAGCAGC
TGCACGATTTAGATCTACATGTTGGAGATAATTTCTTCCTTAAATATGAAGCCTTTGATCTGAATG
GCGGAAGTCTTGGTGGAAGTATCTTTTCTCAGCCTTCGGTGATTTTCGAGCCAGCTGCAG

INTRON 2C/2D (SEQ ID NO:148)

GTATGTTTTAAATGTCACTTATCCGTGATCTGTAATGAAGTTAGCAATTCACTTTATCAACTGTTT
GGCTGTACTGTTTCAGTGCGAGTTTTACTTAGGTTGGATTAATTAAAATATTCAAGCTCATAAATG
TTTTGATTCAACTTTTGTTATTTATTTCAAACAG

DOMAIN 2D

GTTCACACCAGGCTGATGAATATCGTGAGGCAGTAACAAGCGCTAGCCACATAAGAAAAAATATCC
GGGACCTCTCAGAGGGAGAAATTGAGAGCATCAGATCTGCTTTCCTCCAAATTCAAAAAGAGGGTA
TATATGAAAACATTGCAAAGTTCCATGGAAAACCAGGACTTTGTGAACATGATGGACATCCTGTTG
CTTGTTGTGTCCATGGCATGCCCACCTTTCCCCACTGGCACAGACTGTACGTTCTTCAGGTGGAGA
ATGCGCTCTTAGAACGAGGGTCTGCAGTTGCTGTTCCTTACTGGGACTGGACCGAGAAAGCTGACT
CTCTGCCATCATTAATCAATGATGCAACTTATTTCAATTCACGATCCCAGACCTTTGATCCTAATC
CTTTCTTCAGGGGACATATTGCCTTCGAGAATGCTGTGACGTCCAGAGATCCTCAGCCAGAACTAT
GGGACAATAAGGACTTCTACGAGAATGTCATGCTGGCTCTTGAGCAAGACAACTTCTGTGACTTTG
AGATTCAGCTTGAGCTGATACACAACGCCCTTCATTCTAGACTTGGAGGAAGGGCTAAATACTCCC
TTTCGTCTCTTGATTATACCGCATTTGATCCTGTATTTTTCCTTCACCATGCAAACGTTGACAGAA
TCTGGGCCATCTGGCAGGACTTGCAGAGATATAGAAAGAAACCATACAATGAGGCTGACTGCGCAG
TCAACGAGATGCGTAAACCTCTTCAACCATTTAATAACCCAGAACTTAACAGTGATTCCATGACGC
TTAAACACAACCTCCCACAAGACAGTTTTGATTATCAAAACCGCTTCAGGTACCAATATGATAACC
TTCAATTTAACCACTTCAGCATACAAAAGCTAGACCAAACTATTCAGGCTAGAAAACAACACGACA
GAGTTTTTGCTGGCTTTATTCTTCACAACATTGGGACATCTGCTGTTGTAGATATTTATATTTGCG
TTGAACAAGGAGGAGAACAAAACTGCAAGACAAAGGCGGGTTCCTTCACGATTCTGGGGGGAGAAA
CAGAAATGCCATTCCACTTTGACCGCTTGTACAAATTTGACATAACGTCTGCTCTGCATAAACTTG
GTGTTCCCTTGGACGGACATGGATTCGACATCAAAGTTGACGTCAGAGCTGTCAATGGATCGCATC
TTGATCAACACATCCTCAACGAACCGAGTCTGCTTTTTGTTCCTGGTGAACGTAAGAATATATATT
ATG

Fig. 10c

INTRON 2D/2E (SEQ ID NO:149)

GTTATAAAGCAGTATATTCTCTTCAAAAAAGTAGGGGAACTTGGAATTTCAAGGTAAATAACATAA
CTACCTTCAACGGCACAATATCCATATGATGCCCTGGCCAGCAATGAGGCCTGATCTTTTCCCCAT
TAAAAATGTCTGGAACATCTTGGGCAAACGTGTGCGTCAACGTAAAACGCCACCAGTCACGCTAGA
TGAACTTGTCCAGGCGTTGGTGGAAGAATGGGACAGACTGCATCAATTACCATAAGTAGACTCATT
TGCAGCGAATCAGTCAGTGTTTGACCAATAACGGGGCATTACGCACTACTGACGCAAAACAATGT
CAATTTCCGTTTCTTACCCATTCCTTCTTTCACGGACCATAACAGCAAGAGAAACTGNTTAGGTAA
TGAAATACCGGTGAATTATTGTTAACTGGATTCCTTCTTTGTAAAGATACAATTAGTTTGGGACCA
ATTATTATTATCATTAGTTTGTTATTGACCTTGAAATTCGAAGTTCCTCTACATTTTTTAAGGAGT
TTATTTGATTGACAATGAAATGTAAGAAAAGAGCAAATCGTAAAATACGTTAAAAATTATTCCTTA
AACATCAGTCTCTAACTTCAGTTTAAATTGCCAGTAACACGTGTTATATGATGTTTCCGTTTCTCT
TTGTTTTTTAGCATTCAACTTATTTGATATAACGTTTTACTGTTTTAGATTCACATCAAACTGCAG

DOMAIN 2E

ATGGGCTTTCACAACATAATCTTGTGCGAAAAGAAGTAAGCTCTCTTACAACACTGGAGAAACATT
TTTTGAGGAAAGCTCTCAAGAACATGCAAGCAGATGATTCTCCAGACGGATATCAAGCTATTGCTT
CTTTCCACGCTTTGCCTCCTCTTTGTCCAAGTCCATCTGCTGCACATAGACACGCTTGTTGCCTCC
ATGGTATGGCTACCTTCCCTCAGTGGCACAGACTCTACACAGTTCAGTTCGAAGATTCTTTGAAAC
GACATGGTTCTATTGTCGGACTTCCATATTGGGATTGGCTGAAACCGCAGTCTGCACTCCCTGATT
TGGTGACACAGGAGACATACGAGCACCTGTTTTCACACAAAACCTTCCCAAATCCGTTCCTCAAGG
CAAATATAGAATTTGAGGGAGAGGGAGTAACAACAGAGAGGGATGTTGATGCTGAACACCTCTTTG
CAAAAGGAAATCTGGTTTACAACAACTGGTTTTGCAATCAGGCACTATATGCACTAGAACAAGAAA
ATTACTGTGACTTTGAAATACAGTTCGAAATTTTGCATAATGGAATTCATTCATGGGTTGGAGGAT
CAAAGACCCATTCAATAGGTCATCTTCATTACGCATCATACGATCCACTGTTCTATATCCACCATT
CGCAGACAGATCGCATTTGGGCTATCTGGCAAGCTCTCCAGGAGCACAGAGGTCTTTCAGGGAAGG
AAGCACACTGCGCCCTGGAGCAAATGAAAGACCCTCTCAAACCTTTCAGCTTTGGAAGTCCCTATA
ATTTGAACAAACGCACTCAAGAGTTCTCCAAGCCTGAAGACACATTTGATTATACCGATTCGGGT
ATGAGTATGATTCCCTCGAATTTGTTGGCATGTCTGTTTCAAGTTTACATAACTATATAAAACAAC
AACAGGAAGCTGATAGAGTCTTCGCAGGATTCCTTCTTAAAGGATTTGGACAATCAGCATCCGTAT
CGTTTGATATCTGCAGACCAGACCAGAGTTGCCAAGAAGCTGGATACTTCTCAGTTCTCGGTGAA
GTTCAGAAATGCCGTGGCAGTTTGACAGGCTTTACAAGTACGACATTACAAAAACGTTGAAAGACA
TGAAACTGCGATACGATGACACATTTACCATCAAGGTTCACATAAAGGATATAGCTGGAGCTGAGT
TGGACAGCGATCTGATTCCAACTCCTTCTGTTCTCCTTGAAGAAGGAAAGC

INTRON 2E/2F (SEQ ID NO:150)

GTATGTATCTCATGTTTCTCAAATAATTTGATTTTCAATGCCCTTACTATAAAGCACAGTTATTGT
TCAGTGCCAGTAACCGTTTATTTACGTAAATGTTACAGGCTATTATAATCAAAAATACATTACCGA
TATTGTTTACCACACAATTATATCATTGTCAAAATCTACCCCCATTACCTGCGTTTTGAATTTGTA
ACCTTCTGACAAAAATGAATTAGCAAGAGCTCTGATGAAGAACATAATGAACAACACCTATCTTTC
TTCTTTCAATGACGGTTTAACAATACAATGCACAATGTAAAAAAATATATATATATATATAATTTT
ATATCTACAGTTAATGCAAATGACTCCACTAATTCAGGGAAACACATTTTCAG

DOMAIN 2F-1 (1st part of domain f)

ATGGGATCAATGTACGTCACGTTGGTCGTAATCGGATTCGTATGGAACTATCTGAACTCACCGAGA
GAGATCTCGCCAGCCTGAAATCTGCAATGAGGTCTCTACAAGCTGACGATGGGGTGAACGGTTATC
AAGCCATTGCATCATTCCACGGTCTCCCGGCTTCTTGTCATGATGATGAGGGACATGAG

Fig. 10d

INTRON 2F (SEQ ID NO:151)

GTAAAATAAAACGTCCAGTCATCGGAAACCCGCCCAGATATATGGGTTTTTTTCTATTTAAACAAA
AAAGCAGAGACAAAAAGATTATTAAAAGTCACATTTAACTTGATATCAGATCAATAGTTTGGCTAG
TTAGTGCTCTATATCCCTCAAATCCTTCGAATCTTTAAGCCTCGTGATATTTTGACAAACAGAGAA
GACTTAGTAGCCCAGACTTTCCCTTATTTTTTCCTGAAAATCTTAATACGGATATTAAATGGATTC
ATTCTGCAACCTACAACCATAGCCCATATGTTATTATTTCAG

DOMAIN 2F-2 (2nd part of domain f)

ATTGCCTGTTGTATCCACGGAATGCCAGTATTCCCACACTGGCACAGGCTTTACACCCTGCAAATG
GACATGGCTCTGTTATCTCACGGATCTGCTGTTGCTATTCCATACTGGGACTGGACCAAACCTATC
AGCAAACTGCCTGATCTCTTCACCAGCCCTGAATATTACGATCCTTGGAGGGATGCAGTTGTCAAT
AATCCATTTGCTAAAGGCTACATTAAATCCGAGGACGCTTACACGGTTAGGGATCCTCAGGACATT
TTGTACCACTTGCAGGACGAAACGGGAACATCTGTTTTGTTAGATCAAACTCTTTTAGCCTTAGAG
CAGACAGATTTCTGTGATTTTGAGGTTCAATTTGAGGTCGTCCATAATGCTATTCACTACTTGGTG
GGTGGTCGACAAGTTTATGCTCTTTCTTCTCAACACTATGCTTCATATGACCCAGCCTTCTTTATT
CATCACTCCTTTGTTGACAAAATATGGGCAGTCTGGCAAGCTCTGCAAAAGAAGAGAAAGCGTCCC
TATCATAAAGCGGATTGTGCTCTTAACATGATGACCAAACCAATGCGACCATTTGCACACGATTTC
AATCACAATGGATTCACAAAAATGCACGCAGTCCCCAACACTCTATTTGACTTTCAGGACCTTTTC
TACACGTATGACAACTTAGAAATTGCTGGCATGAATGTTAATCAGTTGGAAGCGGAAATCAACCGG
CGAAAAAGCCAAACAAGAGTCTTTGCCGGGTTCCTTCTACATGGCATTGGAAGATCAGCTGATGTA
CGATTTTGGATTTGCAAGACAGCTGACGACTGCCACGCATCTGGCATGATCTTTATCTTAGGAGGT
TCTAAAGAGATGCACTGGGCCTATGACAGGAACTTTAAATACGACATCACCCAAGCTTTGAAGGCT
CAGTCCATACACCCTGAAGATGTGTTTGACACTGATGCTCCTTTCTTCATTAAAGTGGAGGTCCAT
GGTGTAAACAAGACTGCTCTCCCATCTTCAGCTATCCCAGCACCTACTATAATCTACTCAGCTGGT
GAAG

INTRON 2F-2/2G (SEQ ID NO:152)

GTGAGAGAAACTATAATAGTGTATGTCGGCAAAAAATGTGCTCATATCATGACTCTGTTGGCCGGT
GGTTGCTCTCCTCTCCTCCTCCACCACCACCGGTACCTCCACCTGTCAGGGCATCAATGTACCATG
AAAATGTCTACAATACTAGGCCTCCTGTAGAAGCACGTAAGATTTACATGGCCGGTTTGTAACTAG
TTTAAAGTGCTTCACAGTAACCAAAACCAGTCTCTAAAGATTAATGTCTGTTTAAAATTTAATGCC
ACATTTTCAACTGACATATTCTTGCAATTAAGTACAAATGAAGTAGTATAAATTATCCACAAATAG
CGTGATGCACCACAAATATAAACCGAGTGCTTTTTTGGCATTCCCCACTTGTTCTGGCATGATCAC
ATCATAGATCTCGTTCATGAAGATACTGTTGGATGCTTTTTCCCAATATGCCCCAATCTGTTAAAT
TATTTACACGACCGCAGTGTGTACTTTCATCACTCAGATCTTTACAATGTGTTTGTAACGTTTACA
ATTAGCGTTATGATTGAAATATTACCCCCTGCTACGTTAAATCACATTCACTCACTCATCTGATGT
ACTTTACAGGTCATACCGATGATCACGGCTCAG

DOMAIN 2G-1 (1st part of domain g)

ATCATATTGCTGGCAGTGGAGTCAGGAAAGACGTGACGTCTCTTACCGCATCTGAGATAGAGAACC
TGAGGCATGCTCTGCAAAGCGTGATGGATGATGATGGACCCAATGGATTCCAGGCAATTGCTGCTT
ATCACGGAAGTCCTCCCATGTGTCACATGCCTGATGGTAGAGACGTTGCATGTTGTACTCATG

INTRON 2G-1/2G-2 (SEQ ID NO:153)

GTCAGTATTCTCCAATATGTTTGACTAGTGTCTTGCTCATGTATCAACTATTTTAGGCAACGTTTT
TGATTGTTATGGTATTTTCATGATATGATTTTATTGCTACCTCTATACCCAAACAAAAATGTTTTA

Fig. 11a

Primary structure of the KLH2 protein

DOMAIN B

GLPYWDWTMPMSHLPELATSETYLDPVTGETKNNPFHHAQVAFENGVTSRNPDAKLFMKPTYGDHT
YLFDSMIYAFEQEDFCDFEVQYELTHNAIHAWVGGSEKYSMSSLHYTAFDPIFYLHHSNVDRLWAI
WQALQIRRGKSYKAHCASSQEREPLKPFAFSSPLNNNEKTYHNSVPTNVYDYVGVLHYRYDDLQFG
GMTMSELEEYIHKQTQHDRTFAGFFLSYIGTSASVDIFINREGHDKYKVGSFVVLGGSKEMKWGFD
RMYKYEITEALKTLNVAVDDGFSITVEITDVDGSPPSADLIPPPAIIFDVVR

DOMAIN C

ADAKDFGHSRKIRKAVDSLTVEEQTSLRRAMADLQDDKTSGGFQQIAAFHGEPKWCPSPEAEKKFA
CCVHGMAVFPHWHRLLTVQGENALRKHGFTGGLPYWDWTRPMSALPHFVADPTYNDSVSSLEEDNP
WYHGHIDSVGHDTTRAVRDDLYQSPGFGHYTDIAKQVLLAFEQDDFCDFEVQFEIAHNFIHALVGG
NEPYSMSSLRYTTYDPIFFLHRSNTDRLWAIWQALQKYRGKPYNTANCAIASMRKPLQPFGLDSVI
NPDDETREHSVPFRVFDYKNNFDYEYESLAFNGLSIAQLDRELQRRKSHDRVFAGFLLHEIGQSAL
VKFYVCKHNVSDCDHYAGEFYILGDEAEMPWRYDRVYKYEITQQLHDLDLHVGDNFFLKYEAFDLN
GGSLGGSIFSQPSVIFEPAA

DOMAIN D

GSHQADEYREAVTSASHIRKNIRDLSEGEIESIRSAFLQIQKEGIYENIAKFHGKPGLCEHDGHPV
ACCVHGMPTFPHWHRLYVLQVENALLERGSAVAVPYWDWTEKADSLPSLINDATYFNSRSQTFDPN
PFFRGHIAFENAVTSRDPQPELWDNKDFYENVMLALEQDNFCDFEIQLELIHNALHSRLGGRAKYS
LSSLDYTAFDPVFFLHHANVDRIWAIWQDLQRYRKKPYNEADCAVNEMRKPLQPFNNPELNSDSMT
LKHNLPQDSFDYQNRFRYQYDNLQFNHFSIQKLDQTIQARKQHDRVFAGFILHNIGTSAVVDIYIC
VEQGGEQNCKTKAGSFTILGGETEMPFHFDRLYKFDITSALHKLGVPLDGHGFDIKVDVRAVNGSH
LDQHILNEPSLLFVPGERKNIYY

DOMAIN E

DGLSQHNLVRKEVSSLTTLEKHFLRKALKNMQADDSPDGYQAIASFHALPPLCPSPSAAHRHACCL
HGMATFPQWHRLYTVQFEDSLKRHGSIVGLPYWDWLKPQSALPDLVTQETYEHLFSHKTFPNPFLK
ANIEFEGEGVTTERDVDAEHLFAKGNLVYNNWFCNQALYALEQENYCDFEIQFEILHNGIHSWVGG
SKTHSIGHLHYASYDPLFYIHHSQTDRIWAIWQALQEHRGLSGKEAHCALEQMKDPLKPFSFGSPY
NLNKRTQEFSKPEDTFDYHRFGYEYDSLEFVGMSVSSLHNYIKQQQEADRVFAGFLLKGFGQSASV
SFDICRPDQSCQEAGYFSVLGGSSEMPWQFDRLYKYDITKTLKDMKLRYDDTFTIKVHIKDIAGAE
LDSDLIPTPSVLLEEGK

DOMAIN F

HGINVRHVGRNRIRMELSELTERDLASLKSAMRSLQADDGVNGYQAIASFHGLPASCHDDEGHEIA
CCIHGMPVFPHWHRLYTLQMDMALLSHGSAVAIPYWDWTKPISKLPDLFTSPEYYDPWRDAVVNNP
FAKGYIKSEDAYTVRDPQDILYHLQDETGTSVLLDQTLLALEQTDFCDFEVQFEVVHNAIHYLVGG
RQVYALSSQHYASYDPAFFIHHSFVDKIWAVWQALQKKRKRPYHKADCALNMMTKPMRPFAHDFNH
NGFTKMHAVPNTLFDFQDLFYTYDNLEIAGMNVNQLEAEINRRKSQTRVFAGFLLHGIGRSADVRF
WICKTADDCHASGMIFILGGSKEMHWAYDRNFKYDITQALKAQSIHPEDVFDTDAPFFIKVEVHGV
NKTALPSSAIPAPTIIYSAGE

Fig. 11b

DOMAIN G

DHIAGSGVRKDVTSLTASEIENLRHALQSVMDDDGPNGFQAIAAYHGSPPMCHMPDGRDVACCTHG
MASFPHWHRLFVKQMEDALAAHGAHIGIPYWDWTSAFSHLPALVTDHEHNPFHHGHIAHRNVDTSR
SPRDMLFNDPEHGSESFFYRQVLLALEQTDFCQFEVQFEITHNAIHSWTGGHTPYGMSSLEYTAYD
PLFYLHHSNTDRIWAIWQALQKYRGFQYNAAHCDIQVLKQPLKPFSESRNPNPVTRANSRAVDSFD
YERLNYQYDTLTFHGHSISELDAMLQERKKEERTFAAFLLHGFGASADVSFDVCTPDGHCAFAGTF
AVLGGELEMPWSFERLFRYDITKVLKQMNLHYDSEFHFELKIVGTDGTELPSDRIKSPTIEHHGG

DOMAIN H (SEQ ID NO:158)

GHDHSERHDGFFRKEVGSLSLDEANDLKNALYKLQNDQGPNGYESIAGYHGYPFLCPEHGEDQYAC
CVHGMPVFPHWHRLHTIQFERALKEHGSHLGLPYWDW

```
                       SEQUENCE LISTING

<160> NUMBER OF SEQ ID NOS: 239

<210> SEQ ID NO 1
<211> LENGTH: 1269
<212> TYPE: DNA
<213> ORGANISM: Hailotis tuberculata

<400> SEQUENCE: 1
ggcttgttca gtttctactc gtcgcccttg tggcgggggc tggagcagac aacgtcgtca      60
gaaaggacgt gagtcaccte acggatgacg aggtgcaagc tctccacggc gccctccatg     120
acgtcactgc atctacaggg cctctgagtt tcgaagacat aacatcttac catgccgcac     180
cagcgtcgtg tgactacaag ggacggaaga tcgcctgctg tgtccacggt atgcccagtt     240
tccccttctg gcacagggca tatgtcgtcc aagccgagcg ggcactgttg tccaaacgga     300
agactgtcgg aatgccttac tgggactgga cgcaaacgct gactcactta ccatctcttg     360
tgactgaacc catctacatt gacagtaaag gtggaaaggc tcaaaccaac tactggtacc     420
gcggcgagat agcgttcatc aataagaaga ctgcgcgagc tgtagatgat cgcctattcg     480
agaaggtgga gcctggtcac tacacacatc ttatggagac tgtcctcgac gctctcgaac     540
aggacgaatt ctgtaaattt gaaatccagt tcgagttggc tcataatgct atccattact     600
tggttggcgg taaatttgaa tattcaatgt caaacttgga atacacctcc tacgacccca     660
tcttcttcct ccaccactcc aacgttgacc gcctcttcgc catctggcag cgtcttcagg     720
aactgcgagg aaagaatccc aatgcaatgg actgtgcaca tgaactcgct caccagcaac     780
tccaaccctt caacagggac agcaatccag tccagctcac aaaggaccac tcgacacctg     840
```

```
ctgacctctt tgattacaaa caacttggat acagctacga cagcttaaac ctgaatggaa    900
tgacgccaga acagctgaaa acagaactag acgaacgcca ctccaaagaa cgtgcgtttg    960
caagcttccg actcagtggc tttgggggtt ctgccaacgt tgttgtctat gcatgtgtcc   1020
ctgatgatga tccacgcagt gatgactact gcgagaaagc aggcgacttc ttcattcttg   1080
ggggtcaaag cgaaatgccg tggagattct acagaccctt cttctatgat gtaactgaag   1140
cggtacatca ccttggagtc ccgctaagtg gccactacta tgtgaaaaca gaactcttca   1200
gcgtgaatgg cacagcactt tcacctgatc ttcttcctca accaactgtt gcctaccgac   1260
ctgggaaag                                                          1269

<210> SEQ ID NO 2
<211> LENGTH: 1257
<212> TYPE: DNA
<213> ORGANISM: Haliotis tuberculata

<400> SEQUENCE: 2
gtcaccttga cccacctgtg catcatcgcc acgatgacga tcttattgtt cgaaaaaata     60
tagatcattt gactcgtgaa gaggaatacg agctaaggat ggctctggag agattccagg    120
ccgacacatc cgttgatggg taccaggcta cagtagagta ccatggcctt cctgctcgtt    180
gtccacgacc agatgcaaaa gtcaggttcg cctgttgtat gcatggcatg gcatccttcc    240
ctcactggca ccggctgttc gttacccagg tggaagatgc tcttgtacgg cgtggatcgc    300
ctatcggtgt tccttattgg gactggacaa aacctatgac tcaccttcca gacttggcat    360
caaatgagac gtacgtagac ccgtatggac atacacatca taatccattc ttcaatgcaa    420
atatatcttt tgaggaggga caccatcaca cgagcaggat gatagattcg aaactgtttg    480
ccccagtcgc ttttggggag cattcccatc tgtttgatgg aatcctgtac gcatttgagc    540
aggaagattt ctgcgacttt gagattcagt ttgagttagt ccataattct attcatgcgt    600
ggataggcgg ttccgaagat tactccatgg ccaccctgca ttacacagcc tttgacccca    660
ttttctacct tcatcattcc aatgtcgatc gtctatgggc aatctggcaa gctcttcaaa    720
tcaggagaca caagccatat caagcccact gtgcacagtc tgtggaacag ttgccaatga    780
agccatttgc tttcccatca cctcttaaca acaacgagaa gacacatagt cattcagtcc    840
cgactgacat ttatgactac gaggaagtgc tgcactacag ctacgatgat ctaacgtttg    900
gtgggatgaa ccttgaagaa atagaagaag ctatacatct cagacaacag catgaacgag    960
tcttcgcggg atttctcctt gctggaatag gaacatctgc acttgttgac attttcataa   1020
ataaaccggg gaaccaacca ctcaaagctg gagatattgc cattcttggt ggtgccaagg   1080
aaatgccttg ggcgtttgac cgcttgtata aggtcgaaat aactgactca ttgaagacac   1140
tttctctcga tgtcgatgga gattatgaag tcacttttaa aattcatgat atgcacggaa   1200
acgtcttgta tacggacctg attccacacg cagcagttgt ttctgagcca gctcacc      1257

<210> SEQ ID NO 3
<211> LENGTH: 1242
<212> TYPE: DNA
<213> ORGANISM: Haliotis tuberculata

<400> SEQUENCE: 3
ctacctttga ggatgaaaag cacagcttac gaatcagaaa aaatgtcgac agcttgactc     60
ctgaagaaac aaatgaactg cgtaaagccc tggagcttct tgaaaatgat catactgcag    120
```

| | |
|---|---|
| gtggattcaa tcagcttggc gccttccatg gagagcctaa atggtgccct aatcctgaag | 180 |
| cggagcacaa ggttgcatgc tgtgttcatg gcatggctgt tttccctcat ggcacaggc | 240 |
| ttcttgctct ccaggcggag aatgctctta gaaagcatgg gtacagtggt gctctaccat | 300 |
| actgggattg gactcgcccc ctttcccaac ttcctgatct ggttagtcat gagcagtata | 360 |
| cagatccttc cgaccatcac gtgaagcata acccgtggtt caatggccac atcgatacag | 420 |
| taaatcagga taccaccaga agcgtacggg aggatcttta tcaacaacct gaatttggac | 480 |
| atttcacgga tattgctcaa caagtcctct tagcattaga acaagatgac ttctgttcgt | 540 |
| ttgaagtgca gtatgagatt tcccataatt ttatccatgc acttgtagga ggaaccgacg | 600 |
| cttatggcat ggcatcgctg agatatacag catacgatcc aatcttttc ttgcatcatt | 660 |
| caaacaccga caggatctgg gctatttggc aatccctgca aaaatacaga ggcaaaccgt | 720 |
| acaacactgc caactgcgcc atagaatcta tgagaaggcc cctgcaacca tttggactaa | 780 |
| gcagtgccat taaccctgac agaatcacca gagagcatgc tatcccgttt gatgtcttca | 840 |
| actatagaga taaccttcat tacgtatatg atacccctgga atttaatggt ttgtcgattt | 900 |
| cacaacttga tagagagctg gaaaaaatca agagtcacga aagagtattt gctggattct | 960 |
| tgctgtcggg gattaaaaaa tctgctcttg tgaaattcga agtttgtact ccacctgata | 1020 |
| attgtcataa gcaggggag ttttatctac tcggggacga aaacgagatg gcttgggcct | 1080 |
| atgaccgact tttcaagtat gatattactc aggttctgga agcaaaccat ctacacttct | 1140 |
| atgatcatct cttcattcgc tacgaagtct ttgatcttaa aggagtgagt ttgggaactg | 1200 |
| acctgttcca cactgcaaat gtggtacatg attccggcac ag | 1242 |

<210> SEQ ID NO 4
<211> LENGTH: 1239
<212> TYPE: DNA
<213> ORGANISM: Haliotis tuberculata

<400> SEQUENCE: 4

| | |
|---|---|
| gcacccgtga tcgtgataac tacgttgaag aagttactgg ggccagtcat atcaggaaga | 60 |
| atttgaacga cctcaatacc ggagaaatgg aaagccttag agctgctttc ctgcatattc | 120 |
| aggacgacgg aacatatgaa tctattgccc agtaccatgg caaaccaggc aaatgtcaat | 180 |
| tgaatgatca taatattgcg tgttgtgtcc atggtatgcc taccttcccc cagtggcaca | 240 |
| gactgtatgt ggttcaggtg gagaatgctc tcctaaacag gggatctggt gtggctgttc | 300 |
| cttactggga gtggactgct cccatagacc atctacctca tttcattgat gatgcaacat | 360 |
| acttcaattc ccgacaacag cggtacgacc ctaacccttt cttcagggga aaggttactt | 420 |
| ttgaaaacgc agtcacaaca agggacccac aagccgggct cttcaactca gattatatgt | 480 |
| atgagaatgt tttacttgca ctggagcagg aaaattattg tgactttgaa attcagtttg | 540 |
| agcttgttca taacgcactt cattccatgc tgggaggtaa agggcagtac tccatgtcct | 600 |
| ccctggacta ttctgcgttt gatcccgtct tcttcctaca tcatgccaac acggacagac | 660 |
| tgtgggcaat ctggcaggaa ctacaaagat tccgagaact gccttatgaa gaagcgaact | 720 |
| gtgcaatcaa cctcatgcat caaccactga agccgttcag tgatccacat gagaatcacg | 780 |
| acaatgtcac tttgaaatac tcaaaaccac aggacggatt cgactaccag aaccacttcg | 840 |
| gatacaagta tgacaaccct gagttccatc acttatctat cccaagtctt gatgctaccc | 900 |
| tgaagcaaag gagaaatcac gacagagtgt ttgcgggctt ccttcttcat aacataggaa | 960 |
| cttctgctga cataactatc tacatatgtc tgcctgacgg acggcgtggc aatgactgca | 1020 |

-continued

```
gtcatgaggc gggaacattc tatatcctcg gaggcgaaac agagatgcct tttatctttg   1080
accgtttgta taaatttgaa atcaccaaac cactgcaaca gttaggagtc aagctgcatg   1140
gtggagtttt cgaactggag cttgagatca aggcatacaa cggttcctat ctggatcccc   1200 ataccttga tccaactatc atctttgaac ctggaacag                            1239
```

<210> SEQ ID NO 5
<211> LENGTH: 1260
<212> TYPE: DNA
<213> ORGANISM: Haliotis tuberculata

<400> SEQUENCE: 5

```
atacccatat cttggaccac gaccatgagg aagagatact tgtcaggaag aatataattg     60
atttgagccc aagggagagg gtttctctag tcaaagcttt gcaaagaatg aagaatgatc    120
gctccgctga tgggtaccaa gccattgcct ctttccatgc cctgccacca ctctgtccca    180
atccatctgc agctcaccgt tatgcttgct gtgtccatgc catggctaca tttccccagt    240
ggcacagact gtacactgtt caggttcagg atgccctgag gagacatggt tcacttgttg    300
gtattcctta ctgggactgg acaaaaccag tcaacgagtt acccgagctt ctttcttcag    360
caacatttta tcatccaatc cggaatatta atatttcaaa tccattcctc ggggctgaca    420
tagaatttga aggaccgggc gttcatacag agaggcacat aaatactgag cgcctgtttc    480
acagtgggga tcatgacgga taccacaact ggttcttcga actgttctc tttgctttgg     540 aacaggaaga ttactgcgat tttgaaatac aatttgagat agcccataat ggcatccaca    600
catggattgg tggaagcgca gtatatggca tgggacacct tcactatgca tcatatgatc    660
caattttcta catccaccat tcacagacgg acagaatatg ggctatttgg caagagctgc    720
agaagtacag gggtctatct ggttcggaag caaactgtgc cattgaacat atgagaacac    780
ccttgaagcc tttcagcttt gggccaccct acaatttgaa tagtcatacg caagaatatt    840
caaagcctga ggacacgttt gactataaga gtttggata cagatatgat agtctggaat    900 tggagggggcg atcaatttct cgcattgatg aacttatcca gcagagacag agaaagaca    960 gaacttttgc agggttcctc cttaaaggtt ttggtacatc cgcatctgtg tcattgcaag   1020
tttgcagagt tgatcacacc tgtaaagatg cgggctattt cactattctg ggaggatcag   1080
ccgaaatgcc atgggcattc gacaggcttt ataagtatga cattactaaa actcttcacg   1140
acatgaacct gaggcacgag gacactttct ctatagacgt aactatcacg tcttacaatg   1200
gaacagtact ctcgggagac ctcattcaga cgccctccat tatatttgta cctggacgcc   1260
```

<210> SEQ ID NO 6
<211> LENGTH: 1251
<212> TYPE: DNA
<213> ORGANISM: Haliotis tuberculata

<400> SEQUENCE: 6

```
ataaactcaa ctcacggaaa catacaccta acagagtccg ccatgagcta agtagcctta     60
gttcccgtga catagcaagc ttgaaggcag ctttgacaag ccttcaacat gataatggga    120
ctgatggtta tcaagctatt gctgccttcc atggcgttcc tgcgcagtgc cacgagccat    180
ctggacgtga gatcgcctgt tgcatccacg gcatggcgac gtttcctcac tggcaccggt    240
tgtacactct gcagttggag caagcgctgc gcagacacgg gtccagtgtt gctgttccat    300
actgggactg gaccaagcca atcaccgaac tgccacacat tctgacagac ggagaatatt    360
```

```
atgacgtttg gcaaaatgcc gtcttggcca atccgtttgc aagaggttat gtgaaaatta      420
aagatgcatt tacggtgaga aatgtccagg aaagtctgtt caaaatgtca agttttggaa      480
agcactcgct tctgtttgac caggctttgt tggctcttga acaaactgac tactgtgact      540
tcgaagttca gtttgaagtg atgcataaca cgatccatta tctcgtagga gggcgtcaaa      600
cgtacgcctt ctcctctctc gagtattcct catacgatcc aatcttcttt attcaccact      660
cgtttgttga caaaatatgg gctgtatggc aagaactgca aagcaggaga catctacagt      720
ttagaacagc tgattgtgct gtgggcctca tgggtcaggc aatgaggcct tcaacaagg       780 atttcaacca caactcgttc accaagaagc acgcagtccc taatacagta tttgattatg      840
aagatcttgg ctataactat gacaaccttg aaatcagtgg tttaaactta aatgagatcg      900
aggcgttaat agcaaaacgc aagtcacatg ctagagtctt tgctgggttc ctgttgtttg      960
gattaggaac ttcggctgat atacatctgg aaatttgcaa gacatcggaa aactgccatg     1020
atgctggtgt gattttcatc cttggaggtt ctgcagagat gcattgggca tacaaccgcc     1080
tctacaagta tgacattaca gaagcattgc aggaatttga catcaaccct gaagatgttt     1140
tccatgctga tgaaccattt ttcctgaggc tgtcggttgt tgctgtgaat ggaactgtca     1200
ttccatcgtc tcatcttcac cagccaacga taatctatga accaggcgaa g              1251

<210> SEQ ID NO 7
<211> LENGTH: 1209
<212> TYPE: DNA
<213> ORGANISM: Haliotis tuberculata

<400> SEQUENCE: 7
atcaccatga cgaccatcag tcgggaagca tagcaggatc cggggtccgc aaggacgtga       60
acaccttgac taaggctgag accgacaacc tgagggaggc gctgtggggt gtcatggcag      120
accacggtcc caatggcttt caagctattg ctgctttcca tggaaaacca gctttgtgtc      180
ccatgcctga tggccacaac tactcatgtt gtactcacgg catggctacc ttcccacact      240
ggcatcgcct ctacaccaag cagatggagg atgcaatgag ggcgcatggg tctcatgtcg      300
gcctgcccta ctgggactgg actgctgcct tcacccacct gccaacactg gtcaccgaca      360
cggacaacaa ccccttccaa catggacaca ttgattatct caatgtcagc acaactcgat      420
ctccccgaga catgctgttc aacgaccccg agcatggatc agagtcgttc ttctacagac      480
aagtcctctt agctctggaa caaactgatt tctgcaaatt cgaagttcag tttgagataa      540
cccacaatgc catccattcc tggacaggtg gccacagccc ctacggaatg tccactctcg      600
acttcactgc ctacgatcct ctcttctggc ttcaccactc caacaccgac agaatctggg      660
ctgtctggca agctttgcaa gaatacagag gacttccata caaccatgcc aattgtgaga      720
tccaggcaat gaaaacgccc ctgaggcctt tcagtgacga tatcaaccac aacccagtca      780
caaaggctaa cgcgaagcca ttagatgtgt tcgagtataa tcggttgagc ttccagtacg      840
acaacctcat cttccatgga tacagtattc cggaacttga tcgcgtgctt gaagaaagaa      900
aggaggagga cagaatattt gctgccttcc ttctcagtgg aatcaagcgt agtgctgatg      960
tagtgttcga catatgccag ccagaacacg aatgtgtgtt cgcagggact tttgcgattt     1020 tgggaggggga gctagaaatg ccctggtcct cgacagact gttccgctat gatatcacca     1080
aggtgatgaa gcagctacac ctgaggcatg actctgactt taccttcagg gtgaagattg     1140
tcggcaccga cgaccacgag cttccttcag acagtgtcaa agcaccaact attgaatttg     1200
aaccgggcg                                                            1209
```

<210> SEQ ID NO 8
<211> LENGTH: 1535
<212> TYPE: DNA
<213> ORGANISM: Haliotis tuberculata

<400> SEQUENCE: 8

| | | | | | |
|---|---|---|---|---|---|
| tgcacagagg | cggaaaccac | gaagatgaac | accatgatga | cagactcgca | gatgtcctga | 60 |
| tcaggaaaga | agttgacttc | ctctccctgc | aagaggccaa | cgcaattaag | gatgcactgt | 120 |
| acaagctcca | gaatgacgac | agtaaagggg | gctttgaggc | catagctggc | tatcacgggt | 180 |
| atcctaatat | gtgtccagaa | agaggtaccg | acaagtatcc | ctgctgtgtc | cacggaatgc | 240 |
| ccgtgttccc | ccactggcac | cgcctgcata | ccattcagat | ggagagagct | ctgaaaaacc | 300 |
| atggctctcc | aatgggcatt | ccttactggg | attggacaaa | gaagatgtcg | agtcttccat | 360 |
| cttttctttgg | agattccagc | aacaacaacc | ctttctacaa | atattacatc | cggggcgtgc | 420 |
| agcacgaaac | aaccagggac | attaatcaga | gactctttaa | tcaaaccaag | tttggtgaat | 480 |
| ttgattacct | atattaccta | actctgcaag | tcctggagga | aaactcgtac | tgtgactttg | 540 |
| aagttcagta | tgagatcctc | cataacgccg | tccactcctg | gcttggagga | actggaaagt | 600 |
| attccatgtc | taccctggag | cattcggcct | ttgaccctgt | cttcatgatt | caccactcga | 660 |
| gtttggatag | aatctggatc | cttttggcaga | agttgcaaaa | gataagaatg | aagccttact | 720 |
| acgcattgga | ttgtgctggc | gacagactta | tgaaagaccc | cctgcatccc | ttcaactacg | 780 |
| aaaccgttaa | tgaagatgaa | ttcacccgca | tcaactcttt | cccaagcata | ctgtttgacc | 840 |
| actacaggtt | caactatgaa | tacgataaca | tgagaatcag | gggtcaggac | atacatgaac | 900 |
| ttgaagaggt | aattcaggaa | ttaagaaaca | agatcgcat | atttgctggt | tttgttttgt | 960 |
| cgggcttacg | gatatcagct | acagtgaaag | tattcattca | ttcgaaaaac | gatacaagtc | 1020 |
| acgaagaata | tgcaggagaa | tttgcagttt | tgggaggtga | aaggagatg | ccgtgggcat | 1080 |
| atgaaagaat | gctgaaattg | gacatctccg | atgctgtaca | caagcttcac | gtgaaagatg | 1140 |
| aagcatccg | ttttagagtg | gttgttactg | cctacaacgg | tgacgttgtt | accaccaggc | 1200 |
| tgtctcagcc | attcatcgtc | caccgtccag | cccatgtggc | tcacgacatc | ttggtaatcc | 1260 |
| cagtaggtgc | gggccatgac | cttccgccta | agtcgtagt | aaagagcggc | accaaagtcg | 1320 |
| agtttacacc | aatagattcg | tcggtgaaca | agcaatggt | ggagctgggc | agctatactg | 1380 |
| ctatggctaa | atgcatcgtt | ccccctttct | cttaccacgg | ctttgaactg | gacaaagtct | 1440 |
| acagcgtcga | tcacggagac | tactacattg | ctgcaggtac | ccacgcgttg | tgtgagcaga | 1500 |
| acctcaggct | ccacatccac | gtggaacacg | agtag | | | 1535 |

<210> SEQ ID NO 9
<211> LENGTH: 1003
<212> TYPE: DNA
<213> ORGANISM: Haliotis tuberculata

<400> SEQUENCE: 9

| | | | | | |
|---|---|---|---|---|---|
| cacagactgt | tcgtcaccca | ggtggaagat | gctctgatca | ggcgaggatc | gcctataggg | 60 |
| gtcccctact | gggactggac | tcagcctatg | gcgcatctcc | caggacttgc | agacaacgcc | 120 |
| acctatagag | atcccatcag | cggggacagc | agacacaacc | ccttccacga | tgttgaagtt | 180 |
| gccttttgaaa | atggacgtac | agaacgtcac | ccagatagta | gattgtttga | acaaccttta | 240 |
| tttggcaaac | atacgcgtct | cttcgacagt | atagtctatg | cttttgagca | ggaggacttc | 300 |

```
tgcgattttg aagttcaatt tgagatgacc cataataata ttcacgcctg gattggtggc      360
ggcgagaagt attccatgtc ttctctacac tacacagcct tcgaccctat cttctacctt      420
cgtcactcca acactgaccg gctctgggca atttggcaag cgttgcagat acgaagaaac      480
aggccttaca aggctcattg tgcttggtct gaggaacgcc agcctctcaa acctttcgcc      540
ttcagttccc cactgaacaa caacgaaaaa acctacgaaa actcggtgcc caccaacgtt      600
tacgactacg aaggagtcct tggctatact tatgatgacc tcaacttcgg gggcatggac      660
ctgggtcagc ttgaggaata catccagagg cagagacaga gagacaggac ctttgctggt      720
ttctttctgt cacatattgg tacatcagcg aatgttgaaa tcattataga ccatgggact      780
cttcatacct ccgtgggcac gtttgctgtt cttggcggag agaaggagat gaaatgggga      840
tttgaccgtt tgtacaaata tgagattaca atgaactgag gcaacttaa tctccgtgct       900 gatgatgttt tcagcatctc tgttaaagta actgatgttg atggcagtga gctgtcctct      960
gaactcatcc catctgctgc tatcatcttc gaacgaagcc ata                       1003

<210> SEQ ID NO 10
<211> LENGTH: 1251
<212> TYPE: DNA
<213> ORGANISM: Haliotis tuberculata

<400> SEQUENCE: 10
ttgaccatca ggacccgcat catgacacaa tcattaggaa aaatgttgat aatcttacac        60
ccgaggaaat taattctctg aggcgggcaa tggcagacct tcaatcagac aaaaccgccg       120
gtggattcca gcaaattgct gcttttcacg gggaacccaa atggtgccca agtcccgatg       180
ctgagaagaa gttctcctgc tgtgtccatg gaatggctgt cttccctcac tggcacagac       240
tcctgaccgt gcaaggcgag aatgccctga aaagcatgga atgtctcgga gctctcccct       300
actgggactg gactcggccc ctgtctcacc tacctgattt ggttttggta agtagcagaa       360
ctacaccgat gccatattcc accgtggaag cccgaaaccc ctggtacagc ggccatattg       420
atacagttgg tgttgacaca acaagaagcg tccgtcaaga actgtatgaa gctcctggat       480
ttggccatta tactgggggtc gctaagcaag tgcttctggc tttggagcag gatgacttct       540
gtgattttga agtccagttt gagatagctc acaatttcat tcacgctctt gtcggcggaa       600
gcgagccata tggtatggcg tcactccgtt acactactta tgatccaatt ttctacctcc       660
atcattctaa cactgacaga ctctgggcta tatggcaggc tctacaaaag tacaggggca       720
aaccttacaa ttccgccaac tgcgccattg cttctatgag aaaacccta caacccttg        780 gtctgactga tgagatcaac ccggatgatg agacaagaca gcatgctgtt cctttcagtg      840
tctttgatta caagaacaac ttcaattatg aatatgcaca ccttgacttc aacggactat     900
caatctccca gctggaccgt gaactgtcac ggagaaagtc tcatgacaga gtatttgccg     960 gattttgct gcatggtatt cagcagtctg cactagttaa attctttgtc tgcaaatcag     1020
atgatgactg tgaccactat gctggtgaat tctacatcct tggtgatgaa gctgaaatgc    1080 catgggcta tgatcgtctt tacaaatatg agatcactga gcagctcaat gccctggatc     1140
tacacatcgg agatagattc ttcatcagat acgaagcgtt tgatcttcat ggtacaagtc    1200
ttggaagcaa catcttcccc aaaccttctg tcatacatga cgaagggca g               1251

<210> SEQ ID NO 11
<211> LENGTH: 1244
<212> TYPE: DNA
<213> ORGANISM: Haliotis tuberculata
```

<400> SEQUENCE: 11

```
gtcaccatca ggctgacgag tacgacgaag ttgtaactgc tgcaagccac atcagaaaga        60
atttaaaaga tctgtcaaag ggagaagtag agagcctaag gtctgccttc ctgcaacttc       120
agaacgacgg agtctatgag aatattgcca agttccacgg caagcctggg ttgtgtgatg       180
ataacggtcg caaggttgcc tgttgtgtcc atggaatgcc caccttcccc cagtggcaca       240
ggctctatgt cctccaggtg gagaatgctt tgctggagag aggatctgcc gtctctgtgc       300
catactggga ctggactgaa acatttacag agctgccatc tttgattgct gaggctacct       360
atttcaattc ccgtcaacaa acgtttgacc ctaatccttt cttcagaggt aaaatcagtt       420
ttgagaatgc tgttacaaca cgtgatcccc agcctgagct gtacgttaac aggtactact       480
accaaaacgt catgttggtt tttgaacagg acaactactg cgacttcgag atacagtttg       540
agatggttca caatgttctc catgcttggc ttggtggaag agctacttat tctatttctt       600
ctcttgatta ttctgcattc gaccctgtgt ttttccttca ccatgcgaac acagatagat       660
tgtgggccat ctggcaggag ctgcagaggt acaggaagaa gccatacaat gaagcggatt       720
gtgccattaa cctaatgcgc aaacctctac atcccttcga caacagtgat ctcaatcatg       780
atcctgtaac ctttaaatac tcaaaaccca ctgatggctt tgactaccag aacaactttg       840
gatacaagta tgacaacctt gagttcaatc atttcagtat tcccaggctt gaagaaatca       900
ttcgtattag acaacgtcaa gatcgtgtgt ttgcaggatt cctccttcac aacattggga       960
catccgcaac tgttgagata ttcgtctgtg tccctaccac cagcggtgag caaaactgtg      1020
aaaacaaagc cggaacattt gccgtactcg gaggagaaac agagatggcg tttcattttg      1080
acagactcta caggtttgac atcagtgaaa cactgaggga cctcggcata cagctggaca      1140
gccatgactt tgacctcagc atcaagattc aaggagtaaa tggatcctac cttgatccac      1200
acatcctgcc agagccatcc ttgattttg tgcctggttc aagt                        1244
```

<210> SEQ ID NO 12
<211> LENGTH: 1255
<212> TYPE: DNA
<213> ORGANISM: Haliotis tuberculata

<400> SEQUENCE: 12

```
tctttcctgc gtcctgatgg gcattcagat gacatccttg tgagaaaaga agtgaacagc        60
ctgacaacca gggagactgc atctctgatc catgctctga aaagtatgca ggaagaccat       120
tcacctgacg ggttccaagc cattgcctct ttccatgctc tgccaccact ctgcccttca       180
ccatctgcag ctcaccgtta tgcttgctgt gtccacggca tggctacatt tccccagtgg       240
cacagattgt acactgtaca gttccaggat gcactgagga acatggagc tacggtaggt       300
gtaccgtatt gggattggct gcgaccgcag tctcacctac cagagcttgt caccatggag       360
acataccatg atatttggag taacagagat ttccccaatc ctttctacca gccaatatt       420
gagtttgaag gagaaaacat tacaacagag agagaagtca ttgcagacaa acttttttgtc      480
aaaggtggac acgtttttga taaactggtt cttcaaacaa gccatcctag cgctgagcag       540
gaaaactact gtgactttga gattcagttt gaaattcttc acaacggcgt tcacacgtgg       600
gtcggaggca gtcgtaccta ctctatcgga catcttcatt acgcattcta cgaccctctt       660
ttctaccttc accatttcca gacagaccgt atttgggcaa tctggcaaga actccaggaa       720
cagagagggc tctcgggtga tgaggctcac tgtgctctcg agcaaatgag agaaccattg       780
```

| aagcctttca gcttcggcgc tccttataac tggaatcagc tcacacagga tttctcccga | 840 |
| cccgaggaca ccttcgacta caggaagttt ggttatgaat atgacaattt agaattcctg | 900 |
| ggaatgtcag ttgctgaact ggatcaatac attattgaac atcaagaaaa tgatagagta | 960 |
| ttcgctgggt tcctgttgag tggattcgga ggttccgcat cagttaattt ccaggtttgt | 1020 |
| agagctgatt ccacatgtca ggatgctggg tacttcaccg ttcttggtgg cagtgctgag | 1080 |
| atggcgtggg catttgacag gctttacaaa tatgacatta ctgaaactct ggagaaaatg | 1140 |
| caccttcgat atgatgatga cttcacaatc tctgtcagtc tgaccgccaa caacggaact | 1200 |
| gtcctgagca gcagtctaat cccaacaccg agtgtcatat ccagcgggg acatc | 1255 |

<210> SEQ ID NO 13
<211> LENGTH: 1248
<212> TYPE: DNA
<213> ORGANISM: Haliotis tuberculata

<400> SEQUENCE: 13

| gtgacataaa taccaggagc atgtcaccga accgtgttcg ccgtgagctg agcgatctgt | 60 |
| ctgcgaggga cctgtctagt ctcaagtctg ctctgcgaga cctacaggag gatgatggcc | 120 |
| ccaacggata ccaggctctt gcagccttcc atgggctacc agcaggctgc catgatagcc | 180 |
| ggggaaatga gatcgcatgt tgcattcacg ggatgccgac cttcccccag tgcacagac | 240 |
| tgtacaccct gcagttggag atggctctga ggagacatgg atcatctgtc gccatcccct | 300 |
| actgggactg gacaaagcct atctccgaac tcccctcgct cttcaccagc cctgagtatt | 360 |
| atgacccatg gcatgatgct gtggtaaaca acccattctc caaggttttt gtcaaatttg | 420 |
| caaatacccta cacagtaaga gacccacagg agatgctgtt ccagctttgt gaacatggag | 480 |
| agtcaatcct ctatgagcaa actcttcttg ctcttgagca aaccgactac tgtgattttg | 540 |
| aggtacagtt tgaggtcctc cataacgtga tccactacct tgttggtgga cgtcagacct | 600 |
| acgcattgtc ttctctgcat tatgcctcct acgacccatt cttctttata caccattcct | 660 |
| ttgtggataa gatgtgggta gtatggcaag ctcttcaaaa gaggaggaaa cttccataca | 720 |
| agcgagctga ctgtgctgtc aacctaatga ctaaaccaat gaggccattt gactccgata | 780 |
| tgaatcagaa cccattcaca aagatgcacg cagttcccaa cacactctat gactacgaga | 840 |
| cactgtacta cagctacgat aatctcgaaa taggtggcag gaatctcgac cagcttcagg | 900 |
| ctgaaattga cagaagcaga agccacgatc gcgttttgc tggattcttg cttcgtggaa | 960 |
| tcggaacttc tgctgatgtc aggttttgga tttgtagaaa tgaaaatgac tgccacaggg | 1020 |
| gtggaataat tttcatctta ggtggagcca aggaaatgcc atggtcattt gacagaaact | 1080 |
| tcaagtttga tatcacccat gtactcgaga atgctggcat tagcccagag gacgtgtttg | 1140 |
| atgctgagga gccatttat atcaaggttg agatccatgc tgttaacaag accatgatac | 1200 |
| cgtcgtctgt gatcccagcc ccaactatca tctattctcc tggggaag | 1248 |

<210> SEQ ID NO 14
<211> LENGTH: 1207
<212> TYPE: DNA
<213> ORGANISM: Haliotis tuberculata

<400> SEQUENCE: 14

| gtcgcgctgc tgacagtgcg cactctgcca acattgctgg ctctggggtg aggaaggacg | 60 |
| tcacgaccct cactgtgtct gagaccgaga acctaagaca ggctcttcaa ggtgtcatcg | 120 |
| atgatactgg tcccaatggt taccaagcaa tagcatcctt ccacggaagt cctccaatgt | 180 |

```
gcgagatgaa cggccgcaag gttgcctgtt gtgctcacgg tatggcctcc ttcccacact      240
ggcacagact gtatgtgaag cagatggaag atgccctggc tgaccacggg tcacatatcg      300
gcatccctta ctgggactgg acaactgcct tcacagagtt acccgccctt gtcacagact      360
ccgagaacaa tcccttccat gagggtcgca ttgatcatct cggtgtaacc acgtcacgtt      420
cccccagaga catgctgttt aacgacccag agcaaggatc agagtcgttc ttctatagac      480
aagtcctcct ggctttggag cagactgact actgccagtt cgaagtccag tttgagctga      540
cccacaacgc cattcactcc tggacaggtg gacgtagccc ttacgaaatg tcgaccctcg      600
agttcacagc ctacgatcct ctcttctggc ttcaccactc caacaccgac agaatctggg      660
ctgtctggca agcactgcag aaataccgag gactcccata caacgaagca cactgtgaaa      720
tccaggttct gaaacagccc ttgaggccat tcaacgatga catcaaccac aatccaatca      780
ccaagactaa tgccaggcct atcgattcat ttgattatga gaggtttaac tatcagtatg      840
acacccttag cttccatggt aagagcatcc ctgaactgaa tgacctgctc gaggaaagaa      900
aaagagaaga gagaacattt gctgccttcc ttcttcgtgg aatcggttgc agtgctgatg      960
tcgtctttga catctgccgg cccaatggtg actgtgtctt tgcaggaacc tttgctgtgc     1020
tgggagggga gctagaaatg ccttggtcct cgacagact gttccgctat gacatcacca     1080
gagtcatgaa tcagctccat ctccagtatg attcagattt cagtttcagg gtgaagcttg     1140
ttgccaccaa tggcactgag ctttcatcag accttctcaa gtcaccaaca attgaacatg     1200
aacttgg                                                              1207
```

<210> SEQ ID NO 15
<211> LENGTH: 1546
<212> TYPE: DNA
<213> ORGANISM: Haliotis tuberculata
<220> FEATURE:
<221> NAME/KEY: misc_feature
<222> LOCATION: (1273)..(1273)
<223> OTHER INFORMATION: n is a, c, g, or t

<400> SEQUENCE: 15

```
agcccacaga ggaccagttg aagaaacaga agtcactcgc caacatactg acggcaatgc       60
acactttcat cgtaaggaag ttgattcgct gtccctggat gaagcaaaca acttgaagaa      120 tgcccttta c aagctacaga acgaccacag tctaacggga tacgaagcaa tctctggtta      180
ccatggatac cccaatctgt gtccggaaga aggcgatgac aaaataccc  tgctgcgtcc      240 ccggatgggc atctttcctt actggcacag actcttgacc attcaactgg aaagagctct      300
tgagcacaat ggtgcactgc ttggtgttcc ttactgggac tggaacaagg acctgtcgtc      360
actgccggcg ttcttctccg actccagcaa caacaatccc tacttcaagt accacatcgc      420
cggtgttggt cacgacaccg tcagagagcc aactagtctt atatataacc agccccaaat      480
ccatggttat gattatctct attacctagc attgaccacg cttgaagaaa acaattactg      540
ggactttgag gttcagtatg agatcctcca caacgccgtc cactcctggc ttggaggatc      600
ccagaagtat tccatgtcta ccctggagta ttcggccttt gaccctgtct ttatgatcct      660
tcactcgggt ctagacagac tttggatcat ctggcaagaa cttcagaaga tcaggagaaa      720
gccctacaac ttcgctaaat gtgcttatca tatgatggaa gagccactgg cgcccttcag      780
ctatccatct atcaaccagg acgagttcac ccgtgccaac tccaagcctt ctacagtttt      840
tgacagccat aagttcggct accattacga taacctgaat gttagaggtc acagcatcca      900
```

| | |
|---|---:|
| agaactcaac acaatcatca atgacttgag aaacacagac agaatctacg caggatttgt | 960 |
| tttgtcaggc atcggtacgt ctgctagtgt caagatctat ctccgaacag atgacaatga | 1020 |
| cgaagaagtt ggaactttca ctgtcctggg aggagagagg gaaatgccat gggcctacga | 1080 |
| gcgagttttc aagtatgaca tcacagaggt tgcagataga cttaaaatta agttatgggg | 1140 |
| acacccttta acttccggaa ctggagatca catccttacg aatggaatcg gtggtaaaca | 1200 |
| agagcctacc caaatccttt catcatctac agacctgcca atcatgacta cgatgttctt | 1260 |
| gttatcccag tanggaagaa accttcacat ccctcccaaa gttgtcgtca agaaaggcac | 1320 |
| ccgcatcgag ttccacccag tcgatgattc agttacgaga ccagttgttg atcttggaag | 1380 |
| ctacactgca ctcttcaact gtgtggtacc accgttcaca taccacggat tcgaactgaa | 1440 |
| ccacgtctat tctgtcaagc ctggtgacta ctatgttact ggacccacga gagacctttg | 1500 |
| ccagaatgca gatgtcagga ttcatatcca tgttgaggat gagtaa | 1546 |

<210> SEQ ID NO 16
<211> LENGTH: 967
<212> TYPE: DNA
<213> ORGANISM: Megathrua crenulata

<400> SEQUENCE: 16

| | |
|---|---:|
| ggcctaccgt actgggactg gactgaaccc atgacacaca ttccgggtct ggcaggaaac | 60 |
| aaaacttatg tggattctca tggtgcatcc cacacaaatc cttttcatag ttcagtgatt | 120 |
| gcatttgaag aaaatgctcc ccacaccaaa agacaaatag atcaaagact ctttaaaccc | 180 |
| gctacctttg gacaccacac agacctgttc aaccagattt tgtatgcctt tgaacaagaa | 240 |
| gattactgtg actttgaagt ccaatttgag attacccata acacgattca cgcttggaca | 300 |
| ggaggaagcg aacatttctc aatgtcgtcc ctacattaca cagctttcga tcctttgttt | 360 |
| tactttcacc attctaacgt tgatcgtctt tgggccgttt ggcaagcctt acagatgaga | 420 |
| cggcataaac cctacagggc ccactgcgcc atatctctgg aacatatgca tctgaaacca | 480 |
| ttcgcctttt catctcccct taacaataac gaaaagactc atgccaatgc catgccaaac | 540 |
| aagatctacg actatgaaaa tgtcctccat tacacatacg aagatttaac atttggaggc | 600 |
| atctctctgg aaaacataga aaagatgatc cacgaaaacc agcaagaaga cagaatatat | 660 |
| gccggttttc tcctggctgg catacgtact tcagcaaatg ttgatatctt cattaaaact | 720 |
| accgattccg tgcaacataa ggctggaaca tttgcagtgc tcggtggaag caaggaaatg | 780 |
| aagtggggat ttgatcgcgt tttcaagttt gacatcacgc acgttttgaa agatctcgat | 840 |
| ctcactgctg atggcgattt cgaagttact gttgacatca ctgaagtcga tggaactaaa | 900 |
| cttgcatcca gtcttattcc acatgcttct gtcattcgtg agcatgcacg tggtaagctg | 960 |
| aatagag | 967 |

<210> SEQ ID NO 17
<211> LENGTH: 1242
<212> TYPE: DNA
<213> ORGANISM: Megathura crenulata

<400> SEQUENCE: 17

| | |
|---|---:|
| ttaaatttga caaagtgcca aggagtcgtc ttattcgaaa aaatgtagac cgtttgagcc | 60 |
| ccgaggagat gaatgaactt cgtaaagccc tagccttact gaaagaggac aaaagtgccg | 120 |
| gtggatttca gcagcttggt gcattccatg gggagccaaa atggtgtcct agtcccgaag | 180 |
| catctaaaaa atttgcctgc tgtgttcacg gcatgtctgt gttccctcac tggcatcgac | 240 |

```
tgttgacggt tcagagtgaa aatgctttga gacgacatgg ctacgatgga gctttgccgt      300
actgggattg gacctctcct cttaatcacc ttcccgaact ggcagatcat gagaagtacg      360
tcgaccctga agatggggta gagaagcata acccttggtt cgatggtcat atagatacag      420
tcgacaaaac aacaacaaga agtgttcaga ataaactctt cgaacagcct gagtttggtc      480
attatacaag cattgccaaa caagtactgc tagcgttgga acaggacaat ttctgtgact      540
ttgaaatcca atatgagatt gcccataact acatccatgc acttgtagga ggcgctcagc      600
cttatggtat ggcatcgctt cgctacactg cttttgatcc actattctac ttgcatcact      660
ctaatacaga tcgtatatgg gcaatatggc aggctttaca gaagtacaga ggaaaaccgt      720
acaacgttgc taactgtgct gttacatcga tgagagaacc tttgcaacca tttggcctct      780
ctgccaatat caacacagac catgtaacca aggagcattc agtgccattc aacgtttttg      840
attacaagac caatttcaat tatgaatatg cactttggaa atttaacggt ctctcaatct      900
ctcagttgaa taaaaagctc gaagcgataa agagccaaga caggttcttt gcaggcttcc      960
tgttatctgg tttcaagaaa tcatctcttg ttaaattcaa tatttgcacc gatagcagca     1020
actgtcaccc cgctggagag ttttaccttc tgggtgatga aaacgagatg ccatgggcat     1080
acgatagagt cttcaaatat gacataaccg aaaaactcca cgatctaaag ctgcatgcag     1140
aagaccactt ctacattgac tatgaagtat ttgacccttaa accagcaagc ctgggaaaag     1200
atttgttcaa gcagccttca gtcattcatg aaccaagaat ag                        1242

<210> SEQ ID NO 18
<211> LENGTH: 1236
<212> TYPE: DNA
<213> ORGANISM: Megathura crenulata

<400> SEQUENCE: 18
gtcaccatga aggcgaagta tatcaagctg aagtaacttc tgccaaccgt attcgaaaaa       60
acattgaaaa tctgagcctt ggtgaactcg aaagtctgag agctgccttc ctggaaattg      120
aaaacgatgg aacttacgaa tcaatagcta aattccatgg tagccctggt ttgtgccagt      180
taaatggtaa ccccatctct tgttgtgtcc atggcatgcc aactttccct cactggcaca      240
gactgtacgt ggttgtcgtt gagaatgccc tcctgaaaaa aggatcatct gtagctgttc      300
cctattggga ctggacaaaa cgaatcgaac atttacctca cctgatttca gacgccactt      360
actacaattc caggcaacat cactatgaga caaaccccatt ccatcatggc aaaatcacac      420
acgagaatga aatcactact agggatccca aggacagcct cttccattca gactactttt      480
acgagcaggt cctttacgcc ttggagcagg ataacttctg tgatttcgag attcagttgg      540
agatattaca caatgcattg cattctttac ttggtggcaa aggtaaatat tccatgtcaa      600
accttgatta cgctgctttt gatcctgtgt tcttccttca tcacgcaacg actgacagaa      660
tctgggcaat ctggcaagac cttcagaggt tccgaaaacg gccataccga aagcgaatt      720 gcgctatcca attgatgcac acgccactcc agccgtttga taagagcgac aacaatgacg      780
aggcaacgaa aacgcatgcc actccacatg atggttttga atatcaaaac agctttggtt      840
atgcttacga taatctggaa ctgaatcact actcgattcc tcagcttgat cacatgctgc      900
aagaaagaaa aaggcatgac agagtattcg ctggcttcct ccttcacaat attggaacat      960
ctgccgatgg ccatgtattt gtatgtctcc caactgggga acacacgaag gactgcagtc     1020
atgaggctgg tatgttctcc atcttaggcg gtcaaacgga gatgtccttt gtatttgaca     1080
```

```
gactttacaa acttgacata actaaagcct tgaaaagaa cggtgtgcac ctgcaagggg    1140
atttcgatct ggaaattgag attacggctg tgaatggatc tcatctagac agtcatgtca    1200
tccactctcc cactatactg tttgaggccg aacag                              1236

<210> SEQ ID NO 19
<211> LENGTH: 241
<212> TYPE: DNA
<213> ORGANISM: Megathura crenulata

<400> SEQUENCE: 19
attctgccca cacagatgat ggacacactg aaccagtgat gattcgcaaa gatatcacac      60
aattggacaa gcgtcaacaa ctgtcactgg tgaaagccct cgagtccatg aaagccgacc     120
attcatctga tgggttccag gcaatcgctt ccttccatgc tcttcctcct ctttgtccat     180
caccagctgc ttcaaagagg tttgcgtgct gcgtccatgg catgccaacc ttcccgcaat     240
g                                                                    241

<210> SEQ ID NO 20
<211> LENGTH: 949
<212> TYPE: DNA
<213> ORGANISM: Megathura crenulata

<400> SEQUENCE: 20
ggcctgccct actgggattg gaccatgcca atgagtcatt tgccagaact ggctacaagt      60
gagacctacc tcgatccagt tactggggaa actaaaaaca ccctttcca tcacgcccaa     120 gtggcgtttg aaaatggtgt aacaagcagg aatcctgatg ccaaactttt tatgaaacca     180
acttacggag accacactta cctcttcgac agcatgatct acgcatttga gcaggaagac     240
ttctgcgact ttgaagtcca atatgagctc acgcataatg caatacatgc atgggttgga     300
ggcagtgaaa agtattcaat gtcttctctt cactacactg cttttgatcc tatattttac     360
ctccatcact caaatgttga tcgtctctgg gccatttggc aagctcttca aatcaggaga     420
ggcaagtctt acaaggccca ctgcgcctcg tctcaagaaa gagaaccatt aaagcctttt     480
gcattcagtt ccccactgaa caacaacgag aaaacgtacc acaactctgt ccccactaac     540
gtttatgact atgtgggagt tttgcactat cgatatgatg accttcagtt tggcggtatg     600
accatgtcag aacttgagga atatattcac aagcagacac aacatgatag aacctttgca     660
ggattcttcc tttcatatat tggaacatca gcaagcgtag atatcttcat caatcgagaa     720
ggtcatgata aatacaaagt gggaagtttt gtagtacttg gtggatccaa agaaatgaaa     780
tggggctttg atagaatgta caagtatgag atcactgagg ctctgaagac gctgaatgtt     840
gcagtggatg atgggttcag cattactgtt gagatcaccg atgttgatgg atctccccca     900
tctgcagatc tcattccacc tcctgctata atctttgaac gtggtcatg               949

<210> SEQ ID NO 21
<211> LENGTH: 760
<212> TYPE: DNA
<213> ORGANISM: Megathura crenulata

<400> SEQUENCE: 21
ctgatgccaa agactttggc catagcagaa aaatcaggaa agccgttgat tctctgacag      60
tcgaagaaca aacttcgttg aggcgagcta tggcagatct acaggacgac aaaacatcag    120
ggggtttcca gcagattgca gcattccacg gagaaccaaa atggtgtcca gcccccgaag    180
cggagaaaaa atttgcatgc tgtgttcatg gaatggctgt tttccctcac tggcacagat    240
```

-continued

```
tgctgacagt tcaaggagaa aatgctctga ggaaacatgg ctttactggt ggactgccct    300
actgggactg gactcgatca atgagcgccc ttccacattt tgttgctgat cctacttaca    360
atgatgctat ttccagccag gaagaagata acccatggca tcatggtcac atagactctg    420
ttgggcatga tactacaaga gatgtgcgtg atgatcttta tcaatctcct ggtttcggtc    480
actacacaga tattgcacaa caagtccttc tggcctttga gcaggacagt ttctgtgatt    540
ttgaggtaca atttgaaatt gcccataatt tcatacatgc actgattggt ggtaacgaac    600
catacagtat gtcatctttg aggtatacta catacgatcc aatcttcttc ttgcaccact    660
ccagtacaga ccgactttgg gccatctggc aagcaatcac tagtgcggcc gcctgcaggt    720
cgaccataag ggagagctcc caacgcgttg gatgcaatct                           760
```

<210> SEQ ID NO 22
<211> LENGTH: 323
<212> TYPE: DNA
<213> ORGANISM: Megathura crenulata

<400> SEQUENCE: 22

```
gttcacacca ggctgatgaa tatcgtgagg cagtaacaag cgctagccac ataagaaaaa     60
atatccggga cctctcagag ggagaaattg agagcatcag atctgctttc ctccaaattc    120
aaaaagaggg tatatatgaa aacattgcaa agttccatgg aaaaccagga ctttgtgaac    180
atgatggaca tcctgttgct tgttgtgtcc atggcatgcc cacctttccc cactggcaca    240
gactgtacgt tcttcaggtg gagaatgcgc tcttagaacg agggtctgca gttgctgttc    300
cttactggga ctggacccta cct                                            323
```

<210> SEQ ID NO 23
<211> LENGTH: 988
<212> TYPE: DNA
<213> ORGANISM: Megathura crenulata

<400> SEQUENCE: 23

```
atggctgtgt ttccgcactg gcacagactg tttgtgaaac agatggagga cgcacttgct     60
gctcatggag ctcatattgg cataccatac tgggattgga caagtgcgtt tagtcatctg    120
cccgccctag tgactgacca cgagaacaat cccttccacc acggccatat tggtcatctg    180
aatgtggata catctcgatc tccaagagac atgctgttta atgatcctga caaggctca     240 gaatcattct tctacagaca ggttctcttg actctagaac agacagactt ctgccaattt    300
gaagttcagt ttgaacttac acacaatgcc atccactctt ggactggagg acatactcca    360 tatgaatgt catcactgga atatacagca tatgatccac tcttttatct ccaccattcc    420
aacactgatc gtatctgggc catctggcag gcactccaga aatatagagg tcttccatac    480
aacgcagctc actgcgatat ccaagttctg aaacaacctc ttaaaccatt cagcgagtcc    540
aggaatccaa acccagtcac cagagccaat tctagggccg ttgattcatt tgattatgag    600
aaattcaatt atcaatatga cacacttacc ttccacggac tttctatccc agaacttgat    660
gccatgcttc aagagagaaa gaaggaagag agaacatttg cagccttcct gttgcacgga    720
tttggcgcca gtgctgatgt ttcgttttgat gtctgcacac ctgatggtca ttgtgccttt    780 gctggaaccct tcgcggtact tggtggggag cttgagatgc cctggtcctt tgaaagattg    840
ttccgttacg atatcacaaa ggttctcaag cagatgaatc ttcactatga ttctgagttc    900
cactttgagt tgaagattgt tggcacagat ggaacagaac tgccatcgga tcgtatcaag    960
```
agccctacca ttgaacacca tggaggag 988

<210> SEQ ID NO 24
<211> LENGTH: 310
<212> TYPE: DNA
<213> ORGANISM: Megathura crenulata

<400> SEQUENCE: 24

| | | | | |
|---|---|---|---|---|
| gtcacgatca cagtgaacgt cacgatggat ttttcaggaa ggaagtcggt tccctgtccc | 60 |
| tggatgaagc caatgacctt aaaaatgcac tgtacaagct gcagaatgat cagggtccca | 120 |
| atggatatga atcaatagcc ggttaccatg gctatccatt cctctgccct gaacatggtg | 180 |
| aagaccagta cgcatgctgt gtccacggaa tgcctgtatt ccacattgg cacagacttc | 240 |
| atacaatcca gtttgagaga gctctcaaag aacatggttc tcatttgggt ctgccatact | 300 |
| gggactggac | 310 |

<210> SEQ ID NO 25
<211> LENGTH: 422
<212> TYPE: PRT
<213> ORGANISM: Haliotis tuberculata

<400> SEQUENCE: 25

Leu Val Gln Phe Leu Leu Val Ala Leu Val Ala Gly Ala Gly Ala Asp
1               5                   10                  15

Asn Val Val Arg Lys Asp Val Ser His Leu Thr Asp Asp Glu Val Gln
                20                  25                  30

Ala Leu His Gly Ala Leu His Asp Val Thr Ala Ser Thr Gly Pro Leu
            35                  40                  45

Ser Phe Glu Asp Ile Thr Ser Tyr His Ala Ala Pro Ala Ser Cys Asp
        50                  55                  60

Tyr Lys Gly Arg Lys Ile Ala Cys Cys Val His Gly Met Pro Ser Phe
65                  70                  75                  80

Pro Phe Trp His Arg Ala Tyr Val Val Gln Ala Glu Arg Ala Leu Leu
                85                  90                  95

Ser Lys Arg Lys Thr Val Gly Met Pro Tyr Trp Asp Trp Thr Gln Thr
                100                 105                 110

Leu Thr His Leu Pro Ser Leu Val Thr Glu Pro Ile Tyr Ile Asp Ser
            115                 120                 125

Lys Gly Gly Lys Ala Gln Thr Asn Tyr Trp Tyr Arg Gly Glu Ile Ala
        130                 135                 140

Phe Ile Asn Lys Lys Thr Ala Arg Ala Val Asp Asp Arg Leu Phe Glu
145                 150                 155                 160

Lys Val Glu Pro Gly His Tyr Thr His Leu Met Glu Thr Val Leu Asp
                165                 170                 175

Ala Leu Glu Gln Asp Glu Phe Cys Lys Phe Glu Ile Gln Phe Glu Leu
            180                 185                 190

Ala His Asn Ala Ile His Tyr Leu Val Gly Gly Lys Phe Glu Tyr Ser
        195                 200                 205

Met Ser Asn Leu Glu Tyr Thr Ser Tyr Asp Pro Ile Phe Phe Leu His
        210                 215                 220

His Ser Asn Val Asp Arg Leu Phe Ala Ile Trp Gln Arg Leu Gln Glu
225                 230                 235                 240

Leu Arg Gly Lys Asn Pro Asn Ala Met Asp Cys Ala His Glu Leu Ala
                245                 250                 255

His Gln Gln Leu Gln Pro Phe Asn Arg Asp Ser Asn Pro Val Gln Leu

```
                    260                 265                 270
Thr Lys Asp His Ser Thr Pro Ala Asp Leu Phe Asp Tyr Lys Gln Leu
        275                 280                 285
Gly Tyr Ser Tyr Asp Ser Leu Asn Leu Asn Gly Met Thr Pro Glu Gln
    290                 295                 300
Leu Lys Thr Glu Leu Asp Glu Arg His Ser Lys Glu Arg Ala Phe Ala
305                 310                 315                 320
Ser Phe Arg Leu Ser Gly Phe Gly Gly Ser Ala Asn Val Val Tyr
                325                 330                 335
Ala Cys Val Pro Asp Asp Pro Arg Ser Asp Tyr Cys Glu Lys
                340                 345                 350
Ala Gly Asp Phe Phe Ile Leu Gly Gln Ser Glu Met Pro Trp Arg
                355                 360                 365
Phe Tyr Arg Pro Phe Phe Tyr Asp Val Thr Glu Ala Val His His Leu
    370                 375                 380
Gly Val Pro Leu Ser Gly His Tyr Tyr Val Lys Thr Glu Leu Phe Ser
385                 390                 395                 400
Val Asn Gly Thr Ala Leu Ser Pro Asp Leu Leu Pro Gln Pro Thr Val
                405                 410                 415
Ala Tyr Arg Pro Gly Lys
                420

<210> SEQ ID NO 26
<211> LENGTH: 419
<212> TYPE: PRT
<213> ORGANISM: Haliotis tuberculata

<400> SEQUENCE: 26

Gly His Leu Asp Pro Pro Val His His Arg His Asp Asp Leu Ile
1               5                   10                  15
Val Arg Lys Asn Ile Asp His Leu Thr Arg Glu Glu Tyr Glu Leu
                20                  25                  30
Arg Met Ala Leu Glu Arg Phe Gln Ala Asp Thr Ser Val Asp Gly Tyr
            35                  40                  45
Gln Ala Thr Val Glu Tyr His Gly Leu Pro Ala Arg Cys Pro Arg Pro
        50                  55                  60
Asp Ala Lys Val Arg Phe Ala Cys Cys Met His Gly Met Ala Ser Phe
65                  70                  75                  80
Pro His Trp His Arg Leu Phe Val Thr Gln Val Glu Asp Ala Leu Val
                85                  90                  95
Arg Arg Gly Ser Pro Ile Gly Val Pro Tyr Trp Asp Trp Thr Lys Pro
                100                 105                 110
Met Thr His Leu Pro Asp Leu Ala Ser Asn Glu Thr Tyr Val Asp Pro
            115                 120                 125
Tyr Gly His Thr His His Asn Pro Phe Asn Ala Asn Ile Ser Phe
        130                 135                 140
Glu Glu Gly His His His Thr Ser Arg Met Ile Asp Ser Lys Leu Phe
145                 150                 155                 160
Ala Pro Val Ala Phe Gly Glu His Ser His Leu Phe Asp Gly Ile Leu
                165                 170                 175
Tyr Ala Phe Glu Gln Glu Asp Phe Cys Asp Phe Glu Ile Gln Phe Glu
                180                 185                 190
Leu Val His Asn Ser Ile His Ala Trp Ile Gly Gly Ser Glu Asp Tyr
                195                 200                 205
```

-continued

```
Ser Met Ala Thr Leu His Tyr Thr Ala Phe Asp Pro Ile Phe Tyr Leu
210                 215                 220

His His Ser Asn Val Asp Arg Leu Trp Ala Ile Trp Gln Ala Leu Gln
225                 230                 235                 240

Ile Arg Arg His Lys Pro Tyr Gln Ala His Cys Ala Gln Ser Val Glu
                245                 250                 255

Gln Leu Pro Met Lys Pro Phe Ala Phe Pro Ser Pro Leu Asn Asn Asn
                260                 265                 270

Glu Lys Thr His Ser His Ser Val Pro Thr Asp Ile Tyr Asp Tyr Glu
            275                 280                 285

Glu Val Leu His Tyr Ser Tyr Asp Asp Leu Thr Phe Gly Gly Met Asn
290                 295                 300

Leu Glu Glu Ile Glu Glu Ala Ile His Leu Arg Gln Gln His Glu Arg
305                 310                 315                 320

Val Phe Ala Gly Phe Leu Leu Ala Gly Ile Gly Thr Ser Ala Leu Val
                325                 330                 335

Asp Ile Phe Ile Asn Lys Pro Gly Asn Gln Pro Leu Lys Ala Gly Asp
                340                 345                 350

Ile Ala Ile Leu Gly Gly Ala Lys Glu Met Pro Trp Ala Phe Asp Arg
            355                 360                 365

Leu Tyr Lys Val Glu Ile Thr Asp Ser Leu Lys Thr Leu Ser Leu Asp
370                 375                 380

Val Asp Gly Asp Tyr Glu Val Thr Phe Lys Ile His Asp Met His Gly
385                 390                 395                 400

Asn Ala Leu Asp Thr Asp Leu Ile Pro His Ala Ala Val Val Ser Glu
                405                 410                 415

Pro Ala His

<210> SEQ ID NO 27
<211> LENGTH: 414
<212> TYPE: PRT
<213> ORGANISM: Haliotis tuberculata

<400> SEQUENCE: 27

Pro Thr Phe Glu Asp Glu Lys His Ser Leu Arg Ile Arg Lys Asn Val
1               5                   10                  15

Asp Ser Leu Thr Pro Glu Glu Thr Asn Glu Leu Arg Lys Ala Leu Glu
                20                  25                  30

Leu Leu Glu Asn Asp His Thr Ala Gly Gly Phe Asn Gln Leu Gly Ala
            35                  40                  45

Phe His Gly Glu Pro Lys Trp Cys Pro Asn Pro Glu Ala Glu His Lys
    50                  55                  60

Val Ala Cys Cys Val His Gly Met Ala Val Phe Pro His Trp His Arg
65                  70                  75                  80

Leu Leu Ala Leu Gln Ala Glu Asn Ala Leu Arg Lys His Gly Tyr Ser
                85                  90                  95

Gly Ala Leu Pro Tyr Trp Asp Trp Thr Arg Pro Leu Ser Gln Leu Pro
            100                 105                 110

Asp Leu Val Ser His Glu Gln Tyr Thr Asp Pro Ser Asp His His Val
        115                 120                 125

Lys His Asn Pro Trp Phe Asn Gly His Ile Asp Thr Val Asn Gln Asp
    130                 135                 140

Thr Thr Arg Ser Val Arg Glu Asp Leu Tyr Gln Gln Pro Glu Phe Gly
145                 150                 155                 160
```

-continued

```
His Phe Thr Asp Ile Ala Gln Gln Val Leu Leu Ala Leu Glu Gln Asp
            165                 170                 175

Asp Phe Cys Ser Phe Glu Val Gln Tyr Glu Ile Ser His Asn Phe Ile
        180                 185                 190

His Ala Leu Val Gly Gly Thr Asp Ala Tyr Gly Met Ala Ser Leu Arg
    195                 200                 205

Tyr Thr Ala Tyr Asp Pro Ile Phe Phe Leu His Ser Asn Thr Asp
210                 215                 220

Arg Ile Trp Ala Ile Trp Gln Ser Leu Gln Lys Tyr Arg Gly Lys Pro
225                 230                 235                 240

Tyr Asn Thr Ala Asn Cys Ala Ile Glu Ser Met Arg Arg Pro Leu Gln
            245                 250                 255

Pro Phe Gly Leu Ser Ser Ala Ile Asn Pro Asp Arg Ile Thr Arg Glu
        260                 265                 270

His Ala Ile Pro Phe Asp Val Phe Asn Tyr Arg Asp Asn Leu His Tyr
    275                 280                 285

Val Tyr Asp Thr Leu Glu Phe Asn Gly Leu Ser Ile Ser Gln Leu Asp
290                 295                 300

Arg Glu Leu Glu Lys Ile Lys Ser His Glu Arg Val Phe Ala Gly Phe
305                 310                 315                 320

Leu Leu Ser Gly Ile Lys Lys Ser Ala Leu Val Lys Phe Glu Val Cys
            325                 330                 335

Thr Pro Pro Asp Asn Cys His Lys Ala Gly Glu Phe Tyr Leu Leu Gly
        340                 345                 350

Asp Glu Asn Glu Met Ala Trp Ala Tyr Asp Arg Leu Phe Lys Tyr Asp
    355                 360                 365

Ile Thr Gln Val Leu Glu Ala Asn His Leu His Phe Tyr Asp His Leu
370                 375                 380

Phe Ile Arg Tyr Glu Val Phe Asp Leu Lys Gly Val Ser Leu Gly Thr
385                 390                 395                 400

Asp Leu Phe His Thr Ala Asn Val Val His Asp Ser Gly Thr
            405                 410
```

<210> SEQ ID NO 28
<211> LENGTH: 413
<212> TYPE: PRT
<213> ORGANISM: Haliotis tuberculata

<400> SEQUENCE: 28

```
Gly Thr Arg Asp Arg Asp Asn Tyr Val Glu Val Thr Gly Ala Ser
1               5                   10                  15

His Ile Arg Lys Asn Leu Asn Asp Leu Asn Thr Gly Glu Met Glu Ser
            20                  25                  30

Leu Arg Ala Ala Phe Leu His Ile Gln Asp Asp Gly Thr Tyr Glu Ser
        35                  40                  45

Ile Ala Gln Tyr His Gly Lys Pro Gly Lys Cys Gln Leu Asn Asp His
    50                  55                  60

Asn Ile Ala Cys Cys Val His Gly Met Pro Thr Phe Pro Gln Trp His
65                  70                  75                  80

Arg Leu Tyr Val Val Gln Val Glu Asn Ala Leu Leu Asn Arg Gly Ser
            85                  90                  95

Gly Val Ala Val Pro Tyr Trp Glu Trp Thr Ala Pro Ile Asp His Leu
        100                 105                 110

Pro His Phe Ile Asp Asp Ala Thr Tyr Phe Asn Ser Arg Gln Gln Arg
    115                 120                 125
```

-continued

```
Tyr Asp Pro Asn Pro Phe Phe Arg Gly Lys Val Thr Phe Glu Asn Ala
    130                 135                 140

Val Thr Thr Arg Asp Pro Gln Ala Gly Leu Phe Asn Ser Asp Tyr Met
145                 150                 155                 160

Tyr Glu Asn Val Leu Leu Ala Leu Glu Gln Glu Asn Tyr Cys Asp Phe
                165                 170                 175

Glu Ile Gln Phe Glu Leu Val His Asn Ala Leu His Ser Met Leu Gly
            180                 185                 190

Gly Lys Gly Gln Tyr Ser Met Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Phe Arg Glu Leu Pro Tyr Glu Glu Ala Asn
225                 230                 235                 240

Cys Ala Ile Asn Leu Met His Gln Pro Leu Lys Pro Phe Ser Asp Pro
                245                 250                 255

His Glu Asn His Asp Asn Val Thr Leu Lys Tyr Ser Lys Pro Gln Asp
            260                 265                 270

Gly Phe Asp Tyr Gln Asn His Phe Gly Tyr Lys Tyr Asp Asn Leu Glu
        275                 280                 285

Phe His His Leu Ser Ile Pro Ser Leu Asp Ala Thr Leu Lys Gln Arg
    290                 295                 300

Arg Asn His Asp Arg Val Phe Ala Gly Phe Leu Leu His Asn Ile Gly
305                 310                 315                 320

Thr Ser Ala Asp Ile Thr Ile Tyr Ile Cys Leu Pro Asp Gly Arg Arg
                325                 330                 335

Gly Asn Asp Cys Ser His Glu Ala Gly Thr Phe Tyr Ile Leu Gly Gly
            340                 345                 350

Glu Thr Glu Met Pro Phe Ile Phe Asp Arg Leu Tyr Lys Phe Glu Ile
        355                 360                 365

Thr Lys Pro Leu Gln Gln Leu Gly Val Lys Leu His Gly Gly Val Phe
    370                 375                 380

Glu Leu Glu Leu Glu Ile Lys Ala Tyr Asn Gly Ser Tyr Leu Asp Pro
385                 390                 395                 400

His Thr Phe Asp Pro Thr Ile Ile Phe Glu Pro Gly Thr
                405                 410

<210> SEQ ID NO 29
<211> LENGTH: 420
<212> TYPE: PRT
<213> ORGANISM: Haliotis tuberculata

<400> SEQUENCE: 29

Asp Thr His Ile Leu Asp His Asp His Glu Glu Ile Leu Val Arg
1               5                   10                  15

Lys Asn Ile Ile Asp Leu Ser Pro Arg Glu Arg Val Ser Leu Val Lys
                20                  25                  30

Ala Leu Gln Arg Met Lys Asn Asp Arg Ser Ala Asp Gly Tyr Gln Ala
            35                  40                  45

Ile Ala Ser Phe His Ala Leu Pro Pro Leu Cys Pro Asn Pro Ser Ala
    50                  55                  60

Ala His Arg Tyr Ala Cys Cys Val His Gly Met Ala Thr Phe Pro Gln
65                  70                  75                  80

Trp His Arg Leu Tyr Thr Val Gln Val Gln Asp Ala Leu Arg Arg His
```

```
                    85                  90                  95
Gly Ser Leu Val Gly Ile Pro Tyr Trp Asp Trp Thr Lys Pro Val Asn
            100                 105                 110

Glu Leu Pro Glu Leu Leu Ser Ser Ala Thr Phe Tyr His Pro Ile Arg
            115                 120                 125

Asn Ile Asn Ile Ser Asn Pro Phe Leu Gly Ala Asp Ile Glu Phe Glu
130                 135                 140

Gly Pro Gly Val His Thr Glu Arg His Ile Asn Thr Glu Arg Leu Phe
145                 150                 155                 160

His Ser Gly Asp His Asp Gly Tyr His Asn Trp Phe Phe Glu Thr Val
                165                 170                 175

Leu Phe Ala Leu Glu Gln Glu Asp Tyr Cys Asp Phe Glu Ile Gln Phe
            180                 185                 190

Glu Ile Ala His Asn Gly Ile His Thr Trp Ile Gly Gly Ser Ala Val
            195                 200                 205

Tyr Gly Met Gly His Leu His Tyr Ala Ser Tyr Asp Pro Ile Phe Tyr
        210                 215                 220

Ile His His Ser Gln Thr Asp Arg Ile Trp Ala Ile Trp Gln Glu Leu
225                 230                 235                 240

Gln Lys Tyr Arg Gly Leu Ser Gly Ser Glu Ala Asn Cys Ala Ile Glu
                245                 250                 255

His Met Arg Thr Pro Leu Lys Pro Phe Ser Phe Gly Pro Pro Tyr Asn
            260                 265                 270

Leu Asn Ser His Thr Gln Glu Tyr Ser Lys Pro Glu Asp Thr Phe Asp
            275                 280                 285

Tyr Lys Lys Phe Gly Tyr Arg Tyr Asp Ser Leu Glu Leu Glu Gly Arg
        290                 295                 300

Ser Ile Ser Arg Ile Asp Glu Leu Ile Gln Gln Arg Gln Glu Lys Asp
305                 310                 315                 320

Arg Thr Phe Ala Gly Phe Leu Lys Gly Phe Gly Thr Ser Ala Ser
                325                 330                 335

Val Ser Leu Gln Val Cys Arg Val Asp His Thr Cys Lys Asp Ala Gly
            340                 345                 350

Tyr Phe Thr Ile Leu Gly Gly Ser Ala Glu Met Pro Trp Ala Phe Asp
        355                 360                 365

Arg Leu Tyr Lys Tyr Asp Ile Thr Lys Thr Leu His Asp Met Asn Leu
        370                 375                 380

Arg His Glu Asp Thr Phe Ser Ile Asp Val Thr Ile Thr Ser Tyr Asn
385                 390                 395                 400

Gly Thr Val Leu Ser Gly Asp Leu Ile Gln Thr Pro Ser Ile Ile Phe
                405                 410                 415

Val Pro Gly Arg
            420

<210> SEQ ID NO 30
<211> LENGTH: 417
<212> TYPE: PRT
<213> ORGANISM: Haliotis tuberculata

<400> SEQUENCE: 30

His Lys Leu Asn Ser Arg Lys His Thr Pro Asn Arg Val Arg His Glu
1               5                   10                  15

Leu Ser Ser Leu Ser Ser Arg Asp Ile Ala Ser Leu Lys Ala Ala Leu
            20                  25                  30
```

```
Thr Ser Leu Gln His Asp Asn Gly Thr Asp Gly Tyr Gln Ala Ile Ala
         35                  40                  45
Ala Phe His Gly Val Pro Ala Gln Cys His Glu Pro Ser Gly Arg Glu
 50                  55                  60
Ile Ala Cys Cys Ile His Gly Met Ala Thr Phe Pro His Trp His Arg
 65                  70                  75                  80
Leu Tyr Thr Leu Gln Leu Glu Gln Ala Leu Arg Arg His Gly Ser Ser
                 85                  90                  95
Val Ala Val Pro Tyr Trp Asp Trp Thr Lys Pro Ile Thr Glu Leu Pro
                100                 105                 110
His Ile Leu Thr Asp Gly Glu Tyr Asp Val Trp Gln Asn Ala Val
            115                 120                 125
Leu Ala Asn Pro Phe Ala Arg Gly Tyr Val Lys Ile Lys Asp Ala Phe
130                 135                 140
Thr Val Arg Asn Val Gln Glu Ser Leu Phe Lys Met Ser Ser Phe Gly
145                 150                 155                 160
Lys His Ser Leu Leu Phe Asp Gln Ala Leu Leu Ala Leu Glu Gln Thr
                165                 170                 175
Asp Tyr Cys Asp Phe Glu Val Gln Phe Glu Val Met His Asn Thr Ile
            180                 185                 190
His Tyr Leu Val Gly Gly Arg Gln Thr Tyr Ala Phe Ser Ser Leu Glu
        195                 200                 205
Tyr Ser Ser Tyr Asp Pro Ile Phe Phe Ile His His Ser Phe Val Asp
    210                 215                 220
Lys Ile Trp Ala Val Trp Gln Glu Leu Gln Ser Arg Arg His Leu Gln
225                 230                 235                 240
Phe Arg Thr Ala Asp Cys Ala Val Gly Leu Met Gly Gln Ala Met Arg
                245                 250                 255
Pro Phe Asn Lys Asp Phe Asn His Asn Ser Phe Thr Lys Lys His Ala
            260                 265                 270
Val Pro Asn Thr Val Phe Asp Tyr Glu Asp Leu Gly Tyr Asn Tyr Asp
        275                 280                 285
Asn Leu Glu Ile Ser Gly Leu Asn Leu Asn Glu Ile Glu Ala Leu Ile
    290                 295                 300
Ala Lys Arg Lys Ser His Ala Arg Val Phe Ala Gly Phe Leu Leu Phe
305                 310                 315                 320
Gly Leu Gly Thr Ser Ala Asp Ile His Leu Glu Ile Cys Lys Thr Ser
                325                 330                 335
Glu Asn Cys His Asp Ala Gly Val Ile Phe Ile Leu Gly Gly Ser Ala
            340                 345                 350
Glu Met His Trp Ala Tyr Asn Arg Leu Tyr Lys Tyr Asp Ile Thr Glu
        355                 360                 365
Ala Leu Gln Glu Phe Asp Ile Asn Pro Glu Asp Val Phe His Ala Asp
    370                 375                 380
Glu Pro Phe Phe Leu Arg Leu Ser Val Val Ala Val Asn Gly Thr Val
385                 390                 395                 400
Ile Pro Ser Ser His Leu His Gln Pro Thr Ile Ile Tyr Glu Pro Gly
                405                 410                 415
Glu

<210> SEQ ID NO 31
<211> LENGTH: 403
<212> TYPE: PRT
<213> ORGANISM: Haliotis tuberculata
```

<400> SEQUENCE: 31

Asp His His Asp Asp His Gln Ser Gly Ser Ile Ala Gly Ser Gly Val
1               5                   10                  15

Arg Lys Asp Val Asn Thr Leu Thr Lys Ala Glu Thr Asp Asn Leu Arg
            20                  25                  30

Glu Ala Leu Trp Gly Val Met Ala Asp His Gly Pro Asn Gly Phe Gln
        35                  40                  45

Ala Ile Ala Ala Phe His Gly Lys Pro Ala Leu Cys Pro Met Pro Asp
    50                  55                  60

Gly His Asn Tyr Ser Cys Cys Thr His Gly Met Ala Thr Phe Pro His
65                  70                  75                  80

Trp His Arg Leu Tyr Thr Lys Gln Met Glu Asp Ala Met Arg Ala His
                85                  90                  95

Gly Ser His Val Gly Leu Pro Tyr Trp Asp Trp Thr Ala Ala Phe Thr
            100                 105                 110

His Leu Pro Thr Leu Val Thr Asp Thr Asp Asn Asn Pro Phe Gln His
        115                 120                 125

Gly His Ile Asp Tyr Leu Asn Val Ser Thr Thr Arg Ser Pro Arg Asp
    130                 135                 140

Met Leu Phe Asn Asp Pro Glu His Gly Ser Glu Ser Phe Phe Tyr Arg
145                 150                 155                 160

Gln Val Leu Leu Ala Leu Glu Gln Thr Asp Phe Cys Lys Phe Glu Val
                165                 170                 175

Gln Phe Glu Ile Thr His Asn Ala Ile His Ser Trp Thr Gly His
            180                 185                 190

Ser Pro Tyr Gly Met Ser Thr Leu Asp Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Glu Tyr Arg Gly Leu Pro Tyr Asn His Ala Asn Cys Glu
225                 230                 235                 240

Ile Gln Ala Met Lys Thr Pro Leu Arg Pro Phe Ser Asp Asp Ile Asn
                245                 250                 255

His Asn Pro Val Thr Lys Ala Asn Ala Lys Pro Leu Asp Val Phe Glu
            260                 265                 270

Tyr Asn Arg Leu Ser Phe Gln Tyr Asp Asn Leu Ile Phe His Gly Tyr
        275                 280                 285

Ser Ile Pro Glu Leu Asp Arg Val Leu Glu Glu Arg Lys Glu Glu Asp
    290                 295                 300

Arg Ile Phe Ala Ala Phe Leu Leu Ser Gly Ile Lys Arg Ser Ala Asp
305                 310                 315                 320

Val Val Phe Asp Ile Cys Gln Pro Glu His Glu Cys Val Phe Ala Gly
                325                 330                 335

Thr Phe Ala Ile Leu Gly Gly Glu Leu Glu Met Pro Trp Ser Phe Asp
            340                 345                 350

Arg Leu Phe Arg Tyr Asp Ile Thr Lys Val Met Lys Gln Leu His Leu
        355                 360                 365

Arg His Asp Ser Asp Phe Thr Phe Arg Val Lys Ile Val Gly Thr Asp
    370                 375                 380

Asp His Glu Leu Pro Ser Asp Ser Val Lys Ala Pro Thr Ile Glu Phe
385                 390                 395                 400

Glu Pro Gly

<210> SEQ ID NO 32
<211> LENGTH: 511
<212> TYPE: PRT
<213> ORGANISM: Haliotis tuberculata

<400> SEQUENCE: 32

| | | | | | | | | | | | | | | |
|---|---|---|---|---|---|---|---|---|---|---|---|---|---|---|
| Val | His | Arg | Gly | Gly | Asn | His | Glu | Asp | Glu | His | His | Asp | Asp | Arg | Leu |
| 1 | | | | 5 | | | | | 10 | | | | | 15 | |
| Ala | Asp | Val | Leu | Ile | Arg | Lys | Glu | Val | Asp | Phe | Leu | Ser | Leu | Gln | Glu |
| | | | 20 | | | | | 25 | | | | | 30 | | |
| Ala | Asn | Ala | Ile | Lys | Asp | Ala | Leu | Tyr | Lys | Leu | Gln | Asn | Asp | Asp | Ser |
| | | 35 | | | | | 40 | | | | | 45 | | | |
| Lys | Gly | Gly | Phe | Glu | Ala | Ile | Ala | Gly | Tyr | His | Gly | Tyr | Pro | Asn | Met |
| | 50 | | | | | 55 | | | | | 60 | | | | |
| Cys | Pro | Glu | Arg | Gly | Thr | Asp | Lys | Tyr | Pro | Cys | Val | His | Gly | Met |
| 65 | | | | 70 | | | | | 75 | | | | | 80 |
| Pro | Val | Phe | Pro | His | Trp | His | Arg | Leu | His | Thr | Ile | Gln | Met | Glu | Arg |
| | | | | 85 | | | | | 90 | | | | | 95 | |
| Ala | Leu | Lys | Asn | His | Gly | Ser | Pro | Met | Gly | Ile | Pro | Tyr | Trp | Asp | Trp |
| | | | 100 | | | | | 105 | | | | | 110 | | |
| Thr | Lys | Lys | Met | Ser | Ser | Leu | Pro | Ser | Phe | Phe | Gly | Asp | Ser | Ser | Asn |
| | | 115 | | | | | 120 | | | | | 125 | | | |
| Asn | Asn | Pro | Phe | Tyr | Lys | Tyr | Tyr | Ile | Arg | Gly | Val | Gln | His | Glu | Thr |
| | 130 | | | | | 135 | | | | | 140 | | | | |
| Thr | Arg | Asp | Val | Asn | Gln | Arg | Leu | Phe | Asn | Gln | Thr | Lys | Phe | Gly | Glu |
| 145 | | | | | 150 | | | | | 155 | | | | | 160 |
| Phe | Asp | Tyr | Leu | Tyr | Tyr | Leu | Thr | Leu | Gln | Val | Leu | Glu | Glu | Asn | Ser |
| | | | | 165 | | | | | 170 | | | | | 175 | |
| Tyr | Cys | Asp | Phe | Glu | Val | Gln | Tyr | Glu | Ile | Leu | His | Asn | Ala | Val | His |
| | | | 180 | | | | | 185 | | | | | 190 | | |
| Ser | Trp | Leu | Gly | Gly | Thr | Gly | Gln | Tyr | Ser | Met | Ser | Thr | Leu | Glu | Tyr |
| | | 195 | | | | | 200 | | | | | 205 | | | |
| Ser | Ala | Phe | Asp | Pro | Val | Phe | Met | Ile | His | His | Ser | Ser | Leu | Asp | Arg |
| | 210 | | | | | 215 | | | | | 220 | | | | |
| Ile | Trp | Ile | Leu | Trp | Gln | Lys | Leu | Gln | Lys | Ile | Arg | Met | Lys | Pro | Tyr |
| 225 | | | | | 230 | | | | | 235 | | | | | 240 |
| Tyr | Ala | Leu | Asp | Cys | Ala | Gly | Asp | Arg | Leu | Met | Lys | Asp | Pro | Leu | His |
| | | | | 245 | | | | | 250 | | | | | 255 | |
| Pro | Phe | Asn | Tyr | Glu | Thr | Val | Asn | Glu | Asp | Glu | Phe | Thr | Arg | Ile | Asn |
| | | | 260 | | | | | 265 | | | | | 270 | | |
| Ser | Phe | Pro | Ser | Ile | Leu | Phe | Asp | His | Tyr | Arg | Phe | Asn | Tyr | Glu | Tyr |
| | | 275 | | | | | 280 | | | | | 285 | | | |
| Asp | Asn | Met | Arg | Ile | Arg | Gly | Gln | Asp | Ile | His | Glu | Leu | Glu | Glu | Val |
| | 290 | | | | | 295 | | | | | 300 | | | | |
| Ile | Gln | Glu | Leu | Arg | Asn | Lys | Asp | Arg | Ile | Phe | Ala | Gly | Phe | Val | Leu |
| 305 | | | | | 310 | | | | | 315 | | | | | 320 |
| Ser | Gly | Leu | Arg | Ile | Ser | Ala | Thr | Val | Lys | Val | Phe | Ile | His | Ser | Lys |
| | | | | 325 | | | | | 330 | | | | | 335 | |
| Asn | Asp | Thr | Ser | His | Glu | Glu | Tyr | Ala | Gly | Glu | Phe | Ala | Val | Leu | Gly |
| | | | 340 | | | | | 345 | | | | | 350 | | |
| Gly | Glu | Lys | Glu | Met | Pro | Trp | Ala | Tyr | Glu | Arg | Met | Leu | Lys | Leu | Asp |
| | | 355 | | | | | 360 | | | | | 365 | | | |
| Ile | Ser | Asp | Ala | Val | His | Lys | Leu | His | Val | Lys | Asp | Glu | Asp | Ile | Arg |

-continued

```
            370                 375                 380
Phe Arg Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
                420                 425                 430

Val Val Lys Ser Gly Thr Lys Val Glu Phe Thr Pro Ile Asp Ser Ser
                435                 440                 445

Val Asn Lys Ala Met Val Glu Leu Gly Ser Tyr Thr Ala Met Ala Lys
450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
                500                 505                 510

<210> SEQ ID NO 33
<211> LENGTH: 334
<212> TYPE: PRT
<213> ORGANISM: Haliotis tuberculata

<400> SEQUENCE: 33

His Arg Leu Phe Val Thr Gln Val Glu Asp Ala Leu Ile Arg Arg Gly
1               5                   10                  15

Ser Pro Ile Gly Val Pro Tyr Trp Asp Trp Thr Gln Pro Met Ala His
                20                  25                  30

Leu Pro Gly Leu Ala Asp Asn Ala Thr Tyr Arg Asp Pro Ile Ser Gly
            35                  40                  45

Asp Ser Arg His Asn Pro Phe His Asp Val Glu Val Ala Phe Glu Asn
50                  55                  60

Gly Arg Thr Glu Arg His Pro Asp Ser Arg Leu Phe Glu Gln Pro Leu
65                  70                  75                  80

Phe Gly Lys His Thr Arg Leu Phe Asp Ser Ile Val Tyr Ala Phe Glu
                85                  90                  95

Gln Glu Asp Phe Cys Asp Phe Glu Val Gln Phe Glu Met Thr His Asn
            100                 105                 110

Asn Ile His Ala Trp Ile Gly Gly Gly Glu Lys Tyr Ser Met Ser Ser
        115                 120                 125

Leu His Tyr Thr Ala Phe Asp Pro Ile Phe Tyr Leu Arg His Ser Asn
    130                 135                 140

Thr Asp Arg Leu Trp Ala Ile Trp Gln Ala Leu Gln Ile Arg Arg Asn
145                 150                 155                 160

Arg Pro Tyr Lys Ala His Cys Ala Trp Ser Glu Glu Arg Gln Pro Leu
                165                 170                 175

Lys Pro Phe Ala Phe Ser Ser Pro Leu Asn Asn Asn Glu Lys Thr Tyr
            180                 185                 190

Glu Asn Ser Val Pro Thr Asn Val Tyr Asp Tyr Glu Gly Val Leu Gly
        195                 200                 205

Tyr Thr Tyr Asp Asp Leu Asn Phe Gly Gly Met Asp Leu Gly Gln Leu
    210                 215                 220

Glu Glu Tyr Ile Gln Arg Gln Arg Gln Arg Asp Arg Thr Phe Ala Gly
225                 230                 235                 240
```

```
Phe Phe Leu Ser His Ile Gly Thr Ser Ala Asn Val Glu Ile Ile Ile
                245                 250                 255

Asp His Gly Thr Leu His Thr Ser Val Gly Thr Phe Ala Val Leu Gly
                260                 265                 270

Gly Glu Lys Glu Met Lys Trp Gly Phe Asp Arg Leu Tyr Lys Tyr Glu
            275                 280                 285

Ile Thr Asp Glu Leu Arg Gln Leu Asn Leu Arg Ala Asp Asp Val Phe
        290                 295                 300

Ser Ile Ser Val Lys Val Thr Asp Val Asp Gly Ser Glu Leu Ser Ser
305                 310                 315                 320

Glu Leu Ile Pro Ser Ala Ala Ile Ile Phe Glu Arg Ser His
                325                 330
```

<210> SEQ ID NO 34
<211> LENGTH: 417
<212> TYPE: PRT
<213> ORGANISM: Haliotis tuberculata

<400> SEQUENCE: 34

```
Ile Asp His Gln Asp Pro His His Asp Thr Ile Ile Arg Lys Asn Val
1               5                   10                  15

Asp Asn Leu Thr Pro Glu Glu Ile Asn Ser Leu Arg Arg Ala Met Ala
                20                  25                  30

Asp Leu Gln Ser Asp Lys Thr Ala Gly Gly Phe Gln Gln Ile Ala Ala
            35                  40                  45

Phe His Gly Glu Pro Lys Trp Cys Pro Ser Pro Asp Ala Glu Lys Lys
        50                  55                  60

Phe Ser Cys Cys Val His Gly Met Ala Val Phe Pro His Trp His Arg
65                  70                  75                  80

Leu Leu Thr Val Gln Gly Glu Asn Ala Leu Arg Lys His Gly Cys Leu
                85                  90                  95

Gly Ala Leu Pro Tyr Trp Asp Trp Thr Arg Pro Leu Ser His Leu Pro
                100                 105                 110

Asp Leu Val Leu Val Ser Ser Arg Thr Thr Pro Met Pro Tyr Ser Thr
            115                 120                 125

Val Glu Ala Arg Asn Pro Trp Tyr Ser Gly His Ile Asp Thr Val Gly
        130                 135                 140

Val Asp Thr Thr Arg Ser Val Arg Gln Glu Leu Tyr Glu Ala Pro Gly
145                 150                 155                 160

Phe Gly His Tyr Thr Gly Val Ala Lys Gln Val Leu Leu Ala Leu Glu
                165                 170                 175

Gln Asp Asp Phe Cys Asp Phe Glu Val Gln Phe Glu Ile Ala His Asn
                180                 185                 190

Phe Ile His Ala Leu Val Gly Gly Ser Glu Pro Tyr Gly Met Ala Ser
            195                 200                 205

Leu Arg Tyr Thr Thr Tyr Asp Pro Ile Phe Tyr Leu His His Ser Asn
        210                 215                 220

Thr Asp Arg Leu Trp Ala Ile Trp Gln Ala Leu Gln Lys Tyr Arg Gly
225                 230                 235                 240

Lys Pro Tyr Asn Ser Ala Asn Cys Ala Ile Ala Ser Met Arg Lys Pro
                245                 250                 255

Leu Gln Pro Phe Gly Leu Thr Asp Glu Ile Asn Pro Asp Asp Glu Thr
                260                 265                 270

Arg Gln His Ala Val Pro Phe Ser Val Phe Asp Tyr Lys Asn Asn Phe
            275                 280                 285
```

-continued

```
Asn Tyr Glu Tyr Asp Thr Leu Asp Phe Asn Gly Leu Ser Ile Ser Gln
    290                 295                 300

Leu Asp Arg Glu Leu Ser Arg Arg Lys Ser His Asp Arg Val Phe Ala
305                 310                 315                 320

Gly Phe Leu Leu His Gly Ile Gln Gln Ser Ala Leu Val Lys Phe Phe
                325                 330                 335

Val Cys Lys Ser Asp Asp Cys Asp His Tyr Ala Gly Glu Phe Tyr
            340                 345                 350

Ile Leu Gly Asp Glu Ala Glu Met Pro Trp Gly Tyr Asp Arg Leu Tyr
                355                 360                 365

Lys Tyr Glu Ile Thr Glu Gln Leu Asn Ala Leu Asp Leu His Ile Gly
    370                 375                 380

Asp Arg Phe Phe Ile Arg Tyr Glu Ala Phe Asp Leu His Gly Thr Ser
385                 390                 395                 400

Leu Gly Ser Asn Ile Phe Pro Lys Pro Ser Val Ile His Asp Glu Gly
                405                 410                 415

Ala
```

<210> SEQ ID NO 35
<211> LENGTH: 415
<212> TYPE: PRT
<213> ORGANISM: Haliotis tuberculata

<400> SEQUENCE: 35

```
Gly His His Gln Ala Asp Glu Tyr Asp Glu Val Val Thr Ala Ala Ser
1               5                   10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240
```

```
Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
        355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser Ser
                405                 410                 415

<210> SEQ ID NO 36
<211> LENGTH: 418
<212> TYPE: PRT
<213> ORGANISM: Haliotis tuberculata

<400> SEQUENCE: 36

Ser Phe Leu Arg Pro Asp Gly His Ser Asp Asp Ile Leu Val Arg Lys
1               5                   10                  15

Glu Val Asn Ser Leu Thr Thr Arg Glu Thr Ala Ser Leu Ile His Ala
            20                  25                  30

Leu Lys Ser Met Gln Glu Asp His Ser Pro Asp Gly Phe Gln Ala Ile
        35                  40                  45

Ala Ser Phe His Ala Leu Pro Pro Leu Cys Pro Ser Pro Ser Ala Ala
    50                  55                  60

His Arg Tyr Ala Cys Cys Val His Gly Met Ala Thr Phe Pro Gln Trp
65                  70                  75                  80

His Arg Leu Tyr Thr Val Gln Phe Gln Asp Ala Leu Arg Arg His Gly
                85                  90                  95

Ala Thr Val Gly Val Pro Tyr Trp Asp Trp Leu Arg Pro Gln Ser His
            100                 105                 110

Leu Pro Glu Leu Val Thr Met Glu Thr Tyr His Asp Ile Trp Ser Asn
        115                 120                 125

Arg Asp Phe Pro Asn Pro Phe Tyr Gln Ala Asn Ile Glu Phe Glu Gly
    130                 135                 140

Glu Asn Ile Thr Thr Glu Arg Glu Val Ile Ala Asp Lys Leu Phe Val
145                 150                 155                 160

Lys Gly Gly His Val Phe Asp Lys Leu Val Leu Gln Thr Ser His Pro
                165                 170                 175

Ser Ala Glu Gln Glu Asn Tyr Cys Asp Phe Glu Ile Gln Phe Glu Ile
            180                 185                 190

Leu His Asn Gly Val His Thr Trp Val Gly Gly Ser Arg Thr Tyr Ser
```

```
                195                 200                 205
Ile Gly His Leu His Tyr Ala Phe Tyr Asp Pro Leu Phe Tyr Leu His
            210                 215                 220
His Phe Gln Thr Asp Arg Ile Trp Ala Ile Trp Gln Glu Leu Gln Glu
225                 230                 235                 240
Gln Arg Gly Leu Ser Gly Asp Glu Ala His Cys Ala Leu Glu Gln Met
                245                 250                 255
Arg Glu Pro Leu Lys Pro Phe Ser Phe Gly Ala Pro Tyr Asn Trp Asn
                260                 265                 270
Gln Leu Thr Gln Asp Phe Ser Arg Pro Glu Asp Thr Phe Asp Tyr Arg
                275                 280                 285
Lys Phe Gly Tyr Glu Tyr Asp Asn Leu Glu Phe Leu Gly Met Ser Val
            290                 295                 300
Ala Glu Leu Asp Gln Tyr Ile Ile Glu His Gln Glu Asn Asp Arg Val
305                 310                 315                 320
Phe Ala Gly Phe Leu Leu Ser Gly Phe Gly Gly Ser Ala Ser Val Asn
                325                 330                 335
Phe Gln Val Cys Arg Ala Asp Ser Thr Cys Gln Asp Ala Gly Tyr Phe
                340                 345                 350
Thr Val Leu Gly Gly Ser Ala Glu Met Ala Trp Ala Phe Asp Arg Leu
            355                 360                 365
Tyr Lys Tyr Asp Ile Thr Glu Thr Leu Glu Lys Met His Leu Arg Tyr
            370                 375                 380
Asp Asp Asp Phe Thr Ile Ser Val Ser Leu Thr Ala Asn Asn Gly Thr
385                 390                 395                 400
Val Leu Ser Ser Ser Leu Ile Pro Thr Pro Ser Val Ile Phe Gln Arg
                405                 410                 415
Gly His

<210> SEQ ID NO 37
<211> LENGTH: 416
<212> TYPE: PRT
<213> ORGANISM: Haliotis tuberculata

<400> SEQUENCE: 37

Arg Asp Ile Asn Thr Arg Ser Met Ser Pro Asn Arg Val Arg Arg Glu
1               5                   10                  15
Leu Ser Asp Leu Ser Ala Arg Asp Leu Ser Ser Leu Lys Ser Ala Leu
            20                  25                  30
Arg Asp Leu Gln Glu Asp Asp Gly Pro Asn Gly Tyr Gln Ala Leu Ala
            35                  40                  45
Ala Phe His Gly Leu Pro Ala Gly Cys His Asp Ser Arg Gly Asn Glu
        50                  55                  60
Ile Ala Cys Cys Ile His Gly Met Pro Thr Phe Pro Gln Trp His Arg
65                  70                  75                  80
Leu Tyr Thr Leu Gln Leu Glu Met Ala Leu Arg Arg His Gly Ser Ser
                85                  90                  95
Val Ala Ile Pro Tyr Trp Asp Trp Thr Lys Pro Ile Ser Glu Leu Pro
            100                 105                 110
Ser Leu Phe Thr Ser Pro Glu Tyr Tyr Asp Pro Trp His Asp Ala Val
            115                 120                 125
Val Asn Asn Pro Phe Ser Lys Gly Phe Val Lys Phe Ala Asn Thr Tyr
        130                 135                 140
Thr Val Arg Asp Pro Gln Glu Met Leu Phe Gln Leu Cys Glu His Gly
```

```
                145                 150                 155                 160
Glu Ser Ile Leu Tyr Glu Gln Thr Leu Ala Leu Glu Gln Thr Asp
                    165                 170                 175
Tyr Cys Asp Phe Glu Val Gln Phe Glu Val Leu His Asn Val Ile His
                180                 185                 190
Tyr Leu Val Gly Gly Arg Gln Thr Tyr Ala Leu Ser Ser Leu His Tyr
                195                 200                 205
Ala Ser Tyr Asp Pro Phe Phe Phe Ile His His Ser Phe Val Asp Lys
            210                 215                 220
Met Trp Val Val Trp Gln Ala Leu Gln Lys Arg Arg Lys Leu Pro Tyr
225                 230                 235                 240
Lys Arg Ala Asp Cys Ala Val Asn Leu Met Thr Lys Pro Met Arg Pro
                245                 250                 255
Phe Asp Ser Asp Met Asn Gln Asn Pro Phe Thr Lys Met His Ala Val
                260                 265                 270
Pro Asn Thr Leu Tyr Asp Tyr Glu Thr Leu Tyr Tyr Ser Tyr Asp Asn
            275                 280                 285
Leu Glu Ile Gly Gly Arg Asn Leu Asp Gln Leu Gln Ala Glu Ile Asp
    290                 295                 300
Arg Ser Arg Ser His Asp Arg Val Phe Ala Gly Phe Leu Leu Arg Gly
305                 310                 315                 320
Ile Gly Thr Ser Ala Asp Val Arg Phe Trp Ile Cys Arg Asn Glu Asn
                325                 330                 335
Asp Cys His Arg Gly Gly Ile Ile Phe Ile Leu Gly Gly Ala Lys Glu
                340                 345                 350
Met Pro Trp Ser Phe Asp Arg Asn Phe Lys Phe Asp Ile Thr His Val
                355                 360                 365
Leu Glu Asn Ala Gly Ile Ser Pro Glu Asp Val Phe Asp Ala Glu Glu
            370                 375                 380
Pro Phe Tyr Ile Lys Val Glu Ile His Ala Val Asn Lys Thr Met Ile
385                 390                 395                 400
Pro Ser Ser Val Ile Pro Ala Pro Thr Ile Ile Tyr Ser Pro Gly Glu
                405                 410                 415

<210> SEQ ID NO 38
<211> LENGTH: 402
<212> TYPE: PRT
<213> ORGANISM: Haliotis tuberculata

<400> SEQUENCE: 38

Gly Arg Ala Ala Asp Ser Ala His Ser Ala Asn Ile Ala Gly Ser Gly
1               5                   10                  15
Val Arg Lys Asp Val Thr Thr Leu Thr Val Ser Glu Thr Glu Asn Leu
                20                  25                  30
Arg Gln Ala Leu Gln Gly Val Ile Asp Asp Thr Gly Pro Asn Gly Tyr
            35                  40                  45
Gln Ala Ile Ala Ser Phe His Gly Ser Pro Pro Met Cys Glu Met Asn
        50                  55                  60
Gly Arg Lys Val Ala Cys Cys Ala His Gly Met Ala Ser Phe Pro His
65                  70                  75                  80
Trp His Arg Leu Tyr Val Lys Gln Met Glu Asp Ala Leu Ala Asp His
                85                  90                  95
Gly Ser His Ile Gly Ile Pro Tyr Trp Asp Trp Thr Thr Ala Phe Thr
            100                 105                 110
```

```
Glu Leu Pro Ala Leu Val Thr Asp Ser Glu Asn Asn Pro Phe His Glu
            115                 120                 125

Gly Arg Ile Asp His Leu Gly Val Thr Thr Ser Arg Ser Pro Arg Asp
        130                 135                 140

Met Leu Phe Asn Asp Pro Glu Gln Gly Ser Glu Ser Phe Phe Tyr Arg
145                 150                 155                 160

Gln Val Leu Leu Ala Leu Glu Gln Thr Asp Tyr Cys Gln Phe Glu Val
                165                 170                 175

Gln Phe Glu Leu Thr His Asn Ala Ile His Ser Trp Thr Gly Gly Arg
            180                 185                 190

Ser Pro Tyr Gly Met Ser Thr Leu Glu Phe Thr Ala Tyr Asp Pro Leu
        195                 200                 205

Phe Trp Leu His His Ser Asn Thr Asp Arg Ile Trp Ala Val Trp Gln
210                 215                 220

Ala Leu Gln Lys Tyr Arg Gly Leu Pro Tyr Asn Glu Ala His Cys Glu
225                 230                 235                 240

Ile Gln Val Leu Lys Gln Pro Leu Arg Pro Phe Asn Asp Asp Ile Asn
                245                 250                 255

His Asn Pro Ile Thr Lys Thr Asn Ala Arg Pro Ile Asp Ser Phe Asp
            260                 265                 270

Tyr Glu Arg Phe Asn Tyr Gln Tyr Asp Thr Leu Ser Phe His Gly Lys
        275                 280                 285

Ser Ile Pro Glu Leu Asn Asp Leu Leu Glu Glu Arg Lys Arg Glu Glu
290                 295                 300

Arg Thr Phe Ala Ala Phe Leu Leu Arg Gly Ile Gly Cys Ser Ala Asp
305                 310                 315                 320

Val Val Phe Asp Ile Cys Arg Pro Asn Gly Asp Cys Val Phe Ala Gly
                325                 330                 335

Thr Phe Ala Val Leu Gly Gly Glu Leu Glu Met Pro Trp Ser Phe Asp
            340                 345                 350

Arg Leu Phe Arg Tyr Asp Ile Thr Arg Val Met Asn Gln Leu His Leu
        355                 360                 365

Gln Tyr Asp Ser Asp Phe Ser Phe Arg Val Lys Leu Val Ala Thr Asn
370                 375                 380

Gly Thr Glu Leu Ser Ser Asp Leu Leu Lys Ser Pro Thr Ile Glu His
385                 390                 395                 400

Glu Leu

<210> SEQ ID NO 39
<211> LENGTH: 517
<212> TYPE: PRT
<213> ORGANISM: Haliotis tuberculata
<220> FEATURE:
<221> NAME/KEY: misc_feature
<222> LOCATION: (425)..(425)
<223> OTHER INFORMATION: Xaa can be any naturally occurring amino acid

<400> SEQUENCE: 39

Gly Ala His Arg Gly Pro Val Glu Glu Thr Glu Val Thr Arg Gln His
1               5                   10                  15

Thr Asp Gly Asn Ala His Phe His Arg Lys Glu Val Asp Ser Leu Ser
            20                  25                  30

Leu Asp Glu Ala Asn Asn Leu Lys Asn Ala Leu Tyr Lys Leu Gln Asn
        35                  40                  45

Asp His Ser Leu Thr Gly Tyr Glu Ala Ile Ser Gly Tyr His Gly Tyr
    50                  55                  60
```

-continued

```
Pro Asn Leu Cys Pro Glu Glu Gly Asp Asp Lys Ile Pro Leu Leu Arg
 65                  70                  75                  80

Pro Arg Met Gly Ile Phe Pro Tyr Trp His Arg Leu Leu Thr Ile Gln
                 85                  90                  95

Leu Glu Arg Ala Leu Glu His Asn Gly Ala Leu Leu Gly Val Pro Tyr
            100                 105                 110

Trp Asp Trp Asn Lys Asp Leu Ser Ser Leu Pro Ala Phe Phe Ser Asp
        115                 120                 125

Ser Ser Asn Asn Asn Pro Tyr Phe Lys Tyr His Ile Ala Gly Val Gly
    130                 135                 140

His Asp Thr Val Arg Glu Pro Thr Ser Leu Ile Tyr Asn Gln Pro Gln
145                 150                 155                 160

Ile His Gly Tyr Asp Tyr Leu Tyr Tyr Leu Ala Leu Thr Thr Leu Glu
                165                 170                 175

Glu Asn Asn Tyr Trp Asp Phe Glu Val Gln Tyr Glu Ile Leu His Asn
            180                 185                 190

Ala Val His Ser Trp Leu Gly Gly Ser Gln Lys Tyr Ser Met Ser Thr
        195                 200                 205

Leu Glu Tyr Ser Ala Phe Asp Pro Val Phe Met Ile Leu His Ser Gly
    210                 215                 220

Leu Asp Arg Leu Trp Ile Ile Trp Gln Glu Leu Gln Lys Ile Arg Arg
225                 230                 235                 240

Lys Pro Tyr Asn Phe Ala Lys Cys Ala Tyr His Met Met Glu Glu Pro
                245                 250                 255

Leu Ala Pro Phe Ser Tyr Pro Ser Ile Asn Gln Asp Glu Phe Thr Arg
            260                 265                 270

Ala Asn Ser Lys Pro Ser Thr Val Phe Asp Ser His Lys Phe Gly Tyr
        275                 280                 285

His Tyr Asp Asn Leu Asn Val Arg Gly His Ser Ile Gln Glu Leu Asn
    290                 295                 300

Thr Ile Ile Asn Asp Leu Arg Asn Thr Asp Arg Ile Tyr Ala Gly Phe
305                 310                 315                 320

Val Leu Ser Gly Ile Gly Thr Ser Ala Ser Val Lys Ile Tyr Leu Arg
                325                 330                 335

Thr Asp Asp Asn Asp Glu Glu Val Gly Thr Phe Thr Val Leu Gly Gly
            340                 345                 350

Glu Arg Glu Met Pro Trp Ala Tyr Glu Arg Val Phe Lys Tyr Asp Ile
        355                 360                 365

Thr Glu Val Ala Asp Arg Leu Lys Ile Lys Leu Trp Gly His Pro Leu
    370                 375                 380

Thr Ser Gly Thr Gly Asp His Ile Leu Thr Asn Gly Ile Gly Gly Lys
385                 390                 395                 400

Gln Glu Pro Thr Gln Ile Leu Ser Ser Thr Asp Leu Pro Ile Met
                405                 410                 415

Thr Thr Met Phe Leu Leu Ser Gln Xaa Ala Ala Gly Arg Asn Leu His
            420                 425                 430

Ile Pro Pro Lys Val Val Lys Lys Gly Thr Arg Ile Glu Phe His
        435                 440                 445

Pro Val Asp Asp Ser Val Thr Arg Pro Val Asp Leu Gly Ser Tyr
    450                 455                 460

Thr Ala Leu Phe Asn Cys Val Val Pro Pro Phe Thr Tyr His Gly Phe
465                 470                 475                 480
```

Glu Leu Asn His Val Tyr Ser Val Lys Pro Gly Asp Tyr Tyr Val Thr
            485                 490                 495

Gly Pro Thr Arg Asp Leu Cys Gln Asn Ala Asp Val Arg Ile His Ile
            500                 505                 510

His Val Glu Asp Glu
        515

<210> SEQ ID NO 40
<211> LENGTH: 322
<212> TYPE: PRT
<213> ORGANISM: Megathura crenulata

<400> SEQUENCE: 40

Gly Leu Pro Tyr Trp Asp Trp Thr Glu Pro Met Thr His Ile Pro Gly
1               5                   10                  15

Leu Ala Gly Asn Lys Thr Tyr Val Asp Ser His Gly Ala Ser His Thr
            20                  25                  30

Asn Pro Phe His Ser Ser Val Ile Ala Phe Glu Glu Asn Ala Pro His
            35                  40                  45

Thr Lys Arg Gln Ile Asp Gln Arg Leu Phe Lys Pro Ala Thr Phe Gly
    50                  55                  60

His His Thr Asp Leu Phe Asn Gln Ile Leu Tyr Ala Phe Glu Gln Glu
65                  70                  75                  80

Asp Tyr Cys Asp Phe Glu Val Gln Phe Glu Ile Thr His Asn Thr Ile
                85                  90                  95

His Ala Trp Thr Gly Gly Ser Glu His Phe Ser Met Ser Ser Leu His
            100                 105                 110

Tyr Thr Ala Phe Asp Pro Leu Phe Tyr Phe His Ser Asn Val Asp
            115                 120                 125

Arg Leu Trp Ala Val Trp Gln Ala Leu Gln Met Arg Arg His Lys Pro
    130                 135                 140

Tyr Arg Ala His Cys Ala Ile Ser Leu Glu His Met His Leu Lys Pro
145                 150                 155                 160

Phe Ala Phe Ser Ser Pro Leu Asn Asn Asn Glu Lys Thr His Ala Asn
                165                 170                 175

Ala Met Pro Asn Lys Ile Tyr Asp Tyr Glu Asn Val Leu His Tyr Thr
            180                 185                 190

Tyr Glu Asp Leu Thr Phe Gly Gly Ile Ser Leu Glu Asn Ile Glu Lys
            195                 200                 205

Met Ile His Glu Asn Gln Gln Glu Asp Arg Ile Tyr Ala Gly Phe Leu
    210                 215                 220

Leu Ala Gly Ile Arg Thr Ser Ala Asn Val Asp Ile Phe Ile Lys Thr
225                 230                 235                 240

Thr Asp Ser Val Gln His Lys Ala Gly Thr Phe Ala Val Leu Gly Gly
                245                 250                 255

Ser Lys Glu Met Lys Trp Gly Phe Asp Arg Val Phe Lys Phe Asp Ile
            260                 265                 270

Thr His Val Leu Lys Asp Leu Asp Leu Thr Ala Asp Gly Asp Phe Glu
            275                 280                 285

Val Thr Val Asp Ile Thr Glu Val Asp Gly Thr Lys Leu Ala Ser Ser
    290                 295                 300

Leu Ile Pro His Ala Ser Val Ile Arg Glu His Ala Arg Gly Lys Leu
305                 310                 315                 320

Asn Arg

<210> SEQ ID NO 41
<211> LENGTH: 414
<212> TYPE: PRT
<213> ORGANISM: Megathrua crenulata

<400> SEQUENCE: 41

| Val | Lys | Phe | Asp | Lys | Val | Pro | Arg | Ser | Arg | Leu | Ile | Arg | Lys | Asn | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asp Arg Leu Ser Pro Glu Glu Met Asn Glu Leu Arg Lys Ala Leu Ala
            20                  25                  30

Leu Leu Lys Glu Asp Lys Ser Ala Gly Gly Phe Gln Gln Leu Gly Ala
        35                  40                  45

Phe His Gly Glu Pro Lys Trp Cys Pro Ser Pro Glu Ala Ser Lys Lys
50                      55                  60

Phe Ala Cys Cys Val His Gly Met Ser Val Phe Pro His Trp His Arg
65                  70                  75                  80

Leu Leu Thr Val Gln Ser Glu Asn Ala Leu Arg Arg His Gly Tyr Asp
                85                  90                  95

Gly Ala Leu Pro Tyr Trp Asp Trp Thr Ser Pro Leu Asn His Leu Pro
            100                 105                 110

Glu Leu Ala Asp His Glu Lys Tyr Val Asp Pro Glu Asp Gly Val Glu
        115                 120                 125

Lys His Asn Pro Trp Phe Asp Gly His Ile Asp Thr Val Asp Lys Thr
130                 135                 140

Thr Thr Arg Ser Val Gln Asn Lys Leu Phe Glu Gln Pro Glu Phe Gly
145                 150                 155                 160

His Tyr Thr Ser Ile Ala Lys Gln Val Leu Leu Ala Leu Glu Gln Asp
                165                 170                 175

Asn Phe Cys Asp Phe Glu Ile Gln Tyr Glu Ile Ala His Asn Tyr Ile
            180                 185                 190

His Ala Leu Val Gly Gly Ala Gln Pro Tyr Gly Met Ala Ser Leu Arg
        195                 200                 205

Tyr Thr Ala Phe Asp Pro Leu Phe Tyr Leu His Ser Asn Thr Asp
210                 215                 220

Arg Ile Trp Ala Ile Trp Gln Ala Leu Gln Lys Tyr Arg Gly Lys Pro
225                 230                 235                 240

Tyr Asn Val Ala Asn Cys Ala Val Thr Ser Met Arg Glu Pro Leu Gln
                245                 250                 255

Pro Phe Gly Leu Ser Ala Asn Ile Asn Thr Asp His Val Thr Lys Glu
            260                 265                 270

His Ser Val Pro Phe Asn Val Phe Asp Tyr Lys Thr Asn Phe Asn Tyr
        275                 280                 285

Glu Tyr Asp Thr Leu Glu Phe Asn Gly Leu Ser Ile Ser Gln Leu Asn
290                 295                 300

Lys Lys Leu Glu Ala Ile Lys Ser Gln Asp Arg Phe Phe Ala Gly Phe
305                 310                 315                 320

Leu Leu Ser Gly Phe Lys Lys Ser Ser Leu Val Lys Phe Asn Ile Cys
                325                 330                 335

Thr Asp Ser Ser Asn Cys His Pro Ala Gly Glu Phe Tyr Leu Leu Gly
            340                 345                 350

Asp Glu Asn Glu Met Pro Trp Ala Tyr Asp Arg Val Phe Lys Tyr Asp
        355                 360                 365

Ile Thr Glu Lys Leu His Asp Leu Lys Leu His Ala Glu Asp His Phe
370                 375                 380

```
Tyr Ile Asp Tyr Glu Val Phe Asp Leu Lys Pro Ala Ser Leu Gly Lys
385                 390                 395                 400

Asp Leu Phe Lys Gln Pro Ser Val Ile His Glu Pro Arg Ile
                405                 410
```

<210> SEQ ID NO 42
<211> LENGTH: 411
<212> TYPE: PRT
<213> ORGANISM: Megathrua crenulata

<400> SEQUENCE: 42

```
Gly His His Glu Gly Glu Val Tyr Gln Ala Glu Val Thr Ser Ala Asn
1               5                   10                  15

Arg Ile Arg Lys Asn Ile Glu Asn Leu Ser Leu Gly Glu Leu Glu Ser
            20                  25                  30

Leu Arg Ala Ala Phe Leu Glu Ile Glu Asn Asp Gly Thr Tyr Glu Ser
                35                  40                  45

Ile Ala Lys Phe His Gly Ser Pro Gly Leu Cys Gln Leu Asn Gly Asn
50                  55                  60

Pro Ile Ser Cys Cys Val His Gly Met Pro Thr Phe Pro His Trp His
65                  70                  75                  80

Arg Leu Tyr Val Val Val Glu Asn Ala Leu Leu Lys Lys Gly Ser
            85                  90                  95

Ser Val Ala Val Pro Tyr Trp Asp Trp Thr Lys Arg Ile Glu His Leu
                100                 105                 110

Pro His Leu Ile Ser Asp Ala Thr Tyr Tyr Asn Ser Arg Gln His His
            115                 120                 125

Tyr Glu Thr Asn Pro Phe His His Gly Lys Ile Thr His Glu Asn Glu
130                 135                 140

Ile Thr Thr Arg Asp Pro Lys Asp Ser Leu Phe His Ser Asp Tyr Phe
145                 150                 155                 160

Tyr Glu Gln Val Leu Tyr Ala Leu Glu Gln Asp Asn Phe Cys Asp Phe
                165                 170                 175

Glu Ile Gln Leu Glu Ile Leu His Asn Ala Leu His Ser Leu Leu Gly
            180                 185                 190

Gly Lys Gly Lys Tyr Ser Met Ser Asn Leu Asp Tyr Ala Ala Phe Asp
        195                 200                 205

Pro Val Phe Phe Leu His His Ala Thr Thr Asp Arg Ile Trp Ala Ile
210                 215                 220

Trp Gln Asp Leu Gln Arg Phe Arg Lys Arg Pro Tyr Arg Glu Ala Asn
225                 230                 235                 240

Cys Ala Ile Gln Leu Met His Thr Pro Leu Gln Pro Phe Asp Lys Ser
                245                 250                 255

Asp Asn Asn Asp Glu Ala Thr Lys Thr His Ala Thr Pro His Asp Gly
            260                 265                 270

Phe Glu Tyr Gln Asn Ser Phe Gly Tyr Ala Tyr Asp Asn Leu Glu Leu
        275                 280                 285

Asn His Tyr Ser Ile Pro Gln Leu Asp His Met Leu Gln Glu Arg Lys
    290                 295                 300

Arg His Asp Arg Val Phe Ala Gly Phe Leu Leu His Asn Ile Gly Thr
305                 310                 315                 320

Ser Ala Asp Gly His Val Phe Val Cys Leu Pro Thr Gly Glu His Thr
                325                 330                 335

Lys Asp Cys Ser His Glu Ala Gly Met Phe Ser Ile Leu Gly Gly Gln
```

```
                   340                 345                 350
Thr Glu Met Ser Phe Val Phe Asp Arg Leu Tyr Lys Leu Asp Ile Thr
                355                 360                 365
Lys Ala Leu Lys Lys Asn Gly Val His Leu Gln Gly Asp Phe Asp Leu
            370                 375                 380
Glu Ile Glu Ile Thr Ala Val Asn Gly Ser His Leu Asp Ser His Val
385                 390                 395                 400
Ile His Ser Pro Thr Ile Leu Phe Glu Ala Gly
                405                 410

<210> SEQ ID NO 43
<211> LENGTH: 111
<212> TYPE: PRT
<213> ORGANISM: Megathrua crenulata

<400> SEQUENCE: 43

Asp Ser Ala His Thr Asp Gly His Thr Glu Pro Val Met Ile Arg
1               5                   10                  15
Lys Asp Ile Thr Gln Leu Asp Lys Arg Gln Gln Leu Ser Leu Val Lys
            20                  25                  30
Ala Leu Glu Ser Met Lys Ala Asp His Ser Ser Asp Gly Phe Gln Ala
        35                  40                  45
Ile Ala Ser Phe His Ala Leu Pro Pro Leu Cys Pro Ser Pro Ala Ala
    50                  55                  60
Ser Lys Arg Phe Ala Cys Cys Val His Gly Met Pro Thr Phe Pro Gln
65                  70                  75                  80
Trp His Arg Leu Tyr Thr Val Gln Phe Gln Asp Ser Leu Arg Lys His
                85                  90                  95
Gly Ala Val Val Gly Leu Pro Tyr Trp Asp Trp Thr Leu Pro Arg
            100                 105                 110

<210> SEQ ID NO 44
<211> LENGTH: 317
<212> TYPE: PRT
<213> ORGANISM: Megathura crenulata

<400> SEQUENCE: 44

Gly Leu Pro Tyr Trp Asp Trp Thr Met Pro Met Ser His Leu Pro Glu
1               5                   10                  15
Leu Ala Thr Ser Glu Thr Tyr Leu Asp Pro Val Thr Gly Glu Thr Lys
            20                  25                  30
Asn Asn Pro Phe His His Ala Gln Val Ala Phe Glu Asn Gly Val Thr
        35                  40                  45
Ser Arg Asn Pro Asp Ala Lys Leu Phe Met Lys Pro Thr Tyr Gly Asp
    50                  55                  60
His Thr Tyr Leu Phe Asp Ser Met Ile Tyr Ala Phe Glu Gln Glu Asp
65                  70                  75                  80
Phe Cys Asp Phe Glu Val Gln Tyr Glu Leu Thr His Asn Ala Ile His
                85                  90                  95
Ala Trp Val Gly Gly Ser Glu Lys Tyr Ser Met Ser Ser Leu His Tyr
            100                 105                 110
Thr Ala Phe Asp Pro Ile Phe Tyr Leu His His Ser Asn Val Asp Arg
        115                 120                 125
Leu Trp Ala Ile Trp Gln Ala Leu Gln Ile Arg Arg Gly Lys Ser Tyr
    130                 135                 140
Lys Ala His Cys Ala Ser Ser Gln Glu Arg Glu Pro Leu Lys Pro Phe
```

```
            145                 150                 155                 160
Ala Phe Ser Ser Pro Leu Asn Asn Glu Lys Thr Tyr His Asn Ser
                165                 170                 175
Val Pro Thr Asn Val Tyr Asp Tyr Val Gly Val Leu His Tyr Arg Tyr
                180                 185                 190
Asp Asp Leu Gln Phe Gly Gly Met Thr Met Ser Glu Leu Glu Glu Tyr
                195                 200                 205
Ile His Lys Gln Thr Gln His Asp Arg Thr Phe Ala Gly Phe Phe Leu
                210                 215                 220
Ser Tyr Ile Gly Thr Ser Ala Ser Val Asp Ile Phe Ile Asn Arg Glu
225                 230                 235                 240
Gly His Asp Lys Tyr Lys Val Gly Ser Phe Val Leu Gly Gly Ser
                245                 250                 255
Lys Glu Met Lys Trp Gly Phe Asp Arg Met Tyr Lys Tyr Glu Ile Thr
                260                 265                 270
Glu Ala Leu Lys Thr Leu Asn Val Ala Val Asp Asp Gly Phe Ser Ile
                275                 280                 285
Thr Val Glu Ile Thr Asp Val Asp Gly Ser Pro Pro Ser Ala Asp Leu
                290                 295                 300
Ile Pro Pro Pro Ala Ile Ile Phe Glu Arg Gly His Ala
305                 310                 315

<210> SEQ ID NO 45
<211> LENGTH: 411
<212> TYPE: PRT
<213> ORGANISM: Megathura crenulata

<400> SEQUENCE: 45

Asp Ala Lys Asp Phe Gly His Ser Arg Lys Ile Arg Lys Ala Val Asp
1               5                   10                  15
Ser Leu Thr Val Glu Glu Gln Thr Ser Leu Arg Arg Ala Met Ala Asp
                20                  25                  30
Leu Gln Asp Asp Lys Thr Ser Gly Gly Phe Gln Gln Ile Ala Ala Phe
                35                  40                  45
His Gly Glu Pro Lys Trp Cys Pro Ser Pro Glu Ala Glu Lys Lys Phe
50                  55                  60
Ala Cys Cys Val His Gly Met Ala Val Phe Pro His Trp His Arg Leu
65                  70                  75                  80
Leu Thr Val Gln Gly Glu Asn Ala Leu Arg Lys His Gly Phe Thr Gly
                85                  90                  95
Gly Leu Pro Tyr Trp Asp Trp Thr Arg Ser Met Ser Ala Leu Pro His
                100                 105                 110
Phe Val Ala Asp Pro Thr Tyr Asn Asp Ala Ile Ser Ser Gln Glu Glu
                115                 120                 125
Asp Asn Pro Trp His His Gly His Ile Asp Ser Val Gly His Asp Thr
                130                 135                 140
Thr Arg Asp Val Arg Asp Leu Tyr Gln Ser Pro Gly Phe Gly His
145                 150                 155                 160
Tyr Thr Asp Ile Ala Gln Gln Val Leu Leu Ala Phe Glu Gln Asp Ser
                165                 170                 175
Phe Cys Asp Phe Glu Val Gln Phe Glu Ile Ala His Asn Phe Ile His
                180                 185                 190
Ala Leu Ile Gly Gly Asn Glu Pro Tyr Ser Met Ser Ser Leu Arg Tyr
                195                 200                 205
```

```
Thr Thr Tyr Asp Pro Ile Phe Phe Leu His His Ser Thr Asp Arg
210                 215                 220

Leu Trp Ala Ile Trp Gln Ala Leu Gln Lys Tyr Arg Gly Lys Pro Tyr
225                 230                 235                 240

Asn Thr Ala Asn Cys Ala Ile Ala Ser Met Arg Lys Pro Leu Gln Pro
                245                 250                 255

Phe Gly Leu Asp Ser Val Ile Asn Pro Asp Glu Thr Arg Glu His
            260                 265                 270

Ser Val Pro Phe Arg Val Phe Asp Tyr Lys Asn Asn Phe Asp Tyr Glu
            275                 280                 285

Tyr Glu Ser Leu Ala Phe Asn Gly Leu Ser Ile Ala Gln Leu Asp Arg
    290                 295                 300

Glu Leu Gln Arg Arg Lys Ser His Asp Arg Val Phe Ala Gly Phe Leu
305                 310                 315                 320

Leu His Glu Ile Gly Gln Ser Ala Lys His Asn Val Ser Asp Cys Asp
                325                 330                 335

His Tyr Ala Gly Glu Phe Tyr Ile Leu Gly Asp Glu Ala Glu Met Pro
            340                 345                 350

Trp Arg Tyr Asp Arg Val Tyr Lys Tyr Glu Ile Thr Gln Gln Leu His
    355                 360                 365

Asp Leu Asp Leu His Val Gly Asp Asn Phe Phe Leu Lys Tyr Glu Ala
    370                 375                 380

Phe Asp Leu Asn Gly Gly Ser Leu Gly Gly Ser Ile Phe Ser Gln Pro
385                 390                 395                 400

Ser Val Ile Phe Glu Pro Ala Ala Gly Met Phe
                405                 410

<210> SEQ ID NO 46
<211> LENGTH: 109
<212> TYPE: PRT
<213> ORGANISM: Megathrua crenulata

<400> SEQUENCE: 46

Gly Ser His Gln Ala Asp Glu Tyr Arg Glu Ala Val Thr Ser Ala Ser
1               5                   10                  15

His Ile Arg Lys Asn Ile Arg Asp Leu Ser Glu Gly Glu Ile Glu Ser
            20                  25                  30

Ile Arg Ser Ala Phe Leu Gln Ile Gln Lys Glu Gly Ile Tyr Glu Asn
        35                  40                  45

Ile Ala Lys Phe His Gly Lys Pro Gly Leu Cys Glu His Asp Gly His
    50                  55                  60

Pro Val Ala Cys Cys Val His Gly Met Pro Thr Phe Pro His Trp His
65                  70                  75                  80

Arg Leu Tyr Val Leu Gln Val Glu Asn Ala Leu Leu Glu Arg Gly Ser
                85                  90                  95

Ala Val Ala Val Pro Tyr Trp Asp Trp Thr Leu Pro Arg
                100                 105

<210> SEQ ID NO 47
<211> LENGTH: 329
<212> TYPE: PRT
<213> ORGANISM: Megathura crenulata

<400> SEQUENCE: 47

Met Ala Val Phe Pro His Trp His Arg Leu Phe Val Lys Gln Met Glu
1               5                   10                  15
```

```
Asp Ala Leu Ala Ala His Gly Ala His Ile Gly Ile Pro Tyr Trp Asp
            20                  25                  30

Trp Thr Ser Ala Phe Ser His Leu Pro Ala Leu Val Thr Asp His Glu
        35                  40                  45

Asn Asn Pro Phe His His Gly His Ile Gly His Leu Asn Val Asp Thr
    50                  55                  60

Ser Arg Ser Pro Arg Asp Met Leu Phe Asn Asp Pro Glu Gln Gly Ser
65                  70                  75                  80

Glu Ser Phe Phe Tyr Arg Gln Val Leu Leu Thr Leu Glu Gln Thr Asp
                85                  90                  95

Phe Cys Gln Phe Glu Val Gln Phe Glu Leu Thr His Asn Ala Ile His
            100                 105                 110

Ser Trp Thr Gly Gly His Thr Pro Tyr Gly Met Ser Ser Leu Glu Tyr
        115                 120                 125

Thr Ala Tyr Asp Pro Leu Phe Tyr Leu His His Ser Asn Thr Asp Arg
    130                 135                 140

Ile Trp Ala Ile Trp Gln Ala Leu Gln Lys Tyr Arg Gly Leu Pro Tyr
145                 150                 155                 160

Asn Ala Ala His Cys Asp Ile Gln Val Leu Lys Gln Pro Leu Lys Pro
                165                 170                 175

Phe Ser Glu Ser Arg Asn Pro Asn Pro Val Thr Arg Ala Asn Ser Arg
            180                 185                 190

Ala Val Asp Ser Phe Asp Tyr Glu Lys Phe Asn Tyr Gln Tyr Asp Thr
        195                 200                 205

Leu Thr Phe His Gly Leu Ser Ile Pro Glu Leu Asp Ala Met Leu Gln
    210                 215                 220

Glu Arg Lys Lys Glu Glu Arg Thr Phe Ala Ala Phe Leu Leu His Gly
225                 230                 235                 240

Phe Gly Ala Ser Ala Asp Val Ser Phe Asp Val Cys Thr Pro Asp Gly
                245                 250                 255

His Cys Ala Phe Ala Gly Thr Phe Ala Val Leu Gly Gly Glu Leu Glu
            260                 265                 270

Met Pro Trp Ser Phe Glu Arg Leu Phe Arg Tyr Asp Ile Thr Lys Val
        275                 280                 285

Leu Lys Gln Met Asn Leu His Tyr Asp Ser Glu Phe His Phe Glu Leu
    290                 295                 300

Lys Ile Val Gly Thr Asp Gly Thr Glu Leu Pro Ser Asp Arg Ile Lys
305                 310                 315                 320

Ser Pro Thr Ile Glu His His Gly Gly
                325

<210> SEQ ID NO 48
<211> LENGTH: 103
<212> TYPE: PRT
<213> ORGANISM: Megathura crenulata

<400> SEQUENCE: 48

Gly His Asp His Ser Glu Arg His Asp Gly Phe Phe Arg Lys Glu Val
1               5                   10                  15

Gly Ser Leu Ser Leu Asp Glu Ala Asn Asp Leu Lys Asn Ala Leu Tyr
            20                  25                  30

Lys Leu Gln Asn Asp Gln Gly Pro Asn Gly Tyr Glu Ser Ile Ala Gly
        35                  40                  45

Tyr His Gly Tyr Pro Phe Leu Cys Pro Glu His Gly Glu Asp Gln Tyr
    50                  55                  60
```

```
Ala Cys Cys Val His Gly Met Pro Val Phe Pro His Trp His Arg Leu
 65                  70                  75                  80

His Thr Ile Gln Phe Glu Arg Ala Leu Lys Glu His Gly Ser His Leu
                 85                  90                  95

Gly Leu Pro Tyr Trp Asp Trp
            100
```

<210> SEQ ID NO 49
<211> LENGTH: 1269
<212> TYPE: DNA
<213> ORGANISM: Haliotis tuberculata

<400> SEQUENCE: 49

| | | | | | |
|---|---|---|---|---|---|
| ggcttgttca | gtttctactc | gtcgcccttg | tggtggggc | tggagcagac | aacgtcgtca | 60 |
| gaaaggacgt | gagtcacctc | acggatgacg | aggtgcaagc | tctccacggc | gccctccatg | 120 |
| acgtcactgc | atctacaggg | cctctgagtt | tcgaagacat | aacatcttac | catgccgcac | 180 |
| cagcgtcgtg | tgactacaag | ggacggaaga | tcgcctgctg | tgtccacggt | atgcccagtt | 240 |
| tccccttctg | gcacagggca | tatgtcgtcc | aagccgagcg | ggcactgttg | tccaaacgga | 300 |
| agactgtcgg | aatgccttac | tgggactgga | cgcaaacgct | gactcactta | ccatctcttg | 360 |
| tgactgaacc | catctacatt | gacagtaaag | gtggaaaggc | tcaaaccaac | tactggtacc | 420 |
| gcggcgagat | agcgttcatc | aataagaaga | ctgcgcgagc | tgtagatgat | cgcctattcg | 480 |
| agaaggtgga | gcctggtcac | tacacacatc | ttatggagac | tgtcctcgac | gctctcgaac | 540 |
| aggacgaatt | ctgtaaattt | gaaatccagt | tcgagttggc | tcataatgct | atccattact | 600 |
| tggttggcgg | taaatttgaa | tattcaatgt | caaacttgga | atacacctcc | tacgacccca | 660 |
| tcttcttcct | ccaccactcc | aacgttgacc | gcctcttcgc | catctggcag | cgtcttcagg | 720 |
| aactgcgagg | aaagaatccc | aatgcaatgg | actgtgcaca | tgaactcgct | caccagcaac | 780 |
| tccaacccctt | caacagggac | agcaatccag | tccagctcac | aaaggaccac | tcgacacctg | 840 |
| ctgacctctt | tgattacaaa | caacttggat | acagctacga | cagcttaaac | ctgaatggaa | 900 |
| tgacgccaga | acagctgaaa | acagaactag | acgaacgcca | ctccaaagaa | cgtgcgtttg | 960 |
| caagcttccg | actcagtggc | tttggggggtt | ctgccaacgt | tgttgtctat | gcatgtgtcc | 1020 |
| ctgatgatga | tccacgcagt | gatgactact | gcgagaaagc | aggcgacttc | ttcattcttg | 1080 |
| ggggtcaaag | cgaaatgccg | tggagattct | acagaccctt | cttctatgat | gtaactgaag | 1140 |
| cggtacatca | ccttggagtc | ccgctaagtg | gccactacta | tgtgaaaaca | gaactcttca | 1200 |
| gcgtgaatgg | cacagcactt | tcacctgatc | ttcttcctca | accaactgtt | gcctaccgac | 1260 |
| ctgggaaag | | | | | 1269 |

<210> SEQ ID NO 50
<211> LENGTH: 569
<212> TYPE: DNA
<213> ORGANISM: Haliotis tuberculata

<400> SEQUENCE: 50

| | | | | | |
|---|---|---|---|---|---|
| ggtcttccgt | actgggactg | gacgcagcat | ctgactcaac | tcccagatct | ggtgtcagac | 60 |
| ccctttgttttg | tcgacccgga | aggaggaaag | gcccatgaca | acgcatggta | tcgtggaaac | 120 |
| atcaagtttg | agaataagaa | gactgcaaga | gctgttgacg | atcgcctttt | cgagaaggtt | 180 |
| ggaccaggag | agaatacccg | actctttgaa | ggaattctcg | atgctcttga | acaggatgaa | 240 |
| ttctgcaact | tcgagatcca | gtttgagttg | gctcacaacg | ctatccacta | cctggttggc | 300 |

```
ggccgtcaca cgtactccat gtctcatctc gagttacacc ctcctacgac cccctcttct    360
tcctccatca ctccaacacc ggaccgcatc ttcgccatct gggaacgtct tcaggtactc    420
agaggaaagg accccaacac cgccgactgc gcacacaacc tcatccatga gcccatggaa    480
ccgttccgtc gggactcgaa ccctcttgac ctcaccaggg aaaactccaa accaattgac    540
agctttgatt atgcccacct tggctacca                                     569

<210> SEQ ID NO 51
<211> LENGTH: 1246
<212> TYPE: DNA
<213> ORGANISM: Haliotis tuerculata

<400> SEQUENCE: 51
gttacagagg ccccagctcc ctcctcggat gctcacctcg ccgtcaggaa ggatatcaac     60
catctgacac gcgaggaggt gtacgagctg cgcagagcta tggagagatt ccaggccgac    120
acatccgttg atgggtacca ggctacggtt gagtatcacg gcttacctgc tcgatgtcca    180
ttccccgagg ccacaaatag gttcgcctgt tgcatccacg gcatggcgac attccctcat    240
tggcacagac tgttcgtcac ccaggtggaa gatgctctga tcaggcgagg atcgcctata    300
ggggtcccct actgggactg gactcagcct atggcgcatc tcccaggact tgcagacaac    360
gccacctata gagatcccat cagcggggac agcagacaca accccttcca cgatgttgaa    420
gttgcctttg aaaatggacg tacagaacgt cacccagata gtagattgtt tgaacaacct    480
ttatttggca acatacgcg tctcttcgac agtatagtct atgcttttga gcaggaggac    540
ttctgcgatt ttgaagttca atttgagatg acccataata atattcacgc ctggattggt    600
ggcggcgaga agtattccat gtcttctcta cactacacag ccttcgaccc tatcttctac    660
cttcgtcact ccaacactga ccggctctgg gcaatttggc aagcgttgca gatacgaaga    720
aacaggcctt acaaggctca ttgtgcttgg tctgaggaac gccagcctct caaacctttc    780
gccttcagtt ccccactgaa caacaacgaa aaaacctacg aaaactcggt gcccaccaac    840
gtttacgact acgaaggagt ccttggctat acttatgatg acctcaactt cgggggcatg    900
gacctgggtc agcttgagga atacatccag aggcagagac agagagacag gacctttgct    960 ggtttcttc tgtcacatat tggtacatca gcgaatgttg aaatcattat agaccatggg   1020
actcttcata cctccgtggg cacgtttgct gttcttggcg gagagaagga gatgaaatgg   1080
ggatttgacc gtttgtacaa atatgagatt acagatgaac tgaggcaact taatctccgt   1140
gctgatgatg ttttcagcat ctctgttaaa gtaactgatg ttgatggcag tgagctgtcc   1200
tctgaactca tcccatctgc tgctatcatc ttcgaacgaa gccata                 1246

<210> SEQ ID NO 52
<211> LENGTH: 1242
<212> TYPE: DNA
<213> ORGANISM: Haliotis tuberculata

<400> SEQUENCE: 52
gtcaccatca ggctgacgag tacgacgaag ttgtaactgc tgcaagccac atcagaaaga     60
atttaaaaga tctgtcaaag ggagaagtag agagcctaag gtctgccttc ctgcaacttc    120
agaacgacgg agtctatgag aatattgcca agttccacgg caagcctggg ttgtgtgatg    180
ataacggtcg caaggttgcc tgttgtgtcc atggaatgcc caccttcccc cagtggcaca    240
ggctctatgt cctccaggtg gagaatgctt tgctggagag aggatctgcc gtctctgtgc    300
```

```
catactggga ctggactgaa acatttacag agctgccatc tttgattgct gaggctacct      360
atttcaattc ccgtcaacaa acgtttgacc ctaatccttt cttcagaggt aaaatcagtt      420
ttgagaatgc tgttacaaca cgtgatcccc agcctgagct gtacgttaac aggtactact      480
accaaaacgt catgttggtt tttgaacagg acaactactg cgacttcgag atacagtttg      540
agatggttca caatgttctc catgcttggc ttggtggaag agctacttat tctatttctt      600
ctcttgatta ttctgcattc gaccctgtgt ttttccttca ccatgcgaac acagatagat      660
tgtgggccat ctggcaggag ctgcagaggt acaggaagaa gccatacaat gaagcggatt      720
gtgccattaa cctaatgcgc aaacctctac atcccttcga caacagtgat ctcaatcatg      780
atcctgtaac ctttaaatac tcaaaaccca ctgatggctt tgactaccag aacaactttg      840
gatacaagta tgacaacctt gagttcaatc atttcagtat tcccaggctt aagaaaatca      900
ttcgtattag acaacgtcaa gatcgtgtgt ttgcaggatt cctccttcac aacattggga      960
catccgcaac tgttgagata ttcgtctgtg tccctaccac cagcggtgag caaaactgtg     1020
aaaacaaagc cggaacattt gccgtactcg gaggagaaac agagatggcg tttcattttg     1080
acagactcta caggttttgac atcagtgaaa cactgaggga cctcggcata cagctggaca     1140
gccatgactt tgacctcagc atcaagattc aaggagtaaa tggatcctac cttgatccac     1200
acatcctgcc agagccatcc ttgattttg tgcctggttc aa                         1242

<210> SEQ ID NO 53
<211> LENGTH: 1257
<212> TYPE: DNA
<213> ORGANISM: Haliotis tuberculata

<400> SEQUENCE: 53
gttctttcct gcgtcctgat gggcattcag atgacatcct tgtgagaaaa gaagtgaaca       60
gcctgacaac cagggagact gcatctctga tccatgctct gaaaagtatg caggaagacc      120
attcacctga cgggttccaa gccattgcct ctttccatgc tctgccacca ctctgcccttt      180 caccatctgc agctcaccgt tatgcttgct gtgtccacgg catggctaca tttccccagt      240
ggcacagatt gtacactgta cagttccagg atgcactgag gagacatgga gctacggtag      300
gtgtaccgta ttgggattgg ctgcgaccgc agtctcacct accagagctt gtcaccatgg      360
agacatacca tgatatttgg agtaacagag atttccccaa tcctttctac caagccaata      420
ttgagtttga aggagaaaac attacaacag agagagaagt cattgcagac aaacttttg      480 tcaaaggtgg acacgttttt gataaactgg ttcttcaaac aagccatcct agcgctgagc      540
aggaaaacta ctgtgacttt gagattcagt ttgaaattct tcacaacggc gttcacacgt      600
gggtcggagg cagtcgtacc tactctatcg gacatcttca ttacgcattc tacgaccctc      660 tttctacct tcaccatttc cagacagacc gtatttgggc aatctggcaa gaactccagg      720
aacagagagg gctctcgggt gatgaggctc actgtgctct cgagcaaatg agagaaccat      780
tgaagccttt cagcttcggc gctccttata actggaatca gctcacacag gatttctccc      840
gacccgagga caccttcgac tacaggaagt ttggttatga atatgacaat ttagaattcc      900
tgggaatgtc agttgctgaa ctggatcaat acattattga acatcaagaa aatgatagag      960
tattcgctgg gttcctgttg agtggattcg gaggttccgc atcagttaat ttccaggttt     1020
gtagagctga ttccacatgt caggatgctg ggtacttcac cgttcttggt ggcagtgctg     1080
agatggcgtg ggcatttgac aggctttaca aatatgacat tactgaaact ctggagaaaa     1140
tgcaccttcg atatgatgat gacttcacaa tctctgtcag tctgaccgcc aacaacggaa     1200
```

```
ctgtcctgag cagcagtcta atcccaacac cgagtgtcat attccagcgg ggacatc      1257
```

<210> SEQ ID NO 54
<211> LENGTH: 1257
<212> TYPE: DNA
<213> ORGANISM: Megathura crenulata

<400> SEQUENCE: 54

```
attctgccca cacagatgat ggacacactg aaccagtgat gattcgcaaa gatatcacac       60
aattggacaa gcgtcaacaa ctgtcactgg tgaaagccct cgagtccatg aaagccgacc      120
attcatctga tgggttccag gcaatcgctt ccttccatgc tcttcctcct ctttgtccat      180
caccagctgc ttcaaagagg tttgcgtgct cgtccatgg catggcaacg ttcccacaat       240
ggcaccgtct gtacacagtc caattccaag attctctcag aaaacatggt gcagtcgttg      300
gacttccgta ctgggactgg accctacctc gttctgaatt accagagctc ctgaccgtct      360
caactattca tgacccggag acaggcagag atataccaaa tccatttatt ggttctaaaa      420
tagagtttga aggagaaaac gtacatacta aagagatat caataggat cgtctcttcc       480
agggatcaac aaaaacacat cataactggt ttattgagca agcactgctt gctcttgaac      540
aaaccaacta ctgcgacttc gaggttcagt ttgaaattat gcataatggt gttcatacct      600
gggttggagg caaggagccc tatggaattg gccatctgca ttatgcttcc tatgatccac      660
ttttctacat ccatcactcc caaactgatc gtatttgggc tatatggcaa tcgttgcagc      720
gtttcagagg actttctgga tctgaggcta actgtgctgt aaatctcatg aaaactcctc      780
tgaagccttt cagctttgga gcaccatata atcttaatga tcacacgcat gatttctcaa      840
agcctgaaga tacattcgac taccaaaagt ttggatacat atatgacact ctggaatttg      900
cagggtggtc aattcgtggc attgaccata ttgtccgtaa caggcaggaa cattcaaggg      960
tctttgccgg attcttgctt gaaggatttg gcacctctgc cactgtcgat ttccaggtct     1020
gtcgcacagc gggagactgt gaagatgcag ggtacttcac cgtgttggga ggtgaaaaag     1080
aaatgccttg ggcctttgat cggctttaca agtacgacat aacagaaacc ttagacaaga     1140
tgaaccttcg acatgacgaa atcttccaga ttgaagtaac cattacatcc tacgatggaa     1200
ctgtactcga tagtggcctt attcccacac cgtcaatcat ctatgatcct gctcatc       1257
```

<210> SEQ ID NO 55
<211> LENGTH: 1254
<212> TYPE: DNA
<213> ORGANISM: Megathura crenulata

<400> SEQUENCE: 55

```
atgatattag ttcgcaccac ctgtcgctca acaaggttcg tcatgatctg agtacactga       60
gtgagcgaga tattggaagc cttaaatatg ctttgagcag cttgcaggca gatacctcag      120
cagatggttt tgctgccatt gcatccttcc atggtctgcc tgccaaatgt aatgacagcc      180
acaataacga ggtggcatgc tgtatccatg gaatgcctac attcccccac tggcacagac      240
tctacaccct ccaatttgag caagctctaa gaagacatgg ctctagtgta gcagtaccct      300
actgggactg gacaaagcca atacataata ttccacatct gttcacagac aaagaatact      360
acgatgtctg gagaaataaa gtaatgccaa tccatttgc ccgagggtat gtcccctcac       420
acgatacata cacggtaaga gacgtccaag aaggcctgtt ccacctgaca tcaacgggtg      480
aacactcagc gcttctgaat caagctcttt tggcgctgga acagcacgac tactgcgatt      540
```

```
ttgcagtcca gtttgaagtc atgcacaaca caatccatta cctagtggga ggacctcaag     600
tctattcttt gtcatccctt cattatgctt catatgatcc gatcttcttc atacaccact     660
cctttgtaga caaggtttgg gctgtctggc aggctcttca agaaaagaga ggccttccat     720
cagaccgtgc tgactgcgct gttagtctga tgactcagaa catgaggcct ttccattacg     780
aaattaacca taaccagttc accaagaaac atgcagttcc aaatgatgtt ttcaagtacg     840
aactcctggg ttacagatac gacaatctgg aaatcggtgg catgaatttg catgaaattg     900
aaaaggaaat caaagacaaa cagcaccatg tgagagtgtt tgcagggttc ctccttcacg     960
gaattagaac ctcagctgat gtccaattcc agatttgtaa acatcagaa gattgtcacc    1020 atggaggcca atcttcgtt cttgggggga ctaaagagat ggcctgggct tataaccgtt    1080
tattcaagta cgatattacc catgctcttc atgacgcaca catcactcca gaagacgtat    1140
tccatccctc tgaaccattc ttcatcaagg tgtcagtgac agccgtcaac ggaacagttc    1200
ttccggcttc aatcctgcat gcaccaacca ttatctatga acctggtctc ggtg          1254

<210> SEQ ID NO 56
<211> LENGTH: 509
<212> TYPE: DNA
<213> ORGANISM: Megathura crenulata

<400> SEQUENCE: 56
accatcacga agatcatcat tcttcttcta tggctggaca tggtgtcaga aggaaatca      60 acacacttac cactgcagag gtggacaatc tcaaagatgc catgagagcc gtcatggcag     120
accacggtcc aaatggatac caggctatag cagcgttcca tggaaaccca ccaatgtgcc     180
ctatgccaga tggaaagaat tactcgtgtt gtacacatgg catggctact ttcccccact     240
ggcacagact gtacacaaaa cagatggaag atgccttgac cgcccatggt gccagagtcg     300
gccttcctta ctgggacggg acaactgcct ttacagcttt gccaactttt gtcacagatg     360
aagaggacaa tcctttccat catggtcaca tagactattt gggagtggat acaactcggt     420
cgccccgaga caagttgttc aatgatccag agcgaggatc agaatcgttc ttctacaggc     480
aggttctctt ggctttggag cagacagat                                       509

<210> SEQ ID NO 57
<211> LENGTH: 943
<212> TYPE: DNA
<213> ORGANISM: Megathura crenulata

<400> SEQUENCE: 57
ggcctgccct actgggattg gaccatgcca atgagtcatt tgccagaact ggctacaagt      60
gagacctacc tcgatccagt tactggggaa actaaaaaca cccttttcca tcacgcccaa     120
gtggcgtttg aaaatggtgt aacaagcagg atcctgatg ccaaacttt tatgaaacca      180 acttacggag accacactta cctcttcgac agcatgatct acgcatttga gcaggaagac     240
ttctgcgact tgaagtcca atatgagctc acgcataatg caatacatgc atgggttgga     300
ggcagtgaaa agtattcaat gtcttctctt cactacactg cttttgatcc tatattttac     360
ctccatcact caaatgttga tcgtctctgg gccatttggc aagctcttca aatcaggaga     420
ggcaagtctt acaaggccca ctgcgcctcg tctcaagaaa gagaaccatt aaagcctttt     480
gcattcagtt ccccactgaa caacaacgag aaaacgtacc acaactctgt ccccactaac     540
gtttatgact atgtgggagt tttgcactat cgatatgatg accttcagtt tggcggtatg     600
accatgtcag aacttgagga atatattcac aagcagacac aacatgatag aaccttttgca     660
```

```
ggattcttcc tttcatatat tggaacatca gcaagcgtag atatcttcat caatcgagaa      720
ggtcatgata aatacaaagt gggaagtttt gtagtacttg gtggatccaa agaaatgaaa      780
tggggctttg atagaatgta caagtatgag atcactgagg ctctgaagac gctgaatgtt      840
gcagtggatg atgggttcag cattactgtt gagatcaccg atgttgatgg atctccccca      900
tctgcagatc tcattccacc tcctgctata atctttgaac gtg                       943

<210> SEQ ID NO 58
<211> LENGTH: 1248
<212> TYPE: DNA
<213> ORGANISM: Megathura crenulata

<400> SEQUENCE: 58
ctgatgccaa agactttggc catagcagaa aaatcaggaa agccgttgat tctctgacag      60
tcgaagaaca aacttcgttg aggcgagcta tggcagatct acaggacgac aaaacatcag      120
ggggtttcca gcagattgca gcattccacg gagaaccaaa atggtgtcca gccccgaag      180 cggagaaaaa atttgcatgc tgtgttcatg aatggctgt tttccctcac tggcacagat      240
tgctgacagt tcaaggagaa aatgctctga ggaaacatgg ctttactggt ggactgccct      300
actgggactg gactcgatca atgagcgccc ttccacattt tgttgctgat cctacttaca      360
atgatgctat ttccagccag gaagaagata acccatggca tcatggtcac atagactctg      420
ttgggcatga tactacaaga gatgtgcgtg atgatcttta tcaatctcct ggtttcggtc      480
actacacaga tattgcaaaa caagtccttc tggcctttga gcaggacgat ttctgtgatt      540
ttgaggtaca atttgaaatt gcccataatt tcatacatgc tctggttggt ggtaacgaac      600
catacagtat gtcatctttg aggtatacta catacgatcc aatcttcttc ttgcaccgct      660
ccaatacaga ccgactttgg gccatttggc aagctttgca aaaataccgg gggaaaccat      720
acaacactgc aaactgtgcc attgcatcca tgagaaaacc acttcagcca tttggtcttg      780
atagtgtcat aaatccagat gacgaaactc gtgaacattc ggttcctttc cgagtcttcg      840
actacaagaa caacttcgac tatgagtatg agagcctggc atttaatggt ctgtctattg      900
cccaactgga ccgagagttg cagagaagaa agtcacatga cagagtcttt gcaggattcc      960
ttcttcatga aattggacag tctgcactcg tgaaattcta cgtttgcaaa cacaatgtat     1020
ctgactgtga ccattatgct ggagaattct acattttggg agatgaagct gagatgcctt     1080
ggaggtatga ccgtgtgtac aagtacgaga taacacagca gctgcacgat ttagatctac     1140
atgttggaga taatttcttc cttaaatatg aagcctttga tctgaatggc ggaagtcttg     1200
gtggaagtat cttttctcag ccttcggtga ttttcgagcc agctgcag                 1248

<210> SEQ ID NO 59
<211> LENGTH: 1257
<212> TYPE: DNA
<213> ORGANISM: Megathura crenulata

<400> SEQUENCE: 59
gttcacacca ggctgatgaa tatcgtgagg cagtaacaag cgctagccac ataagaaaaa      60
atatccggga cctctcagag ggagaaattg agagcatcag atctgctttc ctccaaattc     120
aaaaagaggg tatatatgaa acattgcaa agttccatgg aaaaccagga ctttgtgaac     180
atgatgagca tcctgttgct tgttgtgtcc atggcatgcc cacctttccc cactggcaca     240
gactgtacgt tcttcaggtg gagaatgcgc tcttagaacg agggtctgca gttgctgttc     300
```

```
                                    -continued cttactggga ctggaccgag aaagctgact ctctgccatc attaatcaat gatgcaactt      360
atttcaattc acgatcccag acctttgatc ctaatccttt cttcagggga catattgcct      420
tcgagaatgc tgtgacgtcc agagatcctc agccagaact atgggacaat aaggacttct      480
acgagaatgt catgctggct cttgagcaag acaacttctg tgactttgag attcagcttg      540
agctgataca caacgccctt cattctagac ttggaggaag ggctaaatac tcccttcgt       600 ctcttgatta taccgcattt gatcctgtat ttttccttca ccatgcaaac gttgacagaa      660
tctgggccat ctggcaggac ttgcagagat atagaaagaa accatacaat gaggctgact      720
gcgcagtcaa cgagatgcgt aaacctcttc aaccatttaa taacccagaa cttaacagtg      780
attccatgac gcttaaacac aacctcccac aagacagttt tgattatcaa aaccgcttca      840
ggtaccaata tgataacctt caatttaacc acttcagcat acaaaagcta gaccaaacta      900
ttcaggctag aaaacaacac gacagagttt tgctggctt tattcttcac aacattggga       960
catctgctgt tgtagatatt tatatttgcg ttgaacaagg aggagaacaa aactgcaaga     1020
caaaggcggg ttccttcacg attctggggg gagaaacaga aatgccattc cactttgacc     1080
gcttgtacaa atttgacata acgtctgctc tgcataaact tggtgttccc ttggacggac     1140
atggattcga catcaaagtt gacgtcagag ctgtcaatgg atcgcatctt gatcaacaca     1200
tcctcaacga accgagtctg cttttgttc ctggtgaacg taagaatata tattatg         1257

<210> SEQ ID NO 60
<211> LENGTH: 1239
<212> TYPE: DNA
<213> ORGANISM: Megathura crenulata

<400> SEQUENCE: 60
atgggctttc acaacataat cttgtgcgaa aagaagtaag ctctcttaca acactggaga       60
aacatttttt gaggaaagct ctcaagaaca tgcaagcaga tgattctcca gacggatatc      120
aagctattgc ttctttccac gctttgcctc ctctttgtcc aagtccatct gctgcacata      180
gacacgcttg ttgcctccat ggtatggcta ccttccctca gtggcacaga ctctacacag      240
ttcagttcga agattctttg aaacgacatg gttctattgt cggacttcca tattgggatt      300
ggctgaaacc gcagtctgca ctccctgatt tggtgcacac ggagacatac gagcacctgt      360
tttcacacaa aaccttccca aatccgttcc tcaaggcaaa tatagaattt gagggagagg      420
gagtaacaac agagagggat gttgatgctg aacacctctt tgcaaaagga aatctggttt      480
acaacaactg gttttgcaat caggcactat atgcactaga acaagaaaat tactgtgact      540 tgaaataca gttcgaaatt ttgcataatg gaattcattc atgggttgga ggatcaaaga       600
cccattcaat aggtcatctt cattacgcat catacgatac actgttctat atccaccatt      660
cgcagacaga tcgcatttgg gctatctggc aagctctcca ggagcacaga ggtctttcag      720 gaaggaagc acactgcgcc ctggagcaaa tgaaagaccc tctcaaacct ttcagctttg      780
gaagtcccta taatttgaac aaacgcactc aagagttctc caagcctgaa gacacatttg      840
attatcaccg attcgggtat gagtatgatt ccctcgaatt tgttggcatg tctgtttcaa      900
gtttacataa ctatataaaa caacaacagg aagctgatag agtcttcgca ggattccttc      960
ttaaaggatt tggacaatca gcatccgtat cgtttgatat ctgcagacca gaccagagtt     1020
gccaagaagc tggatacttc tcagttctcg gtggaagttc agaaatgccg tggcagtttg     1080
acaggcttta caagtacgac attacaaaaa cgttgaaaga catgaaactg cgatacgatg     1140
acacatttac catcaaggtt cacataaagg atatagctgg agctgagttg gacagcgatc     1200
```

```
tgattccaac tccttctgtt ctccttgaag aaggaaagc                           1239

<210> SEQ ID NO 61
<211> LENGTH: 1251
<212> TYPE: DNA
<213> ORGANISM: Haliotis tuberculata

<400> SEQUENCE: 61
atgggatcaa tgtacgtcac gttggtcgta atcggattcg tatggaacta tctgaactca     60
ccgagagaga tctcgccagc ctgaaatctg caatgaggtc tctacaagct gacgatgggg    120
tgaacggtta tcaagccatt gcatcattcc acggtctccc ggcttcttgt catgatgatg    180
agggacatga gattgcctgt tgtatccacg gaatgccagt attcccacac tggcacaggc    240
tttacaccct gcaaatggac atggctctgt tatctcacgg atctgctgtt gctattccat    300
actgggactg gaccaaacct atcagcaaac tgcctgatct cttccaccagc cctgaatatt    360 acgatccttg gagggatgca gttgtcaata atccatttgc taaaggctac attaaatccg    420
aggacgctta cacggttagg gatcctcagg acattttgta ccacttgcag gacgaaacgg    480
gaacatctgt tttgttagat caaactcttt tagccttaga gcagacagat ttctgtgatt    540
ttgaggttca atttgaggtc gtccataatg ctattcacta cttggtgggt ggtcgacaag    600
tttatgctct ttcttctcaa cactatgctt catatgaccc agccttcttt attcatcact    660
cctttgttga caaatatgg gcagtctggc aagctctgca aaagaagaga aagcgtccct    720
atcataaagc ggattgtgct cttaacatga tgaccaaacc aatgcgacca tttgcacacg    780
atttcaatca caatggattc acaaaaatgc acgcagtccc caacactcta tttgactttc    840
aggacctttt ctacacgtat gacaactag aaattgctgg catgaatgtt aatcagttgg    900
aagcggaaat caaccggcga aaaagccaaa caagagtctt tgccgggttc cttctacatg    960
gcattggaag atcagctgat gtacgattt ggatttgcaa gacagctgac gactgccacg   1020
catctggcat gatctttatc ttaggaggtt ctaaagagat gcactgggcc tatgacagga   1080
actttaaata cgacatcacc caagctttga aggctcagtc catacaccct gaagatgtgt   1140
ttgacactga tgctcctttc ttcattaaag tggaggtcca tggtgtaaac aagactgctc   1200
tcccatcttc agctatccca gcacctacta taatctactc agctggtgaa g            1251

<210> SEQ ID NO 62
<211> LENGTH: 1185
<212> TYPE: DNA
<213> ORGANISM: Haliotis tuberculata
<220> FEATURE:
<221> NAME/KEY: misc_feature
<222> LOCATION: (163)..(163)
<223> OTHER INFORMATION: n is a, c, g, or t

<400> SEQUENCE: 62
atcatattgc tggcagtgga gtcaggaaag acgtgacgtc tcttaccgca tctgagatag     60
agaacctgag gcatgctctg caaagcgtga tggatgatga tggacccaat ggattccagg    120
caattgctgc ttatcacgga agtcctccca tgtgtcacat gcntgatggt agagacgttg    180
catgttgtac tcatgaatg gcatctttcc ctcactggca cagactgttt gtgaaacaga    240
tggaggatgc actggctgcg catggagctc acattggcat accatactgg gattggacaa    300
gtgcgtttag tcatctgcct gccctagtga ctgaccacga gcacaatccc ttccaccacg    360
gacatattgc tcatcggaat gtggatacat ctcgatctcc gagagacatg ctgttcaatg    420
```

-continued

```
acccgaaca cgggtcagaa tcattcttct atagacaggt tctcttggct ctagaacaga      480
cagacttctg ccaatttgaa gttcagtttg aaataacaca caatgcaatc cactcttgga      540
ctggaggaca tactccatat ggaatgtcat cactggaata tacagcatat gatccactct      600
tttatctcca ccattccaac actgatcgta tctgggccat ctggcaggca ctccagaaat      660
acagaggttt tcaatacaac gcagctcatt gcgatatcca ggttctgaaa caacctctta      720
aaccattcag cgagtccagg aatccaaacc cagtcaccag agccaattct agggcagtcg      780
attcatttga ttatgagaga ctcaattatc aatatgacac acttaccttc cacggacatt      840
ctatctcaga acttgatgcc atgcttcaag agagaaagaa ggaagagaga acatttgcag      900
ccttcctgtt gcacggattt ggcgccagtg ctgatgtttc gtttgatgtc tgcacacctg      960
atggtcattg tgcctttgct ggaaccttcg cggtacttgg tggggagctt gagatgccct     1020
ggtcctttga agattgttc cgttacgata tcacaaaggt tctcaagcag atgaatcttc      1080
actatgattc tgagttccac tttgagttga agattgttgg cacagatgga acagaactgc     1140
catcggatcg tatcaagagc cctaccattg aacaccatgg aggag                     1185
```

<210> SEQ ID NO 63
<211> LENGTH: 422
<212> TYPE: PRT
<213> ORGANISM: Haliotis tuberculata

<400> SEQUENCE: 63

```
Leu Val Gln Phe Leu Leu Val Ala Leu Val Gly Ala Gly Ala Asp
1               5                   10                  15

Asn Val Val Arg Lys Asp Val Ser His Leu Thr Asp Asp Glu Val Gln
            20                  25                  30

Ala Leu His Gly Ala Leu His Asp Val Thr Ala Ser Thr Gly Pro Leu
        35                  40                  45

Ser Phe Glu Asp Ile Thr Ser Tyr His Ala Ala Pro Ala Ser Cys Asp
    50                  55                  60

Tyr Lys Gly Arg Lys Ile Ala Cys Cys Val His Gly Met Pro Ser Phe
65                  70                  75                  80

Pro Phe Trp His Arg Ala Tyr Val Val Gln Ala Glu Arg Ala Leu Leu
                85                  90                  95

Ser Lys Arg Lys Thr Val Gly Met Pro Tyr Trp Asp Trp Thr Gln Thr
            100                 105                 110

Leu Thr His Leu Pro Ser Leu Val Thr Glu Pro Ile Tyr Ile Asp Ser
        115                 120                 125

Lys Gly Gly Lys Ala Gln Thr Asn Tyr Trp Tyr Arg Gly Glu Ile Ala
    130                 135                 140

Phe Ile Asn Lys Lys Thr Ala Arg Ala Val Asp Asp Arg Leu Phe Glu
145                 150                 155                 160

Lys Val Glu Pro Gly His Tyr Thr His Leu Met Glu Thr Val Leu Asp
                165                 170                 175

Ala Leu Glu Gln Asp Glu Phe Cys Lys Phe Glu Ile Gln Phe Glu Leu
            180                 185                 190

Ala His Asn Ala Ile His Tyr Leu Val Gly Gly Lys Phe Glu Tyr Ser
        195                 200                 205

Met Ser Asn Leu Glu Tyr Thr Ser Tyr Asp Pro Ile Phe Phe Leu His
    210                 215                 220

His Ser Asn Val Asp Arg Leu Phe Ala Ile Trp Gln Arg Leu Gln Glu
225                 230                 235                 240
```

```
Leu Arg Gly Lys Asn Pro Asn Ala Met Asp Cys Ala His Glu Leu Ala
                245                 250                 255

His Gln Gln Leu Gln Pro Phe Asn Arg Asp Ser Asn Pro Val Gln Leu
            260                 265                 270

Thr Lys Asp His Ser Thr Pro Ala Asp Leu Phe Asp Tyr Lys Gln Leu
        275                 280                 285

Gly Tyr Ser Tyr Asp Ser Leu Asn Leu Asn Gly Met Thr Pro Glu Gln
    290                 295                 300

Leu Lys Thr Glu Leu Asp Glu Arg His Ser Lys Glu Arg Ala Phe Ala
305                 310                 315                 320

Ser Phe Arg Leu Ser Gly Phe Gly Gly Ser Ala Asn Val Val Val Tyr
                325                 330                 335

Ala Cys Val Pro Asp Asp Pro Arg Ser Asp Asp Tyr Cys Glu Lys
            340                 345                 350

Ala Gly Asp Phe Phe Ile Leu Gly Gly Gln Ser Glu Met Pro Trp Arg
        355                 360                 365

Phe Tyr Arg Pro Phe Phe Tyr Asp Val Thr Glu Ala Val His His Leu
    370                 375                 380

Gly Val Pro Leu Ser Gly His Tyr Tyr Val Lys Thr Glu Leu Phe Ser
385                 390                 395                 400

Val Asn Gly Thr Ala Leu Ser Pro Asp Leu Leu Pro Gln Pro Thr Val
                405                 410                 415

Ala Tyr Arg Pro Gly Lys
                420

<210> SEQ ID NO 64
<211> LENGTH: 511
<212> TYPE: PRT
<213> ORGANISM: Haliotis tuberculata

<400> SEQUENCE: 64

Val His Arg Gly Gly Asn His Glu Asp Glu His His Asp Asp Arg Leu
1               5                   10                  15

Ala Asp Val Leu Ile Arg Lys Glu Val Asp Phe Leu Ser Leu Gln Glu
            20                  25                  30

Ala Asn Ala Ile Lys Asp Ala Leu Tyr Lys Leu Gln Asn Asp Asp Ser
        35                  40                  45

Lys Gly Gly Phe Glu Ala Ile Ala Gly Tyr His Gly Tyr Pro Asn Met
    50                  55                  60

Cys Pro Glu Arg Gly Thr Asp Lys Tyr Pro Cys Cys Val His Gly Met
65                  70                  75                  80

Pro Val Phe Pro His Trp His Arg Leu His Thr Ile Gln Met Glu Arg
                85                  90                  95

Ala Leu Lys Asn His Gly Ser Pro Met Gly Ile Pro Tyr Trp Asp Trp
            100                 105                 110

Thr Lys Lys Met Ser Ser Leu Pro Ser Phe Phe Gly Asp Ser Ser Asn
        115                 120                 125

Asn Asn Pro Phe Tyr Lys Tyr Tyr Ile Arg Gly Val Gln His Glu Thr
    130                 135                 140

Thr Arg Asp Val Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
            180                 185                 190
```

```
Ser Trp Leu Gly Gly Thr Gly Gln Tyr Ser Met Ser Thr Leu Glu His
        195                 200                 205

Ser Ala Phe Asp Pro Val Phe Met Ile His His Ser Ser Leu Asp Arg
    210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
        275                 280                 285

Asp Asn Met Arg Ile Arg Gly Gln Asp Ile His Glu Leu Glu Glu Val
    290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
        355                 360                 365

Ile Ser Asp Ala Val His Lys Leu His Val Lys Asp Glu Asp Ile Arg
    370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510

<210> SEQ ID NO 65
<211> LENGTH: 197
<212> TYPE: PRT
<213> ORGANISM: Haliotis tuberculata

<400> SEQUENCE: 65

Gly Leu Pro Tyr Trp Asp Trp Thr Gln His Leu Thr Gln Leu Pro Asp
1               5                   10                  15

Leu Val Ser Asp Pro Leu Phe Val Asp Pro Glu Gly Gly Lys Ala His
            20                  25                  30

Asp Asn Ala Trp Tyr Arg Gly Asn Ile Lys Phe Glu Asn Lys Lys Thr
        35                  40                  45

Ala Arg Ala Val Asp Asp Arg Leu Phe Glu Lys Val Gly Pro Gly Glu
```

```
                  50                  55                  60
Asn Thr Arg Leu Phe Glu Gly Ile Leu Asp Ala Leu Glu Gln Asp Glu
 65                  70                  75                  80

Phe Cys Asn Phe Glu Ile Gln Phe Glu Leu Ala His Asn Ala Ile His
                 85                  90                  95

Tyr Leu Val Gly Gly Arg His Thr Tyr Ser Met Ser His Leu Glu Tyr
                100                 105                 110

Thr Ser Tyr Asp Pro Leu Phe Phe Leu His His Ser Asn Pro Asp Arg
                115                 120                 125

Ile Phe Ala Ile Trp Glu Arg Leu Gln Val Leu Arg Gly Lys Asp Pro
        130                 135                 140

Asn Thr Ala Asp Cys Ala His Asn Leu Ile His Glu Pro Met Glu Pro
145                 150                 155                 160

Phe Arg Arg His Glu Pro Met Glu Pro Phe Arg Arg Asp Ser Asn Pro
                165                 170                 175

Leu Asp Leu Thr Arg Glu Asn Ser Lys Pro Ile Asp Ser Phe Asp Tyr
                180                 185                 190

Ala His Leu Gly Tyr
        195

<210> SEQ ID NO 66
<211> LENGTH: 415
<212> TYPE: PRT
<213> ORGANISM: Haliotis tuberculata

<400> SEQUENCE: 66

Val Thr Glu Ala Pro Ala Pro Ser Ser Asp Ala His Leu Ala Val Arg
 1               5                  10                  15

Lys Asp Ile Asn His Leu Thr Arg Glu Glu Val Tyr Glu Leu Arg Arg
                 20                  25                  30

Ala Met Glu Arg Phe Gln Ala Asp Thr Ser Val Asp Gly Tyr Gln Ala
             35                  40                  45

Thr Val Glu Tyr His Gly Leu Pro Ala Arg Cys Pro Phe Pro Glu Ala
         50                  55                  60

Thr Asn Arg Phe Ala Cys Cys Ile His Gly Met Ala Thr Phe Pro His
 65                  70                  75                  80

Trp His Arg Leu Phe Val Thr Gln Val Glu Asp Ala Leu Ile Arg Arg
                 85                  90                  95

Gly Ser Pro Ile Gly Val Pro Tyr Trp Asp Trp Thr Gln Pro Met Ala
                100                 105                 110

His Leu Pro Gly Leu Ala Asp Asn Ala Thr Tyr Arg Asp Pro Ile Ser
            115                 120                 125

Gly Asp Ser Arg His Asn Pro Phe His Asp Val Glu Val Ala Phe Glu
        130                 135                 140

Asn Gly Arg Thr Glu Arg His Pro Asp Ser Arg Leu Phe Glu Gln Pro
145                 150                 155                 160

Leu Phe Gly Lys His Thr Arg Leu Phe Asp Ser Ile Val Tyr Ala Phe
                165                 170                 175

Glu Gln Glu Asp Phe Cys Asp Phe Glu Val Gln Phe Glu Met Thr His
                180                 185                 190

Asn Asn Ile His Ala Trp Ile Gly Gly Gly Glu Lys Tyr Ser Met Ser
            195                 200                 205

Ser Leu His Tyr Thr Ala Phe Asp Pro Ile Phe Tyr Leu Arg His Ser
        210                 215                 220
```

-continued

```
Asn Thr Asp Arg Leu Trp Ala Ile Trp Gln Ala Leu Gln Ile Arg Arg
225                 230                 235                 240

Asn Arg Pro Tyr Lys Ala His Cys Ala Trp Ser Glu Glu Arg Gln Pro
            245                 250                 255

Leu Lys Pro Phe Ala Phe Ser Ser Pro Leu Asn Asn Asn Glu Lys Thr
        260                 265                 270

Tyr Glu Asn Ser Val Pro Thr Asn Val Tyr Asp Tyr Glu Gly Val Leu
    275                 280                 285

Gly Tyr Thr Tyr Asp Asp Leu Asn Phe Gly Gly Met Asp Leu Gly Gln
290                 295                 300

Leu Glu Glu Tyr Ile Gln Arg Gln Arg Gln Arg Asp Arg Thr Phe Ala
305                 310                 315                 320

Gly Phe Phe Leu Ser His Ile Gly Thr Ser Ala Asn Val Glu Ile Ile
            325                 330                 335

Ile Asp His Gly Thr Leu His Thr Ser Val Gly Thr Phe Ala Val Leu
        340                 345                 350

Gly Gly Glu Lys Glu Met Lys Trp Gly Phe Asp Arg Leu Tyr Lys Tyr
    355                 360                 365

Glu Ile Thr Asp Glu Leu Arg Gln Leu Asn Leu Arg Ala Asp Asp Val
370                 375                 380

Phe Ser Ile Ser Val Lys Val Thr Asp Val Asp Gly Ser Glu Leu Ser
385                 390                 395                 400

Ser Glu Leu Ile Pro Ser Ala Ala Ile Ile Phe Glu Arg Ser His
            405                 410                 415

<210> SEQ ID NO 67
<211> LENGTH: 414
<212> TYPE: PRT
<213> ORGANISM: Haliotis tuberculata

<400> SEQUENCE: 67

Gly His His Gln Ala Asp Glu Tyr Asp Glu Val Val Thr Ala Ala Ser
1               5                   10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Val Phe Glu Gln Asp Asn Tyr Cys Asp Phe
                165                 170                 175

Glu Ile Gln Phe Glu Met Val His Asn Val Leu His Ala Trp Leu Gly
            180                 185                 190
```

```
Gly Arg Ala Thr Tyr Ser Ile Ser Ser Leu Asp Tyr Ser Ala Phe Asp
            195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
            275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350

Glu Thr Glu Met Ala Phe His Phe Asp Arg Leu Tyr Arg Phe Asp Ile
            355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser
                405                 410

<210> SEQ ID NO 68
<211> LENGTH: 419
<212> TYPE: PRT
<213> ORGANISM: Haliotis tuberculata

<400> SEQUENCE: 68

Ser Ser Phe Leu Arg Pro Asp Gly His Ser Asp Ile Leu Val Arg
1               5                   10                  15

Lys Glu Val Asn Ser Leu Thr Thr Arg Glu Thr Ala Ser Leu Ile His
                20                  25                  30

Ala Leu Lys Ser Met Gln Glu Asp His Ser Pro Asp Gly Phe Gln Ala
            35                  40                  45

Ile Ala Ser Phe His Ala Leu Pro Pro Leu Cys Pro Ser Pro Ser Ala
    50                  55                  60

Ala His Arg Tyr Ala Cys Cys Val His Gly Met Ala Thr Phe Pro Gln
65                  70                  75                  80

Trp His Arg Leu Tyr Thr Val Gln Phe Gln Asp Ala Leu Arg Arg His
                85                  90                  95

Gly Ala Thr Val Gly Val Pro Tyr Trp Asp Trp Leu Arg Pro Gln Ser
            100                 105                 110

His Leu Pro Glu Leu Val Thr Met Glu Thr Tyr His Asp Ile Trp Ser
        115                 120                 125

Asn Arg Asp Phe Pro Asn Pro Phe Tyr Gln Ala Asn Ile Glu Phe Glu
    130                 135                 140

Gly Glu Asn Ile Thr Thr Glu Arg Glu Val Ile Ala Asp Lys Leu Phe
```

-continued

```
                145                 150                 155                 160
Val Lys Gly Gly His Val Phe Asp Lys Leu Val Leu Gln Thr Ser His
                    165                 170                 175
Pro Ser Ala Glu Gln Glu Asn Tyr Cys Asp Phe Glu Ile Gln Phe Glu
                180                 185                 190
Ile Leu His Asn Gly Val His Thr Trp Val Gly Gly Ser Arg Thr Tyr
                195                 200                 205
Ser Ile Gly His Leu His Tyr Ala Phe Tyr Asp Pro Leu Phe Tyr Leu
            210                 215                 220
His His Phe Gln Thr Asp Arg Ile Trp Ala Ile Trp Gln Glu Leu Gln
225                 230                 235                 240
Glu Gln Arg Gly Leu Ser Gly Asp Glu Ala His Cys Ala Leu Glu Gln
                245                 250                 255
Met Arg Glu Pro Leu Lys Pro Phe Ser Phe Gly Ala Pro Tyr Asn Trp
                260                 265                 270
Asn Gln Leu Thr Gln Asp Phe Ser Arg Pro Glu Asp Thr Phe Asp Tyr
                275                 280                 285
Arg Lys Phe Gly Tyr Glu Tyr Asp Asn Leu Glu Phe Leu Gly Met Ser
            290                 295                 300
Val Ala Glu Leu Asp Gln Tyr Ile Ile Glu His Gln Glu Asn Asp Arg
305                 310                 315                 320
Val Phe Ala Gly Phe Leu Leu Ser Gly Phe Gly Ser Ala Ser Val
                325                 330                 335
Asn Phe Gln Val Cys Arg Ala Asp Ser Thr Cys Gln Asp Ala Gly Tyr
                340                 345                 350
Phe Thr Val Leu Gly Gly Ser Ala Glu Met Ala Trp Ala Phe Asp Arg
                355                 360                 365
Leu Tyr Lys Tyr Asp Ile Thr Glu Thr Leu Glu Lys Met His Leu Arg
            370                 375                 380
Tyr Asp Asp Asp Phe Thr Ile Ser Val Ser Leu Thr Ala Asn Asn Gly
385                 390                 395                 400
Thr Val Leu Ser Ser Ser Leu Ile Pro Thr Pro Ser Val Ile Phe Gln
                405                 410                 415
Arg Gly His

<210> SEQ ID NO 69
<211> LENGTH: 378
<212> TYPE: PRT
<213> ORGANISM: Megathrua crenulata

<400> SEQUENCE: 69

Arg Tyr Gln Ala Thr Ala Glu Tyr His Gly Leu Pro Ala Arg Cys Pro
1               5                   10                  15
Arg Pro Asp Ala Lys Asp Arg Tyr Ala Cys Cys Val His Gly Met Pro
                20                  25                  30
Ile Phe Pro His Trp His Arg Leu Phe Val Thr Gln Val Glu Asp Ala
            35                  40                  45
Leu Val Gly Arg Gly Ala Thr Ile Gly Ile Pro Tyr Trp Asp Trp Thr
        50                  55                  60
Glu Pro Met Thr His Ile Pro Gly Leu Ala Gly Asn Lys Thr Tyr Val
65                  70                  75                  80
Asp Ser His Gly Ala Ser His Thr Asn Pro Phe His Ser Ser Val Ile
                85                  90                  95
Ala Phe Glu Glu Asn Ala Pro His Thr Lys Arg Gln Ile Asp Gln Arg
```

```
                   100                 105                 110
Leu Phe Lys Pro Ala Thr Phe Gly His His Thr Asp Leu Phe Asn Gln
            115                 120                 125

Ile Leu Tyr Ala Phe Glu Gln Glu Asp Tyr Cys Asp Phe Glu Val Gln
            130                 135                 140

Phe Glu Ile Thr His Asn Thr Ile His Ala Trp Thr Gly Gly Ser Glu
145                 150                 155                 160

His Phe Ser Met Ser Ser Leu His Tyr Thr Ala Phe Asp Pro Leu Phe
                165                 170                 175

Tyr Phe His His Ser Asn Val Asp Arg Leu Trp Ala Val Trp Gln Ala
            180                 185                 190

Leu Gln Met Arg Arg His Lys Pro Tyr Arg Ala His Cys Ala Ile Ser
            195                 200                 205

Leu Glu His Met His Leu Lys Pro Phe Ala Phe Ser Ser Pro Leu Asn
    210                 215                 220

Asn Asn Glu Lys Thr His Ala Asn Ala Met Pro Asn Lys Ile Tyr Asp
225                 230                 235                 240

Tyr Glu Asn Val Leu His Tyr Thr Tyr Glu Asp Leu Thr Phe Gly Gly
                245                 250                 255

Ile Ser Leu Glu Asn Ile Glu Lys Met Ile His Glu Asn Gln Gln Glu
            260                 265                 270

Asp Arg Ile Tyr Ala Gly Phe Leu Ala Gly Ile Arg Thr Ser Ala
            275                 280                 285

Asn Val Asp Ile Phe Ile Lys Thr Thr Asp Ser Val Gln His Lys Ala
    290                 295                 300

Gly Thr Phe Ala Val Leu Gly Gly Ser Lys Glu Met Lys Trp Gly Phe
305                 310                 315                 320

Asp Arg Val Phe Lys Phe Asp Ile Thr His Val Leu Lys Asp Leu Asp
                325                 330                 335

Leu Thr Ala Asp Gly Asp Phe Glu Val Thr Val Asp Ile Thr Glu Val
            340                 345                 350

Asp Gly Thr Lys Leu Ala Ser Ser Leu Ile Pro His Ala Ser Val Ile
            355                 360                 365

Arg Glu His Ala Arg Gly Lys Leu Asn Arg
    370                 375

<210> SEQ ID NO 70
<211> LENGTH: 419
<212> TYPE: PRT
<213> ORGANISM: Megathura crenulata

<400> SEQUENCE: 70

Asp Ser Ala His Thr Asp Asp Gly His Thr Glu Pro Val Met Ile Arg
1               5                   10                  15

Lys Asp Ile Thr Gln Leu Asp Lys Arg Gln Gln Leu Ser Leu Val Lys
            20                  25                  30

Ala Leu Glu Ser Met Lys Ala Asp His Ser Ser Asp Gly Phe Gln Ala
        35                  40                  45

Ile Ala Ser Phe His Ala Leu Pro Pro Leu Cys Pro Ser Pro Ala Ala
    50                  55                  60

Ser Lys Arg Phe Ala Cys Cys Val His Gly Met Ala Thr Phe Pro Gln
65                  70                  75                  80

Trp His Arg Leu Tyr Thr Val Gln Phe Gln Asp Ser Leu Arg Lys His
                85                  90                  95
```

```
Gly Ala Val Val Gly Leu Pro Tyr Trp Asp Trp Thr Leu Pro Arg Ser
            100                 105                 110

Glu Leu Pro Glu Leu Leu Thr Val Ser Thr Ile His Asp Pro Glu Thr
            115                 120                 125

Gly Arg Asp Ile Pro Asn Pro Phe Ile Gly Ser Lys Ile Glu Phe Glu
            130                 135                 140

Gly Glu Asn Val His Thr Lys Arg Asp Ile Asn Arg Asp Arg Leu Phe
145                 150                 155                 160

Gln Gly Ser Thr Lys Thr His His Asn Trp Phe Ile Glu Gln Ala Leu
                165                 170                 175

Leu Ala Leu Glu Gln Thr Asn Tyr Cys Asp Phe Glu Val Gln Phe Glu
                180                 185                 190

Ile Met His Asn Gly Val His Thr Trp Val Gly Gly Lys Glu Pro Tyr
                195                 200                 205

Gly Ile Gly His Leu His Tyr Ala Ser Tyr Asp Pro Leu Phe Tyr Ile
            210                 215                 220

His His Ser Gln Thr Asp Arg Ile Trp Ala Ile Trp Gln Ser Leu Gln
225                 230                 235                 240

Arg Phe Arg Gly Leu Ser Gly Ser Glu Ala Asn Cys Ala Val Asn Leu
                245                 250                 255

Met Lys Thr Pro Leu Lys Pro Phe Ser Phe Gly Ala Pro Tyr Asn Leu
                260                 265                 270

Asn Asp His Thr His Asp Phe Ser Lys Pro Glu Asp Thr Phe Asp Tyr
                275                 280                 285

Gln Lys Phe Gly Tyr Ile Tyr Asp Thr Leu Glu Phe Ala Gly Trp Ser
            290                 295                 300

Ile Arg Gly Ile Asp His Ile Val Arg Asn Arg Gln Glu His Ser Arg
305                 310                 315                 320

Val Phe Ala Gly Phe Leu Leu Glu Gly Phe Gly Thr Ser Ala Thr Val
                325                 330                 335

Asp Phe Gln Val Cys Arg Thr Ala Gly Asp Cys Glu Asp Ala Gly Tyr
                340                 345                 350

Phe Thr Val Leu Gly Gly Glu Lys Glu Met Pro Trp Ala Phe Asp Arg
            355                 360                 365

Leu Tyr Lys Tyr Asp Ile Thr Glu Thr Leu Asp Lys Met Asn Leu Arg
            370                 375                 380

His Asp Glu Ile Phe Gln Ile Glu Val Thr Ile Thr Ser Tyr Asp Gly
385                 390                 395                 400

Thr Val Leu Asp Ser Gly Leu Ile Pro Thr Pro Ser Ile Ile Tyr Asp
                405                 410                 415

Pro Ala His

<210> SEQ ID NO 71
<211> LENGTH: 418
<212> TYPE: PRT
<213> ORGANISM: Megathura crenulata

<400> SEQUENCE: 71

His Asp Ile Ser Ser His His Leu Ser Leu Asn Lys Val Arg His Asp
1               5                   10                  15

Leu Ser Thr Leu Ser Glu Arg Asp Ile Gly Ser Leu Lys Tyr Ala Leu
            20                  25                  30

Ser Ser Leu Gln Ala Asp Thr Ser Ala Asp Gly Phe Ala Ala Ile Ala
            35                  40                  45
```

```
Ser Phe His Gly Leu Pro Ala Lys Cys Asn Asp Ser His Asn Asn Glu
 50                  55                  60

Val Ala Cys Cys Ile His Gly Met Pro Thr Phe Pro His Trp His Arg
 65                  70                  75                  80

Leu Tyr Thr Leu Gln Phe Glu Gln Ala Leu Arg Arg His Gly Ser Ser
                 85                  90                  95

Val Ala Val Pro Tyr Trp Asp Trp Thr Lys Pro Ile His Asn Ile Pro
            100                 105                 110

His Leu Phe Thr Asp Lys Glu Tyr Tyr Asp Val Trp Arg Asn Lys Val
            115                 120                 125

Met Pro Asn Pro Phe Ala Arg Gly Tyr Val Pro Ser His Asp Thr Tyr
130                 135                 140

Thr Val Arg Asp Val Gln Glu Gly Leu Phe His Leu Thr Ser Thr Gly
145                 150                 155                 160

Glu His Ser Ala Leu Leu Asn Gln Ala Leu Leu Ala Leu Glu Gln His
                165                 170                 175

Asp Tyr Cys Asp Phe Ala Val Gln Phe Glu Val Met His Asn Thr Ile
            180                 185                 190

His Tyr Leu Val Gly Gly Pro Gln Val Tyr Ser Leu Ser Ser Leu His
            195                 200                 205

Tyr Ala Ser Tyr Asp Pro Ile Phe Phe Ile His Ser Phe Val Asp
210                 215                 220

Lys Val Trp Ala Val Trp Gln Ala Leu Gln Glu Lys Arg Gly Leu Pro
225                 230                 235                 240

Ser Asp Arg Ala Asp Cys Ala Val Ser Leu Met Thr Gln Asn Met Arg
                245                 250                 255

Pro Phe His Tyr Glu Ile Asn His Asn Gln Phe Thr Lys Lys His Ala
            260                 265                 270

Val Pro Asn Asp Val Phe Lys Tyr Glu Leu Leu Gly Tyr Arg Tyr Asp
            275                 280                 285

Asn Leu Glu Ile Gly Gly Met Asn Leu His Glu Ile Glu Lys Glu Ile
290                 295                 300

Lys Asp Lys Gln His His Val Arg Val Phe Ala Gly Phe Leu Leu His
305                 310                 315                 320

Gly Ile Arg Thr Ser Ala Asp Val Gln Phe Gln Ile Cys Lys Thr Ser
                325                 330                 335

Glu Asp Cys His His Gly Gly Gln Ile Phe Val Leu Gly Thr Lys
            340                 345                 350

Glu Met Ala Trp Ala Tyr Asn Arg Leu Phe Lys Tyr Asp Ile Thr His
            355                 360                 365

Ala Leu His Asp Ala His Ile Thr Pro Glu Asp Val Phe His Pro Ser
370                 375                 380

Glu Pro Phe Phe Ile Lys Val Ser Val Thr Ala Val Asn Gly Thr Val
385                 390                 395                 400

Leu Pro Ala Ser Ile Leu His Ala Pro Thr Ile Ile Tyr Glu Pro Gly
                405                 410                 415

Leu Gly

<210> SEQ ID NO 72
<211> LENGTH: 241
<212> TYPE: PRT
<213> ORGANISM: Megathura crenulata

<400> SEQUENCE: 72
```

```
Asp His His Glu Asp His His Ser Ser Met Ala Gly His Gly Val
1               5                   10                  15

Arg Lys Glu Ile Asn Thr Leu Thr Thr Ala Glu Val Asp Asn Leu Lys
            20                  25                  30

Asp Ala Met Arg Ala Val Met Ala Asp His Gly Pro Asn Gly Tyr Gln
        35                  40                  45

Ala Ile Ala Ala Phe His Gly Asn Pro Pro Met Cys Pro Met Pro Asp
50                  55                  60

Gly Lys Asn Tyr Ser Cys Cys Thr His Gly Met Ala Thr Phe Pro His
65                  70                  75                  80

Trp His Arg Leu Tyr Thr Lys Gln Met Glu Asp Ala Leu Thr Ala His
                85                  90                  95

Gly Ala Arg Val Gly Leu Pro Tyr Trp Asp Gly Thr Thr Ala Phe Thr
            100                 105                 110

Ala Leu Pro Thr Phe Val Thr Asp Glu Glu Asp Asn Pro Phe His His
        115                 120                 125

Gly His Ile Asp Tyr Leu Gly Val Asp Thr Thr Arg Ser Pro Arg Asp
    130                 135                 140

Lys Leu Phe Asn Asp Pro Glu Arg Gly Ser Ser Phe Phe Tyr Arg
145                 150                 155                 160

Gln Val Leu Leu Ala Leu Glu Gln Thr Asp Phe Cys Gln Phe Glu Val
                165                 170                 175

Gln Phe Glu Ile Thr His Asn Ala Ile His Ser Trp Thr Gly Gly Leu
            180                 185                 190

Thr Pro Tyr Gly Met Ser Thr Leu Glu Tyr Thr Thr Tyr Asp Pro Leu
        195                 200                 205

Phe Trp Leu His His Ala Asn Thr Asp Arg Ile Trp Ala Ile Trp Gln
    210                 215                 220

Ala Leu Gln Glu Tyr Arg Gly Leu Pro Tyr Asp His Ala Asn Cys Glu
225                 230                 235                 240

Ile

<210> SEQ ID NO 73
<211> LENGTH: 98
<212> TYPE: PRT
<213> ORGANISM: Megathura crenulata

<400> SEQUENCE: 73

Lys His His Glu Lys His His Glu Asp His His Glu Asp Ile Leu Val
1               5                   10                  15

Arg Lys Asn Ile His Ser Leu Ser His His Glu Ala Glu Glu Leu Arg
            20                  25                  30

Asp Ala Leu Tyr Lys Leu Gln Asn Asp Glu Ser His Gly Gly Tyr Glu
        35                  40                  45

His Ile Ala Gly Phe His Gly Tyr Pro Asn Leu Cys Pro Glu Lys Gly
50                  55                  60

Asp Glu Lys Tyr Pro Cys Cys Val His Gly Met Ser Ile Phe Pro His
65                  70                  75                  80

Trp His Arg Leu His Thr Ile Gln Leu Glu Arg Ala Leu Lys Lys His
                85                  90                  95

Gly Ser

<210> SEQ ID NO 74
<211> LENGTH: 416
<212> TYPE: PRT
```

<213> ORGANISM: Megathura crenulata

<400> SEQUENCE: 74

```
Ala Asp Ala Lys Asp Phe Gly His Ser Arg Lys Ile Arg Lys Ala Val
1               5                   10                  15
Asp Ser Leu Thr Val Glu Glu Gln Thr Ser Leu Arg Arg Ala Met Ala
            20                  25                  30
Asp Leu Gln Asp Asp Lys Thr Ser Gly Gly Phe Gln Gln Ile Ala Ala
        35                  40                  45
Phe His Gly Glu Pro Lys Trp Cys Pro Ser Pro Glu Ala Glu Lys Lys
    50                  55                  60
Phe Ala Cys Cys Val His Gly Met Ala Val Phe Pro His Trp His Arg
65                  70                  75                  80
Leu Leu Thr Val Gln Gly Glu Asn Ala Leu Arg Lys His Gly Phe Thr
                85                  90                  95
Gly Gly Leu Pro Tyr Trp Asp Trp Thr Arg Ser Met Ser Ala Leu Pro
            100                 105                 110
His Phe Val Ala Asp Pro Thr Tyr Asn Asp Ala Ile Ser Ser Gln Glu
        115                 120                 125
Glu Asp Asn Pro Trp His His Gly His Ile Asp Ser Val Gly His Asp
    130                 135                 140
Thr Thr Arg Asp Val Arg Asp Asp Leu Tyr Gln Ser Pro Gly Phe Gly
145                 150                 155                 160
His Tyr Thr Asp Ile Ala Lys Gln Val Leu Leu Ala Phe Glu Gln Asp
                165                 170                 175
Asp Phe Cys Asp Phe Glu Val Gln Phe Glu Ile Ala His Asn Phe Ile
            180                 185                 190
His Ala Leu Val Gly Gly Asn Glu Pro Tyr Ser Met Ser Ser Leu Arg
        195                 200                 205
Tyr Thr Thr Tyr Asp Pro Ile Phe Phe Leu His Arg Ser Asn Thr Asp
    210                 215                 220
Arg Leu Trp Ala Ile Trp Gln Ala Leu Gln Lys Tyr Arg Gly Lys Pro
225                 230                 235                 240
Tyr Asn Thr Ala Asn Cys Ala Ile Ala Ser Met Arg Lys Pro Leu Gln
                245                 250                 255
Pro Phe Gly Leu Asp Ser Val Ile Asn Pro Asp Asp Glu Thr Arg Glu
            260                 265                 270
His Ser Val Pro Phe Arg Val Phe Asp Tyr Lys Asn Asn Phe Asp Tyr
        275                 280                 285
Glu Tyr Glu Ser Leu Ala Phe Asn Gly Leu Ser Ile Ala Gln Leu Asp
    290                 295                 300
Arg Glu Leu Gln Arg Arg Lys Ser His Asp Arg Val Phe Ala Gly Phe
305                 310                 315                 320
Leu Leu His Glu Ile Gly Gln Ser Ala Leu Val Lys Phe Tyr Val Cys
                325                 330                 335
Lys His Asn Val Ser Asp Cys Asp His Tyr Ala Gly Glu Phe Tyr Ile
                340                 345                 350
Leu Gly Asp Glu Ala Glu Met Pro Trp Arg Tyr Asp Arg Val Tyr Lys
        355                 360                 365
Tyr Glu Ile Thr Gln Gln Leu His Asp Leu Asp Leu His Val Gly Asp
    370                 375                 380
Asn Phe Phe Leu Lys Tyr Glu Ala Phe Asp Leu Asn Gly Gly Ser Leu
385                 390                 395                 400
```

-continued

```
Gly Gly Ser Ile Phe Ser Gln Pro Ser Val Ile Phe Glu Pro Ala Ala
            405                 410                 415
```

<210> SEQ ID NO 75
<211> LENGTH: 416
<212> TYPE: PRT
<213> ORGANISM: Megathura crenulata

<400> SEQUENCE: 75

```
Ala Asp Ala Lys Asp Phe Gly His Ser Arg Lys Ile Arg Lys Ala Val
1               5                   10                  15

Asp Ser Leu Thr Val Glu Glu Gln Thr Ser Leu Arg Arg Ala Met Ala
            20                  25                  30

Asp Leu Gln Asp Asp Lys Thr Ser Gly Gly Phe Gln Gln Ile Ala Ala
        35                  40                  45

Phe His Gly Glu Pro Lys Trp Cys Pro Ser Pro Glu Ala Glu Lys Lys
    50                  55                  60

Phe Ala Cys Cys Val His Gly Met Ala Val Phe Pro His Trp His Arg
65                  70                  75                  80

Leu Leu Thr Val Gln Gly Glu Asn Ala Leu Arg Lys His Gly Phe Thr
                85                  90                  95

Gly Gly Leu Pro Tyr Trp Asp Trp Thr Arg Ser Met Ser Ala Leu Pro
            100                 105                 110

His Phe Val Ala Asp Pro Thr Tyr Asn Asp Ala Ile Ser Ser Gln Glu
        115                 120                 125

Glu Asp Asn Pro Trp His His Gly His Ile Asp Ser Val Gly His Asp
    130                 135                 140

Thr Thr Arg Asp Val Arg Asp Asp Leu Tyr Gln Ser Pro Gly Phe Gly
145                 150                 155                 160

His Tyr Thr Asp Ile Ala Lys Gln Val Leu Leu Ala Phe Glu Gln Asp
                165                 170                 175

Asp Phe Cys Asp Phe Glu Val Gln Phe Glu Ile Ala His Asn Phe Ile
            180                 185                 190

His Ala Leu Val Gly Gly Asn Glu Pro Tyr Ser Met Ser Ser Leu Arg
        195                 200                 205

Tyr Thr Thr Tyr Asp Pro Ile Phe Phe Leu His Arg Ser Asn Thr Asp
    210                 215                 220

Arg Leu Trp Ala Ile Trp Gln Ala Leu Gln Lys Tyr Arg Gly Lys Pro
225                 230                 235                 240

Tyr Asn Thr Ala Asn Cys Ala Ile Ala Ser Met Arg Lys Pro Leu Gln
                245                 250                 255

Pro Phe Gly Leu Asp Ser Val Ile Asn Pro Asp Asp Glu Thr Arg Glu
            260                 265                 270

His Ser Val Pro Phe Arg Val Phe Asp Tyr Lys Asn Asn Phe Asp Tyr
        275                 280                 285

Glu Tyr Glu Ser Leu Ala Phe Asn Gly Leu Ser Ile Ala Gln Leu Asp
    290                 295                 300

Arg Glu Leu Gln Arg Arg Lys Ser His Asp Arg Val Phe Ala Gly Phe
305                 310                 315                 320

Leu Leu His Glu Ile Gly Gln Ser Ala Leu Val Lys Phe Tyr Val Cys
                325                 330                 335

Lys His Asn Val Ser Asp Cys Asp His Tyr Ala Gly Glu Phe Tyr Ile
            340                 345                 350

Leu Gly Asp Glu Ala Glu Met Pro Trp Arg Tyr Asp Arg Val Tyr Lys
        355                 360                 365
```

-continued

```
Tyr Glu Ile Thr Gln Gln Leu His Asp Leu Asp Leu His Val Gly Asp
        370                 375                 380

Asn Phe Phe Leu Lys Tyr Glu Ala Phe Asp Leu Asn Gly Gly Ser Leu
385                 390                 395                 400

Gly Gly Ser Ile Phe Ser Gln Pro Ser Val Ile Phe Glu Pro Ala Ala
                405                 410                 415

<210> SEQ ID NO 76
<211> LENGTH: 419
<212> TYPE: PRT
<213> ORGANISM: Megathura crenulata

<400> SEQUENCE: 76

Gly Ser His Gln Ala Asp Glu Tyr Arg Glu Ala Val Thr Ser Ala Ser
1               5                   10                  15

His Ile Arg Lys Asn Ile Arg Asp Leu Ser Glu Gly Glu Ile Glu Ser
            20                  25                  30

Ile Arg Ser Ala Phe Leu Gln Ile Gln Lys Glu Gly Ile Tyr Glu Asn
        35                  40                  45

Ile Ala Lys Phe His Gly Lys Pro Gly Leu Cys Glu His Asp Gly His
    50                  55                  60

Pro Val Ala Cys Cys Val His Gly Met Pro Thr Phe Pro His Trp His
65                  70                  75                  80

Arg Leu Tyr Val Leu Gln Val Glu Asn Ala Leu Leu Glu Arg Gly Ser
                85                  90                  95

Ala Val Ala Val Pro Tyr Trp Asp Trp Thr Glu Lys Ala Asp Ser Leu
            100                 105                 110

Pro Ser Leu Ile Asn Asp Ala Thr Tyr Phe Asn Ser Arg Ser Gln Thr
        115                 120                 125

Phe Asp Pro Asn Pro Phe Phe Arg Gly His Ile Ala Phe Glu Asn Ala
    130                 135                 140

Val Thr Ser Arg Asp Pro Gln Pro Glu Leu Trp Asp Asn Lys Asp Phe
145                 150                 155                 160

Tyr Glu Asn Val Met Leu Ala Leu Glu Gln Asp Asn Phe Cys Asp Phe
                165                 170                 175

Glu Ile Gln Leu Glu Leu Ile His Asn Ala Leu His Ser Arg Leu Gly
            180                 185                 190

Gly Arg Ala Lys Tyr Ser Leu Ser Ser Leu Asp Tyr Thr Ala Phe Asp
        195                 200                 205

Pro Val Phe Phe Leu His His Ala Asn Val Asp Arg Ile Trp Ala Ile
    210                 215                 220

Trp Gln Asp Leu Gln Arg Tyr Arg Lys Lys Pro Tyr Asn Glu Ala Asp
225                 230                 235                 240

Cys Ala Val Asn Glu Met Arg Lys Pro Leu Gln Pro Phe Asn Asn Pro
                245                 250                 255

Glu Leu Asn Ser Asp Ser Met Thr Leu Lys His Asn Leu Pro Gln Asp
            260                 265                 270

Ser Phe Asp Tyr Gln Asn Arg Phe Arg Tyr Gln Tyr Asp Asn Leu Gln
        275                 280                 285

Phe Asn His Phe Ser Ile Gln Lys Leu Asp Gln Thr Ile Gln Ala Arg
    290                 295                 300

Lys Gln His Asp Arg Val Phe Ala Gly Phe Ile Leu His Asn Ile Gly
305                 310                 315                 320

Thr Ser Ala Val Val Asp Ile Tyr Ile Cys Val Glu Gln Gly Gly Glu
```

```
                    325                 330                 335
Gln Asn Cys Lys Thr Lys Ala Gly Ser Phe Thr Ile Leu Gly Gly Glu
                340                 345                 350
Thr Glu Met Pro Phe His Phe Asp Arg Leu Tyr Lys Phe Asp Ile Thr
            355                 360                 365
Ser Ala Leu His Lys Leu Gly Val Pro Leu Asp Gly His Gly Phe Asp
        370                 375                 380
Ile Lys Val Asp Val Arg Ala Val Asn Gly Ser His Leu Asp Gln His
385                 390                 395                 400
Ile Leu Asn Glu Pro Ser Leu Leu Phe Val Pro Gly Glu Arg Lys Asn
                405                 410                 415
Ile Tyr Tyr

<210> SEQ ID NO 77
<211> LENGTH: 413
<212> TYPE: PRT
<213> ORGANISM: Megathura crenulata

<400> SEQUENCE: 77

Asp Gly Leu Ser Gln His Asn Leu Val Arg Lys Glu Val Ser Ser Leu
1               5                   10                  15
Thr Thr Leu Glu Lys His Phe Leu Arg Lys Ala Leu Lys Asn Met Gln
            20                  25                  30
Ala Asp Asp Ser Pro Asp Gly Tyr Gln Ala Ile Ala Ser Phe His Ala
        35                  40                  45
Leu Pro Pro Leu Cys Pro Ser Pro Ala Ala His Arg His Ala Cys
    50                  55                  60
Cys Leu His Gly Met Ala Thr Phe Pro Gln Trp His Arg Leu Tyr Thr
65                  70                  75                  80
Val Gln Phe Glu Asp Ser Leu Lys Arg His Gly Ser Ile Val Gly Leu
                85                  90                  95
Pro Tyr Trp Asp Trp Leu Lys Pro Gln Ser Ala Leu Pro Asp Leu Val
            100                 105                 110
Thr Gln Glu Thr Tyr Glu His Leu Phe Ser His Lys Thr Phe Pro Asn
        115                 120                 125
Pro Phe Leu Lys Ala Asn Ile Glu Phe Glu Gly Glu Gly Val Thr Thr
    130                 135                 140
Glu Arg Asp Val Asp Ala Glu His Leu Phe Ala Lys Gly Asn Leu Val
145                 150                 155                 160
Tyr Asn Asn Trp Phe Cys Asn Gln Ala Leu Tyr Ala Leu Glu Gln Glu
                165                 170                 175
Asn Tyr Cys Asp Phe Glu Ile Gln Phe Glu Ile Leu His Asn Gly Ile
            180                 185                 190
His Ser Trp Val Gly Gly Ser Lys Thr His Ser Ile Gly His Leu His
        195                 200                 205
Tyr Ala Ser Tyr Asp Pro Leu Phe Tyr Ile His His Ser Gln Thr Asp
    210                 215                 220
Arg Ile Trp Ala Ile Trp Gln Ala Leu Gln Glu His Arg Gly Leu Ser
225                 230                 235                 240
Gly Lys Glu Ala His Cys Ala Leu Glu Gln Met Lys Asp Pro Leu Lys
                245                 250                 255
Pro Phe Ser Phe Gly Ser Pro Tyr Asn Leu Asn Lys Arg Thr Gln Glu
            260                 265                 270
Phe Ser Lys Pro Glu Asp Thr Phe Asp Tyr His Arg Phe Gly Tyr Glu
```

```
                275                 280                 285
Tyr Asp Ser Leu Glu Phe Val Gly Met Ser Val Ser Leu His Asn
            290                 295                 300

Tyr Ile Lys Gln Gln Gln Glu Ala Asp Arg Val Phe Ala Gly Phe Leu
305                 310                 315                 320

Leu Lys Gly Phe Gly Gln Ser Ala Ser Val Ser Phe Asp Ile Cys Arg
                325                 330                 335

Pro Asp Gln Ser Cys Gln Glu Ala Gly Tyr Phe Ser Val Leu Gly Gly
            340                 345                 350

Ser Ser Glu Met Pro Trp Gln Phe Asp Arg Leu Tyr Lys Tyr Asp Ile
        355                 360                 365

Thr Lys Thr Leu Lys Asp Met Lys Leu Arg Tyr Asp Asp Thr Phe Thr
    370                 375                 380

Ile Lys Val His Ile Lys Asp Ile Ala Gly Ala Glu Leu Asp Ser Asp
385                 390                 395                 400

Leu Ile Pro Thr Pro Ser Val Leu Leu Glu Glu Gly Lys
                405                 410

<210> SEQ ID NO 78
<211> LENGTH: 417
<212> TYPE: PRT
<213> ORGANISM: Megathura crenulata

<400> SEQUENCE: 78

His Gly Ile Asn Val Arg His Val Gly Arg Asn Arg Ile Arg Met Glu
1               5                   10                  15

Leu Ser Glu Leu Thr Glu Arg Asp Leu Ala Ser Leu Lys Ser Ala Met
            20                  25                  30

Arg Ser Leu Gln Ala Asp Asp Gly Val Asn Gly Tyr Gln Ala Ile Ala
        35                  40                  45

Ser Phe His Gly Leu Pro Ala Ser Cys His Asp Asp Glu Gly His Glu
    50                  55                  60

Ile Ala Cys Cys Ile His Gly Met Pro Val Phe Pro His Trp His Arg
65                  70                  75                  80

Leu Tyr Thr Leu Gln Met Asp Met Ala Leu Leu Ser His Gly Ser Ala
                85                  90                  95

Val Ala Ile Pro Tyr Trp Asp Trp Thr Lys Pro Ile Ser Lys Leu Pro
            100                 105                 110

Asp Leu Phe Thr Ser Pro Glu Tyr Tyr Asp Pro Trp Arg Asp Ala Val
        115                 120                 125

Val Asn Asn Pro Phe Ala Lys Gly Tyr Ile Lys Ser Glu Asp Ala Tyr
    130                 135                 140

Thr Val Arg Asp Pro Gln Asp Ile Leu Tyr His Leu Gln Asp Glu Thr
145                 150                 155                 160

Gly Thr Ser Val Leu Leu Asp Gln Thr Leu Leu Ala Leu Glu Gln Thr
                165                 170                 175

Asp Phe Cys Asp Phe Glu Val Gln Phe Glu Val Val His Asn Ala Ile
            180                 185                 190

His Tyr Leu Val Gly Gly Arg Gln Val Tyr Ala Leu Ser Ser Gln His
        195                 200                 205

Tyr Ala Ser Tyr Asp Pro Ala Phe Phe Ile His His Ser Phe Val Asp
    210                 215                 220

Lys Ile Trp Ala Val Trp Gln Ala Leu Gln Lys Lys Arg Lys Arg Pro
225                 230                 235                 240
```

-continued

Tyr His Lys Ala Asp Cys Ala Leu Asn Met Met Thr Lys Pro Met Arg
                245                 250                 255

Pro Phe Ala His Asp Phe Asn His Asn Gly Phe Thr Lys Met His Ala
            260                 265                 270

Val Pro Asn Thr Leu Phe Asp Phe Gln Asp Leu Phe Tyr Thr Tyr Asp
        275                 280                 285

Asn Leu Glu Ile Ala Gly Met Asn Val Asn Gln Leu Glu Ala Glu Ile
    290                 295                 300

Asn Arg Arg Lys Ser Gln Thr Arg Val Phe Ala Gly Phe Leu Leu His
305                 310                 315                 320

Gly Ile Gly Arg Ser Ala Asp Val Arg Phe Trp Ile Cys Lys Thr Ala
                325                 330                 335

Asp Asp Cys His Ala Ser Gly Met Ile Phe Ile Leu Gly Gly Ser Lys
            340                 345                 350

Glu Met His Trp Ala Tyr Asp Arg Asn Phe Lys Tyr Asp Ile Thr Gln
        355                 360                 365

Ala Leu Lys Ala Gln Ser Ile His Pro Glu Asp Val Phe Asp Thr Asp
    370                 375                 380

Ala Pro Phe Phe Ile Lys Val Glu Val His Gly Val Asn Lys Thr Ala
385                 390                 395                 400

Leu Pro Ser Ser Ala Ile Pro Ala Pro Thr Ile Ile Tyr Ser Ala Gly
                405                 410                 415

Glu

<210> SEQ ID NO 79
<211> LENGTH: 397
<212> TYPE: PRT
<213> ORGANISM: Megathura crenulata
<220> FEATURE:
<221> NAME/KEY: misc_feature
<222> LOCATION: (55)..(55)
<223> OTHER INFORMATION: Xaa can be any naturally occurring amino acid

<400> SEQUENCE: 79

Asp His Ile Ala Gly Ser Gly Val Arg Lys Asp Val Thr Ser Leu Thr
1               5                   10                  15

Ala Ser Glu Ile Glu Asn Leu Arg His Ala Leu Gln Ser Val Met Asp
            20                  25                  30

Asp Asp Gly Pro Asn Gly Phe Gln Ala Ile Ala Ala Tyr His Gly Ser
        35                  40                  45

Pro Pro Met Cys His Met Xaa Ala Ala Asp Gly Arg Asp Val Ala Cys
    50                  55                  60

Cys Thr His Gly Met Ala Ser Phe Pro His Trp His Arg Leu Phe Val
65                  70                  75                  80

Lys Gln Met Glu Asp Ala Leu Ala Ala His Gly Ala His Ile Gly Ile
                85                  90                  95

Pro Tyr Trp Asp Trp Thr Ser Ala Phe Ser His Leu Pro Ala Leu Val
            100                 105                 110

Thr Asp His Glu His Asn Pro Phe His His Gly His Ile Ala His Arg
        115                 120                 125

Asn Val Asp Thr Ser Arg Ser Pro Arg Asp Met Leu Phe Asn Asp Pro
    130                 135                 140

Glu His Gly Ser Glu Ser Phe Phe Tyr Arg Gln Val Leu Leu Ala Leu
145                 150                 155                 160

Glu Gln Thr Asp Phe Cys Gln Phe Glu Val Gln Phe Glu Ile Thr His
                165                 170                 175

```
Asn Ala Ile His Ser Trp Thr Gly Gly His Thr Pro Tyr Gly Met Ser
            180                 185                 190
Ser Leu Glu Tyr Thr Ala Tyr Asp Pro Leu Phe Tyr Leu His His Ser
        195                 200                 205
Asn Thr Asp Arg Ile Trp Ala Ile Trp Gln Ala Leu Gln Lys Tyr Arg
    210                 215                 220
Gly Phe Gln Tyr Asn Ala Ala His Cys Asp Ile Gln Val Leu Lys Gln
225                 230                 235                 240
Pro Leu Lys Pro Phe Ser Glu Ser Arg Asn Pro Asn Pro Val Thr Arg
                245                 250                 255
Ala Asn Ser Arg Ala Val Asp Ser Phe Asp Tyr Glu Arg Leu Asn Tyr
            260                 265                 270
Gln Tyr Asp Thr Leu Thr Phe His Gly His Ser Ile Ser Glu Leu Asp
        275                 280                 285
Ala Met Leu Gln Glu Arg Lys Lys Glu Glu Arg Thr Phe Ala Ala Phe
    290                 295                 300
Leu Leu His Gly Phe Gly Ala Ser Ala Asp Val Ser Phe Asp Val Cys
305                 310                 315                 320
Thr Pro Asp Gly His Cys Ala Phe Ala Gly Thr Phe Ala Val Leu Gly
                325                 330                 335
Gly Glu Leu Glu Met Pro Trp Ser Phe Glu Arg Leu Phe Arg Tyr Asp
            340                 345                 350
Ile Thr Lys Val Leu Lys Gln Met Asn Leu His Tyr Asp Ser Glu Phe
        355                 360                 365
His Phe Glu Leu Lys Ile Val Gly Thr Asp Gly Thr Glu Leu Pro Ser
    370                 375                 380
Asp Arg Ile Lys Ser Pro Thr Ile Glu His His Gly Gly
385                 390                 395

<210> SEQ ID NO 80
<211> LENGTH: 1266
<212> TYPE: DNA
<213> ORGANISM: Haliotis tuberculata

<400> SEQUENCE: 80
cttgttcagt ttctactcgt cgcccttgtg gtgggggctg gagcagacaa cgtcgtcaga      60
aaggacgtga gtcacctcac ggatgacgag gtgcaagctc tccacggcgc cctccatgac     120
gtcactgcat ctacagggcc tctgagtttc gaagacataa catcttacca tgccgcacca     180
gcgtcgtgtg actacaaggg acggaagatc gcctgctgtg tccacggtat gcccagtttc     240
cccttctggc acagggcata tgtcgtccaa gccgagcggg cactgttgtc caaacggaag     300
actgtcggaa tgccttactg ggactggacg caaacgctga ctcacttacc atctcttgtg     360
actgaaccca tctacattga cagtaaaggt ggaaaggctc aaaccaacta ctggtaccgc     420
ggcgagatag cgttcatcaa taagaagact gcgcgagctg tagatgatcg cctattcgag     480
aaggtggagc tggtcactca cacacatctt atggagactg tcctcgacgc tctcgaacag     540
gacgaattct gtaaatttga atccagttc gagttggctc ataatgctat ccattacttg     600
gttggcggta aatttgaata ttcaatgtca aacttggaat acacctccta cgaccccatc     660
ttcttcctcc accactccaa cgttgaccgc tcttcgcca tctggcagcg tcttcaggaa     720
ctgcgaggaa agaatcccaa tgcaatggac tgtgcacatg aactcgctca ccagcaactc     780
caacccttca cagggacag caatccagtc cagctcacaa aggaccactc gacacctgct     840
```

| | | |
|---|---|---|
| gacctctttg attacaaaca acttggatac agctacgaca gcttaaacct gaatggaatg | 900 |
| acgccagaac agctgaaaac agaactagac gaacgccact ccaaagaacg tgcgtttgca | 960 |
| agcttccgac tcagtggctt tgggggttct gccaacgttg ttgtctatgc atgtgtccct | 1020 |
| gatgatgatc cacgcagtga tgactactgc gagaaagcag gcgacttctt cattcttggg | 1080 |
| ggtcaaagcg aaatgccgtg gagattctac agacccttct tctatgatgt aactgaagcg | 1140 |
| gtacatcacc ttggagtccc gctaagtggc cactactatg tgaaaacaga actcttcagc | 1200 |
| gtgaatggca cagcactttc acctgatctt cttcctcaac caactgttgc ctaccgacct | 1260 |
| gggaaa | 1266 |

<210> SEQ ID NO 81
<211> LENGTH: 1257
<212> TYPE: DNA
<213> ORGANISM: Haliotis tuberculata

<400> SEQUENCE: 81

| | |
|---|---|
| ggtcaccttg acccacctgt gcatcatcgc cacgatgacg atcttattgt tcgaaaaaat | 60 |
| atagatcatt tgactcgtga agaggaatac gagctaagga tggctctgga gagattccag | 120 |
| gccgacacat ccgttgatgg gtaccaggct acagtagagt accatggcct tcctgctcgt | 180 |
| tgtccacgac cagatgcaaa agtcaggttc gcctgttgta tgcatggcat ggcatccttc | 240 |
| cctcactggc accggctgtt cgttacccag gtggaagatg ctcttgtacg gcgtggatcg | 300 |
| cctatcggtg ttccttattg ggactggaca aaacctatga ctcaccttcc agacttggca | 360 |
| tcaaatgaga cgtacgtaga cccgtatgga catacacatc ataatccatt cttcaatgca | 420 |
| aatatatctt ttgaggaggg acaccatcac acgagcagga tgatagattc gaaactgttt | 480 |
| gccccagtcg cttttgggga gcattcccat ctgtttgatg gaatcctgta cgcatttgag | 540 |
| caggaagatt tctgcgactt tgagattcag tttgagttag tccataattc tattcatgcg | 600 |
| tggataggcg gttccgaaga ttactccatg gccaccctgc attacacagc ctttgacccc | 660 |
| attttctacc ttcatcattc caatgtcgat cgtctatggg caatctggca agctcttcaa | 720 |
| atcaggagac acaagccata tcaagcccac tgtgcacagt ctgtggaaca gttgccaatg | 780 |
| aagccatttg ctttcccatc acctcttaac aacaacgaga agacacatag tcattcagtc | 840 |
| ccgactgaca tttatgacta cgaggaagtg ctgcactaca gctacgatga tctaacgttt | 900 |
| ggtgggatga accttgaaga aatagaagaa gctatacatc tcagacaaca gcatgaacga | 960 |
| gtcttcgcgg gatttctcct tgctggaata ggaacatctg cacttgttga cattttcata | 1020 |
| aataaaccgg ggaaccaacc actcaaagct ggagatattg ccattcttgg tggtgccaag | 1080 |
| gaaatgcctt gggcgtttga ccgcttgtat aaggtcgaaa taactgactc attgaagaca | 1140 |
| cttttctctcg atgtcgatgg agattatgaa gtcacttttta aaattcatga tatgcacgga | 1200 |
| aacgctcttg atacggacct gattccacac gcagcagttg tttctgagcc agctcac | 1257 |

<210> SEQ ID NO 82
<211> LENGTH: 1242
<212> TYPE: DNA
<213> ORGANISM: Haliotis tuberculata

<400> SEQUENCE: 82

| | |
|---|---|
| cctacctttg aggatgaaaa gcacagctta cgaatcagaa aaaatgtcga cagcttgact | 60 |
| cctgaagaaa caaatgaact gcgtaaagcc ctggagcttc ttgaaaatga tcatactgca | 120 |
| ggtggattca atcagcttgg cgccttccat ggagagccta aatggtgccc taatcctgaa | 180 |

```
gcggagcaca aggttgcatg ctgtgttcat ggcatggctg ttttccctca ttggcacagg      240
cttcttgctc tccaggcgga gaatgctctt agaaagcatg ggtacagtgg tgctctacca      300
tactgggatt ggactcgccc cctttcccaa cttcctgatc tggttagtca tgagcagtat      360
acagatcctt ccgaccatca cgtgaagcat aacccgtggt tcaatggcca catcgataca      420
gtaaatcagg ataccaccag aagcgtacgg gaggatcttt atcaacaacc tgaatttgga      480
catttcacgg atattgctca acaagtcctc ttagcattag aacaagatga cttctgttcg      540
tttgaagtgc agtatgagat ttcccataat tttatccatg cacttgtagg aggaaccgac      600
gcttatggca tggcatcgct gagatataca gcatacgatc caatctttt cttgcatcat       660 tcaaacaccg acaggatctg ggctatttgg caatccctgc aaaaatacag aggcaaaccg      720
tacaacactg ccaactgcgc catagaatct atgagaaggc ccctgcaacc atttggacta      780
agcagtgcca ttaaccctga cagaatcacc agagagcatg ctatcccgtt tgatgtcttc      840
aactatagag ataaccttca ttacgtatat gatacccctgg aatttaatgg tttgtcgatt     900
tcacaacttg atagagagct ggaaaaaatc aagagtcacg aaagagtatt tgctggattc      960
ttgctgtcgg ggattaaaaa atctgctctt gtgaaattcg aagtttgtac tccacctgat     1020
aattgtcata agcagggga gttttatcta ctcggggacg aaaacgagat ggcttgggcc      1080
tatgaccgac ttttcaagta tgatattact caggttctgg aagcaaacca tctacacttc     1140
tatgatcatc tcttcattcg ctacgaagtc tttgatctta aaggagtgag tttgggaact     1200
gacctgttcc acactgcaaa tgtggtacat gattccggca ca                        1242

<210> SEQ ID NO 83
<211> LENGTH: 1239
<212> TYPE: DNA
<213> ORGANISM: Haliotis tuberculata

<400> SEQUENCE: 83
ggcacccgtg atcgtgataa ctacgttgaa gaagttactg gggccagtca tatcaggaag       60
aatttgaacg acctcaatac cggagaaatg gaaagcctta gagctgcttt cctgcatatt      120
caggacgacg gaacatatga atctattgcc cagtaccatg gcaaaccagg caaatgtcaa      180
ttgaatgatc ataatattgc gtgttgtgtc catggtatgc ctaccttccc ccagtggcac      240
agactgtatg tggttcaggt ggagaatgct ctcctaaaca ggggatctgg tgtggctgtt      300
ccttactggg agtggactgc tcccatagac catctacctc atttcattga tgatgcaaca      360
tacttcaatt cccgacaaca gcggtacgac cctaaccctt tcttcagggg aaaggttact      420
tttgaaaacg cagtcacaac aagggaccca caagccgggc tcttcaactc agattatatg      480
tatgagaatg ttttacttgc actggagcag gaaaattatt gtgactttga aattcagttt      540
gagcttgttc ataacgcact tcattccatg ctgggaggta aagggcagta ctccatgtcc      600
tccctggact attctgcgtt tgatcccgtc ttcttcctac atcatgccaa cacggacaga      660
ctgtgggcaa tctggcagga actacaaaga ttccgagaac tgccttatga agaagcgaac      720
tgtgcaatca acctcatgca tcaaccactg aagccgttca gtgatccaca tgagaatcac      780
gacaatgtca ctttgaaata ctcaaaacca caggacggat tcgactacca gaaccacttc      840
ggatacaagt atgacaacct tgagttccat cacttatcta tcccaagtct tgatgctacc      900
ctgaagcaaa ggagaaatca cgacagagtg tttgcgggct tccttcttca taacatagga      960
acttctgctg acataactat ctacatatgt ctgcctgacg gacggcgtgg caatgactgc     1020
```

| -continued | |
|---|---|
| agtcatgagg cgggaacatt ctatatcctc ggaggcgaaa cagagatgcc tttatctttt | 1080 |
| gaccgtttgt ataaatttga aatcaccaaa ccactgcaac agttaggagt caagctgcat | 1140 |
| ggtggagttt tcgaactgga gcttgagatc aaggcataca acggttccta tctggatccc | 1200 |
| cataccttg atccaactat catctttgaa cctggaaca | 1239 |

<210> SEQ ID NO 84
<211> LENGTH: 1260
<212> TYPE: DNA
<213> ORGANISM: Haliotis tuberculata

<400> SEQUENCE: 84

| | |
|---|---|
| gatacccata tcttggacca cgaccatgag gaagagatac ttgtcaggaa gaatataatt | 60 |
| gatttgagcc caagggagag ggtttctcta gtcaaagctt tgcaaagaat gaagaatgat | 120 |
| cgctccgctg atgggtacca agccattgcc tctttccatg ccctgccacc actctgtccc | 180 |
| aatccatctg cagctcaccg ttatgcttgc tgtgtccatg gcatggctac atttccccag | 240 |
| tggcacagac tgtacactgt tcaggttcag gatgccctga ggagacatgg ttcacttgtt | 300 |
| ggtattcctt actgggactg gacaaaacca gtcaacgagt acccgagct tctttcttca | 360 |
| gcaacatttt atcatccaat ccggaatatt aatatttcaa atccattcct cggggctgac | 420 |
| atagaatttg aaggaccggg cgttcataca gagaggcaca taaatactga gcgcctgttt | 480 |
| cacagtgggg atcatgacgg ataccacaac tggttcttcg aaactgttct ctttgctttg | 540 |
| gaacaggaag attactgcga ttttgaaata caatttgaga tagcccataa tggcatccac | 600 |
| acatggattg gtggaagcgc agtatatggc atgggacacc ttcactatgc atcatatgat | 660 |
| ccaattttct acatccacca ttcacagacg gacagaatat gggctatttg caagagctg | 720 |
| cagaagtaca ggggtctatc tggttcggaa gcaaactgtg ccattgaaca tatgagaaca | 780 |
| cccttgaagc ctttcagctt tgggccaccc tacaatttga atagtcatac gcaagaatat | 840 |
| tcaaagcctg aggacacgtt tgactataag aagtttggat acagatatga tagtctggaa | 900 |
| ttggaggggc gatcaatttc tcgcattgat gaacttatcc agcagagaca ggagaaagac | 960 |
| agaacttttg cagggttcct ccttaaaggt tttggtacat ccgcatctgt gtcattgcaa | 1020 |
| gtttgcagag ttgatcacac ctgtaaagat gcgggctatt tcactattct gggaggatca | 1080 |
| gccgaaatgc catgggcatt cgacaggctt tataagtatg acattactaa aactcttcac | 1140 |
| gacatgaacc tgaggcacga ggacactttc tctatagacg taactatcac gtcttacaat | 1200 |
| ggaacagtac tctcgggaga cctcattcag acgccctcca ttatatttgt acctggacgc | 1260 |

<210> SEQ ID NO 85
<211> LENGTH: 1251
<212> TYPE: DNA
<213> ORGANISM: Haliotis tuberculata

<400> SEQUENCE: 85

| | |
|---|---|
| cataaactca actcacggaa acatacacct aacagagtcc gccatgagct aagtagcctt | 60 |
| agttcccgtg acatagcaag cttgaaggca gctttgacaa gccttcaaca tgataatggg | 120 |
| actgatggtt atcaagctat tgctgccttc catggcgttc ctgcgcagtg ccacgagcca | 180 |
| tctggacgtg agatcgcctg ttgcatccac ggcatggcga cgtttcctca ctggcaccgg | 240 |
| ttgtacactc tgcagttgga gcaagcgctg cgcagacacg ggtccagtgt tgctgttcca | 300 |
| tactgggact ggaccaagcc aatcaccgaa ctgccacaca ttctgacaga cggagaatat | 360 |
| tatgacgttt ggcaaaatgc cgtcttggcc aatccgtttg caagaggtta tgtgaaaatt | 420 |

```
aaagatgcat ttacggtgag aaatgtccag gaaagtctgt tcaaaatgtc aagttttgga      480
aagcactcgc ttctgtttga ccaggctttg ttggctcttg aacaaactga ctactgtgac      540
ttcgaagttc agtttgaagt gatgcataac acgatccatt atctcgtagg agggcgtcaa      600
acgtacgcct tctcctctct cgagtattcc tcatacgatc caatcttctt tattcaccac      660
tcgtttgttg acaaaatatg ggctgtatgg caagaactgc aaagcaggag acatctacag      720
tttagaacag ctgattgtgc tgtgggcctc atgggtcagg caatgaggcc tttcaacaag      780
gatttcaacc acaactcgtt caccaagaag cacgcagtcc ctaatacagt atttgattat      840
gaagatcttg gctataacta tgacaacctt gaaatcagtg gtttaaactt aaatgagatc      900
gaggcgttaa tagcaaaacg caagtcacat gctagagtct ttgctgggtt cctgttgttt      960
ggattaggaa cttcggctga tatacatctg gaaatttgca agacatcgga aaactgccat     1020
gatgctggtg tgattttcat ccttggaggt tctgcagaga tgcattgggc atacaaccgc     1080
ctctacaagt atgacattac agaagcattg caggaatttg acatcaaccc tgaagatgtt     1140
ttccatgctg atgaaccatt tttcctgagg ctgtcggttg ttgctgtgaa tggaactgtc     1200
attccatcgt ctcatcttca ccagccaacg ataatctatg aaccaggcga a              1251

<210> SEQ ID NO 86
<211> LENGTH: 1209
<212> TYPE: DNA
<213> ORGANISM: Haliotis tuberculata

<400> SEQUENCE: 86
gatcaccatg acgaccatca gtcgggaagc atagcaggat ccggggtccg caaggacgtg       60
aacaccttga ctaaggctga gaccgacaac ctgagggagg cgctgtgggg tgtcatggca      120
gaccacggtc ccaatggctt tcaagctatt gctgctttcc atggaaaacc agctttgtgt      180
cccatgcctg atggccacaa ctactcatgt tgtactcacg gcatggctac cttcccacac      240
tggcatcgcc tctacaccaa gcagatggag gatgcaatga gggcgcatgg gtctcatgtc      300
ggcctgccct actgggactg gactgctgcc ttcacccacc tgccaacact ggtcaccgac      360
acggacaaca ccccttcca acatggacac attgattatc tcaatgtcag cacaactcga      420
tctccccgag acatgctgtt caacgacccc gagcatggat cagagtcgtt cttctacaga      480
caagtcctct tagctctgga acaaactgat ttctgcaaat tcgaagttca gtttgagata      540
acccacaatg ccatccattc ctggacaggt ggccacagcc ctacggaat gtccactctc      600 gacttcactg cctacgatcc tctcttctgg cttcaccact ccaacaccga cagaatctgg      660
gctgtctggc aagcttttgca agaatacaga ggacttccat acaaccatgc caattgtgag      720
atccaggcaa tgaaaacgcc cctgaggcct ttcagtgacg atatcaacca caacccagtc      780
acaaaggcta acgcgaagcc attagatgtg ttcgagtata atcggttgag cttccagtac      840
gacaacctca tcttccatgg atacagtatt ccggaacttg atcgcgtgct tgaagaaaga      900
aaggaggagg acagaatatt tgctgccttc cttctcagtg aatcaagcg tagtgctgat      960 gtagtgttcg acatatgcca gccagaacac gaatgtgtgt tcgcagggac ttttgcgatt     1020
ttgggagggg agctagaaat gccctggtcc ttcgacagac tgttccgcta tgatatcacc     1080
aaggtgatga agcagctaca cctgaggcat gactctgact ttaccttcag ggtgaagatt     1140
gtcggcaccg acgaccacga gcttccttca gacagtgtca agcaccaac tattgaattt     1200 gaaccgggc                                                             1209
```

<210> SEQ ID NO 87
<211> LENGTH: 1536
<212> TYPE: DNA
<213> ORGANISM: Haliotis tuberculata

<400> SEQUENCE: 87

| | | | | | |
|---|---|---|---|---|---|
| gtgcacagag | gcggaaacca | cgaagatgaa | caccatgatg | acagactcgc | agatgtcctg | 60 |
| atcaggaaag | aagttgactt | cctctccctg | caagaggcca | acgcaattaa | ggatgcactg | 120 |
| tacaagctcc | agaatgacga | cagtaaaggg | ggctttgagg | ccatagctgg | ctatcacggg | 180 |
| tatcctaata | tgtgtccaga | aagaggtacc | gacaagtatc | cctgctgtgt | ccacggaatg | 240 |
| cccgtgttcc | cccactggca | ccgcctgcat | accattcaga | tggagagagc | tctgaaaaac | 300 |
| catggctctc | caatgggcat | tccttactgg | gattggacaa | agaagatgtc | gagtcttcca | 360 |
| tctttctttg | gagattccag | caacaacaac | cctttctaca | atattacat | ccggggcgtg | 420 |
| cagcacgaaa | caaccaggga | cattaatcag | agactcttta | tcaaaccaa | gtttggtgaa | 480 |
| tttgattacc | tatattacct | aactctgcaa | gtcctggagg | aaaactcgta | ctgtgacttt | 540 |
| gaagttcagt | atgagatcct | ccataacgcc | gtccactcct | ggcttggagg | aactggaaag | 600 |
| tattccatgt | ctaccctgga | gcattcggcc | tttgaccctg | tcttcatgat | tcaccactcg | 660 |
| agtttggata | gaatctggat | cctttggcag | aagttgcaaa | agataagaat | gaagccttac | 720 |
| tacgcattgg | attgtgctgg | cgacagactt | atgaaagacc | ccctgcatcc | cttcaactac | 780 |
| gaaaccgtta | tgaagatga | attcacccgc | atcaactctt | tcccaagcat | actgtttgac | 840 |
| cactacaggt | tcaactatga | atacgataac | atgagaatca | ggggtcagga | catacatgaa | 900 |
| cttgaagagg | taattcagga | attaagaaac | aaagatcgca | tatttgctgg | ttttgttttg | 960 |
| tcgggcttac | ggatatcagc | tacagtgaaa | gtattcattc | attcgaaaaa | cgatacaagt | 1020 |
| cacgaagaat | atgcaggaga | atttgcagtt | ttgggaggtg | agaaggagat | gccgtgggca | 1080 |
| tatgaaagaa | tgctgaaatt | ggacatctcc | gatgctgtac | acaagcttca | cgtgaaagat | 1140 |
| gaagacatcc | gttttagagt | ggttgttact | gcctacaacg | tgacgttgt | taccaccagg | 1200 |
| ctgtctcagc | cattcatcgt | ccaccgtcca | gcccatgtgg | ctcacgacat | cttggtaatc | 1260 |
| ccagtaggtg | cgggccatga | ccttccgcct | aaagtcgtag | taaagagcgg | caccaaagtc | 1320 |
| gagtttacac | caatagattc | gtcggtgaac | aaagcaatgg | tggagctggg | cagctatact | 1380 |
| gctatggcta | aatgcatcgt | tccccctttc | tcttaccacg | gctttgaact | ggacaaagtc | 1440 |
| tacagcgtcg | atcacggaga | ctactacatt | gctgcaggta | cccacgcgtt | gtgtgagcag | 1500 |
| aacctcaggc | tccacatcca | cgtggaacac | gagtag | | | 1536 |

<210> SEQ ID NO 88
<211> LENGTH: 591
<212> TYPE: DNA
<213> ORGANISM: Haliotis tuberculata

<400> SEQUENCE: 88

| | | | | | |
|---|---|---|---|---|---|
| ggtcttccgt | actgggactg | gacgcagcat | ctgactcaac | tcccagatct | ggtgtcagac | 60 |
| cccttgtttg | tcgacccgga | aggaggaaag | gcccatgaca | acgcatggta | tcgtggaaac | 120 |
| atcaagtttg | agaataagaa | gactgcaaga | gctgttgacg | atcgccttt | cgagaaggtt | 180 |
| ggaccaggag | agaatacccg | actctttgaa | ggaattctcg | atgctcttga | acaggatgaa | 240 |
| ttctgcaact | tcgagatcca | gtttgagttg | gctcacaacg | ctatccacta | cctggttggc | 300 |
| ggccgtcaca | cgtactccat | gtctcatctc | gagtacacct | cctacgaccc | cctcttcttc | 360 |

| | |
|---|---:|
| ctccatcact ccaacccgga ccgcatcttc gccatctggg aacgtcttca ggtactcaga | 420 |
| ggaaaggacc ccaacaccgc cgactgcgca cacaacctca tccatgagcc catggaaccg | 480 |
| ttccgtcggc atgagcccat ggaaccgttc cgtcgggact cgaaccctct tgacctcacc | 540 |
| agggaaaact ccaaaccaat tgacagcttt gattatgccc accttggcta c | 591 |

<210> SEQ ID NO 89
<211> LENGTH: 1245
<212> TYPE: DNA
<213> ORGANISM: Haliotis tuberculata

<400> SEQUENCE: 89

| | |
|---|---:|
| gttacagagg ccccagctcc ctcctcggat gctcacctcg ccgtcaggaa ggatatcaac | 60 |
| catctgacac gcgaggaggt gtacgagctg cgcagagcta tggagagatt ccaggccgac | 120 |
| acatccgttg atgggtacca ggctacggtt gagtatcacg gcttacctgc tcgatgtcca | 180 |
| ttccccgagg ccacaaatag gttcgcctgt tgcatccacg gcatggcgac attccctcat | 240 |
| tggcacagac tgttcgtcac ccaggtggaa gatgctctga tcaggcgagg atcgcctata | 300 |
| ggggtcccct actgggactg gactcagcct atggcgcatc tcccaggact tgcagacaac | 360 |
| gccacctata gagatcccat cagcggggac agcagacaca acccttcca cgatgttgaa | 420 |
| gttgcctttg aaaatggacg tacagaacgt cacccagata gtagattgtt tgaacaacct | 480 |
| ttatttggca acatacgcg tctcttcgac agtatagtct atgcttttga gcaggaggac | 540 |
| ttctgcgatt ttgaagttca atttgagatg acccataata atattcacgc ctggattggt | 600 |
| ggcggcgaga agtattccat gtcttctcta cactacacag ccttcgaccc tatcttctac | 660 |
| cttcgtcact ccaacactga ccggctctgg caatttggc aagcgttgca gatacgaaga | 720 |
| aacaggcctt acaaggctca ttgtgcttgg tctgaggaac gccagcctct caaacctttc | 780 |
| gccttcagtt ccccactgaa caacaacgaa aaacctacg aaaactcggt gcccaccaac | 840 |
| gtttacgact acgaaggagt ccttggctat acttatgatg acctcaactt cggggggcatg | 900 |
| gacctgggtc agcttgagga atacatccag aggcagagac agagagacag gacctttgct | 960 |
| ggtttctttc tgtcacatat tggtacatca gcgaatgttg aaatcattat agaccatggg | 1020 |
| actcttcata cctccgtggg cacgtttgct gttcttggcg gagagaagga gatgaaatgg | 1080 |
| ggatttgacc gttttgtacaa atatgagatt acagatgaac tgaggcaact taatctccgt | 1140 |
| gctgatgatg ttttcagcat ctctgttaaa gtaactgatg ttgatggcag tgagctgtcc | 1200 |
| tctgaactca tcccatctgc tgctatcatc ttcgaacgaa gccat | 1245 |

<210> SEQ ID NO 90
<211> LENGTH: 1251
<212> TYPE: DNA
<213> ORGANISM: Haliotis tuberculata

<400> SEQUENCE: 90

| | |
|---|---:|
| attgaccatc aggacccgca tcatgacaca atcattagga aaaatgttga taatcttaca | 60 |
| cccgaggaaa ttaattctct gaggcgggca atggcagacc ttcaatcaga caaaaccgcc | 120 |
| ggtggattcc agcaaattgc tgcttttcac ggggaaccca aatggtgccc aagtcccgat | 180 |
| gctgagaaga agttctcctg ctgtgtccat ggaatggctg tcttccctca ctggcacaga | 240 |
| ctcctgaccg tgcaaggcga gaatgccctg agaaagcatg gatgtctcgg agctctcccc | 300 |
| tactgggact ggactcggcc cctgtctcac ctacctgatt tggttttggt aagtagcaga | 360 |

| | |
|---|---|
| actacaccga tgccatattc caccgtggaa gcccgaaacc cctggtacag cggccatatt | 420 |
| gatacagttg gtgttgacac aacaagaagc gtccgtcaag aactgtatga agctcctgga | 480 |
| tttggccatt atactggggt cgctaagcaa gtgcttctgg cttttggagca ggatgacttc | 540 |
| tgtgattttg aagtccagtt tgagatagct cacaatttca ttcacgctct tgtcggcgga | 600 |
| agcgagccat atggtatggc gtcactccgt tacactactt atgatccaat tttctacctc | 660 |
| catcattcta acactgacag actctgggct atatggcagg tctacaaaa gtacagggc | 720 |
| aaaccttaca attccgccaa ctgcgccatt gcttctatga aaaacccct acaacccttt | 780 |
| ggtctgactg atgagatcaa cccggatgat gagacaagac agcatgctgt tcctttcagt | 840 |
| gtctttgatt acaagaacaa cttcaattat gaatatgaca cccttgactt caacggacta | 900 |
| tcaatctccc agctggaccg tgaactgtca cggagaaagt ctcatgacag agtatttgcc | 960 |
| ggattttgc tgcatggtat tcagcagtct gcactagtta aattctttgt ctgcaaatca | 1020 |
| gatgatgact gtgaccacta tgctggtgaa ttctacatcc ttggtgatga agctgaaatg | 1080 |
| ccatggggct atgatcgtct ttacaaatat gagatcactg agcagctcaa tgccctggat | 1140 |
| ctacacatcg gagatagatt cttcatcaga tacgaagcgt ttgatcttca tggtacaagt | 1200 |
| cttggaagca acatcttccc caaaccttct gtcatacatg acgaaggggc a | 1251 |

<210> SEQ ID NO 91
<211> LENGTH: 1242
<212> TYPE: DNA
<213> ORGANISM: Haliotis tuberculata

<400> SEQUENCE: 91

| | |
|---|---|
| ggtcaccatc aggctgacga gtacgacgaa gttgtaactg ctgcaagcca catcagaaag | 60 |
| aatttaaaag atctgtcaaa gggagaagta gagagcctaa ggtctgcctt cctgcaactt | 120 |
| cagaacgacg gagtctatga gaatattgcc aagttccacg gcaagcctgg gttgtgtgat | 180 |
| gataacggtc gcaaggttgc ctgttgtgtc catggaatgc ccaccttccc ccagtggcac | 240 |
| aggctctatg tcctccaggt ggagaatgct ttgctggaga aggatctgc cgtctctgtg | 300 |
| ccatactggg actggactga acatttaca gagctgccat ctttgattgc tgaggctacc | 360 |
| tatttcaatt cccgtcaaca aacgtttgac cctaatcctt tcttcagagg taaaatcagt | 420 |
| tttgagaatg ctgttacaac acgtgatccc cagcctgagc tgtacgttaa caggtactac | 480 |
| taccaaaacg tcatgttggt ttttgaacag gacaactact gcgacttcga gatacagttt | 540 |
| gagatggttc acaatgttct ccatgcttgg cttggtggaa gagctactta ttctatttct | 600 |
| tctcttgatt attctgcatt cgaccctgtg ttttccttc accatgcgaa cacagataga | 660 |
| ttgtgggcca tctggcagga gctgcagagg tacaggaaga agccatacaa tgaagcggat | 720 |
| tgtgccatta acctaatgcg caaacctcta catcccttcg acaacagtga tctcaatcat | 780 |
| gatcctgtaa cctttaaata ctcaaaaccc actgatggct ttgactacca gaacaacttt | 840 |
| ggatacaagt atgacaacct tgagttcaat catttcagta ttcccaggct tgaagaaatc | 900 |
| attcgtatta gacaacgtca agatcgtgtg tttgcaggat tcctccttca caacattggg | 960 |
| acatccgcaa ctgttgagat attcgtctgt gtccctacca ccagcggtga gcaaaactgt | 1020 |
| gaaaacaaag ccggaacatt tgccgtactc ggaggagaaa cagagatggc gtttcatttt | 1080 |
| gacagactct acaggtttga catcagtgaa acactgaggg acctcggcat acagctggac | 1140 |
| agccatgact ttgacctcag catcaagatt caaggagtaa atggatccta ccttgatcca | 1200 |
| cacatcctgc cagagccatc cttgattttt gtgcctggtt ca | 1242 |

<210> SEQ ID NO 92
<211> LENGTH: 1257
<212> TYPE: DNA
<213> ORGANISM: Haliotis tuberculata

<400> SEQUENCE: 92

| | | | | | |
|---|---|---|---|---|---|
| agttctttcc | tgcgtcctga | tgggcattca | gatgacatcc | ttgtgagaaa | agaagtgaac | 60 |
| agcctgacaa | ccagggagac | tgcatctctg | atccatgctc | tgaaaagtat | gcaggaagac | 120 |
| cattcacctg | acgggttcca | agccattgcc | tctttccatg | ctctgccacc | actctgccct | 180 |
| tcaccatctg | cagctcaccg | ttatgcttgc | tgtgtccacg | gcatggctac | atttccccag | 240 |
| tggcacagat | tgtacactgt | acagttccag | gatgcactga | ggagacatgg | agctacggta | 300 |
| ggtgtaccgt | attgggattg | gctgcgaccg | cagtctcacc | taccagagct | tgtcaccatg | 360 |
| gagacatacc | atgatatttg | gagtaacaga | gatttcccca | atcctttcta | ccaagccaat | 420 |
| attgagtttg | aaggagaaaa | cattacaaca | gagagagaag | tcattgcaga | caaacttttt | 480 |
| gtcaaaggtg | gacacgtttt | tgataaactg | gttcttcaaa | caagccatcc | tagcgctgag | 540 |
| caggaaaact | actgtgactt | tgagattcag | tttgaaattc | ttcacaacgg | cgttcacacg | 600 |
| tgggtcggag | gcagtcgtac | ctactctatc | ggacatcttc | attacgcatt | ctacgaccct | 660 |
| cttttctacc | ttcaccattt | ccagacagac | cgtatttggg | caatctggca | agaactccag | 720 |
| gaacagagag | gctctcgggg | tgatgaggct | cactgtgctc | tcgagcaaat | gagagaacca | 780 |
| ttgaagcctt | tcagcttcgg | cgctccttat | aactggaatc | agctcacaca | ggatttctcc | 840 |
| cgacccgagg | acaccttcga | ctacaggaag | tttggttatg | aatatgacaa | tttagaattc | 900 |
| ctgggaatgt | cagttgctga | actggatcaa | tacattattg | aacatcaaga | aaatgataga | 960 |
| gtattcgctg | ggttcctgtt | gagtggattc | ggaggttccg | catcagttaa | tttccaggtt | 1020 |
| tgtagagctg | attccacatg | tcaggatgct | gggtacttca | ccgttcttgg | tggcagtgct | 1080 |
| gagatggcgt | gggcatttga | caggctttac | aaatatgaca | ttactgaaac | tctggagaaa | 1140 |
| atgcaccttc | gatatgatga | tgacttcaca | atctctgtca | gtctgaccgc | caacaacgga | 1200 |
| actgtcctga | gcagcagtct | aatcccaaca | ccgagtgtca | tattccagcg | gggacat | 1257 |

<210> SEQ ID NO 93
<211> LENGTH: 1248
<212> TYPE: DNA
<213> ORGANISM: Haliotis tuberculata

<400> SEQUENCE: 93

| | | | | | |
|---|---|---|---|---|---|
| cgtgacataa | ataccaggag | catgtcaccg | aaccgtgttc | gccgtgagct | gagcgatctg | 60 |
| tctgcgaggg | acctgtctag | tctcaagtct | gctctgcgag | acctacagga | ggatgatggc | 120 |
| cccaacggat | accaggctct | tgcagccttc | catgggctac | cagcaggctg | ccatgatagc | 180 |
| cggggaaatg | agatcgcatg | ttgcattcac | gggatgccga | ccttcccca | gtggcacaga | 240 |
| ctgtacaccc | tgcagttgga | gatggctctg | aggagacatg | gatcatctgt | cgccatcccc | 300 |
| tactgggact | ggacaaagcc | tatctccgaa | ctcccctcgc | tcttcaccag | ccctgagtat | 360 |
| tatgacccat | ggcatgatgc | tgtggtaaac | aacccattct | ccaaaggttt | tgtcaaattt | 420 |
| gcaaatacct | acacagtaag | agacccacag | gagatgctgt | tccagctttg | tgaacatgga | 480 |
| gagtcaatcc | tctatgagca | aactcttctt | gctcttgagc | aaaccgacta | ctgtgattt | 540 |
| gaggtacagt | ttgaggtcct | ccataacgtg | atccactacc | ttgttggtgg | acgtcagacc | 600 |

| | |
|---|---|
| tacgcattgt cttctctgca ttatgcctcc tacgacccat tcttctttat acaccattcc | 660 |
| tttgtggata agatgtgggt agtatggcaa gctcttcaaa agaggaggaa acttccatac | 720 |
| aagcgagctg actgtgctgt caacctaatg actaaaccaa tgaggccatt tgactccgat | 780 |
| atgaatcaga acccattcac aaagatgcac gcagttccca acacactcta tgactacgag | 840 |
| acactgtact acagctacga taatctcgaa ataggtggca ggaatctcga ccagcttcag | 900 |
| gctgaaattg acagaagcag aagccacgat cgcgttttg ctggattctt gcttcgtgga | 960 |
| atcggaactt ctgctgatgt caggttttgg atttgtagaa atgaaaatga ctgccacagg | 1020 |
| ggtggaataa ttttcatctt aggtggagcc aaggaaatgc catggtcatt tgacagaaac | 1080 |
| ttcaagtttg atatcaccca tgtactcgag aatgctggca ttagcccaga ggacgtgttt | 1140 |
| gatgctgagg agccatttta tatcaaggtt gagatccatg ctgttaacaa gaccatgata | 1200 |
| ccgtcgtctg tgatcccagc cccaactatc atctattctc ctggggaa | 1248 |

<210> SEQ ID NO 94
<211> LENGTH: 1206
<212> TYPE: DNA
<213> ORGANISM: Haliotis tuberculata

<400> SEQUENCE: 94

| | |
|---|---|
| ggtcgcgctg ctgacagtgc gcactctgcc aacattgctg gctctgggt gaggaaggac | 60 |
| gtcacgaccc tcactgtgtc tgagaccgag aacctaagac aggctcttca aggtgtcatc | 120 |
| gatgatactg gtcccaatgg ttaccaagca atagcatcct tccacggaag tcctccaatg | 180 |
| tgcgagatga acggccgcaa ggttgcctgt tgtgctcacg gtatggcctc cttcccacac | 240 |
| tggcacagac tgtatgtgaa gcagatggaa gatgccctgg ctgaccacgg gtcacatatc | 300 |
| ggcatccctt actgggactg gacaactgcc ttcacagagt tacccgccct tgtcacagac | 360 |
| tccgagaaca tcccttcca tgagggtcgc attgatcatc tcggtgtaac cacgtcacgt | 420 |
| tcccccagag acatgctgtt taacgaccca gagcaaggat cagagtcgtt cttctataga | 480 |
| caagtcctcc tggctttgga gcagactgac tactgccagt tcgaagtcca gtttgagctg | 540 |
| acccacaacg ccattcactc ctggacaggt ggacgtagcc cttacggaat gtcgaccctc | 600 |
| gagttcacag cctacgatcc tctcttctgg cttcaccact ccaacaccga cagaatctgg | 660 |
| gctgtctggc aagcactgca gaaataccga ggactcccat acaacgaagc acactgtgaa | 720 |
| atccaggttc tgaaacagcc cttgaggcca ttcaacgatg acatcaacca caatccaatc | 780 |
| accaagacta atgccaggcc tatcgattca tttgattatg agaggtttaa ctatcagtat | 840 |
| gacaccctta gcttccatgg taagagcatc cctgaactga atgacctgct cgaggaaaga | 900 |
| aaaagagaag agagaacatt tgctgccttc cttcttcgtg aatcggttg cagtgctgat | 960 |
| gtcgtctttg acatctgccg gcccaatggt gactgtgtct ttgcaggaac ctttgctgtg | 1020 |
| ctgggagggg agctagaaat gccttggtcc ttcgacagac tgttccgcta tgacatcacc | 1080 |
| agagtcatga atcagctcca tctccagtat gattcagatt tcagtttcag ggtgaagctt | 1140 |
| gttgccacca atggcactga gctttcatca gaccttctca agtcaccaac aattgaacat | 1200 |
| gaactt | 1206 |

<210> SEQ ID NO 95
<211> LENGTH: 1548
<212> TYPE: DNA
<213> ORGANISM: Haliotis tuberculata
<220> FEATURE:
<221> NAME/KEY: misc_feature

```
<222> LOCATION: (1275)..(1275)
<223> OTHER INFORMATION: n is a, c, g, or t

<400> SEQUENCE: 95
ggagcccaca gaggaccagt tgaagaaaca gaagtcactc gccaacatac tgacggcaat      60
gcacactttc atcgtaagga agttgattcg ctgtccctgg atgaagcaaa caacttgaag    120
aatgccctt  acaagctaca gaacgaccac agtctaacgg atacgaagc  aatctctggt    180
taccatggat accccaatct gtgtccggaa gaaggcgatg acaaaatacc cctgctgcgt    240
ccccggatgg gcatctttcc ttactggcac agactcttga ccattcaact ggaaagagct    300
cttgagcaca atggtgcact gcttggtgtt ccttactggg actggaacaa ggacctgtcg    360
tcactgccgg cgttcttctc cgactccagc aacaacaatc cctacttcaa gtaccacatc    420
gccggtgttg gtcacgacac cgtcagagag ccaactagtc ttatatataa ccagccccaa    480
atccatggtt atgattatct ctattaccta gcattgacca cgcttgaaga aaacaattac    540
tgggactttg aggttcagta tgagatcctc cacaacgccg tccactcctg gcttggagga    600
tcccagaagt attccatgtc taccctggag tattcggcct ttgacctgt  ctttatgatc    660
cttcactcgg gtctagacag actttggatc atctggcaag aacttcagaa gatcaggaga    720
aagccctaca acttcgctaa atgtgcttat catatgatgg aagagccact ggcgcccttc    780
agctatccat ctatcaacca ggacgagttc acccgtgcca actccaagcc ttctacagtt    840
tttgacagcc ataagttcgg ctaccattac gataacctga atgttagagg tcacagcatc    900
caagaactca acacaatcat caatgacttg agaaacacag acagaatcta cgcaggattt    960
gttttgtcag gcatcggtac gtctgctagt gtcaagatct atctccgaac agatgacaat   1020
gacgaagaag ttggaacttt cactgtcctg ggaggagaga gggaaatgcc atgggcctac   1080
gagcgagttt tcaagtatga catcacagag gttgcagata gacttaaaat taagttatgg   1140
ggacacccttt aacttccgg  aactggagat cacatcctta cgaatggaat cggtggtaaa   1200
caagagccta cccaaatcct ttcatcatct acagacctgc caatcatgac tacgatgttc   1260
ttgttatccc agtanggaag aaaccttcac atccctccca aagttgtcgt caagaaaggc   1320
acccgcatcg agttccaccc agtcgatgat tcagttacga gaccagttgt tgatcttgga   1380
agctacactg cactcttcaa ctgtgtggta ccaccgttca cataccacgg attcgaactg   1440
aaccacgtct attctgtcaa gcctggtgac tactatgtta ctggacccac gagagacctt   1500
tgccagaatg cagatgtcag gattcatatc catgttgagg atgagtaa               1548

<210> SEQ ID NO 96
<211> LENGTH: 966
<212> TYPE: DNA
<213> ORGANISM: Megathura crenulata

<400> SEQUENCE: 96
ggcctaccgt actgggactg gactgaaccc atgacacaca ttccgggtct ggcaggaaac     60
aaaacttatg tggattctca tggtgcatcc cacacaaatc ctttcatag  ttcagtgatt   120
gcatttgaag aaaatgctcc ccacaccaaa agacaaatag atcaaagact ctttaaaccc    180
gctacctttg acaccacac  agacctgttc aaccagattt tgtatgcctt tgaacaagaa    240
gattactgtg acttttgaagt ccaatttgag attacccata acacgattca cgcttggaca    300
ggaggaagcg aacatttctc aatgtcgtcc ctacattaca cagctttcga tccttttgttt   360
tactttcacc attctaacgt tgatcgtctt tgggccgttt ggcaagcctt acagatgaga    420
```

| | |
|---|---|
| cggcataaac cctacagggc ccactgcgcc atatctctgg aacatatgca tctgaaacca | 480 |
| ttcgccttt catctcccct taacaataac gaaaagactc atgccaatgc catgccaaac | 540 |
| aagatctacg actatgaaaa tgtcctccat tacacatacg aagatttaac atttggaggc | 600 |
| atctctctgg aaaacataga aaagatgatc cacgaaaacc agcaagaaga cagaatatat | 660 |
| gccggttttc tcctggctgg catacgtact tcagcaaatg ttgatatctt cattaaaact | 720 |
| accgattccg tgcaacataa ggctggaaca tttgcagtgc tcggtggaag caaggaaatg | 780 |
| aagtggggat ttgatcgcgt tttcaagttt gacatcacgc acgttttgaa agatctcgat | 840 |
| ctcactgctg atggcgattt cgaagttact gttgacatca ctgaagtcga tggaactaaa | 900 |
| cttgcatcca gtcttattcc acatgcttct gtcattcgtg agcatgcacg tggtaagctg | 960 |
| aataga | 966 |

<210> SEQ ID NO 97
<211> LENGTH: 1242
<212> TYPE: DNA
<213> ORGANISM: Megathura crenulata

<400> SEQUENCE: 97

| | |
|---|---|
| gttaaatttg acaaagtgcc aaggagtcgt cttattcgaa aaaatgtaga ccgtttgagc | 60 |
| cccgaggaga tgaatgaact tcgtaaagcc ctagccttac tgaaagagga caaaagtgcc | 120 |
| ggtggatttc agcagcttgg tgcattccat ggggagccaa aatggtgtcc tagtcccgaa | 180 |
| gcatctaaaa aatttgcctg ctgtgttcac ggcatgtctg tgttccctca ctggcatcga | 240 |
| ctgttgacgg ttcagagtga aaatgctttg agacgacatg gctacgatgg agctttgccg | 300 |
| tactgggatt ggacctctcc tcttaatcac cttcccgaac tggcagatca tgagaagtac | 360 |
| gtcgaccctg aagatggggt agagaagcat aacccttggt tcgatggtca tatagataca | 420 |
| gtcgacaaaa caacaacaag aagtgttcag aataaactct tcgaacagcc tgagtttggt | 480 |
| cattatacaa gcattgccaa acaagtactg ctagcgttgg aacaggacaa tttctgtgac | 540 |
| tttgaaatcc aatatgagat tgcccataac tacatccatg cacttgtagg aggcgctcag | 600 |
| ccttatggta tggcatcgct tcgctacact gcttttgatc cactattcta cttgcatcac | 660 |
| tctaatacag atcgtatatg ggcaatatgg caggctttac agaagtacag aggaaaaccg | 720 |
| tacaacgttg ctaactgtgc tgttacatcg atgagagaac ctttgcaacc atttggcctc | 780 |
| tctgccaata tcaacacaga ccatgtaacc aaggagcatt cagtgccatt caacgttttt | 840 |
| gattacaaga ccaatttcaa ttatgaatat gacactttgg aatttaacgg tctctcaatc | 900 |
| tctcagttga ataaaaagct cgaagcgata aagagccaag acaggttctt tgcaggcttc | 960 |
| ctgttatctg gtttcaagaa atcatctctt gttaaattca atatttgcac cgatagcagc | 1020 |
| aactgtcacc ccgctggaga gttttacctt ctgggtgatg aaaacgagat gccatgggca | 1080 |
| tacgatagag tcttcaaata tgacataacc gaaaaactcc acgatctaaa gctgcatgca | 1140 |
| gaagaccact tctacattga ctatgaagta tttgacctta accagcaag cctgggaaaa | 1200 |
| gatttgttca gcagccttc agtcattcat gaaccaagaa ta | 1242 |

<210> SEQ ID NO 98
<211> LENGTH: 1236
<212> TYPE: DNA
<213> ORGANISM: Megathura crenulata

<400> SEQUENCE: 98

| | |
|---|---|
| ggtcaccatg aaggcgaagt atatcaagct gaagtaactt ctgccaaccg tattcgaaaa | 60 |

-continued

```
aacattgaaa atctgagcct tggtgaactc gaaagtctga gagctgcctt cctggaaatt        120
gaaaacgatg gaacttacga atcaatagct aaattccatg gtagccctgg tttgtgccag        180
ttaaatggta accccatctc ttgttgtgtc catggcatgc caactttccc tcactggcac        240
agactgtacg tggttgtcgt tgagaatgcc ctcctgaaaa aggatcatc tgtagctgtt         300 ccctattggg actggacaaa acgaatcgaa catttacctc acctgatttc agacgccact        360
tactacaatt ccaggcaaca tcactatgag acaaacccat tccatcatgg caaaatcaca        420
cacgagaatg aaatcactac tagggatccc aaggacagcc tcttccattc agactacttt       480
tacgagcagg tcctttacgc cttggagcag gataacttct gtgatttcga gattcagttg       540
gagatattac acaatgcatt gcattcttta cttggtggca aggtaaaata ttccatgtca        600
aaccttgatt acgctgcttt tgatcctgtg ttcttccttc atcacgcaac gactgacaga        660
atctgggcaa tctggcaaga ccttcagagg ttccgaaaac ggccataccg agaagcgaat        720
tgcgctatcc aattgatgca cacgccactc cagccgtttg ataagagcga caacaatgac        780
gaggcaacga aaacgcatgc cactccacat gatggttttg aatatcaaaa cagctttggt        840
tatgcttacg ataatctgga actgaatcac tactcgattc ctcagcttga tcacatgctg        900
caagaaagaa aaaggcatga cagagtattc gctggcttcc tccttcacaa tattggaaca       960
tctgccgatg gccatgtatt tgtatgtctc ccaactgggg aacacacgaa ggactgcagt      1020
catgaggctg gtatgttctc catcttaggc ggtcaaacgg agatgtcctt tgtatttgac      1080
agactttaca aacttgacat aactaaagcc ttgaaaaaga acggtgtgca cctgcaaggg      1140
gatttcgatc tggaaattga gattacggct gtgaatggat ctcatctaga cagtcatgtc      1200
atccactctc ccactatact gtttgaggcc ggaaca                                 1236
```

<210> SEQ ID NO 99
<211> LENGTH: 1257
<212> TYPE: DNA
<213> ORGANISM: Megathura crenulata

<400> SEQUENCE: 99

```
gattctgccc acacagatga tggacacact gaaccagtga tgattcgcaa agatatcaca        60
caattggaca agcgtcaaca actgtcactg gtgaaagccc tcgagtccat gaaagccgac       120
cattcatctg atgggttcca ggcaatcgct tccttccatg ctcttcctcc tctttgtcca       180
tcaccagctg cttcaaagag gtttgcgtgc tgcgtccatg gcatggcaac gttcccacaa       240
tggcaccgtc tgtacacagt ccaattccaa gattctctca gaaaacatgg tgcagtcgtt       300
ggacttccgt actgggactg gaccctacct cgttctgaat taccagagct cctgaccgtc       360
tcaactattc atgacccgga gacaggcaga gatataccaa atccatttat tggttctaaa       420
atagagtttg aaggagaaaa cgtacatact aaaagagata tcaataggga tcgtctcttc       480
cagggatcaa caaaaacaca tcataactgg tttattgagc aagcactgct tgctcttgaa       540
caaaccaact actgcgactt cgaggttcag tttgaaatta tgcataatgg tgttcatacc       600
tgggttggag gcaaggagcc ctatggaatt ggccatctgc attatgcttc ctatgatcca       660
cttttctaca tccatcactc ccaaactgat cgtatttggg ctatatgcca atcgttgcag       720
cgtttcagag gactttctgg atctgaggct aactgtgctg taaatctcat gaaaactcct       780
ctgaagcctt tcagctttgg agcaccatat aatcttaatg atcacacgca tgatttctca       840
aagcctgaag atacattcga ctaccaaaag tttggataca tatatgacac tctggaattt       900
```

```
gcagggtggt caattcgtgg cattgaccat attgtccgta acaggcagga acattcaagg    960
gtctttgccg gattcttgct tgaaggattt ggcacctctg ccactgtcga tttccaggtc   1020
tgtcgcacag cgggagactg tgaagatgca gggtacttca ccgtgttggg aggtgaaaaa   1080
gaaatgcctt gggcctttga tcggctttac aagtacgaca taacagaaac cttagacaag   1140
atgaaccttc gacatgacga aatcttccag attgaagtaa ccattacatc ctacgatgga   1200
actgtactcg atagtggcct tattcccaca ccgtcaatca tctatgatcc tgctcat      1257
```

<210> SEQ ID NO 100
<211> LENGTH: 1254
<212> TYPE: DNA
<213> ORGANISM: Megathura crenulata

<400> SEQUENCE: 100

```
catgatatta gttcgcacca cctgtcgctc aacaaggttc gtcatgatct gagtacactg     60
agtgagcgag atattggaag ccttaaatat gctttgagca gcttgcaggc agatacctca    120
gcagatggtt ttgctgccat tgcatccttc catggtctgc ctgccaaatg taatgacagc    180
cacaataacg aggtggcatg ctgtatccat ggaatgccta cattccccca ctggcacaga    240
ctctacaccc tccaatttga gcaagctcta agaagacatg gctctagtgt agcagtaccc    300
tactgggact ggacaaagcc aatacataat attccacatc tgttcacaga caagaatac     360 tacgatgtct ggagaaataa agtaatgcca atccatttg cccgagggta tgtcccctca     420
cacgatacat acacggtaag agacgtccaa gaaggcctgt tccacctgac atcaacgggt    480
gaacactcag cgcttctgaa tcaagctctt ttggcgctgg aacagcacga ctactgcgat    540
tttgcagtcc agtttgaagt catgcacaac acaatccatt acctagtggg aggacctcaa    600
gtctattctt tgtcatccct tcattatgct tcatatgatc cgatcttctt catacaccac    660
tcctttgtag acaaggtttg ggctgtctgg caggctcttc aagaaaagag aggccttcca    720
tcagaccgtg ctgactgcgc tgttagtctg atgactcaga acatgaggcc tttccattac    780
gaaattaacc ataaccagtt caccaagaaa catgcagttc caaatgatgt tttcaagtac    840
gaactcctgg gttacagata cgacaatctg gaaatcggtg gcatgaattt gcatgaaatt    900
gaaaaggaaa tcaaagacaa acagcaccat gtgagagtgt ttgcagggtt cctccttcac    960
ggaattagaa cctcagctga tgtccaattc cagatttgta aaacatcaga agattgtcac   1020
catggaggcc aaatcttcgt tcttgggggg actaaagaga tggcctgggc ttataaccgt   1080
ttattcaagt acgatattac ccatgctctt catgacgcac acatcactcc agaagacgta   1140
ttccatccct ctgaaccatt cttcatcaag gtgtcagtga cagccgtcaa cggaacagtt   1200
cttccggctt caatcctgca tgcaccaacc attatctatg aacctggtct cggt         1254
```

<210> SEQ ID NO 101
<211> LENGTH: 510
<212> TYPE: DNA
<213> ORGANISM: Megathura crenulata

<400> SEQUENCE: 101

```
gaccatcacg aagatcatca ttcttcttct atggctggac atggtgtcag aaaggaaatc     60
aacacactta ccactgcaga ggtggacaat ctcaaagatg ccatgagagc cgtcatggca    120
gaccacggtc caaatggata ccaggctata gcagcgttcc atggaaaccc accaatgtgc    180
cctatgccag atgaaagaa ttactcgtgt tgtacacatg gcatggctac tttcccccac     240
tggcacagac tgtacacaaa acagatggaa gatgccttga ccgcccatgg tgccagagtc    300
```

```
ggccttcctt actgggacgg gacaactgcc tttacagctt tgccaactttt tgtcacagat       360 gaagaggaca atcctttcca tcatggtcac atagactatt tgggagtgga tacaactcgg       420
tcgccccgag acaagttgtt caatgatcca gagcgaggat cagaatcgtt cttctacagg       480
caggttctct tggctttgga gcagacagat                                         510

<210> SEQ ID NO 102
<211> LENGTH: 942
<212> TYPE: DNA
<213> ORGANISM: Megathura crenulata

<400> SEQUENCE: 102
ggcctgccct actgggattg gaccatgcca atgagtcatt tgccagaact ggctacaagt        60
gagacctacc tcgatccagt tactggggaa actaaaaaca acccttttcca tcacgcccaa      120 gtggcgtttg aaaatggtgt aacaagcagg aatcctgatg ccaaactttt tatgaaacca      180
acttacggag accacactta cctcttcgac agcatgatct acgcatttga gcaggaagac      240
ttctgcgact ttgaagtcca atatgagctc acgcataatg caatacatgc atgggttgga      300
ggcagtgaaa agtattcaat gtcttctctt cactacactg cttttgatcc tatattttac      360
ctccatcact caaatgttga tcgtctctgg gccatttggc aagctcttca aatcaggaga      420
ggcaagtctt acaaggccca ctgcgcctcg tctcaagaaa gagaaccatt aaagcctttt      480
gcattcagtt ccccactgaa caacaacgag aaaacgtacc acaactctgt ccccactaac      540
gtttatgact atgtgggagt tttgcactat cgatatgatg accttcagtt tggcggtatg      600
accatgtcag aacttgagga atatattcac aagcagacac aacatgatag aacctttgca      660
ggattcttcc tttcatatat tggaacatca gcaagcgtag atatcttcat caatcgagaa      720
ggtcatgata aatacaaagt gggaagtttt gtagtacttg gtggatccaa agaaatgaaa      780
tggggctttg atagaatgta caagtatgag atcactgagg ctctgaagac gctgaatgtt      840
gcagtggatg atgggttcag cattactgtt gagatcaccg atgttgatgg atctccccca      900
tctgcagatc tcattccacc tcctgctata atctttgaac gt                          942

<210> SEQ ID NO 103
<211> LENGTH: 1248
<212> TYPE: DNA
<213> ORGANISM: Megathura crenulata

<400> SEQUENCE: 103
gctgatgcca aagactttgg ccatagcaga aaaatcagga aagccgttga ttctctgaca        60
gtcgaagaac aaacttcgtt gaggcgagct atggcagatc tacaggacga caaaacatca      120
gggggtttcc agcagattgc agcattccac ggagaaccaa aatggtgtcc aagccccgaa      180
gcggagaaaa aatttgcatg ctgtgttcat ggaatggctg ttttccctca ctggcacaga      240
ttgctgacag ttcaaggaga aaatgctctg aggaaacatg gctttactgg tggactgccc      300
tactgggact ggactcgatc aatgagcgcc cttccacatt tgttgctga tcctacttac       360 aatgatgcta tttccagcca ggaagaagat aacccatggc atcatggtca catagactct      420
gttgggcatg atactacaag agatgtgcgt gatgatcttt atcaatctcc tggtttcggt      480
cactacacag atattgcaaa acaagtcctt ctggcctttg agcaggacga tttctgtgat      540
tttgaggtac aatttgaaat tgcccataat ttcatacatg ctctggttgg tggtaacgaa      600
ccatacagta tgtcatcttt gaggtatact acatacgatc caatcttctt cttgcaccgc      660
```

```
tccaatacag accgactttg ggccatttgg caagctttgc aaaaataccg ggggaaacca      720
tacaacactg caaactgtgc cattgcatcc atgagaaaac cacttcagcc atttggtctt      780
gatagtgtca taaatccaga tgacgaaact cgtgaacatt cggttccttt ccgagtcttc      840
gactacaaga acaacttcga ctatgagtat gagagcctgg catttaatgg tctgtctatt      900
gcccaactgg accgagagtt gcagagaaga agtcacatg acagagtctt tgcaggattc       960
cttcttcatg aaattggaca gtctgcactc gtgaaattct acgtttgcaa acacaatgta     1020
tctgactgtg accattatgc tggagaattc tacattttgg gagatgaagc tgagatgcct     1080
tggaggtatg accgtgtgta caagtacgag ataacacaga gctgcacga tttagatcta      1140 catgttggag ataatttctt ccttaaatat gaagcctttg atctgaatgg cggaagtctt     1200
ggtggaagta tcttttctca gccttcggtg attttcgagc cagctgca               1248
```

```
<210> SEQ ID NO 104
<211> LENGTH: 1257
<212> TYPE: DNA
<213> ORGANISM: Megathura crenulata

<400> SEQUENCE: 104
ggttcacacc aggctgatga atatcgtgag gcagtaacaa gcgctagcca cataagaaaa       60
aatatccggg acctctcaga gggagaaatt gagagcatca gatctgcttt cctccaaatt      120 caaaagagg gtatatatga aacattgca aagttccatg gaaaaccagg actttgtgaa        180
catgatggac atcctgttgc ttgttgtgtc catggcatgc ccacctttcc ccactggcac      240
agactgtacg ttcttcaggt ggagaatgcg ctcttagaac gagggtctgc agttgctgtt      300
ccttactggg actggaccga gaaagctgac tctctgccat cattaatcaa tgatgcaact      360
tatttcaatt cacgatccca gacctttgat cctaatcctt tcttcagggg acatattgcc      420
ttcgagaatg ctgtgacgtc cagagatcct cagccagaac tatgggacaa taaggacttc      480
tacgagaatg tcatgctggc tcttgagcaa gacaacttct gtgactttga gattcagctt      540
gagctgatac acaacgccct tcattctaga cttggaggaa gggctaaata ctccctttcg      600
tctcttgatt ataccgcatt tgatcctgta tttttccttc accatgcaaa cgttgacaga      660
atctgggcca tctggcagga cttgcagaga tatagaaaga accatacaa tgaggctgac       720 tgcgcagtca acgagatgcg taaacctctt caaccattta ataacccaga acttaacagt     780
gattccatga cgcttaaaca caacctccca caagacagtt ttgattatca aaaccgcttc     840
aggtaccaat atgataacct tcaatttaac cacttcagca tacaaaagct agaccaaact     900
attcaggcta gaaaacaaca cgacagagtt tttgctggct ttattcttca caacattggg      960
acatctgctg ttgtagatat ttatatttgc gttgaacaag gaggagaaca aaactgcaag     1020
acaaaggcgg gttccttcac gattctgggg ggagaaacag aaatgccatt ccactttgac     1080
cgcttgtaca aatttgacat aacgtctgct ctgcataaac ttggtgttcc cttggacgga     1140
catggattcg acatcaaagt tgacgtcaga gctgtcaatg gatcgcatct tgatcaacac     1200
atcctcaacg aaccgagtct gcttttttgtt cctggtgaac gtaagaatat atattat      1257
```

```
<210> SEQ ID NO 105
<211> LENGTH: 1239
<212> TYPE: DNA
<213> ORGANISM: Megathura crenulata

<400> SEQUENCE: 105
gatgggcttt cacaacataa tcttgtgcga aagaagtaa gctctcttac aacactggag        60
```

```
aaacattttt tgaggaaagc tctcaagaac atgcaagcag atgattctcc agacggatat      120
caagctattg cttctttcca cgctttgcct cctctttgtc caagtccatc tgctgcacat      180
agacacgctt gttgcctcca tggtatggct accttccctc agtggcacag actctacaca      240
gttcagttcg aagattcttt gaaacgacat ggttctattg tcggacttcc atattgggat      300
tggctgaaac cgcagtctgc actccctgat ttggtgacac aggagacata cgagcacctg      360
ttttcacaca aaaccttccc aaatccgttc ctcaaggcaa atatagaatt tgagggagag      420
ggagtaacaa cagagaggga tgttgatgct gaacacctct ttgcaaaagg aaatctggtt      480
tacaacaact ggttttgcaa tcaggcacta tatgcactag aacaagaaaa ttactgtgac      540
tttgaaatac agttcgaaat tttgcataat ggaattcatt catgggttgg aggatcaaag      600
acccattcaa taggtcatct tcattacgca tcatacgatc cactgttcta tatccaccat      660
tcgcagacac atcgcatttg gctatctgg caagctctcc aggagcacag aggtctttca      720
gggaaggaag cacactgcgc cctggagcaa atgaaagacc ctctcaaacc tttcagcttt      780
ggaagtccct ataatttgaa caaacgcact caagagttct ccaagcctga agacacattt      840
gattatcacc gattcgggta tgagtatgat tccctcgaat tgttggcat gtctgtttca      900 agtttacata actatataaa acaacaacag gaagctgata gagtcttcgc aggattcctt      960
cttaaaggat ttggacaatc agcatccgta tcgtttgata tctgcagacc agaccagagt     1020
tgccaagaag ctggatactt ctcagttctc ggtggaagtt cagaaatgcc gtggcagttt     1080
gacaggcttt acaagtacga cattacaaaa acgttgaaag acatgaaact gcgatacgat     1140
gacacattta ccatcaaggt tcacataaag gatatagctg gagctgagtt ggacagcgat     1200
ctgattccaa ctccttctgt tctccttgaa gaaggaaag                            1239

<210> SEQ ID NO 106
<211> LENGTH: 1251
<212> TYPE: DNA
<213> ORGANISM: Megathura crenulata

<400> SEQUENCE: 106
catgggatca atgtacgtca cgttggtcgt aatcggattc gtatggaact atctgaactc       60
accgagagag atctcgccag cctgaaatct gcaatgaggt ctctacaagc tgacgatggg      120
gtgaacggtt atcaagccat tgcatcattc cacggtctcc cggcttcttg tcatgatgat      180
gagggacatg agattgcctg ttgtatccac ggaatgccag tattcccaca ctggcacagg      240
ctttacaccc tgcaaatgga catggctctg ttatctcacg gatctgctgt tgctattcca      300
tactgggact ggaccaaacc tatcagcaaa ctgcctgatc tcttcaccag ccctgaatat      360
tacgatcctt ggagggatgc agttgtcaat aatccatttg ctaaaggcta cattaaatcc      420
gaggacgctt acacggttag ggatcctcag gacattttgt accacttgca ggacgaaacg      480
ggaacatctg ttttgttaga tcaaactctt ttagccttag agcagacaga tttctgtgat      540
tttgaggttc aatttgaggt cgtccataat gctattcact acttggtggg tggtcgacaa      600
gtttatgctc tttcttctca acactatgct tcatatgacc cagccttctt tattcatcac      660
tcctttgttg acaaaatatg ggcagtctgg caagctctgc aaaagaagag aaagcgtccc      720
tatcataaag cggattgtgc tcttaacatg atgaccaaac caatgcgacc atttgcacac      780
gatttcaatc acaatggatt cacaaaaatg cacgcagtcc ccaacactct atttgacttt      840
caggaccttt tctacacgta tgacaactta gaaattgctg gcatgaatgt taatcagttg      900
```

```
gaagcggaaa tcaaccggcg aaaaagccaa acaagagtct tgccgggtt ccttctacat    960 ggcattggaa gatcagctga tgtacgattt tggatttgca agacagctga cgactgccac   1020
gcatctggca tgatctttat cttaggaggt tctaaagaga tgcactgggc ctatgacagg   1080
aactttaaat acgacatcac ccaagctttg aaggctcagt ccatacaccc tgaagatgtg   1140
tttgacactg atgctccttt cttcattaaa gtggaggtcc atggtgtaaa caagactgct   1200
ctcccatctt cagctatccc agcacctact ataatctact cagctggtga a            1251
```

<210> SEQ ID NO 107
<211> LENGTH: 1185
<212> TYPE: DNA
<213> ORGANISM: Megathura crenulata
<220> FEATURE:
<221> NAME/KEY: misc_feature
<222> LOCATION: (164)..(164)
<223> OTHER INFORMATION: n is a, c, g, or t

<400> SEQUENCE: 107

```
gatcatattg ctggcagtgg agtcaggaaa gacgtgacgt ctcttaccgc atctgagata     60
gagaacctga ggcatgctct gcaaagcgtg atggatgatg atggacccaa tggattccag    120
gcaattgctg cttatcacgg aagtcctccc atgtgtcaca tgcntgatgg tagagacgtt    180
gcatgttgta ctcatggaat ggcatctttc cctcactggc acagactgtt tgtgaaacag    240
atggaggatg cactggctgc gcatggagct cacattggca taccatactg ggattggaca    300
agtgcgttta gtcatctgcc tgccctagta actgaccacg agcacaatcc cttccaccac    360
ggacatattg ctcatcggaa tgtggataca tctcgatctc cgagagacat gctgttcaat    420
gaccccgaac acgggtcaga atcattcttc tatagacagg ttctcttggc tctagaacag    480
acagacttct gccaatttga agttcagttt gaaataacac acaatgcaat ccactcttgg    540
actggaggac atactccata tggaatgtca tcactggaat atacagcata tgatccactc    600
ttttatctcc accattccaa cactgatcgt atctgggcca tctggcaggc actccagaaa    660
tacagaggtt ttcaatacaa cgcagctcat tgcgatatcc aggttctgaa acaacctctt    720
aaaccattca gcgagtccag gaatccaaac ccagtcacca gagccaattc tagggcagtc    780
gattcatttg attatgagag actcaattat caatatgaca cacttacctt ccacggacat    840
tctatctcag aacttgatgc catgcttcaa gagagaaaga aggaagagag aacatttgca    900
gccttcctgt tgcacggatt tggcgccagt gctgatgttt cgtttgatgt ctgcacacct    960
gatggtcatt gtgcctttgc tggaaccttc gcggtacttg gtggggagct tgagatgccc   1020
tggtcctttg aaagattgtt ccgttacgat atcacaaagg ttctcaagca gatgaatctt   1080
cactatgatt ctgagttcca cttttgagttg aagattgttg gcacagatgg aacagaactg   1140
ccatcggatc gtatcaagag ccctaccatt gaacaccatg gagga                   1185
```

<210> SEQ ID NO 108
<211> LENGTH: 309
<212> TYPE: DNA
<213> ORGANISM: Megathura crenulata

<400> SEQUENCE: 108

```
ggtcacgatc acagtgaacg tcacgatgga ttttttcagga aggaagtcgg ttccctgtcc     60
ctggatgaag ccaatgacct taaaaatgca ctgtacaagc tgcagaatga tcagggtccc    120
aatggatatg aatcaatagc cggttaccat ggctatccat tcctctgccc tgaacatggt    180
gaagaccagt acgcatgctg tgtccacgga atgcctgtat ttccacattg gcacagactt    240
```

| | |
|---|---|
| catacaatcc agtttgagag agctctcaaa gaacatggtt ctcatttggg tctgccatac | 300 |
| tgggactgg | 309 |

<210> SEQ ID NO 109
<211> LENGTH: 2561
<212> TYPE: DNA
<213> ORGANISM: Haliotis tuberculata

<400> SEQUENCE: 109

| | |
|---|---|
| gtaagtcaac gtctttgttt taagtttgat gcatatctat cattgcgttt taaaatacca | 60 |
| ttacaaccaa cgtgtctcta ttggtcttca cctgtttaac gtatatattg tttttaatgt | 120 |
| gaaaatctga gattattttc atttccgtca atattcgtaa atactatac aaataaaatt | 180 |
| gcttcagcct attgcattgg cagttttcgc agaataacga gggaaggcgt acataaaata | 240 |
| taaaccagtg tatattcaag catgtttata atttctttat agattataac atcatatcaa | 300 |
| aacaccaatc tggatttaaa cccgtgaatc caaagtatac caattaacgg aactttatca | 360 |
| tgttttatca aaggttttag atgagggtaa agaagtccga gctatatttt gcgatatcag | 420 |
| caaagccttc tatcacgtct tgcacacagg gctggtatct aaactcgaat ccacaggaat | 480 |
| aaatatttca gccgatagag aacagtcggt ggctatcatt ggtcacaaaa caagtccaaa | 540 |
| atctgcatta gccggtgttc cccaaggctc tgtcttgggg ccactattat ttctcaccta | 600 |
| tataaacgat tcaactaatg gaatataaag caacgtaaac ctcaccgcag atgaaacact | 660 |
| aagttataga caatccgttt aaaacccagc cactgcttaa taatgactta ggccgtcttt | 720 |
| cagactgggc tagtaagcgg caggttaaat ttccccttga aaagacagaa accatggtat | 780 |
| atttcaaaaa cacgaatgca agtcctaaac ttcaactact acttgatgat actgggattt | 840 |
| ctaaagtgtg tgaacaaaaa cacattggcc tgatcctaca agataaccag acagaaacca | 900 |
| tgttttttt caataacacg aatgcaagtc taaacttca actactactt gatgatactg | 960 |
| ggatttctaa agtgtgtggt gaacacaaac accttggcct gattctgcaa gataatggaa | 1020 |
| aatgtcagaa acataagcaa gttgatgtgg ggttttctgg gggttgtgac acaccgaaa | 1080 |
| gaccctgcaa ctaatgttag ctcaaagggt tttacacccg gtcacaagtg gggatcgacc | 1140 |
| caggcaccett ttgcctttga cagctcgcct ttcaaaaaat ctcaattcga aaacgaaatc | 1200 |
| taataatttc atgagcgata caaccgtttt tcataatgct gtggtaccgc atactgtgga | 1260 |
| aacatctgtc tacccatttg gtagtccccc ataaaatgta tttatgttta aaacacaat | 1320 |
| gtttataggg ttacagttag aagaagcatt tctattggct aatgtacatt gcttgttttt | 1380 |
| actattgtgc aaaggcatat tacaggtctt ttaggaaatt aaatactgtt taaatcacat | 1440 |
| acactaccgg taatcctatt atgcttatcc tgccaacatt ctgcccaagc aaacgcatga | 1500 |
| aagttaaagc tgagtgtaaa atactgattg ctgtgttact tcacaaccag tggactgaat | 1560 |
| acaaccatgt tttttcttga aagtcacaaa catccagtcg gtttctaatg tgttaagttt | 1620 |
| ctagtttcat aaagagcatg acgtaatggt gaataggagt tatcaatgtt tctatctaat | 1680 |
| gactcctagt tcgttacttt tttaataaaa catccatgtg tttaatgttt ggccacagat | 1740 |
| ataacaagaa agaaatcgga taaaatctac attttgacca atcggaaggc tgcccctcc | 1800 |
| ctaatcctaa tcattttgt gcctcaaaac atactcaacc agacatttga actatgtata | 1860 |
| tatcagaatg aaatggtaac aataaacttg tatgttgacc agacagaatt agggtgaatc | 1920 |
| tgaataccaa ctattgtcac atatgaatat ggataagctc tgcgcgtgcg tgcgggcggt | 1980 |

```
gtagtgcgtg tgtgtctgtg tgtgtgtgtg tgtgcgtttg tgtgtgtgtc tgcgtgcgtg    2040
tgtgtgcgcg tgtgtgcgtg tgtgtgtgtg tgcagtgtgc cgagtgtgtg tgtgtgtgtg    2100
tgcacagaca tgtggttgag acacacttga ttcagtgcag gattatgtcc ttcaaccgag    2160
tgtagtcttt aagtgtgcct ggaaacaaaa aactgcgttg ggttgcatcg cctctgtagc    2220
aagcttggac gcgtcacgca gctctgatac cacgtattgg caccatgttt catcggtctc    2280
acgcgaatat tatgctatgt gtggcgtatc ataccatagg ttgggaacgt ttcaatactg    2340
taccgagctt gggcgtgtca caaagctatg ataagatgac aacacgtctt ggcatcttgt    2400
ttcctcggta tcacgcgctg ttatgctatg tgtggctatc acaccttagg ttgggaaagt    2460
ttccacattt tccagcctcg tacatgtttc cttttgtttt ttccttagtt atcagcatac    2520
cgtatattct atatttaatg agcatttgta tttttctaca g                       2561
```

<210> SEQ ID NO 110
<211> LENGTH: 5043
<212> TYPE: DNA
<213> ORGANISM: Haliotis tuberculata
<220> FEATURE:
<221> NAME/KEY: misc_feature
<222> LOCATION: (2928)..(2928)
<223> OTHER INFORMATION: n is a, c, g, or t

<400> SEQUENCE: 110

```
gtgagtttct taacattgtc atggtacatg gatatacgct cagtgggaaa gcaggatatc     60
cccttggttc aagtattcac ttgtcacgcc aagtgttcga ttcccaacat ggaatactgt    120
catatagtaa attgatacac tacttacatt taattctcca ctaaacgtca acgtccttta    180
cttcatggcc cacatggtcc gtattagtga gtgagtgagt cagggcataa gtatttaacg    240
tcaaatcagc aatatttcag ccatattgtg acaagaattg aatataaata attatactta    300
taatgcttat aaatataaat tatataaata cctataacta taaattagtt atactagtat    360
ttatcaaaac atatttgcca cgacactgca cgccgatact tcaagtgtct tcacctcaag    420
cgtgtaactc ctcatactct gtaataagta tgtacactaa gtgagtgcta tcatctccat    480
gcttcattag tttcgtcaga tgcgtgtatc catacgagta cattcagatt atgggatcca    540
gagctttctt atctcaagta tttccgattg taaagccata ctacttcccc aatgactgac    600
gagacagatg gcaaccgttc tttcctcctg actaggtgag tgccactgat aaatcattat    660
gcctttaaca ttaggaatgt tagcagtgca catgtttcag aattgcgacc ttatggttgt    720
aaagattaca aactttacaa cttacttgag acaggttcca tatgtcgtat ctgaaatagt    780
gtgaaggtat ctgattcgat gcaatacaca gacatataaa catattgtcg ccctgctatt    840
ccggaaaggt cattttgtat gtaacgttcc ttaatggaca caaacggaat tattagttaa    900
acatactcaa caaaactatg ttattttgca atgggtagca ccgaaatcta ccgacagtgg    960
ttcgtaaaag tagaacattc tgacataaag aaaaatcatt ggctttaaat atatgcaagt   1020
tacttgtctc taacaaccag ttttatacac atttcagaga acggggaatc cgcgatgaca   1080
atatcaacga gtatatacag aatatataat taaaaacgat gagtgcctgg caagggaaag   1140
agcgagattt gccaaacagg ggggtggtgt tgagcttgaa tcgtggagaa acgtagattg   1200
aaagacaaga tgcatctaa tgatccgaaa atcaaacaca ggattaactg ggatgcagaa   1260
gaatgaatat ctcaagcata catgcaacac ttcatgaatg catctcaaac attttcgtca   1320
gatcggatgc atgaagattt gtaaagcaat ggtttaaatt gtccctaaac gtttagttgg   1380
agatgtatga ggctaggctg tatgttgaac gaaaccattt aacattgttg ttcatgatta   1440
```

```
tttaatattt tttcatttta tagatgtaca ataaaattgg aaactaaaca tttcccttta      1500
ttgttttgta tttacctgtt catgggtatg ttttgaaaga tcgtgatatt tagttggcat      1560
tcacaagttg gaaaaaggtc actcagtttg atttcaagtt tatgtaacct ctttatctga      1620
cgctccaaaa tatgtatagc cttgttcatc tgtcggtatg tggatattcc tacttcaggg      1680
tagggtagca ttaatactta caaaacataa cgtgtaccag atttcagtca cctcagagat      1740
gataatgcat gtcgatatga taggtcaaaa ctttcgatat caatcacaat gaacctatgg      1800
accctgaatc ggaatgatac gttacacttt agaaacaatt cacaaatatg actgtcaccc      1860
tttcaggtaa taatgtttga cggactacga tagtgctgaa cagcaggaga ggcaacatgg      1920
ttcgattgtg agacaggttt agtgtatttg tttgcgaatt taaggttctg aatcacaata      1980
gacacggttc agtaatggga taaccaatc attagataga tagagattag tcgcgatatt       2040
gctgggataa agcttagtgg gacgttaagt cccatctcaa tctctctcat ttttccaaa       2100 acagttttaa ttcaggctca tgacaaggtc gtactgttgc aaaggattct acttcaagca      2160
gagatgtctc atgaatacag tacagggttt ttgaagttta tccagtgcag cgctggcacc      2220
atctctgcat gcgaattata ccatccatgc cgctctaggc tatttgtatt aagtctgtag      2280
aattaaattc gcgagttgca atactgctc accattatct gcctcaaccc agtttgggta       2340
catgcgattt acacaatatt atgtataatg ttcgcttttc gaaaacaaaa cacctaaatt      2400
catccaaagt tttgggagat tttattcgag aaatcaacct gagatgttga atcgggagct      2460
gcgcttattc aatggtggac tcggaaggga agtaaccgct gatgaggcaa acaataacg       2520 caaacatatg gaagtggaac tctttgaacc agtattatgt ttgtgtggac atgtatgtgt      2580
taatttgacc attcgaacaa ctttactatt ctattcataa tgtgtttaga tttacatttg      2640
aattaaaaga gatgagttta agatattaat attttccttt tatagtctgt cgtgattgta      2700
gggcaatatt tatgtatgtt cgttcatttt tcatttatca tttggaaagg tatatcataa      2760
gattattatt atcattcttg aagtaatgta tacatatata tatgtcttga gtagcttatt      2820
ttcaatttat tatcatccgt catccaattt tatttcacga aagtataaga aataacgaga      2880
gagagagaga gagagagaga aaagacagaa atgaagttag gagatatnag ttatcaagaa      2940
aacaacagtt tgaattttt gtttagacaa gatatcatat caataacctc gcactattac       3000
gggaataggc gggcgttcca tatgcacaat gaatcgtcag ttaaaatcaa cattaaactt      3060
aaaatactcc tcatatttaa agttgatcta cctcttgtat tattgtagac tattagacag      3120
aagtcgacag tgacaccagc aaccagatat catacccaga cttaaaaagc tgtttccttg      3180
atgtttcaat ttatttccat ttccattatt tcccttatt ggtttccatt tatcaaactt       3240
accatctgca ccagtgggag attgatatgt tgtatttatt tatatttctt gtactacaat      3300
atcaagaatg tataggagct attccttgtt cctaaaaccg gatagatcca taatttccat      3360
tttgggataa atggaaacta aacacaactt ttacagtaaa cacgagtgag caagttgagt      3420
tttacgccgt ttttagtagt attccagcaa tatcgcggcg ggggacacca gaaatgggct      3480
tcacacagtg aatgcatgtg gggattcgaa cccgggtctt cggcgtgacg agtgaacgct      3540
ttagccacta ggctaccca ccgcctattt atagttaaga cgaatacttt tctcaagcct       3600
caaatatgtc cattctagag agactgaatc tgatcctgaa tctgcggacc ggtcttgaat      3660
atcatcccac taactcattg tacaaagtac ctgtagattg tcagttcaaa gacagatttc      3720
acaaccctat tatattttgt cctgctcatt aagatattca gactcactca aactgctaaa      3780
```

-continued

```
tgatttttaat cctactttga gatgttttaa cttttattcg atgcattttt gcgttctgcg    3840
tcctgtataa aggtaaagca ggtaaactaa cctaaccctgt tgatttattt catagttttg    3900
cgatcagatt gaaaccggaa tgcacagtga agtgtggcat acatctttcc acagagatac    3960
tggatactag gtggtacaac cgcattggct ttgtgaaagg atattagtgt tttatgagac    4020
tgactcatgt ttcaatgctt agagcggaat gatctcggtc ttcatgaaaa atattgtgtt    4080
gaagtaaccc cccagtccct aacagaacgt ggggaaagca gatggatatg ccaagacatc    4140
ttcgcatggt gtgaagatga tcgttacaac atctgcagaa aaagttatt ctgtgaagaa     4200
tatgccaaag catcactgtg agtgttttga agatgtgata tggcaacacg cagcgtgtaa    4260
ttatgctttg tgtgtatttc tgaagatccg tatgagcatg gcgccaaact atcagttaaa    4320
tggctatgcg aagatcttcc cgagatggta aacacatatt ttggccatttt ctttgtaag   4380
tgggcgacac agaagatccc cctgattgtg tggatgagga cacaaaaacg ggtcccccttt   4440
cctttgctga tgctaatgac gccctggaaa cattgaaaga cttcttctcc agcaagcaag    4500
ccaccaacca caagttgtat aaatcgcttg cggacttgaa tacggcagtt ggacagatac    4560
atacagccag agagggccga actaaaacat ctaaacatgg aaaaactgta aagacaggct    4620
ttgttgtacg acgtacgtaa attcattgaa tgtttgaaaa ggtagaaaat tattaaatct    4680
ttgaaacctc gctctgtttg tttgttattg tcccccacat ttgcaaatgg tatccaaaaa    4740
gggcagacac atttgttta atcttagcca ggttcaattt agccttgcgc ccagactcat     4800
tgtatctggt gaaggctata ggtggccacg tcttctaaga tgctatgcta ttcttaccag    4860
aatccaatgt aaagagttca aacgcatggt tcgctttgat tgtgattctt tcttagcacc    4920
tctctcctac ccagagttca cctgcactgc tcctgactca caataagctg acgtgctgtc    4980
atatatgtgc aacattgtat acgttggcgt taagcccaac tcacttccgc tgtcttttgg    5040
cag                                                                   5043
```

<210> SEQ ID NO 111
<211> LENGTH: 659
<212> TYPE: DNA
<213> ORGANISM: Halitotis tuberculata

<400> SEQUENCE: 111

```
gtaactacaa acgtcgtccc attcatacag gagaaatata caattgtgtt gtaagagcgg     60
tatactgttt gccaactgtg taattgaaac gttgatgatg tgtctttgt atttcaattt      120
gtatgcactt agacatgatc aatgtttctg atgtgtcaag gatgttcggt gtgtcacttt    180
caaaagatca aattcatatg acgtacacag agcaagaacc aacagtaaga agtctgtatg    240
acttcgctct taaaagcaat ggaaaaatat tttcacttaa cacctagccc ataatcacgc    300
atattagatt attcaagcga tgtcaacatg tttttaatat caatctcatg gttctgatat    360
taccggagac atgcaacagg ctgccattat agccaggaaa tcttatgaat atgtgcatat    420
ttttttctttg attctgtatg acgagaaata ttcggaggca agattgtgt tttcagaaca    480
gaatcagggt atcagtgaca tcgtcactgc atggctacaa tattgctgat gtgactgttt    540
ctccaaggat tttcatctca ctgtctgtac tttgaatcta caaattcgta ttaaagttat    600
gacaattta cccctgccta tttgtaaacg aaatataaca tgagtgttta tgctgacag      659
```

<210> SEQ ID NO 112
<211> LENGTH: 904
<212> TYPE: DNA
<213> ORGANISM: Haliotis tuberculata

<400> SEQUENCE: 112

| | |
|---|---|
| gtaagtttgg tttacagttt cattataaaa acatagcagt tttaagttta ggggcagatt | 60 |
| ctaatctcta atattccttt caactcactt tattggtgcc ttcttggagt gacatttaga | 120 |
| aactaagaca agaggaagat gaacaatgtt tgtagggata gacagcttgg atgcaatttc | 180 |
| ggaccagatt ctaacagcgt catgaagcaa gtgatacaca acgttatcaa taacgagaat | 240 |
| atacacatag atggtttgag tttataaatg aactattaac ggcattgtgg ttatagacag | 300 |
| tgaggaagac gccagataga caaagggtag gggccttggt tagataatga gaagttgaag | 360 |
| aggtgtaata acttaaatct ctcttgacta ttgattgtgt ctaagagttt tcttatctta | 420 |
| cagtcggcca gttgggtcaa agatggtgtg attcggatgt gctttgtgtg ttctgcgatg | 480 |
| gctgatttag agtcagttta cttcagatga atgaagttcc ccgattctta tgtttaagtt | 540 |
| tgtttcacct acgcatgaag acatcaccag cagggtcgtc tttatttcta gtagcttatt | 600 |
| tacagcaagc ttgtaacgta tgctgaattg ctgtgcctct gtagaacaca gcatctatgt | 660 |
| ttgcttgctt ctttagtaga ctgcggatgt gatggttggt tacctggtat gctgacgaaa | 720 |
| gaattgttga cgtggtggtt tgccttgatg ggttcgttga cttggtttgt tggatactga | 780 |
| ttaaggtgac tctgctggga ggcttggatt ctggggccgg tgttctttgc tctcctgtct | 840 |
| agggtggcga ttatttccca acccacttgt tccattacac tcaaaacctg ctatcaattt | 900 |
| acag | 904 |

<210> SEQ ID NO 113
<211> LENGTH: 543
<212> TYPE: DNA
<213> ORGANISM: Haliotis tuberculata

<400> SEQUENCE: 113

| | |
|---|---|
| gtgagacatt attacacttc tatttagtag tgggggcggg atagctcagg tggtagagcg | 60 |
| tcggccttca gcttctagtc tcgcccacaa gagcgcgctg gctaaagggc cggagttaga | 120 |
| ttcccgcggg cggcaggcaa tatctccgaa ggggagaaca gttctccagt cggtgaaatt | 180 |
| ggggtgcaat gttgtaccac tgaaatgcgt gcagcaccaa ccatccaaat accagccttg | 240 |
| ccgcgctggt ctgactacat agtaccaccc ggattcaacc gggctatata ggttctcctc | 300 |
| cagcagtaaa tctgacagtc gccatatagc tgggatattg ctgagtgcga cgttaagccc | 360 |
| caactcactc actttatatt tagtattcta tttagtatcg acgcatgacc atgtgtggtg | 420 |
| gtctactcat ctcaacacga ccgattaacg ttaagagctg ccaacatgat tctctttctc | 480 |
| tctttagcct ctttatgcca aaagctatat attaatgtag gaccctacat atattatttc | 540 |
| cag | 543 |

<210> SEQ ID NO 114
<211> LENGTH: 2689
<212> TYPE: DNA
<213> ORGANISM: Haliotis tuberculata

<400> SEQUENCE: 114

| | |
|---|---|
| gtaagttgat tgtcttaata ttgtttaat ttttgcagaa atttgatttt aaattgtgta | 60 |
| ataacagtac acatttttac gcaacagcag tcattattgt gtgtgaagat gtcaaaccag | 120 |
| aaaggtttca atcgtgaaaa caaaaacaat tctctatctg tataccctc aataccagta | 180 |
| tgatcacaaa tctaggaaat attacaatac tgcttcatag agtaactgct gtttgtggca | 240 |

-continued

| | |
|---|---|
| gagctggata cgaagtttct gatagttcac agctacatga tagtaaatga acctgtacac | 300 |
| atcaacggtt gatcatgaaa attttgtatg tgtgaaagtg ctacctgtat tagtgaacgt | 360 |
| gctacctgta taactgaaag tgctacctgt atgactgaaa gtgctacctg tatgctgaaa | 420 |
| gtgctacctg tattagtgaa cgtgctacct gtataactga aagtgctacc tgtatgactg | 480 |
| aaagtgctac ctgtattagt gaaagtgcta cctgtatgag tgaacgtgct acctgtataa | 540 |
| ctgaaagtgc tacctgtatg actgaaagtg ctacctgtat tagtgaaagt gctgcctgta | 600 |
| ttagtgaaag tgctacctgt atgactgagc gtgttacctg tatgactgaa cgtgctacct | 660 |
| gtattagtga aagtgtaatc tgtatgagtg aaagtgctac ctgtattagt gaaagtgcta | 720 |
| cttgtattag tgaaagtgct acatgtatga ctgaaagtgc tacatgtatg aatgagagtg | 780 |
| ctacctgtgt gactgaaagt gctacctgta ttagtgaaag tgctacctgt atgactgaac | 840 |
| gtgctacctg tattagtgat agtgtcactg gtaccaactg gatgttctca cttctttggc | 900 |
| gaatatctgg gctcaaaaca gttttcagt atcatagtcg tatcagtttg atttgtatgt | 960 |
| gcagtggaat cattttcgtc aaataatcaa aactggtgtt gaactggcgt tcacgtttta | 1020 |
| tggttgtaaa acaaattctg taagtaaaga tattttaggg atatctgtat gacatgaact | 1080 |
| gaattgctta aggttagcat gccatgacaa attgctgaat gtctgaggat tggtggagca | 1140 |
| ataaatcatt attaagacaa aaatcagaaa cgtccatttt cacttttaac agtgtatctg | 1200 |
| tctgaatgcc ccctactttt tggaagagta tatatgaatt atcggcaata taaaacgtta | 1260 |
| aatggcaaat gtcgggcata tgtcaggaca ttattaccgc agtttatagt catatttacc | 1320 |
| gggtctagga caattgtcac cccgacaatt gccacccgga caattgccac ccaaaaataa | 1380 |
| aatatacgta aacagaaaac aaatattgct ttcagccttt attgagttag ataatgacat | 1440 |
| ttatgttgat aaatatgtcg tttgataata ataataacaa taatataata ttacaatact | 1500 |
| gcaatagtac tatcagtact tatcattta tcacagatta tatatagatt ctagagtccg | 1560 |
| atgttgtagg caacacttcg tcggtaggcc gttaggtagt tatcattagg gctgagtatt | 1620 |
| gcgccaaatt tcgtattgct atatactgcg atacacggtt acctgttttg caatacgtaa | 1680 |
| acttaggcaa atatgacagt ttttccatga ttattttcac gtttcaatgc ttaaaatggt | 1740 |
| cttatctgtt atctccttga aggtttaata aaataacaat aaacataaat cattattgaa | 1800 |
| aattaatgaa caaagtaaa gcgcttctca gttaccttaa cctaacttat ttatgaatgg | 1860 |
| gattactatc caagaatgtg aaattccaaa acaccttggg ataacactgc aaaacgactg | 1920 |
| ttcatgggac ggacatgaaa aaggtgagtc ccatgttaaa ctgttgagaa gtttcctat | 1980 |
| actgtttgtc ccgaaaaagg ctaaagacca tgtactaatc aattattcta tctattttcg | 2040 |
| attactgttc tcatatttgg gacaactgtg cagatcggta gcatccaagc tcgtctaaat | 2100 |
| cggtttgata aaccttgtca ataacatgt tgtctcaaca tccaagctca cctaaacctt | 2160 |
| gtcaatacct gcatctgaac aaatgtatat ttaagacgat agcatccaag ctcatctta | 2220 |
| aaatgaatat tttctctttt tctaccaaaa cattatttgg ttgacagttg tcctccctat | 2280 |
| tatagtaaaa agaactgggt ggcaattgtc ctaggtggca attgtccgga tggcaattgt | 2340 |
| ccgggtggca attgtccggg tggcagttgt ccaggtggct attgtcctgt tcccatattt | 2400 |
| acgtatccca tttctgctc tgtaatttta aataaactca cctgcctaag gtaagacgac | 2460 |
| atgtgtcacg tgaacatcgt ttgggggcaa gggcggaatc ccttcgttga agtaaatga | 2520 |
| atactgtaca tagagatgcg tatcttgaac tctttattag ctttgatatt gtgcttaata | 2580 |
| ttacatgaat gtatttcaat atgtaattat gtgttcaaat gaatggttga cttgaatggt | 2640 |

-continued tttattgctt tatatgctac atcaacatgt gtgtttcttt tcatttcag    2689

<210> SEQ ID NO 115
<211> LENGTH: 561
<212> TYPE: DNA
<213> ORGANISM: Haliotis tuberculata

<400> SEQUENCE: 115
gtaagtaaat ttacaaaatt tggtgttctc taactatcct aagtattcaa tcgttagcgt    60
gtacctatct gcataatgca ataccctgac tccatataag tatagtatat ttactctggt   120
cgaaaacaaa caaattgaaa acaagagtgg acgtgctgtt atgatttctt tttcattctt   180
ggttcgttgt gtaatgccac agccagcaat tccagatata tagcgacggt ctatgaatac   240
tccagtctgg accagacaat cgtgtggaat ggtttaggca cattatatca aattcattgt   300
tgaagatatg agttatgagg tcacaatgtt gtcttgttac cccgtgtcag tagtgacgtc   360
atttcatgac tgaaatctct tcaacgccgt ttagcaataa taggctcagt agtattcaac   420
caattacaat cagtagaaaa ttctctatac tattcttatg ttgcatcctg atatccctat   480
gcaaaaatta gtcatctaat ataatcattt tcgataaata ctttgggcaa acaaatcaat   540
gtaacatcta ttttctttca g                                             561

<210> SEQ ID NO 116
<211> LENGTH: 334
<212> TYPE: DNA
<213> ORGANISM: Haliotis tuberculata

<400> SEQUENCE: 116
gtacgtggat ttgattacat agcaatgcta tatgatttca gtaattacaa cctcaagtca    60
tgtagccgtt ttagattgca ttacatcaaa cagcattgga ttaaattggg ggattgtcca   120
ggccgcatta tgttgcattc cgaaaatagt ttgtgtccag tgtccacgtt taaaattaaa   180 ccatttaat catattaggg ataattttaa tagatgttat agtgctttat ttcatattgt   240
tacagtggac agtcaccaag gacatatttt actctataga tacacaaaca ccaattaaaa   300
ccctgctttg gaaagtctaa cttttttcccc acag                              334

<210> SEQ ID NO 117
<211> LENGTH: 283
<212> TYPE: DNA
<213> ORGANISM: Haliotis tuberculata

<400> SEQUENCE: 117
gtaatgccat cttaatacag ttcgttcgtt aaattatata tgttcgttta caacaccata    60
ccttgaattg aggtaataca tcacttgata ttgataatgt aatggtaatt gttcttgttt   120
gtaaaaccgt ttctggggtg tttattcact atccacctgg tggatagtga gtaaacacat   180
tcggtttaat atgggtatct aatggacagt gaagtgtgct ggctaggcag ataccttggt   240
ttctgtgaat ggaggtagta gaaagggggtt ttgatgattg cag                    283

<210> SEQ ID NO 118
<211> LENGTH: 174
<212> TYPE: DNA
<213> ORGANISM: Haliotis tuberculata

<400> SEQUENCE: 118
gtgagtacct gtttgcacta agacttctgt aggctaaaag tgtaagaaat atcaattaat    60

```
ttcaattcac ccaaacttga aaacggtacc tatataggtt aacttttgt ctacagtaaa      120 ctgaacatac ctacacattt catgaaatga tctctcaata ttttccacca acag           174

<210> SEQ ID NO 119
<211> LENGTH: 703
<212> TYPE: DNA
<213> ORGANISM: Haliotis tuberculata
<220> FEATURE:
<221> NAME/KEY: misc_feature
<222> LOCATION: (478)..(478)
<223> OTHER INFORMATION: n is a, c, g, or t

<400> SEQUENCE: 119
gtaaatttac agagctttat gaagtgtgtt cagagtgaag agaccaagat atacttatac      60
ccaaaactag ctagcaacag acgatttcac ttgtttcgga cactttgtat tatacgttgg    120
atcccaaggt aaacggaaac gtaaccgaga atcagtccgt aaagtgagtg agtgagtttg    180
gggcttaacg tcgcactcag caataccca gctatgtggc gactctcaga tttactgctg    240
gaggagaacc tacatagccc ggtttaaccc gtgtggtatg tagtaagacc agcgcggcat    300
ggctggtatc tgacggacga agggtggcgc tgcacgtatt ccagtggtac aacactgcac    360
cccaatttca ccgaccggag aactgatctc cccttcggag atatcgcctg ccttccacgg    420
gattcgaact cggtgacctt caagccagcg cgcttctagc gggggcgatt agaggttnaa    480
ggccgacggc tctaccacct taactatccc ccggcccac tcctgacgga aatgtttata    540
attcagcctt tgttttctta ttaaacactc ttggcagatt ttctatagat aatggattca    600
catgtagaca gtctcccatt gttgtaactg gtagtcaaga gttagaatct gaatacattc    660
tccaagatgg atcaaggaaa acaataatta cttgatgttg cag                      703

<210> SEQ ID NO 120
<211> LENGTH: 298
<212> TYPE: DNA
<213> ORGANISM: Haliotis tuberculata

<400> SEQUENCE: 120
gtgagatata tgcaaattga atgttgtcca gatgcgttgt ttacatttat atgcttggaa     60
ttgtcctgaa cgaatacagt ggaataacca aaagctgaaa aataaaaaga tatatacttc    120
attctgaatt tgtcagtatt gctgacccaa aaacacgtta tccatgtcga cactatattt    180
gcctttctga atctgagact gcgttatgtt tctaataatc acgaaatatg gtatacaggt    240
tgtgtatctg tagaataccc aaggcagaat ttaaagggtc acaccctgtt taatacag     298

<210> SEQ ID NO 121
<211> LENGTH: 963
<212> TYPE: DNA
<213> ORGANISM: Haliotis tuberculata

<400> SEQUENCE: 121
gtaagtttgt gttggttagt gttggttgca tgttttgcca tatcgatagt atcagtgtgg     60
taacatctgg tttctagttc attcagttca ccttatcaga agctgtttgc tctcgtctac    120
aatagtgacg tcttttcagtt ttagaaccgt gtacatccgg gttatattgg tctccagcaa    180
cccgtgcttg tcgtgggagg ccactgatgg gaacgggtgg tcagactcgc tcacttagtt    240
gacacatgtc aattgcgaag atcgatgctg aggttgttaa acattggatt gtctggtcca    300
gactcgatta tttacagaca gccgccatgt acctggaata ttgctgagtg cggcgttaaa    360
caacaaacta gtcagactaa tctttcactg tttataatga tggctcgaac ctagcactca    420
```

```
tgtcccaagt tggcgaacat ctggaaggga atttcaaatg aaaagaacaa tctttcacgt      480
ctattggtat cacgctcctg agaagaaca tgatgttcac ggcgttactt cctcttacct      540
gttttacttg ttcccacgtt tcttcatatt taaagagtat ttgggtatta gagctttggt      600
gctgttacaa tgctactcaa ctgttcagtg cgggcgaccg cgcttgttta cacattaagt      660
tttgtttgtt ggttggtttg tgtgtgtgtg tgtatgtgtg tgtgtgtgtg tgtgtgtgta      720
tgtgtgtgtg tgtgtatcta tgtctatgtg tctgtgtctg tgtgtctgtc tatgtgtgtg      780
tgtgtctgtg tctatgtgtg tgtctgcgtg tgtgtctgtg tccgtatgtg gctgtgtcta      840
tgtgtgtgtg tgtctgtgtt tatgtgtgta tatgcgtgtg tgtctgtgtc cgtatgtggc      900
tgtgtctatg tgtgtgacat gcaatacatg ctgtgatact cactagctgc gtctatcgac      960
cag                                                                   963

<210> SEQ ID NO 122
<211> LENGTH: 650
<212> TYPE: DNA
<213> ORGANISM: Haliotis tuberculata

<400> SEQUENCE: 122
gtaagagcgg ggtagggatg gggtggtagg gggtgggttg ttctattact tcccgcttca       60
cttgtatgaa atggataacc ttggctgcat cccaattgcg tgatcgattc tctttcgatt      120
cactcgtgcg attagactgc cttatttact atagtagtta gaatgttgct cagtgcgccg      180
ttaaacaact aatacacaaa accgcatttg ttttatatgg tcactctact gtttatcacg      240
tatatgtatg ttccgactca ctggttggtg cgtaccattc tactgtcaca ctgagagcca      300
atgttctcag atgtgtgaaa tgtttgaaag ccgtttctac ataatattgc aggaatacca      360
ttgtagaatg tagtcaaaca ggtaacaatc tgttagtgag cccagttcga ggttgcgttg      420
tagggtgtag tccaacaggt aggcagtcca taagcatagt ttttaagcat tttagatcat      480
ctataattaa ccacatggtt agccgctatg tttagtttaa tccagtataa gttagaactg      540
ttatatttcg aagggaagtg agtaaatcct tattccttga ctaccattta atagatttcc      600
caatgactcc attcaactcc taactttcac atcactgctc tcttcaacag                 650

<210> SEQ ID NO 123
<211> LENGTH: 583
<212> TYPE: DNA
<213> ORGANISM: Haliotis tuberculata

<400> SEQUENCE: 123
gtgagtacga caggcatttc tagtaaaaac ctacttttgg taaaaggttc gagaaatcac       60
ttgaagcaac aacatgattt tgtaacgcct attacacgtg aacatgtcac acccggtgat      120
gccgtttaat ggacatgcct ctgttaatga aaggggtaag tacatgtgta tgggatgggg      180
atgggagcca cctgtcccaa tttcataggt ccctaggatc ccagttgcgt aggaatcccc      240
tgattaatgc cttgtgaatt cctcctggaa ttgtcctggc ccaaattttt acaaacccgc      300
cccgatatac cttggaaata attgggccta agggtggggc ttttaaggac caagaaccca      360
acctaaaccc caacccattt ttcccaccc attccaggtt ttgttttacc aaataaaaag      420
gtttccactt tgaggaaacc ctttaagggt tcttttcagg gctttttttc ttttctggga      480
attccaattc cggggaaaca aaatacatat atttcacaga cctttggtca aatttatata      540
atttccgact tcatgtcata ggtttgtctt tcttcctaca cag                       583
```

<210> SEQ ID NO 124
<211> LENGTH: 475
<212> TYPE: DNA
<213> ORGANISM: Haliotis tuberculata

<400> SEQUENCE: 124

| | | | | | |
|---|---|---|---|---|---|
| gtgaggagaa | ggccccaggc | tagcagggca | atggatgaag | gaaatagggg | caaagggaat | 60 |
| agcagttaca | ccatcgacat | ttccaacctc | ctcagaaact | aatatatagc | cttaatacaa | 120 |
| ccagccaaga | ctcaacgggc | agccggggtg | gggggatttg | gtggtcgctg | tttcagacca | 180 |
| gggtgcaaaa | tatcagtgcg | caaatcaaca | tgttgcgtgt | cagacactga | cacagcagtc | 240 |
| attgaacctg | cagacccata | acaggaaaat | ggggcagata | cgatcaaaga | cagtgtaaaa | 300 |
| tagggataag | taggcatatg | caaccacctg | atggaaatga | aaaggggtaa | gtttaaaccc | 360 |
| cggctaccaa | aggtccaatg | gttccttaac | ccagcttacg | ctatccctct | aatttcagta | 420 |
| ttgagctgat | ttctgtcgag | ttcatgtaaa | ctgtatactt | tctgtattat | tacag | 475 |

<210> SEQ ID NO 125
<211> LENGTH: 1002
<212> TYPE: DNA
<213> ORGANISM: Haliotis tuberculata

<400> SEQUENCE: 125

| | | | | | |
|---|---|---|---|---|---|
| gtaagggatc | tcagatccgt | cagagtgagt | gagtgagtga | gtgagtgccc | agcaactgaa | 60 |
| gctaggccgc | cctactgggg | atcacaggga | atgtatgtca | atggttgaag | aaaggagcag | 120 |
| tgggttacaa | cgccgcgttc | aaagtcatgg | cagtttcata | gcgcattgtg | cgcgcgtgtg | 180 |
| tatctgtgtg | cgcgcgtgtg | tgcttgcgtg | cgtgtgagtg | agtccgcttg | tgcatttgta | 240 |
| ctagcacaga | ctaatgctgg | ttctagagag | cctactgata | aatgtttaca | ttaagatctt | 300 |
| tacagtatac | tgagattcga | gcccagacca | gcggaacacc | aggcagggta | caacaaata | 360 |
| acgcctttcc | acacaaccga | cgcagcctaa | agtggctctg | ataggctgat | accggtgtat | 420 |
| tcttagaact | tgtaatttgt | gctttgccat | aatacatgta | cttcagttaa | ctgtaataca | 480 |
| gcataagact | ggaccggtgt | ttacgacgca | atgagcaata | attactctac | gaaaagattt | 540 |
| ggttagacat | attcaataat | tgtaacattc | attaacaatg | aacaccacgt | gcactctcgt | 600 |
| ttgtgtcaac | gtattcataa | tcattctcat | gcatctgtta | gctcagatat | tttgatgttt | 660 |
| caagagattt | gtacgaacgt | atgggctggt | gccccatgaa | attacataca | atgaattcag | 720 |
| gtgaaatacc | tggcgagaca | ataagatctt | actagtgctg | ccacttcagt | atggtgtccc | 780 |
| cgatggtgtc | tggtgtatgg | gtgtgttttgg | cgtcagttgt | tactggaaaa | gtcagctcta | 840 |
| attatgtctt | tatgtggtta | aagacccccat | aacctagatg | tctgggttta | acttaacatg | 900 |
| atagtaacag | tcggctgtat | agcctgacgc | ttaaacgtta | gatgaataag | gactatattg | 960 |
| tgttgtataa | catttctata | acctcctttc | tatatcattt | ag | | 1002 |

<210> SEQ ID NO 126
<211> LENGTH: 597
<212> TYPE: DNA
<213> ORGANISM: Haliotis tuberculata

<400> SEQUENCE: 126

| | | | | | |
|---|---|---|---|---|---|
| gtgagtcacg | ttctctgatg | gtcacgagtc | acgttctctg | atggtcacga | gtcacgttct | 60 |
| ctgatggtca | cgagtcacgt | tctctgatgg | tcacgagtca | cattctctga | tggtcacgag | 120 |
| tcacattctc | tgttgagtga | agtctcagta | ccatttattt | ctcttaccctt | cttctaacca | 180 |

```
ggggtttcag cgtggatcgt ctgagaagtt agcgcaaatc tatattgaag tcatttttct      240
atcatataac catcgttata tccacgtgcg aaagtgttca ttaattattt ttattttcat      300
ttatgaaggt ctaaaagaaa atatgtattg ttggaaacta tattcgaagg tgaaggcaac      360
acgagtgtat taatattctc aatatcaatg tacgctctgt cagcacctgt ttcaccagga      420
actacacctt tagcgtacca aaatatcagc tgatgatttc gaagcggact ataccctcac      480
cacttgtttt gtgtgtgtat ttatgtgtgc atgtgtgtgc gtgcgtgcgt gtgtgtgtgt      540
gtcctacgta tgttgatatt tgttctgac tgtatatgtt cgtgcttacc attgaag         597
```

<210> SEQ ID NO 127
<211> LENGTH: 689
<212> TYPE: DNA
<213> ORGANISM: Haliotis tuberculata

<400> SEQUENCE: 127

```
gtatgtatga ttctaataat gaatgttttt acctccggtt taaacaatat tttagtatta       60
cgaaaggaga agtacctcga gaggtctagg tctcagatgt ttagaaaccc atgaagacag      120
gtatgcttct gaaaaacaaa gtaacatcat gaggctaaag ttcagattca aaccatcgta      180
gttcgaatcc agcatgcaaa gggccctaac cctgtagatg cgctgcttg aaacagagta      240 gtctgttcag ggtcagtact gtccccacaa acatcatagt cagggtcagt actgtcccca      300
caaacatcat agtcagggtc agtactgtcc cacaaacat cacagtcagg ttaattttg       360 gattcggttt cgaatgcgaa gaagacagtc acgccctgac actggaccga ggttgccgag      420
aaagctcgtg atattgctgg aatactgccc agtaaaacca tcatttattt taggctattt      480
attacgaaaa ataataatat gtatagaaat gcatatgatc gctgtttgaa tgtaaaattt      540
agaatgggtt tgggagtgtt cactattttt tcatcaaaat ttcatgtatt ttaaccgatc      600
gacgctgaag acaaactacc gttaatcagg cagttcattc atatctgata gggaatattg      660
gttgttaacc aacgctacat tgtgtccag                                        689
```

<210> SEQ ID NO 128
<211> LENGTH: 846
<212> TYPE: DNA
<213> ORGANISM: Haliotis tuberculata

<400> SEQUENCE: 128

```
gtaaatggcc attgtataca tgcattcatt tggactttga gtgagtgagt ggatgcgtat       60
tcagtaagtg agagtgtgag tgggtattag gtctgtgagt gggttggtga gtggatgggt      120
gagtaagagt gggttggtga gaaagtgagt gagtcacttg gtgggtgcgt tagtggaagc      180
gtgattgagt ggatgggagg taggtgagtg agtgaattgg tgggggggtg agtgaggtta      240
acgctgttct gctgttcaat cacaccacat gttgccagct tactgtgcag gacgaatcca      300
gggttgtgtt aaattttata tgtttatata taacgatgga cgtgtctgga tgtggcgaat      360
gtgtcaagag aattatgcgg cttttgtgctg ctccgcgtat ttattgcacg cgcgttggta    420
cgcggttgat aaagtagttc aaaacatttc ccagccatct ttgtctgttg tgaaaaccta      480
ctccaggacc atccatttca atatgtgtct gcgttcatgg agttatacat gttaaactgt      540
agagcgcaga tgagcacact tgagcatttc ttcagtaaat cagaatgtgt atatttcaaa      600
atttaccaaa tgcaatatca tcaagcaaat tatgcagctc tatagtaaca tcggagtcaa      660
tggtccagtg tgccctcggc tgccattccg acctccctgg ccagaataca ccccggtcag      720
```

```
gatcagttat ccgtcagaag gcacggtgcg gaatgaaaac ataaacacat agtcgcttag    780
tagtatgctg atttaggcac gcaaaatccg aatgtgaatt actgtgaatt gcattacctg    840
ttacag                                                               846
```

<210> SEQ ID NO 129
<211> LENGTH: 474
<212> TYPE: DNA
<213> ORGANISM: Halitotis tuberculata
<400> SEQUENCE: 129

```
gtaagtagct acctgtttat tcaattttttt cgctttgcca atcaattcat tcagcttgaa     60
attcaataat tgtgttttgc atggctgaaa accaatttga actcttttct tttctcaggt    120
cgaactcaaa taaataatca ctaattgtta tgcacgcggg tagggcatac atactatatc    180
cacatcggtc atctcaaaat gcaaacaaat tgtcttattt ccgttgggac aagcaaaccc    240
cctttcctgt aatcttgcct ttggcatcca ctggaattaa tgttgactgg taattgatac    300
tggctctctt cttgcataga gttaatatct atagtttgta aatctttatg attttgctat    360
ttatatttcg acagcatgct atagacaccc tagactattg tatagccact tgtattgttt    420
ttccatttat tatttataac agaacatggc ttgtaatttt tatttacctt ccag          474
```

<210> SEQ ID NO 130
<211> LENGTH: 290
<212> TYPE: DNA
<213> ORGANISM: Halitotis tuberculata
<400> SEQUENCE: 130

```
gtgagaacat tgataatagt tcaaatgaag tatatccgat tcaagctgtc gatacaagat     60
gagatacata atcacaatgt tgtattaga tatctctctt aatttaatgc cgcttttatc    120
aatattcgag caatccttca gcaacataca ccagcaaatg tttcatcaac agactatatt    180
atttaatatt ttaaaaatcc ttctctgttg ttataaatac ttaaagtatc gaattccttg    240
aatgcgtctt ctctgcagca tatagttaag ttgttgtgtt tctctgtcag               290
```

<210> SEQ ID NO 131
<211> LENGTH: 298
<212> TYPE: DNA
<213> ORGANISM: Halitotis tuberculata
<400> SEQUENCE: 131

```
gtaagaaagt ttcactgtct aaatcttttt ttatgataga gggtagagaa gtggagacaa     60
tgtgacaata tattgaataa agttgtttaa aatttataac tctcataagt tcatattatg    120
ctgaagctgt agccatctat aactgtgtaa catgaaatgt taagacatta acctaaatac    180
ttcagctgat aacaaaacaa tgttaataca tacgtcaatg taacattttc ttatctttag    240
gttatagcat aaacacttca gagatacagt gacgaaaacc tctatttaaa tatttcag     298
```

<210> SEQ ID NO 132
<211> LENGTH: 189
<212> TYPE: DNA
<213> ORGANISM: Halitotis tuberculata
<400> SEQUENCE: 132

```
gtaagtagta aactgctcag attgtttttca taattactcc actattaagt aaaaagtact     60
agtaattcaa tagtactgtt cacagagaaa tgtaacacaa tagaccacag agtccatttg    120
ttaaacgcct ttggcttggt aagtctgaga ttttggtgac tgatggaaag ctaaaatata    180
```

-continued

| | |
|---|---|
| ttttgacag | 189 |

<210> SEQ ID NO 133
<211> LENGTH: 821
<212> TYPE: DNA
<213> ORGANISM: Halitotis tuberculata

<400> SEQUENCE: 133

| | |
|---|---|
| gtatatttaa gtattttatc ttacgcatga ccctgaccct atttatttt ttttaatcct | 60 |
| cggatttgtt taatcctgtt accagcgaag gtccgggtta gaattgatct tcagtcaact | 120 |
| attcttgtcg taggactaac gagttgtctg gcttgcttac tcggttgaca cgtgtcaacg | 180 |
| gatcccaatt gcaattagat cgatgctcat gctgttgatc cctggattgc ctggtccgga | 240 |
| ctccacatac cgccgccata ttgctggtat attgtcgaat gcgacgctaa acagcaagcc | 300 |
| aaccaacaat actgagacct ggtggtacat gtcagttctc tattgctggg gttccaaaca | 360 |
| tagccatcag ttgaaatatt tcatacatag aagaatacct ctgaatatga tgatgaaaca | 420 |
| tttacttaga cttgcctgtg agccccaggc aaaatgcact gtaaaaatac actgacagag | 480 |
| gattaggcat tcttgggagt actgtatagt tagttgcata catattagcg ttccctcact | 540 |
| aaaacgaatc tctgaatgct atcaattaaa gatcatgatg cttgattgt gtctactgta | 600 |
| tttaaaatgg tgttaagatt tgcaattaca atatacacaa acacgtttcc tgcatctcgg | 660 |
| agaatgcaat ctttcgttgt acgcgtctgt tttcatattt ttatgcatgt agtttgcact | 720 |
| acttagcgtc caataaatcc attcacaaaa tcacacaaac aaacgatttt aggaatgtga | 780 |
| ctgtagctgc aacgaatata cctgatcctt tcttgttcca g | 821 |

<210> SEQ ID NO 134
<211> LENGTH: 866
<212> TYPE: DNA
<213> ORGANISM: Haliotis tuberculata

<400> SEQUENCE: 134

| | |
|---|---|
| gtgagagaac cagtaatagc tactgtctac aaagaatgtg ttcatttaaa gacctgactg | 60 |
| taggccgatg gctgctgtca tctcctccgc ctcctcctcc tgttcctcct ccgaagggt | 120 |
| cagcttcagg ttctccttgcc aatatgccaa gcagacctcc tgagcaggca gtatatatac | 180 |
| gtaagggaag caagtatgga ccatcgcgcg gcatgtagag atacaatgat cagctgtctg | 240 |
| ctgttccact cctgtcagac aatgagataa acatgaaatac agtattactc agcagcgttc | 300 |
| caattttcaa ccctcgtatt tattaaaaaa aggaattttt aatatatttt tctccttgtt | 360 |
| gaaatatttt agtaactgtt aatcgatata gagtggagta gtgacgcttt atttcggttc | 420 |
| attctcgaaa caaaaatata atagtccact gaactctctt aaattgtttt tacaaccttc | 480 |
| aactgccaca gacgtaatcc ctcacgttat tttgagctga caacgtgttg aattgagtgt | 540 |
| gttccgaatt ctaaataagc atgtatatat ttacgtctca tgcaagtaat atatgtttaa | 600 |
| ctgatgacgt cacttggtga ccactgattt agttcctttg tcataattgc agtttctgtt | 660 |
| gtcacgggga cggtggggaa gccaggttcc tcctgtcacg ctgaatatcc cgttcgaatc | 720 |
| ccccacatgg gtacaaagtg tgatgcctat ttctggtgtc ccccaccgtg atattgctgg | 780 |
| aataagtggc ttaataccat atacactcac tctattgtca cactactgcc accggctcac | 840 |
| acctctgatg cttctgttct atccag | 866 |

<210> SEQ ID NO 135

```
<211> LENGTH: 785
<212> TYPE: DNA
<213> ORGANISM: Haliotis tuberculata

<400> SEQUENCE: 135
gtaattaatg gatgtgaagt caatgtccga gggtataata aggatttaaa tacttcagtc      60
gtgtaatact gtatgacatg tgtattggat ggtgtaggta ttacaggtta taaggccagt     120
gtgtgttggg acggttactt tcctgcacta gtaataagca ttgtatttag ctagctttta     180
tcatataact ttagtttcat ggtttgtggc aattgaaatc gaaattttct ttcatttcaa     240
ggttatcgca ctcgtgtgtt agaatagtta ctatgctgca ttgagaataa cactatagta     300
ataaagcata tcatacagta agaataacac tatagtaata agtatatca tacagtaaga     360
atgtcattgt atgataaata ggttatcaca ctcgtgtgtt ttagaatggt tactatccca     420
ggaataacca ctatgtatta catgtatatt gggcagtgta agtagtagca ttgtatatta     480
aatcagtata tcgtgcttca aaacaccagg atatatgggg tatacagtgg gcagtgtaag     540
tagcaacatt gtatattaaa tcagtatatc gtacttcaaa acaccaggat tatgggtat      600
acagtgggca gtgtaagtag tagcattgta tattaaatca gtatatcgta cttcaaaaca     660
ccaggatata attcagtata tcgtgcttca aaacaccagg atataattca gtatatcgtg     720
cttcaaaaca ccaggatata tgggatatac agtgcgggtt tgcatacaac ctccacccct     780
tacag                                                                785

<210> SEQ ID NO 136
<211> LENGTH: 378
<212> TYPE: DNA
<213> ORGANISM: Haliotis tuberculata

<400> SEQUENCE: 136
gtcagtttag tctcctgtct gagctaacga taccaatttc ctatttttcga gaaccacgat     60
gacgagaaaa caagcaatat agatatagat gcagtataga tcaagttaat gaattcattg    120
ctatatgttt gcttgtaata aactttaaga aaacgagagc atgcacacaa atgaaacaaa    180
caattatgtg tttgatagga atatgatata tgtatttggg ggctgacgtg agcagggttg    240
aagggacagt ttacattgtc agtaacactg ggagtattct ttgatccaca atatatagtt    300
tcattgtgtt cagcagttac aactaacatt atatcataca ttacgtcgta acatgcttct    360
tttgtcctct tctgccag                                                  378

<210> SEQ ID NO 137
<211> LENGTH: 398
<212> TYPE: DNA
<213> ORGANISM: Haliotis tuberculata

<400> SEQUENCE: 137
gtatgttatc ttattatcaa atgtgtaatc agatactgga gacgttttca tattaacttg     60
gtcagcatta gttgatgatt ttggtgcgat attgacgaca aggagttaag cattaacacg    120
ttcaacacat cttaatctg atatgagaag ggaataaatt gatccagtat tgatgattga    180
agttagatta acagtgaaag ataccagt tttgataatc gtataaaaca gtagcagaat     240
tgtatcgtga aaactaaatg tgggaaggcg aacgccaagc agattttaga ttacgatcgt    300
gtgctagaat aattcacaat aacccagacg tcggaaatgt ggttgtctat ggcaatagtt    360
acgattaatt gctaacatgc acgatttacc tatttcag                            398
```

<210> SEQ ID NO 138
<211> LENGTH: 522
<212> TYPE: DNA
<213> ORGANISM: Haliotis tuberculata

<400> SEQUENCE: 138

| | | | | | |
|---|---|---|---|---|---|
| gtgagataag | aaacccttct | aacagtaata | cgacaccaca | ttacagctta | aacatgattg | 60 |
| ccatcgatgt | tttcatgtgt | agtatacgct | tttcagttct | acataatttt | gtttttcaaa | 120 |
| tcaagtttag | caaatgaatc | tatcactgga | aaatagggta | gggtagccaa | gtggttaaag | 180 |
| cggtcactga | tcacgccaaa | gacgagtgtc | ctaacctgca | tgggtacaaa | agtgaagacc | 240 |
| attgctggtg | tctaccgccg | taatattgtt | tttagtattg | ctaaaactta | tactcaccca | 300 |
| tgcgctgtaa | aagtggaata | ataatcatat | ttcaacaaaa | gcacaaaacc | atttcatttt | 360 |
| catgaaagcc | tcttgttcac | ctgaaagacg | caagagaaca | atagttccta | acattatttt | 420 |
| cagacattgg | aaatgtcctg | cacgtgtaaa | ccatatatcc | tttgaaattt | ttacgactgc | 480 |
| atcgtataca | atttatgata | taaatttaaa | actttatttc | ag | | 522 |

<210> SEQ ID NO 139
<211> LENGTH: 673
<212> TYPE: DNA
<213> ORGANISM: Megathura crenulata

<400> SEQUENCE: 139

| | | | | | |
|---|---|---|---|---|---|
| gttttgtaat | aattatgtag | aattctttac | ctcagaataa | gatgaggtca | catgggtttt | 60 |
| gcaaaactat | tacgttcgaa | ttaatattaa | taataccgga | ccctccactg | gtacatattt | 120 |
| atctttataa | cgataatagc | gatgatgatg | atgatgatga | tgatgatgat | gatgatgata | 180 |
| atgatgatgc | cggtattgca | cgtaatccag | ccgacttaga | tgcacaccta | agggtgcaga | 240 |
| aagtataaca | attagattgc | gtttgcatct | gtgtatgcgt | gtgctttaac | caaaagtcaa | 300 |
| aataaaagtg | caaaccctta | gtttattcat | ttgatagagc | cttttacgat | aagaacaatg | 360 |
| taataaatta | gaacataact | gaaacctccg | aaagaaggcc | tgtttgtcaa | gagaggtatc | 420 |
| gacatgattg | acttataaac | ctgtgcttct | atattttgga | actgtccact | ttcttgttgt | 480 |
| gtgtactgta | atcacatcgc | actatggctg | caagacgtgt | acgagtacac | tatatactta | 540 |
| cctaatgacc | aaccacaagg | ctggctttgt | taatattgtt | atttcacaga | ataaacaca | 600 |
| gaattccagc | atttggctgg | tgtatttagc | aaaacaccga | tatgacactc | atgttttatt | 660 |
| acattttttt | cag | | | | | 673 |

<210> SEQ ID NO 140
<211> LENGTH: 273
<212> TYPE: DNA
<213> ORGANISM: Megathura crenulata

<400> SEQUENCE: 140

| | | | | | |
|---|---|---|---|---|---|
| gtacttgtta | tatgtttcga | atattgccga | taccttcaat | atatatactt | tatcaaagta | 60 |
| attgattaat | ctgaagtaat | tttcctttcc | agtagagatt | cagttgatac | aacaagaatt | 120 |
| cgccctgttg | tatgtcactt | tatttcatc | aaacgattcg | aagtgagctg | tccatgccac | 180 |
| aatggggtct | ctgtaacttt | ctcgtatggg | gtatagatta | tatagacgtg | gcagaccta | 240 |
| cgtataacta | atatttgtgt | aatgtcgttt | cag | | | 273 |

<210> SEQ ID NO 141
<211> LENGTH: 241
<212> TYPE: DNA

<213> ORGANISM: Megathura crenulata

<400> SEQUENCE: 141

```
gtaactattt tgtcactgta accaacaact gcagtctatt ttgcaattac gataataaca     60
atttttgaaa tatatcttta ttaaagcaaa ggtttctaga gacaaacagc cggctctaat    120
tattttttcg aacttacgct tgagtaaaga tctgcaaatg caaccctac ctatactatt    180
aaaaatataa tgttacattc gtatctgaat gtttaataaa tcacttcata ttctgttgca    240
g                                                                    241
```

<210> SEQ ID NO 142
<211> LENGTH: 327
<212> TYPE: DNA
<213> ORGANISM: Megathura crenulata

<400> SEQUENCE: 142

```
gtaagtatac acacattatt tctcttctgc tatatcagat gaagagaacg ttgtatcact     60
aacctagtct tgtttgattt gtggtttcgt ttgcttcctg aacagtaggg ttgatttaac    120
ttctctgttt cgtctgtacc aatgaaagac tatgatgctt gtgtgaagat gctttgttca    180
tgagtcagtc tgttcttgta atgctttgat ctttgccatc aacattcttg aaattaatta    240
tggtttccct taaatactta catattacat ttaaacgtcg ctgcttgtct gattgcatat    300
tctttcaaaa ataactatat attccag                                        327
```

<210> SEQ ID NO 143
<211> LENGTH: 958
<212> TYPE: DNA
<213> ORGANISM: Megathura crenulata
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t

<400> SEQUENCE: 143

```
gtaaatatac agtgaaatcc ggataagtaa aatccagata agaaaaaaaa cattttctgt     60
ggtcccggca tgtttcttct tcatctatca ttattttgat acggataagt aaaaatcggc    120
tgagtaaaac atccgggtaa gtaaaatgat tttcgaggtc tcttcatcgg ataagtaaga    180
tacacaagtg atcattccaa taaacactaa ctgatgcaac acaataccag cgcacagtgt    240
tttcactacg tttgtttgta ttgtaattaa caattaacac ttaagtgttt cccaatgtgt    300
ccgtgtgcaa actgattggg acaaagcttg caacaagccc ggcaattcca tgtcgtttat    360
gtctacgttt gttattctga ctgcttggag gggttcggaa aaaataaaa acgggtaaa     420
tattataaaa aattcacggt gccttgaaat tttaggtgtc cggatttcac tgtagatgat    480
taatttctca cttgtaaaca aaaggacccc agtaccctca ttcgtgacgt acgttataaa    540
atgtaattat aaaaagccca ttatcatgtt atacgtgatc ttgncttgca attatnctac    600
cgctttcttg atttttttaaa gcaatttctc cctctatgaa cttattaaca tagcactcct    660
gcaaagaaa acagtcactg catggatcca tattgaatgt tgctgcttat ttctcatttt    720
attactcaca gatatttcaa gaacatcgta ctctctaacc aggctaaagc aaagagggtt    780
acattttagc cgacaagttc actagctgag tggaacacgt atatattaat ggagatgact    840
ctggtcatga tgattaggac aattatcatg acgttatcat tgatcatgac catgtcagta    900
```
taatagatag ctaacaaata atgtaattac taattatgaa gcaatggtgc atttgcag    958

<210> SEQ ID NO 144
<211> LENGTH: 868
<212> TYPE: DNA
<213> ORGANISM: Megathura crenulata

<400> SEQUENCE: 144
gtctcggtga gttattaaaa gaaacaaaat atttaccatt accattgtta actacaaaaa     60
tgagtgagat atcttatatc actggtacac tactgatatt ttatgcaatg aaattactat    120
ttttccaggt acgcttcaac ccctccccccc cccccccccc cccccccccc cccccccccc    180
cccatcatgc ttttctgtaa aacataaaac accaattaac aatgttctta gtgtgtttgt    240
tgactccctt ccactgcaac gcctacataa tcaaagtgtt cgttttttc caaactttcc     300
agttagtgtt gaagactaaa aagttaaata agcattcaca taacttctaa gagcaactgg    360
gaccatgcag ttacgtattg atatttctgt gagagtgaag caaaacactg tttttcaagc    420
ttaggtttat caatcaaaat gtccaatagt tcatgttatc gaaaaggcag cgaaggataa    480
gaggctccga gacatcttgt ctattctcgt gttcatatga tatcaactga ggagcttcca    540
ttacattttt gaccttatca tttaaagaca tacatggaac attttcattt tacagttaaa    600
gtgaaccact tcaggttcaa cttcaacttc gaattcaact tctgttgtgt gttttatgag    660
ccgactgaaa tagagtgcct tactttcact tctagtttcg ttctgtctcg tcatcgttgt    720
ttctttcagt gtgcatagta cacgccagt atagaacaca cgaacttgtc cttacttaat    780
agattctgaa actattatgt ggaaagttgg caggctatag taacatcctg gcaaaattat    840
catgtatcct cttgtttgtc ataattag                                      868

<210> SEQ ID NO 145
<211> LENGTH: 1766
<212> TYPE: DNA
<213> ORGANISM: Megathura crenulata

<400> SEQUENCE: 145
gtatgtattt cccactggtg gtcgctgact gccaacacat acttgtaatt tattcatgaa     60
agtataaatg tttgtttgaa agtatatttta taaccatctt gcacaagcgt cacgaatttt    120
caccacaaag cttcaaaacg cccaaaacat tctaatagcg atatatttgt taaaagacca    180
aaatatagcc ttacaacaat agattatttt aataagacca gtcagtgcat gcaaatcgat    240
tggaaacttt gaaataaaat attctatgta ctaactgcca atctcataat acttgccttg    300
gatgtgcttc ttttttcacat tcgcgtcgag cttcaactcc aatgcataag cttaaaaata    360
atcataaaca caaacaaata gccacagagg cgacgatccc tccaggccag gctttatttg    420
tctcttatag aatatatcgc tattagaatg ttttttgacgt tttgaagctt tgtgggtgaa    480
aattcgtgat gtttatgcgt ggtatttatg taagatgaaa ataaatatat cttttcaaac    540
aagatttttag tattttgaag acttctatga ataaattaca cttatgtgtt aggttattgg    600
tcactgagcg cttgtggtat tttcccttct tcaatttgtt tgttctttgt tcaatttcga    660
atagttatcc tactgtggat agtctatatg agaatcgttg aaagaataat acaattctaa    720
tggattgcaa cttctttaac ttttatttgc aactgccacg tttcggtata cgttcttatg    780
ccgtcatcaa gcatacgagt gtacatgtat gccaaacgc tgcaaataaa aattaaagaa    840
gttgcaatcc ataagaattt caatgttctt tcatcatcac atcaacttct aaaaatgcct    900

```
ataaaacaat caacaaacgt acaatagtac attaccggat ctcgcagcat gaccacgtcg      960
atatctaaac aatatcacta tccattaata ggatcaagag taggtacaga catgttcagt     1020
tataaatact cttcaaaaaa gtaggggaac ttggaatttc aaggtcaata acaaactaat     1080
gataataaca attggtccca aataataaca attggtccca aactaattgt atctttacaa     1140
agaagaaatt gagtgaacaa ttcacccggt attttattac ctaaaccgtt tctcttgctg     1200
ttatggtgcg tgaaagaaga aatgggtaag aaacggaaat tgacatttt gcgtcagtgg     1260
tgcgtaatgc ccccattgtt ggccaaacac tgattgattc gctgaggcat cgtgcatacg     1320
cgtctaccta tggtaatttg atgcagtctg tcccattctt ccaccaacgc ctggacaagt     1380
tcatctagcg tggctggtgg cctttcacgt tgacgcacac gtcggcccaa gatgtcccag     1440
acattttcaa tggccaggc tcattgctgg tcagggcatc ctatgatat tgtgccgttg     1500
aaggtggtta tgttgttcac attgaaattc caagttctcc tactcttttt aagaggaggt     1560
tcacaaagta cgttctttca tgttggtgaa gagaatatca aggtcttcta agggattgtg     1620
tcttataata tttgatttta agaagtttga tattatctgc atccttccca agaaattgca     1680
aatgttcaca cactattgcg tttgataatg ttttgggga aataaactgt ccaggactgc     1740
taaatagtaa ttattgctac ttttag                                         1766

<210> SEQ ID NO 146
<211> LENGTH: 1049
<212> TYPE: DNA
<213> ORGANISM: Megathura crenulata
<220> FEATURE:
<221> NAME/KEY: misc_feature
<222> LOCATION: (290)..(318)
<223> OTHER INFORMATION: n is a, c, g, or t

<400> SEQUENCE: 146
gtgagttcac gtaagcctac gagatcaaca ttactcctta acagccacgg catcatgtac       60
cgatatatca caaacaaaag tattcaaagc tttaaacacg atatgtatgg ttcaagaatg      120
acatcattaa acaaggacat gagtctgaaa taaacatgac ttgacaccgt tgtggtcaca      180
gttttgtttc tcattggtga acctgtgaaa caacctttca aaccaaaaga tgcctattaa      240
tattgttaat tcccatgaat taggagatac acacattcta ctgtcatttn nnnnnnnnn      300
nnnnnnnnn nnnnnnnaa taaccgcttc cagcatgaaa acacaatatg attatctcaa      360
ttctaccatt actaattata attttgactg gcattatttg acgacgcgta aaacatcgct      420
gctttacaga ctgcactgcg gtaactgtga cgttttcatg acgtcactac attctattca      480
aaacatttcc acagaagagc gagaccacgg ccgtgatggg ttctgggcag atgattaccc      540
aagtatatat ttataataac ttgactgctt gcctgaataa tgttgacaca tgacaacgaa      600
tttgtgatag cgtaagaagc gtgaatactg tgaatagtgt gagggtgtt tgctgagagt      660
taaccaccgt taattgcaaa attcccgaat acttgcattt gcagtcgaag aagaattgca      720
ttcttactcc tgtgaatgga ctcattgtta tttagcagcg gttattgagg ttttgatcac      780
ctctaaatag acaatcagga tgcggcaaac cggaaaatta tagcagaatc tgtaattcaa      840
gatgggcttg cctgtgaaaa tatgctgcga gttcagtaac acttttccct ttcgatcatg      900
gcctgttttg ctctgaatct ggtctttcag aggatccctg cttttttaaa actaaagtcc      960
tcccaactca cttatattta tgttttttaa ttatttatag ttttaatatg aacaacaaat     1020
catatttatt tacacattat atttttcag                                      1049
```

<210> SEQ ID NO 147
<211> LENGTH: 1846
<212> TYPE: DNA
<213> ORGANISM: Megathura crenulata

<400> SEQUENCE: 147

| | | | | | | |
|---|---|---|---|---|---|---|
| gtatttaaaa | aagtaataaa | accatatttt | cgaatgcgct | ttatgaaata | tcgtgtgact | 60 |
| ggttctttag | tttacatgga | gtgtaacaac | atgctccatc | agttgacata | tactgctcac | 120 |
| acaaagtaag | ggatatttga | taatgataac | aaatataatc | aaagcggtta | tactatcaag | 180 |
| acttattcac | ataattacag | gtgaagggag | gtgtgatcgt | gttcactgat | caggttgagg | 240 |
| ccagagaagt | cccagtttga | gtcttgcaga | agatgatgtt | taggcatggg | gtcgaatcac | 300 |
| caaaatcaca | tgacttcaat | aacgggttgg | accacctcga | gcgacgatgc | aagcagtaga | 360 |
| gcgtctacgc | atgctcctga | taaggcgacc | aatctgttcc | tggggaatca | gtcgccactc | 420 |
| ctcttgtagt | gccacgctca | tttctgctac | ggtcctgggt | acctgctatc | gggtcttgat | 480 |
| ccgtatccca | aggatgtccc | acacatgttc | aaggtgagag | gtcggggaac | atcgctggcc | 540 |
| acggtaaggt | ctgaatttga | tgccgttgaa | agtgagctct | gacaacctga | gcatggtgag | 600 |
| ctctgacgtt | gtcgtcctga | aagatgaatc | cagctccatg | acagcgagca | aagggcagga | 660 |
| cgtgttggtc | aatgcagttg | tctctgcagt | acacacctgt | cactcgccac | tcacaagcgt | 720 |
| gtagatctgt | acgaccagtc | atggagatcc | cagcccacat | cataacgac | ccctatccat | 780 |
| accgatcatg | agccaccata | gcagcgtctt | gatgacgttc | tccctgtcgc | ctcgacatcc | 840 |
| tcacacggcc | aaaaggaacg | tggactcgtc | actgaacatg | acattagcca | acctggcact | 900 |
| tgtccaccgc | tgatgttggc | gagaccattc | cagtcgagct | cttcggtgtc | tggctttcat | 960 |
| cgataacacg | acgtaaggtc | tgcgggcgtg | caagacggc | ctatgcaggc | gatttcggat | 1020 |
| tgtctgggtg | ctaactctga | tcccaggtgc | ctgctgaagt | tgatgctgga | tctgtgtggc | 1080 |
| attgagatgg | cgattcctta | ggactgtgga | gatgatgaat | cgatcttgac | ttatggtggt | 1140 |
| gacattagga | cgtcgggttc | gtgtcctatc | ctgcactctt | ccagttgttc | ggtgacgctc | 1200 |
| tggtacccgg | ctgattactg | actgagaata | tccatctgcc | gtgcgacatg | agcctgtgtt | 1260 |
| ggcccagcct | gaagcattgc | aatcgccaga | gacgctcttc | aaaagtcatt | cgacgcatgg | 1320 |
| tttttctgttc | acaaatgaca | gcgtaaaaca | gttttttggtg | cttttatgct | tcccaagagc | 1380 |
| atgaaaaaca | cgttctatgg | gtcgtgcaca | ccttacatga | caagtgtgaa | aagtgacttg | 1440 |
| cacccccttg | tgtgttcgga | tgcacactct | gtttacgtac | tgatgcgatt | tggcgtctaa | 1500 |
| acatgttttg | gcgtctaaac | atgttttcct | gcatgattca | tatactattt | tgtcatattc | 1560 |
| ctggcatcaa | accaaactac | agtgaaatat | atttcaatat | cccctacttt | gtgtgagtag | 1620 |
| tatagatcac | tgcagacaac | atatagacaa | tgcagttaca | ccgtcaacaa | tcccagtcat | 1680 |
| taattatgat | gacacttcca | cacatagtgt | cagtgattgt | aattcaactg | tacacacttt | 1740 |
| tcccgtgaac | attcaggatc | tatatgacta | aatatataac | attagtatac | gtgcagtttt | 1800 |
| gtatcgctac | gacattgttg | taactctttg | tttaatcatt | taacag | | 1846 |

<210> SEQ ID NO 148
<211> LENGTH: 166
<212> TYPE: DNA
<213> ORGANISM: Megathura crenulata

<400> SEQUENCE: 148

| | | | | | | |
|---|---|---|---|---|---|---|
| gtatgtttta | aatgtcactt | atccgtgatc | tgtaatgaag | ttagcaattc | actttatcaa | 60 |

-continued

```
ctgtttggct gtactgtttc agtgcgagtt ttacttaggt tggattaatt aaaatattca        120
agctcataaa tgttttgatt caacttttgt tatttatttc aaacag                      166
```

<210> SEQ ID NO 149
<211> LENGTH: 726
<212> TYPE: DNA
<213> ORGANISM: Megathura crenulata
<220> FEATURE:
<221> NAME/KEY: misc_feature
<222> LOCATION: (388)..(388)
<223> OTHER INFORMATION: n is a, c, g, or t

<400> SEQUENCE: 149

```
gttataaagc agtatattct cttcaaaaaa gtaggggaac ttggaatttc aaggtaaata        60
acataactac cttcaacggc acaatatcca tatgatgccc tggccagcaa tgaggcctga       120
tcttttcccc attaaaaatg tctggaacat cttgggcaaa cgtgtgcgtc aacgtaaaac       180
gccaccagtc acgctagatg aacttgtcca ggcgttggtg gaagaatggg acagactgca       240
tcaattacca taagtagact catttgcagc gaatcagtca gtgtttgacc aataacgggg       300
gcattacgca ctactgacgc aaaacaatgt caatttccgt ttcttaccca ttccttcttt       360
cacggaccat aacagcaaga gaaactgntt aggtaatgaa ataccggtga attattgtta       420
actggattcc ttcttgtaa agatacaatt agtttgggac caattattat tatcattagt        480
ttgttattga ccttgaaatt cgaagttcct ctacattttt taaggagttt atttgattga       540
caatgaaatg taagaaaaga gcaaatcgta aaatacgtta aaaattattc cttaaacatc       600
agtctctaac ttcagtttaa attgccagta acacgtgtta tatgatgttt ccgtttctct       660
ttgtttttta gcattcaact tatttgatat aacgttttac tgttttagat tcacatcaaa       720
ctgcag                                                                  726
```

<210> SEQ ID NO 150
<211> LENGTH: 383
<212> TYPE: DNA
<213> ORGANISM: Megathura crenulata

<400> SEQUENCE: 150

```
gtatgtatct catgtttctc aaataatttg attttcaatg cccttactat aaagcacagt        60
tattgttcag tgccagtaac cgtttattta cgtaaatgtt acaggctatt ataatcaaaa       120
atacattacc gatattgttt accacacaat tatatcattg tcaaaatcta cccccattac       180
ctgcgttttg aatttgtaac cttctgacaa aaatgaatta gcaagagctc tgatgaagaa       240
cataatgaac aacacctatc tttcttcttt caatgacggt ttaacaatac aatgcacaat       300
gtaaaaaaat atatatatat atataatttt atatctacag ttaatgcaaa tgactccact       360
aattcaggga aacacatttt cag                                               383
```

<210> SEQ ID NO 151
<211> LENGTH: 306
<212> TYPE: DNA
<213> ORGANISM: Megathura crenulata

<400> SEQUENCE: 151

```
gtaaaataaa acgtccagtc atcggaaacc cgcccagata tatgggtttt tttctattta        60
aacaaaaaag cagagacaaa aagattatta aaagtcacat ttaacttgat atcagatcaa       120
tagtttggct agttagtgct ctatatccct caaatccttc gaatctttaa gcctcgtgat       180
attttgacaa acagagaaga cttagtagcc cagactttcc cttattttt cctgaaaatc        240
```

```
ttaatacgga tattaaatgg attcattctg caacctacaa ccatagccca tatgttatta    300
tttcag                                                               306

<210> SEQ ID NO 152
<211> LENGTH: 627
<212> TYPE: DNA
<213> ORGANISM: Megathura crenulata

<400> SEQUENCE: 152
gtgagagaaa ctataatagt gtatgtcggc aaaaaatgtg ctcatatcat gactctgttg    60
gccggtggtt gctctcctct cctcctccac caccaccggt acctccacct gtcagggcat   120
caatgtacca tgaaaatgtc tacaatacta ggcctcctgt agaagcacgt aagatttaca   180
tggccggttt gtaactagtt taaagtgctt cacagtaacc aaaaccagtc tctaaagatt   240
aatgtctgtt taaaatttaa tgccacattt tcaactgaca tattcttgca attaagtaca   300
aatgaagtag tataaattat ccacaaatag cgtgatgcac cacaaatata aaccgagtgc   360
ttttttggca ttccccactt gttctggcat gatcacatca tagatctcgt tcatgaagat   420
actgttggat gcttttcccc aatatgcccc aatctgttaa attatttaca cgaccgcagt   480
gtgtactttc atcactcaga tctttacaat gtgtttgtaa cgtttacaat tagcgttatg   540
attgaaatat taccccctgc tacgttaaat cacattcact cactcatctg atgtactta   600 caggtcatac cgatgatcac ggctcag                                      627

<210> SEQ ID NO 153
<211> LENGTH: 266
<212> TYPE: DNA
<213> ORGANISM: Megathura crenulata

<400> SEQUENCE: 153
gtcagtattc tccaatatgt ttgactagtg tcttgctcat gtatcaacta ttttaggcaa    60 cgttttgat tgttatggta ttttcatgat atgatttat tgctacctct atacccaaac    120
aaaaatgttt tatcaacaat tgtttgagtt ttaatgcaag aaaattatca ggagtagcgt   180
gcaaaaatga ctggaaggca tggtgtactt ctgtgtgtac atacaagtgg gtaatgcctt   240
attgaactcg taatcactcg tttcag                                       266

<210> SEQ ID NO 154
<211> LENGTH: 266
<212> TYPE: DNA
<213> ORGANISM: Megathura crenulata

<400> SEQUENCE: 154
gtcagtattc tccaatatgt ttgactagtg tcttgctcat gtatcaacta ttttaggcaa    60 cgttttgat tgttatggta ttttcatgat atgatttat tgctacctct atacccaaac    120
aaaaatgttt tatcaacaat tgtttgagtt ttaatgcaag aaaattatca ggagtagcgt   180
gcaaaaatga ctggaaggca tggtgtactt ctgtgtgtac atacaagtgg gtaatgcctt   240
attgaactcg taatcactcg tttcag                                       266

<210> SEQ ID NO 155
<211> LENGTH: 190
<212> TYPE: DNA
<213> ORGANISM: Megathura crenulata

<400> SEQUENCE: 155
```

```
gtatgttttg agatccacat aatcttctac cctgtctcat ttctaatgct cttcaataca      60
caatttatat agcctttgag cttcagatgt attacggaca ggcattacag tatacatgta     120
atatggtttt ctgctatttg caaaaattgt gtcctatctc tgttcagatc atcatggcgg     180
tgacacctag                                                             190
```

<210> SEQ ID NO 156
<211> LENGTH: 403
<212> TYPE: PRT
<213> ORGANISM: Haliotis tuberculata

<400> SEQUENCE: 156

```
Gly Leu Pro Tyr Trp Asp Trp Thr Gln His Leu Thr Gln Leu Pro Asp
1               5                   10                  15

Leu Val Ser Asp Pro Leu Phe Val Asp Pro Glu Gly Gly Lys Ala His
            20                  25                  30

Asp Asn Ala Trp Tyr Arg Gly Asn Ile Lys Phe Glu Asn Lys Lys Thr
        35                  40                  45

Ala Arg Ala Val Asp Asp Arg Leu Phe Glu Lys Val Gly Pro Gly Glu
    50                  55                  60

Asn Thr Arg Leu Phe Glu Gly Ile Leu Asp Ala Leu Glu Gln Asp Glu
65                  70                  75                  80

Phe Cys Asn Phe Glu Ile Gln Phe Glu Leu Ala His Asn Ala Ile His
                85                  90                  95

Tyr Leu Val Gly Gly Arg His Thr Tyr Ser Met Ser His Leu Glu Tyr
            100                 105                 110

Thr Ser Tyr Asp Pro Leu Phe Phe Leu His His Ser Asn Thr Asp Arg
        115                 120                 125

Ile Phe Ala Ile Trp Gln Arg Leu Gln Val Leu Arg Gly Lys Asp Pro
    130                 135                 140

Asn Thr Ala Asp Cys Ala His Asn Leu Ile His Glu Pro Met Glu Pro
145                 150                 155                 160

Phe Arg Arg Asp Ser Asn Pro Leu Asp Leu Thr Arg Glu Asn Ser Lys
                165                 170                 175

Pro Ile Asp Ser Phe Asp Tyr Ala His Leu Gly Tyr Gln Tyr Asp Asp
            180                 185                 190

Leu Thr Leu Asn Gly Met Thr Pro Glu Glu Leu Asn Ser Tyr Leu His
        195                 200                 205

Glu Arg Ser Gly Lys Glu Gly Val Phe Ala Ser Phe Arg Leu Ser Gly
    210                 215                 220

Phe Gly Gly Ser Ala Asn Val Val Tyr Ala Cys Arg Pro Ala His
225                 230                 235                 240

Asp Glu Met Ala Val Asp Gln Cys Asp Lys Ala Gly Asp Phe Phe Val
                245                 250                 255

Leu Gly Gly Pro Thr Glu Met Pro Trp Arg Phe Tyr Arg Ala Phe His
            260                 265                 270

Phe Asp Val Thr Asp Ser Ile Asp Asn Ile Asp Lys Asp Arg His Gly
        275                 280                 285

His Tyr Tyr Val Lys Ala Glu Leu Phe Ser Val Asn Gly Ser Ala Leu
    290                 295                 300

Pro Asn Asp Leu Leu Pro Gln Pro Thr Ile Ser His Arg Pro Ala Arg
305                 310                 315                 320

Gly His Val Asp Glu Ala Pro Ala Pro Ser Ser Asp Ala His Leu Ala
                325                 330                 335
```

```
Val Arg Lys Asp Ile Asn His Leu Thr Arg Glu Glu Val Tyr Glu Leu
            340                 345                 350

Arg Arg Ala Met Glu Arg Phe Gln Ala Asp Thr Ser Val Asp Gly Tyr
        355                 360                 365

Gln Ala Thr Val Glu Tyr His Gly Leu Pro Ala Arg Cys Pro Phe Pro
    370                 375                 380

Glu Ala Thr Asn Arg Phe Ala Cys Cys Ile His Gly Met Ala Thr Phe
385                 390                 395                 400

Pro His Trp
```

```
<210> SEQ ID NO 157
<211> LENGTH: 973
<212> TYPE: DNA
<213> ORGANISM: Haliotis tuberculata

<400> SEQUENCE: 157
ggtcttccgt actgggactg gacgcagcat ctgactcaac tcccagatct ggtgtcagac      60
cccttgtttg tcgacccgga aggaggaaag gcccatgaca acgcatggta tcgtggaaac     120
atcaagtttg agaataagaa gactgcaaga gctgttgacg atcgcctttt cgagaaggtt     180
ggaccaggag agaatacccg actctttgaa ggaattctcg atgctcttga acaggatgaa     240
ttctgcaact tcgagatcca gtttgagttg gctcacaacg ctatccacta cctggttggc     300
ggccgtcaca cgtactccat gtctcatctc gagtacacct cctacgaccc cctcttcttc     360
ctccatcact ccaacaccga ccgcatcttc gccatctggc aacgtcttca ggtactcaga     420
ggaaaggacc ccaacaccgc cgactgcgca cacaacctca tccatgagcc catggaaccg     480
ttccgtcggg actcgaaccc tcttgacctc accagggaaa actccaaacc aattgacagc     540
tttgattatg cccaccttgg ctaccagtat gatgacttga ccctgaacgg tatgacccca     600
gaggaattga actcatatct gcatgaacgg tcaggcaagg aggggtgtt cgcaagcttc     660
cgactctcag gttttggcgg ctctgctaac gttgttgtct acgcatgccg tcctgcccac     720
gatgaaatgg ctgtcgatca gtgcgacaaa gccggcgact tctttgtgtt gggcggaccc     780
accgagatgc cctggaggtt ttacagagca ttccacttcg acgtcaccga cagcatcgac     840
aacatcgaca aggaccgcca cggccactat tatgtaaagg cggaattatt cagtgtaaat     900
ggaagtgcgc taccgaatga tctcctgcct caacccacca tctcacacag gccagcccgc     960
ggacacgttg atg                                                       973
```

```
<210> SEQ ID NO 158
<211> LENGTH: 103
<212> TYPE: PRT
<213> ORGANISM: Megathura crenulata

<400> SEQUENCE: 158

Gly His Asp His Ser Glu Arg His Asp Gly Phe Phe Arg Lys Glu Val
1               5                   10                  15

Gly Ser Leu Ser Leu Asp Glu Ala Asn Asp Leu Lys Asn Ala Leu Tyr
            20                  25                  30

Lys Leu Gln Asn Asp Gln Gly Pro Asn Gly Tyr Glu Ser Ile Ala Gly
        35                  40                  45

Tyr His Gly Tyr Pro Phe Leu Cys Pro Glu His Gly Glu Asp Gln Tyr
    50                  55                  60

Ala Cys Cys Val His Gly Met Pro Val Phe Pro His Trp His Arg Leu
65                  70                  75                  80
```

```
His Thr Ile Gln Phe Glu Arg Ala Leu Lys Glu His Gly Ser His Leu
            85                  90                  95
Gly Leu Pro Tyr Trp Asp Trp
        100
```

<210> SEQ ID NO 159
<211> LENGTH: 310
<212> TYPE: DNA
<213> ORGANISM: Megathura crenulata

<400> SEQUENCE: 159

| | | | | | |
|---|---|---|---|---|---|
| gtcacgatca | cagtgaacgt | cacgatggat | ttttcaggaa | ggaagtcggt | tccctgtccc | 60 |
| tggatgaagc | caatgacctt | aaaaatgcac | tgtacaagct | gcagaatgat | cagggtccca | 120 |
| atggatatga | atcaatagcc | ggttaccatg | gctatccatt | cctctgccct | gaacatggtg | 180 |
| aagaccagta | cgcatgctgt | gtccacggaa | tgcctgtatt | tccacattgg | cacagacttc | 240 |
| atacaatcca | gtttgagaga | gctctcaaag | aacatggttc | tcatttgggt | ctgccatact | 300 |
| gggactggac | | | | | | 310 |

<210> SEQ ID NO 160
<211> LENGTH: 32
<212> TYPE: DNA
<213> ORGANISM: Haliotis tuberculata

<400> SEQUENCE: 160
ggcttgttca gtttctactc gtcgcccttg tg          32

<210> SEQ ID NO 161
<211> LENGTH: 16
<212> TYPE: DNA
<213> ORGANISM: Haliotis tuberculata

<400> SEQUENCE: 161
gtgggggctg gagcag          16

<210> SEQ ID NO 162
<211> LENGTH: 350
<212> TYPE: DNA
<213> ORGANISM: Haliotis tuberculata

<400> SEQUENCE: 162

| | | | | | |
|---|---|---|---|---|---|
| acaacgtcgt | cagaaaggac | gtgagtcacc | tcacagttga | cgaggtgcaa | gctcttcacg | 60 |
| gcgccctcca | tgacgtcact | gcatctacag | ggcctctgag | tttcgaagac | ataacatctt | 120 |
| accatgccgc | accagcgtcg | tgtgactaca | agggacggaa | gatcgcctgc | tgtgtccacg | 180 |
| gtatgcccag | tttccccttc | tggcacaggg | catatgtcgt | ccaagccgag | cgggcactgt | 240 |
| tgtccaaacg | gaagactgtc | ggaatgcctt | actgggactg | gacgcaaacg | ctgactcact | 300 |
| taccatctct | tgtgactgaa | cccatctaca | ttgacagtaa | aggtggaaag | | 350 |

<210> SEQ ID NO 163
<211> LENGTH: 221
<212> TYPE: DNA
<213> ORGANISM: Haliotis tuberculata

<400> SEQUENCE: 163

| | | | | | |
|---|---|---|---|---|---|
| gctcaaacca | actactggta | ccgcggcgag | atagcgttca | tcaataagaa | gactgcgcga | 60 |
| gctgtagatg | atcgcctatt | cgagaaggtg | gagcctggtc | actacacaca | tcttatggag | 120 |
| actgtcctcg | acgctctcga | acaggacgaa | ttctgtaaat | ttgaaatcca | gttcgagttg | 180 |

```
gctcataatg ctatccatta cttggttggc ggtaaatttg a                221
```

<210> SEQ ID NO 164
<211> LENGTH: 255
<212> TYPE: DNA
<213> ORGANISM: Haliotis tuberculata

<400> SEQUENCE: 164

```
atattcaatg tcaaacttgg aatacacctc ctacgacccc atcttcttcc tccaccactc    60
caacgttgac cgcctcttcg ccatctggca gcgtcttcag gaactgcgag gaaagaatcc   120
caatgcaatg gactgtgcac atgaactcgc tcaccagcaa ctccaaccct caacaggga   180
cagcaatcca gtccagctca caaaggacca ctcgacacct gctgacctct ttgattacaa   240
acaacttgga tacag                                                   255
```

<210> SEQ ID NO 165
<211> LENGTH: 407
<212> TYPE: DNA
<213> ORGANISM: Haliotis tuberculata

<400> SEQUENCE: 165

```
ctacgacagc ttaaacctga atggaatgac gccagaacag ctgaaaacag aactagacga    60
acgccactcc aaagaacgtg cgtttgcaag cttccgactc agtggctttg ggggttctgc   120
caacgttgtt gtctatgcat gtgtccctga tgatgatcca cgcagtgatg actactgcga   180
gaaagcaggc gacttcttca ttcttggggg tcaaagcgaa atgccgtgga gattctacag   240
acccttcttc tatgatgtaa ctgaagcggt acatcacctt ggagtcccgc taagtggcca   300
ctactatgtg aaaacagaac tcttcagcgt gaatggcaca gcactttcac ctgatcttct   360
tcctcaacca actgttgcct accgacctgg gaaaggtcac cttgacc                407
```

<210> SEQ ID NO 166
<211> LENGTH: 1245
<212> TYPE: DNA
<213> ORGANISM: Haliotis tuberculata

<400> SEQUENCE: 166

```
cacctgtgca tcatcgccac gatgacgatc ttattgttcg aaaaaatata gatcatttga    60
ctcgtgaaga ggaatacgag ctaaggatgg ctctggagag attccaggcc gacacatccg   120
ttgatgggta ccaggctaca gtagagtacc atggccttcc tgctcgttgt ccacgaccag   180
atgcaaaagt caggttcgcc tgttgtatgc atggcatggc atccttccct cactggcacc   240
ggctgttcgt tacccaggtg gaagatgctc ttgtacggcg tggatcgcct atcggtgttc   300
cttattggga ctggacaaaa cctatgactc accttccaga cttggcatca aatgagacgt   360
acgtagaccc gtatggacat acacatcata atccattctt caatgcaaat atatctttg   420
aggagggaca ccatcacacg agcaggatga tagattcgaa actgtttgcc ccagtcgctt   480
ttggggagca ttcccatctg tttgatggaa tcctgtacgc atttgagcag gaagatttct   540
gcgactttga gattcagttt gagttagtcc ataattctat tcatgcgtgg ataggcggtt   600
ccgaagatta ctccatggcc accctgcatt cacacagcct tgaccccatt ttctaccttc   660
atcattccaa tgtcgatcgt ctatgggcaa tctggcaagc tcttcaaatc aggagacaca   720
agccatatca agcccactgt gcacagtctg tggaacagtt gccaatgaag ccatttgctt   780
tcccatcacc tcttaacaac aacgagaaga cacatagtca ttcagtcccg actgacattt   840
```

```
atgactacga ggaagtgctg cactacagct acgatgatct aacgtttggt gggatgaacc      900
ttgaagaaat agaagaagct atacatctca gacaacagca tgaacgagtc ttcgcgggat      960
ttctccttgc tggaatagga acatctgcac ttgttgacat tttcataaat aaaccgggga     1020
accaaccact caaagctgga gatattgcca ttcttggtgg tgccaaggaa atgccttggg     1080
cgtttgaccg cttgtataag gtcgaaataa ctgactcatt gaagacactt tctctcgatg     1140
tcgatggaga ttatgaagtc acttttaaaa ttcatgtatt gcacggaaac gctcttgata     1200
cggacctgat tccacacgca gcagttgttt ctgagccagc tcacc                    1245
```

<210> SEQ ID NO 167
<211> LENGTH: 1242
<212> TYPE: DNA
<213> ORGANISM: Haliotis tuberculata

<400> SEQUENCE: 167

```
ctacctttga ggatgaaaag cacagcttac gaatcagaaa aaatgtcgac agcttgactc       60
ctgaagaaac aaatgaactg cgtaaagccc tggagcttct tgaaaatgat catactgcag      120
gtggattcaa tcagcttggc gccttccatg gagagcctaa atggtgccct aatcctgaag      180
cggagcacaa ggttgcatgc tgtgttcatg gcatggctgt tttccctcat ggcacaggc       240
ttcttgctct ccaggcggag aatgctctta gaaagcatgg gtacagtggt gctctaccat      300
actgggattg gactcgcccc cttttcccaac ttcctgatct ggttagtcat gagcagtata     360
cagatccttc cgaccatcac gtgaagcata cccgtggtt caatggccac atcgatacag       420
taaatcagga taccaccaga agcgtacggg aggatcttta tcaacaacct gaatttggac      480
atttcacgga tattgctcaa caagtcctct tagcattaga acaagatgac ttctgttcgt      540
ttgaagtgca gtatgagatt tcccataatt ttatccatgc acttgtagga ggaaccgacg      600
cttatggcat ggcatcgctg agatatacag catacgatcc aatcttttc ttgcatcatt       660
caaacaccga caggatctgg gctatttggc aatccctgca aaatacagaa ggcaaaccgt      720
acaacactgc caactgcgcc atagaatcta tgagaaggcc cctgcaacca tttggactaa     780
gcagtgccat taaccctgac agaatcacca gagagcatgc tatcccgttt gatgtcttca     840
actatagaga taaccttcat tacgtatatg ataccctgga attaatggtt ttgtcgatttt     900
cacaacttga tagagagctg gaaaaaatca gagtcacgaa aagagtattt gctggattct      960
tgctgtcggg gattaaaaaaa tctgctcttg tgaaattcga agtttgtact ccacctgata    1020
attgtcataa agcagggag ttttatctac tcggggacga aaacgagatg gcttgggcct       1080
atgaccgact tttcaagtat gatattactc aggttctgga agcaaaccat ctacacttct     1140
atgatcatct cttcattcgc tacgaagtct ttgatcttaa aggagtgagt ttgggaactg     1200
acctgttcca cactgcaaat gtggtacatg attccggcac ag                       1242
```

<210> SEQ ID NO 168
<211> LENGTH: 1239
<212> TYPE: DNA
<213> ORGANISM: Haliotis tuberculata

<400> SEQUENCE: 168

```
gcacccgtga tcgtgataac tacgttgaag aagttactgg ggccagtcat atcaggaaga       60
atttgaacga cctcaatacc ggagaaatgg aaagccttag agctgctttc ctgcatattc      120
aggacgacgg aacatatgaa tctattgccc agtaccatgg caaaccaggc aaatgtcaat      180
tgaatgatca taatattgcg tgttgtgtcc atggtatgcc taccttcccc cagtggcaca      240
```

```
gactgtatgt ggttcaggtg gagaatgctc tcctaaacag gggatctggt gtggctgttc      300
cttactggga gtggactgct cccatagacc atctacctca tttcattgat gatgcaacat      360
acttcaattc ccgacaacag cggtacgacc ctaacccttt cttcagggga aaggttactt      420
ttgaaaacgc agtcacaaca agggacccac aagccgggct cttcaactca gattatatgt      480
atgagaatgt tttacttgca ctggagcagg aaaattattg tgactttgaa attcagtttg      540
agcttgttca taacgcactt cattccatgc tgggaggtaa agggcagtac tccatgtcct      600
ccctggacta ttctgcgttt gatcccgtct tcttcctaca tcatgccaac acggacagac      660
tgtgggcaat ctggcaggaa ctacaaagat tccgagaact gccttatgaa gaagcgaact      720
gtgcaatcaa cctcatgcat caaccactga agccgttcag tgatccacat gagaatcacg      780
acaatgtcac tttgaaatac tcaaaaccac aggacggatt cgactaccag aaccacttcg      840
gatacaagta tgcaaccctt gagttccatc acttatctat cccaagtctt gatgctaccc      900
tgaagcaaag gagaaatcac gacagagtgt ttgcgggctt ccttcttcat aacataggaa      960
cttctgctga cataactatc tacatatgtc tgcctgacgg acggcgtggc aatgactgca     1020
gtcatgaggc gggaacattc tatatcctcg gaggcgaaac agagatgcct tttatctttg     1080
accgtttgta taaatttgaa atcaccaaac cactgcaaca gttaggagtc aagctgcatg     1140
gtggagtttt cgaactggag cttgagatca aggcatacaa cggttcctat ctggatcccc     1200 ataccttttga tccaactatc atctttgaac ctggaacag                           1239
```

<210> SEQ ID NO 169
<211> LENGTH: 1260
<212> TYPE: DNA
<213> ORGANISM: Haliotis tuberculata

<400> SEQUENCE: 169

```
atacccatat cttggaccac gaccatgagg aagagatact tgtcaggaag aatataattg       60
atttgagccc aagggagagg gtttctctag tcaaagcttt gcaaagaatg aagaatgatc      120
gctccgctga tggtaccaa gccattgcct ctttccatgc cctgccacca ctctgtccca      180
atccatctgc agctcaccgt tatgcttgct gtgtccatgg catggctaca tttccccagt      240
ggcacagact gtacactgtt caggttcagg atgcccctgag gagacatggt tcacttgttg      300
gtattcctta ctgggactgg acaaaaccag tcaacgagtt acccgagctt cttttcttcag      360 caacattta tcatccaatc cggaatatta atatttcaaa tccattcctc ggggctgaca       420
tagaatttga aggaccgggc gttcatacag agaggcacat aaatactgag cgcctgtttc       480
acagtgggga tcatgacgga taccacaact ggttcttcga aactgttctc tttgctttgg       540
aacaggaaga ttactgcgat tttgaaatac aatttgagat agcccataat ggcatccaca       600
catggattgg tggaagcgca gtatatggca tgggacaccct tcactatgca tcatatgatc       660
caattttcta catccaccat tcacagacgg acagaatatg ggctatttgg caagagctgc       720
agaagtacag gggtctatct ggttcggaag caaactgtgc cattgaacat atgagaacac       780
ccttgaagcc tttcagcttt gggccaccct acaatttgaa tagtcatacg caagaatatt       840
caaagcctga ggacacgttt gactataaga agtttggata cagatatgat agtctgaat       900 tggaggggcg atcaatttct cgcattgatg aacttatcca gcagagacag gagaaagaca       960 gaactttgc agggttcctc cttaaaggtt ttggtacatc cgcatctgtg tcattgcaag     1020
tttgcagagt tgatcacacc tgtaaagatg cgggctattg cactattctg ggaggatcag     1080
```

```
ccgaaatgcc atgggcattc gacaggcttt ataagtatga cattactaaa actcttcacg   1140
acatgaacct gaggcacgag gacactttct ctatagacgt aactatcacg tcttacaatg   1200
gaacagtact ctcgggagac ctcattcaga cgccctccat tatatttgta cctggacgcc   1260
```

<210> SEQ ID NO 170
<211> LENGTH: 191
<212> TYPE: DNA
<213> ORGANISM: Haliotis tuberculata

<400> SEQUENCE: 170

```
ataaactcaa ctcacggaaa catacaccta acagagtccg ccatgagcta agtagcctta    60
gttcccgtga catagcaagc ttgaaggcag cttttgacaag ccttcaacat gataatggga  120
ctgatggtta tcaagctatt gctgccttcc atggcgttcc tgcgcagtgc cacgagccat  180
ctggacgtga g                                                      191
```

<210> SEQ ID NO 171
<211> LENGTH: 1060
<212> TYPE: DNA
<213> ORGANISM: Haliotis tuberculata

<400> SEQUENCE: 171

```
atcgcctgtt gcatccacgg catggcgacg tttcctcact ggcaccggtt gtacactctg    60
cagttggagc aagcgctgcg cagacacggg tccagtgttg ctgttccata ctgggactgg  120
accaagccaa tcaccgaact gccacacatt ctgacagacg gagaatatta tgacgtttgg  180
caaaatgccg tcttggccaa tccgtttgca agaggttatg tgaaaattaa agatgcattt  240
acggtgagaa atgtccagga agtctgttc aaaatgtcaa gttttggaaa gcactcgctt   300
ctgtttgacc aggctttgtt ggctcttgaa caaactgact actgtgactt cgaagttcag  360
tttgaagtga tgcataacac gatccattat ctcgtaggag ggcgtcaaac gtacgccttc  420
tcctctctcg agtattcctc atacgatcca atcttcttta ttcaccactc gtttgttgac  480
aaaatatggg ctgtatggca agaactgcaa agcaggagac atctacagtt tagaacagct  540
gattgtgctg tgggcctcat gggtcaggca atgaggcctt tcaacaagga tttcaaccac  600
aactcgttca ccaagaagca cgcagtccct aatacagtat ttgattatga agatcttggc  660
tataactatg acaaccttga aatcagtggt ttaaacttaa atgagatcga ggcgttaata  720
gcaaaacgca agtcacatgc tagagtcttt gctgggttcc tgttgtttgg attaggaact  780
tcggctgata tacatctgga aatttgcaag acatcggaaa actgccatga tgctggtgtg  840
attttcatcc ttggaggttc tgcagagatg cattgggcat acaaccgcct ctacaagtat  900
gacattacag aagcattgca ggaatttgac atcaaccctg aagatgtttt ccatgctgat  960
gaaccatttt tcctgaggct gtcggttgtt gctgtgaatg gaactgtcat tccatcgtct 1020
catcttcacc agccaacgat aatctatgaa ccaggcgaag                       1060
```

<210> SEQ ID NO 172
<211> LENGTH: 219
<212> TYPE: DNA
<213> ORGANISM: Haliotis tuberculata

<400> SEQUENCE: 172

```
atcaccatga cgaccatcag tcgggaagca tagcaggatc cggggtccgc aaggacgtga    60
acaccttgac taaggctgag accgacaacc tgagggaggc gctgtgggt gtcatggcag   120 accacggtcc caatggcttt caagctattg ctgctttcca tggaaaacca gctttgtgtc  180
```

```
ccatgcctga tggccacaac tactcatgtt gtactcacg                              219

<210> SEQ ID NO 173
<211> LENGTH: 164
<212> TYPE: DNA
<213> ORGANISM: Haliotis tuberculata

<400> SEQUENCE: 173
gcatggctac cttcccacac tggcatcgcc tctacaccaa gcagatggag gatgcaatga       60
gggcgcatgg gtctcatgtc ggcctgccct actgggactg gactgctgcc ttcacccacc      120
tgccaacact ggtcaccgac acggacaaca acccttcca acat                        164

<210> SEQ ID NO 174
<211> LENGTH: 826
<212> TYPE: DNA
<213> ORGANISM: Haliotis tuberculata

<400> SEQUENCE: 174
ggacacattg attatctcaa tgtcagcaca actcgatctc cccgagacat gctgttcaac       60
gaccccgagc atggatcaga gtcgttcttc tacagacaag tcctcttagc tctggaacaa      120
actgatttct gcaaattcga agttcagttt gagataaccc acaatgccat ccattcctgg      180
acaggtggcc acagcccta cggaatgtcc actctcgact tcactgccta cgatcctctc      240
ttctggcttc accactccaa caccgacaga atctgggctg tctggcaagc tttgcaagaa      300
tacagaggac ttccatacaa ccatgccaat tgtgagatcc aggcaatgaa aacgcccctg      360
aggcctttca gtgacgatat caaccacaac ccagtcacaa aggctaacgc gaagccatta      420
gatgtgttcg agtataatcg gttgagcttc agtacgaca acctcatctt ccatggatac       480
agtattccgg aacttgatcg cgtgcttgaa gaaagaaagg aggaggacag aatattgct       540 gccttccttc tcagtggaat caagcgtagt gctgatgtag tgttcgacat atgccagcca      600
gaacacgaat gtgtgttcgc agggactttt gcgattttgg gagggagct agaaatgccc        660 tggtccttcg acagactgtt ccgctatgat atcaccaagg tgatgaagca gctacacctg      720
aggcatgact ctgactttac cttcagggtg aagattgtcg gcaccgacga ccacgagctt      780
ccttcagaca gtgtcaaagc accaactatt gaatttgaac cgggcg                     826

<210> SEQ ID NO 175
<211> LENGTH: 1535
<212> TYPE: DNA
<213> ORGANISM: Haliotis tuberculata

<400> SEQUENCE: 175
tgcacagagg cggaaaccac gaagatgaac accatgatga cagactcgca gatgtcctga       60
tcaggaaaga agttgacttc ctctccctgc aagaggccaa cgcaattaag gatgcactgt      120
acaagctcca gaatgacgac agtaaagggg gctttgaggc catagctggc tatcacgggt      180
atcctaatat gtgtccagaa agaggtaccg acaagtatcc ctgctgtgtc cacggaatgc      240
ccgtgttccc ccactggcac cgcctgcata ccattcagat ggagagagct ctgaaaaacc      300
atggctctcc aatgggcatt ccttactggg attggacaaa gaagatgtcg agtcttccat      360
ctttctttgg agattccagc aacaacaacc ctttctacaa atattacatc cggggcgtgc      420
agcacgaaac aaccagggac attaatcaga gactctttaa tcaaaccaag tttggtgaat      480
ttgattacct atattaccta actctgcaag tcctggagga aaactcgtac tgtgactttg      540
```

```
aagttcagta tgagatcctc cataacgccg tccactcctg gcttggagga actggaaagt      600
attccatgtc taccctggag cattcggcct ttgaccctgt cttcatgatt caccactcga      660
gtttggatag aatctggatc ctttggcaga agttgcaaaa gataagaatg aagccttact      720
acgcattgga ttgtgctggc gacagactta tgaaagaccc cctgcatccc ttcaactacg      780
aaaccgttaa tgaagatgaa ttcacccgca tcaactcttt cccaagcata ctgtttgacc      840
actacaggtt caactatgaa tacgataaca tgagaatcag gggtcaggac atacatgaac      900
ttgaagaggt aattcaggaa ttaagaaaca aagatcgcat atttgctggt tttgttttgt      960
cgggcttacg gatatcagct acagtgaaag tattcattca ttcgaaaaac gatacaagtc     1020
acgaagaata tgcaggagaa tttgcagttt tgggaggtga aggagatg ccgtgggcat     1080 atgaaagaat gctgaaattg gacatctccg atgctgtaca aagcttcac gtgaaagatg     1140 aagacatccg ttttagagtg gttgttactg cctacaacgg tgacgttgtt accaccaggc     1200
tgtctcagcc attcatcgtc caccgtccag cccatgtggc tcacgacatc ttggtaatcc     1260
cagtaggtgc gggccatgac cttccgccta agtcgtagt aaagagcggc accaaagtcg     1320
agtttacacc aatagattcg tcggtgaaca agcaatggt ggagctgggc agctatactg     1380
ctatggctaa atgcatcgtt ccccctttct cttaccacgg ctttgaactg gacaaagtct     1440
acagcgtcga tcacggagac tactacattg ctgcaggtac ccacgcgttg tgtgagcaga     1500
acctcaggct ccacatccac gtggaacacg agtag                                1535
```

```
<210> SEQ ID NO 176
<211> LENGTH: 7
<212> TYPE: DNA
<213> ORGANISM: Haliotis tuberculata

<400> SEQUENCE: 176 ttcacag                                                                 7

<210> SEQ ID NO 177
<211> LENGTH: 471
<212> TYPE: DNA
<213> ORGANISM: Haliotis tuberculata

<400> SEQUENCE: 177
gttgctatgc cgactgcgct atattggtga acgagacgat gaggacatct ctgaaagagt       60
tcgccaagtg atgtgtaggt cacggaagta ttgttgagct aacaatatga tgatttcaaa      120
atgacttggc gctctaggac aaagacataa ttcatcagca ccctgtgcac caactctttg      180
tttgctgcaa acgtctgaca agcgacacgt caatcaacaa gctgttcaaa ctcaagtgga      240
tgtaactaga atcgttgggc catcgttcac aaagtattga cagatgtcac acatgatggc      300
gagaaacact ttagaacttt taatgaccta gagtgacttg taaatatgta aatatattct      360
tcaaagactc agctgaacta ttgttggata acacatcaat tccctcaaca aaatgcttta      420
tcttcacatg gatgtatgta atgtggccgg caataaagta tatatatgta t               471

<210> SEQ ID NO 178
<211> LENGTH: 15
<212> TYPE: PRT
<213> ORGANISM: Haliotis tuberculata

<400> SEQUENCE: 178

Leu Val Gln Phe Leu Leu Val Ala Leu Val Val Gly Ala Gly Ala
1               5                   10                  15
```

<210> SEQ ID NO 179
<211> LENGTH: 407
<212> TYPE: PRT
<213> ORGANISM: Haliotis tuberculata

<400> SEQUENCE: 179

```
Asp Asn Val Val Arg Lys Asp Val Ser His Leu Thr Val Asp Glu Val
1               5                   10                  15

Gln Ala Leu His Gly Ala Leu His Asp Val Thr Ala Ser Thr Gly Pro
            20                  25                  30

Leu Ser Phe Glu Asp Ile Thr Ser Tyr His Ala Ala Pro Ala Ser Cys
        35                  40                  45

Asp Tyr Lys Gly Arg Lys Ile Ala Cys Cys Val His Gly Met Pro Ser
    50                  55                  60

Phe Pro Phe Trp His Arg Ala Tyr Val Val Gln Ala Glu Arg Ala Leu
65                  70                  75                  80

Leu Ser Lys Arg Lys Thr Val Gly Met Pro Tyr Trp Asp Trp Thr Gln
                85                  90                  95

Thr Leu Thr His Leu Pro Ser Leu Val Thr Glu Pro Ile Tyr Ile Asp
            100                 105                 110

Ser Lys Gly Gly Lys Ala Gln Thr Asn Tyr Trp Tyr Arg Gly Glu Ile
        115                 120                 125

Ala Phe Ile Asn Lys Lys Thr Ala Arg Ala Val Asp Asp Arg Leu Phe
    130                 135                 140

Glu Lys Val Glu Pro Gly His Tyr Thr His Leu Met Glu Thr Val Leu
145                 150                 155                 160

Asp Ala Leu Glu Gln Asp Glu Phe Cys Lys Phe Glu Ile Gln Phe Glu
                165                 170                 175

Leu Ala His Asn Ala Ile His Tyr Leu Val Gly Gly Lys Phe Glu Tyr
            180                 185                 190

Ser Met Ser Asn Leu Glu Tyr Thr Ser Tyr Asp Pro Ile Phe Phe Leu
        195                 200                 205

His His Ser Asn Val Asp Arg Leu Phe Ala Ile Trp Gln Arg Leu Gln
    210                 215                 220

Glu Leu Arg Gly Lys Asn Pro Asn Ala Met Asp Cys Ala His Glu Leu
225                 230                 235                 240

Ala His Gln Gln Leu Gln Pro Phe Asn Arg Asp Ser Asn Pro Val Gln
                245                 250                 255

Leu Thr Lys Asp His Ser Thr Pro Ala Asp Leu Phe Asp Tyr Lys Gln
            260                 265                 270

Leu Gly Tyr Ser Tyr Asp Ser Leu Asn Leu Asn Gly Met Thr Pro Glu
        275                 280                 285

Gln Leu Lys Thr Glu Leu Asp Glu Arg His Ser Lys Glu Arg Ala Phe
    290                 295                 300

Ala Ser Phe Arg Leu Ser Gly Phe Gly Ser Ala Asn Val Val Val
305                 310                 315                 320

Tyr Ala Cys Val Pro Asp Asp Pro Arg Ser Asp Asp Tyr Cys Glu
                325                 330                 335

Lys Ala Gly Asp Phe Phe Ile Leu Gly Gly Gln Ser Glu Met Pro Trp
            340                 345                 350

Arg Phe Tyr Arg Pro Phe Phe Tyr Asp Val Thr Glu Ala Val His His
        355                 360                 365

Leu Gly Val Pro Leu Ser Gly His Tyr Tyr Val Lys Thr Glu Leu Phe
    370                 375                 380
```

```
Ser Val Asn Gly Thr Ala Leu Ser Pro Asp Leu Leu Pro Gln Pro Thr
385                 390                 395                 400

Val Ala Tyr Arg Pro Gly Lys
                405

<210> SEQ ID NO 180
<211> LENGTH: 419
<212> TYPE: PRT
<213> ORGANISM: Haliotis tuberculata

<400> SEQUENCE: 180

Gly His Leu Asp Pro Pro Val His His Arg His Asp Asp Asp Leu Ile
1               5                   10                  15

Val Arg Lys Asn Ile Asp His Leu Thr Arg Glu Glu Tyr Glu Leu
            20                  25                  30

Arg Met Ala Leu Glu Arg Phe Gln Ala Asp Thr Ser Val Asp Gly Tyr
        35                  40                  45

Gln Ala Thr Val Glu Tyr His Gly Leu Pro Ala Arg Cys Pro Arg Pro
    50                  55                  60

Asp Ala Lys Val Arg Phe Ala Cys Cys Met His Gly Met Ala Ser Phe
65                  70                  75                  80

Pro His Trp His Arg Leu Phe Val Thr Gln Val Glu Asp Ala Leu Val
                85                  90                  95

Arg Arg Gly Ser Pro Ile Gly Val Pro Tyr Trp Asp Trp Thr Lys Pro
            100                 105                 110

Met Thr His Leu Pro Asp Leu Ala Ser Asn Glu Thr Tyr Val Asp Pro
        115                 120                 125

Tyr Gly His Thr His His Asn Pro Phe Phe Asn Ala Asn Ile Ser Phe
    130                 135                 140

Glu Glu Gly His His His Thr Ser Arg Met Ile Asp Ser Lys Leu Phe
145                 150                 155                 160

Ala Pro Val Ala Phe Gly Glu His Ser His Leu Phe Asp Gly Ile Leu
                165                 170                 175

Tyr Ala Phe Glu Gln Glu Asp Phe Cys Asp Phe Glu Ile Gln Phe Glu
            180                 185                 190

Leu Val His Asn Ser Ile His Ala Trp Ile Gly Gly Ser Glu Asp Tyr
        195                 200                 205

Ser Met Ala Thr Leu His Tyr Thr Ala Phe Asp Pro Ile Phe Tyr Leu
    210                 215                 220

His His Ser Asn Val Asp Arg Leu Trp Ala Ile Trp Gln Ala Leu Gln
225                 230                 235                 240

Ile Arg Arg His Lys Pro Tyr Gln Ala His Cys Ala Gln Ser Val Glu
                245                 250                 255

Gln Leu Pro Met Lys Pro Phe Ala Phe Pro Ser Pro Leu Asn Asn Asn
            260                 265                 270

Glu Lys Thr His Ser His Ser Val Pro Thr Asp Ile Tyr Asp Tyr Glu
        275                 280                 285

Glu Val Leu His Tyr Ser Tyr Asp Asp Leu Thr Phe Gly Gly Met Asn
    290                 295                 300

Leu Glu Glu Ile Glu Glu Ala Ile His Leu Arg Gln Gln His Glu Arg
305                 310                 315                 320

Val Phe Ala Gly Phe Leu Leu Ala Gly Ile Gly Thr Ser Ala Leu Val
                325                 330                 335

Asp Ile Phe Ile Asn Lys Pro Gly Asn Gln Pro Leu Lys Ala Gly Asp
```

```
               340                 345                 350
Ile Ala Ile Leu Gly Gly Ala Lys Glu Met Pro Trp Ala Phe Asp Arg
            355                 360                 365

Leu Tyr Lys Val Glu Ile Thr Asp Ser Leu Lys Thr Leu Ser Leu Asp
        370                 375                 380

Val Asp Gly Asp Tyr Glu Val Thr Phe Lys Ile His Asp Met His Gly
385                 390                 395                 400

Asn Ala Leu Asp Thr Asp Leu Ile Pro His Ala Ala Val Val Ser Glu
                405                 410                 415

Pro Ala His

<210> SEQ ID NO 181
<211> LENGTH: 414
<212> TYPE: PRT
<213> ORGANISM: Haliotis tuberculata

<400> SEQUENCE: 181

Pro Thr Phe Glu Asp Glu Lys His Ser Leu Arg Ile Arg Lys Asn Val
1               5                  10                  15

Asp Ser Leu Thr Pro Glu Glu Thr Asn Glu Leu Arg Lys Ala Leu Glu
            20                  25                  30

Leu Leu Glu Asn Asp His Thr Ala Gly Gly Phe Asn Gln Leu Gly Ala
        35                  40                  45

Phe His Gly Glu Pro Lys Trp Cys Pro Asn Pro Glu Ala Glu His Lys
    50                  55                  60

Val Ala Cys Cys Val His Gly Met Ala Val Phe Pro His Trp His Arg
65                  70                  75                  80

Leu Leu Ala Leu Gln Ala Glu Asn Ala Leu Arg Lys His Gly Tyr Ser
                85                  90                  95

Gly Ala Leu Pro Tyr Trp Asp Trp Thr Arg Pro Leu Ser Gln Leu Pro
            100                 105                 110

Asp Leu Val Ser His Glu Gln Tyr Thr Asp Pro Ser Asp His His Val
        115                 120                 125

Lys His Asn Pro Trp Phe Asn Gly His Ile Asp Thr Val Asn Gln Asp
    130                 135                 140

Thr Thr Arg Ser Val Arg Glu Asp Leu Tyr Gln Gln Pro Glu Phe Gly
145                 150                 155                 160

His Phe Thr Asp Ile Ala Gln Gln Val Leu Leu Ala Leu Glu Gln Asp
                165                 170                 175

Asp Phe Cys Ser Phe Glu Val Gln Tyr Glu Ile Ser His Asn Phe Ile
            180                 185                 190

His Ala Leu Val Gly Gly Thr Asp Ala Tyr Gly Met Ala Ser Leu Arg
        195                 200                 205

Tyr Thr Ala Tyr Asp Pro Ile Phe Phe Leu His Ser Asn Thr Asp
    210                 215                 220

Arg Ile Trp Ala Ile Trp Gln Ser Leu Gln Lys Tyr Arg Gly Lys Pro
225                 230                 235                 240

Tyr Asn Thr Ala Asn Cys Ala Ile Glu Ser Met Arg Arg Pro Leu Gln
                245                 250                 255

Pro Phe Gly Leu Ser Ser Ala Ile Asn Pro Asp Arg Ile Thr Arg Glu
            260                 265                 270

His Ala Ile Pro Phe Asp Val Phe Asn Tyr Arg Asp Asn Leu His Tyr
        275                 280                 285

Val Tyr Asp Thr Leu Glu Phe Asn Gly Leu Ser Ile Ser Gln Leu Asp
```

```
            290                 295                 300
Arg Glu Leu Glu Lys Ile Lys Ser His Glu Arg Val Phe Ala Gly Phe
305                 310                 315                 320

Leu Leu Ser Gly Ile Lys Lys Ser Ala Leu Val Lys Phe Glu Val Cys
                325                 330                 335

Thr Pro Pro Asp Asn Cys His Lys Ala Gly Glu Phe Tyr Leu Leu Gly
                340                 345                 350

Asp Glu Asn Glu Met Ala Trp Ala Tyr Asp Arg Leu Phe Lys Tyr Asp
                355                 360                 365

Ile Thr Gln Val Leu Glu Ala Asn His Leu His Phe Tyr Asp His Leu
                370                 375                 380

Phe Ile Arg Tyr Glu Val Phe Asp Leu Lys Gly Val Ser Leu Gly Thr
385                 390                 395                 400

Asp Leu Phe His Thr Ala Asn Val Val His Asp Ser Gly Thr
                405                 410

<210> SEQ ID NO 182
<211> LENGTH: 413
<212> TYPE: PRT
<213> ORGANISM: Haliotis tuberculata

<400> SEQUENCE: 182

Gly Thr Arg Asp Arg Asp Asn Tyr Val Glu Val Thr Gly Ala Ser
1               5                   10                  15

His Ile Arg Lys Asn Leu Asn Asp Leu Asn Thr Gly Glu Met Glu Ser
                20                  25                  30

Leu Arg Ala Ala Phe Leu His Ile Gln Asp Asp Gly Thr Tyr Glu Ser
                35                  40                  45

Ile Ala Gln Tyr His Gly Lys Pro Gly Lys Cys Gln Leu Asn Asp His
            50                  55                  60

Asn Ile Ala Cys Cys Val His Gly Met Pro Thr Phe Pro Gln Trp His
65                  70                  75                  80

Arg Leu Tyr Val Val Gln Val Glu Asn Ala Leu Leu Asn Arg Gly Ser
                85                  90                  95

Gly Val Ala Val Pro Tyr Trp Glu Trp Thr Ala Pro Ile Asp His Leu
                100                 105                 110

Pro His Phe Ile Asp Asp Ala Thr Tyr Phe Asn Ser Arg Gln Gln Arg
            115                 120                 125

Tyr Asp Pro Asn Pro Phe Phe Arg Gly Lys Val Thr Phe Glu Asn Ala
130                 135                 140

Val Thr Thr Arg Asp Pro Gln Ala Gly Leu Phe Asn Ser Asp Tyr Met
145                 150                 155                 160

Tyr Glu Asn Val Leu Leu Ala Leu Glu Gln Glu Asn Tyr Cys Asp Phe
                165                 170                 175

Glu Ile Gln Phe Glu Leu Val His Asn Ala Leu His Ser Met Leu Gly
            180                 185                 190

Gly Lys Gly Gln Tyr Ser Met Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Phe Arg Glu Leu Pro Tyr Glu Glu Ala Asn
225                 230                 235                 240

Cys Ala Ile Asn Leu Met His Gln Pro Leu Lys Pro Phe Ser Asp Pro
                245                 250                 255
```

His Glu Asn His Asp Asn Val Thr Leu Lys Tyr Ser Lys Pro Gln Asp
                260                 265                 270

Gly Phe Asp Tyr Gln Asn His Phe Gly Tyr Lys Tyr Asp Asn Leu Glu
            275                 280                 285

Phe His His Leu Ser Ile Pro Ser Leu Asp Ala Thr Leu Lys Gln Arg
        290                 295                 300

Arg Asn His Asp Arg Val Phe Ala Gly Phe Leu Leu His Asn Ile Gly
305                 310                 315                 320

Thr Ser Ala Asp Ile Thr Ile Tyr Ile Cys Leu Pro Asp Gly Arg Arg
                325                 330                 335

Gly Asn Asp Cys Ser His Glu Ala Gly Thr Phe Tyr Ile Leu Gly Gly
            340                 345                 350

Glu Thr Glu Met Pro Phe Ile Phe Asp Arg Leu Tyr Lys Phe Glu Ile
        355                 360                 365

Thr Lys Pro Leu Gln Gln Leu Gly Val Lys Leu His Gly Gly Val Phe
    370                 375                 380

Glu Leu Glu Leu Glu Ile Lys Ala Tyr Asn Gly Ser Tyr Leu Asp Pro
385                 390                 395                 400

His Thr Phe Asp Pro Thr Ile Ile Phe Glu Pro Gly Thr
                405                 410

<210> SEQ ID NO 183
<211> LENGTH: 420
<212> TYPE: PRT
<213> ORGANISM: Haliotis tuberculata

<400> SEQUENCE: 183

Asp Thr His Ile Leu Asp His Asp His Glu Glu Ile Leu Val Arg
1               5                   10                  15

Lys Asn Ile Ile Asp Leu Ser Pro Arg Glu Val Ser Leu Val Lys
            20                  25                  30

Ala Leu Gln Arg Met Lys Asn Asp Arg Ser Ala Asp Gly Tyr Gln Ala
        35                  40                  45

Ile Ala Ser Phe His Ala Leu Pro Pro Leu Cys Pro Asn Pro Ser Ala
    50                  55                  60

Ala His Arg Tyr Ala Cys Cys Val His Gly Met Ala Thr Phe Pro Gln
65                  70                  75                  80

Trp His Arg Leu Tyr Thr Val Gln Val Gln Asp Ala Leu Arg Arg His
                85                  90                  95

Gly Ser Leu Val Gly Ile Pro Tyr Trp Asp Trp Thr Lys Pro Val Asn
            100                 105                 110

Glu Leu Pro Glu Leu Leu Ser Ser Ala Thr Phe Tyr His Pro Ile Arg
        115                 120                 125

Asn Ile Asn Ile Ser Asn Pro Phe Leu Gly Ala Asp Ile Glu Phe Glu
    130                 135                 140

Gly Pro Gly Val His Thr Glu Arg His Ile Asn Thr Glu Arg Leu Phe
145                 150                 155                 160

His Ser Gly Asp His Asp Gly Tyr His Asn Trp Phe Phe Glu Thr Val
                165                 170                 175

Leu Phe Ala Leu Glu Gln Glu Asp Tyr Cys Asp Phe Glu Ile Gln Phe
            180                 185                 190

Glu Ile Ala His Asn Gly Ile His Thr Trp Ile Gly Gly Ser Ala Val
        195                 200                 205

Tyr Gly Met Gly His Leu His Tyr Ala Ser Tyr Asp Pro Ile Phe Tyr
    210                 215                 220

```
Ile His His Ser Gln Thr Asp Arg Ile Trp Ala Ile Trp Gln Glu Leu
225                 230                 235                 240

Gln Lys Tyr Arg Gly Leu Ser Gly Ser Glu Ala Asn Cys Ala Ile Glu
            245                 250                 255

His Met Arg Thr Pro Leu Lys Pro Phe Ser Phe Gly Pro Pro Tyr Asn
        260                 265                 270

Leu Asn Ser His Thr Gln Glu Tyr Ser Lys Pro Glu Asp Thr Phe Asp
            275                 280                 285

Tyr Lys Lys Phe Gly Tyr Arg Tyr Asp Ser Leu Glu Leu Glu Gly Arg
        290                 295                 300

Ser Ile Ser Arg Ile Asp Glu Leu Ile Gln Gln Arg Gln Glu Lys Asp
305                 310                 315                 320

Arg Thr Phe Ala Gly Phe Leu Lys Gly Phe Gly Thr Ser Ala Ser
            325                 330                 335

Val Ser Leu Gln Val Cys Arg Val Asp His Thr Cys Lys Asp Ala Gly
            340                 345                 350

Tyr Phe Thr Ile Leu Gly Gly Ser Ala Glu Met Pro Trp Ala Phe Asp
        355                 360                 365

Arg Leu Tyr Lys Tyr Asp Ile Thr Lys Thr Leu His Asp Met Asn Leu
        370                 375                 380

Arg His Glu Asp Thr Phe Ser Ile Asp Val Thr Ile Thr Ser Tyr Asn
385                 390                 395                 400

Gly Thr Val Leu Ser Gly Asp Leu Ile Gln Thr Pro Ser Ile Ile Phe
            405                 410                 415

Val Pro Gly Arg
        420

<210> SEQ ID NO 184
<211> LENGTH: 417
<212> TYPE: PRT
<213> ORGANISM: Haliotis tuberculata

<400> SEQUENCE: 184

His Lys Leu Asn Ser Arg Lys His Thr Pro Asn Arg Val Arg His Glu
1               5                   10                  15

Leu Ser Ser Leu Ser Ser Arg Asp Ile Ala Ser Leu Lys Ala Ala Leu
            20                  25                  30

Thr Ser Leu Gln His Asp Asn Gly Thr Asp Gly Tyr Gln Ala Ile Ala
        35                  40                  45

Ala Phe His Gly Val Pro Ala Gln Cys His Glu Pro Ser Gly Arg Glu
    50                  55                  60

Ile Ala Cys Cys Ile His Gly Met Ala Thr Phe Pro His Trp His Arg
65                  70                  75                  80

Leu Tyr Thr Leu Gln Leu Glu Gln Ala Leu Arg Arg His Gly Ser Ser
                85                  90                  95

Val Ala Val Pro Tyr Trp Asp Trp Thr Lys Pro Ile Thr Glu Leu Pro
            100                 105                 110

His Ile Leu Thr Asp Gly Glu Tyr Tyr Asp Val Trp Gln Asn Ala Val
        115                 120                 125

Leu Ala Asn Pro Phe Ala Arg Gly Tyr Val Lys Ile Lys Asp Ala Phe
    130                 135                 140

Thr Val Arg Asn Val Gln Glu Ser Leu Phe Lys Met Ser Ser Phe Gly
145                 150                 155                 160

Lys His Ser Leu Leu Phe Asp Gln Ala Leu Leu Ala Leu Glu Gln Thr
```

```
                165                 170                 175
Asp Tyr Cys Asp Phe Glu Val Gln Phe Glu Val Met His Asn Thr Ile
            180                 185                 190

His Tyr Leu Val Gly Gly Arg Gln Thr Tyr Ala Phe Ser Ser Leu Glu
            195                 200                 205

Tyr Ser Ser Tyr Asp Pro Ile Phe Phe Ile His His Ser Phe Val Asp
    210                 215                 220

Lys Ile Trp Ala Val Trp Gln Glu Leu Gln Ser Arg Arg His Leu Gln
225                 230                 235                 240

Phe Arg Thr Ala Asp Cys Ala Val Gly Leu Met Gly Gln Ala Met Arg
                245                 250                 255

Pro Phe Asn Lys Asp Phe Asn His Asn Ser Phe Thr Lys Lys His Ala
            260                 265                 270

Val Pro Asn Thr Val Phe Asp Tyr Glu Asp Leu Gly Tyr Asn Tyr Asp
            275                 280                 285

Asn Leu Glu Ile Ser Gly Leu Asn Leu Asn Glu Ile Glu Ala Leu Ile
    290                 295                 300

Ala Lys Arg Lys Ser His Ala Arg Val Phe Ala Gly Phe Leu Leu Phe
305                 310                 315                 320

Gly Leu Gly Thr Ser Ala Asp Ile His Leu Glu Ile Cys Lys Thr Ser
                325                 330                 335

Glu Asn Cys His Asp Ala Gly Val Ile Phe Ile Leu Gly Gly Ser Ala
            340                 345                 350

Glu Met His Trp Ala Tyr Asn Arg Leu Tyr Lys Tyr Asp Ile Thr Glu
    355                 360                 365

Ala Leu Gln Glu Phe Asp Ile Asn Pro Glu Asp Val Phe His Ala Asp
            370                 375                 380

Glu Pro Phe Phe Leu Arg Leu Ser Val Val Ala Val Asn Gly Thr Val
385                 390                 395                 400

Ile Pro Ser Ser His Leu His Gln Pro Thr Ile Ile Tyr Glu Pro Gly
                405                 410                 415

Glu

<210> SEQ ID NO 185
<211> LENGTH: 403
<212> TYPE: PRT
<213> ORGANISM: Haliotis tuberculata

<400> SEQUENCE: 185

Asp His His Asp Asp His Gln Ser Gly Ser Ile Ala Gly Ser Gly Val
1               5                   10                  15

Arg Lys Asp Val Asn Thr Leu Thr Lys Ala Glu Thr Asp Asn Leu Arg
            20                  25                  30

Glu Ala Leu Trp Gly Val Met Ala Asp His Gly Pro Asn Gly Phe Gln
        35                  40                  45

Ala Ile Ala Ala Phe His Gly Lys Pro Ala Leu Cys Pro Met Pro Asp
    50                  55                  60

Gly His Asn Tyr Ser Cys Cys Thr His Gly Met Ala Thr Phe Pro His
65                  70                  75                  80

Trp His Arg Leu Tyr Thr Lys Gln Met Glu Asp Ala Met Arg Ala His
                85                  90                  95

Gly Ser His Val Gly Leu Pro Tyr Trp Asp Trp Thr Ala Ala Phe Thr
            100                 105                 110

His Leu Pro Thr Leu Val Thr Asp Thr Asp Asn Asn Pro Phe Gln His
```

```
                115                 120                 125
Gly His Ile Asp Tyr Leu Asn Val Ser Thr Thr Arg Ser Pro Arg Asp
    130                 135                 140

Met Leu Phe Asn Asp Pro Glu His Gly Ser Glu Ser Phe Phe Tyr Arg
145                 150                 155                 160

Gln Val Leu Leu Ala Leu Glu Gln Thr Asp Phe Cys Lys Phe Glu Val
                165                 170                 175

Gln Phe Glu Ile Thr His Asn Ala Ile His Ser Trp Thr Gly Gly His
            180                 185                 190

Ser Pro Tyr Gly Met Ser Thr Leu Asp Phe Thr Ala Tyr Asp Pro Leu
        195                 200                 205

Phe Trp Leu His His Ser Asn Thr Asp Arg Ile Trp Ala Val Trp Gln
    210                 215                 220

Ala Leu Gln Glu Tyr Arg Gly Leu Pro Tyr Asn His Ala Asn Cys Glu
225                 230                 235                 240

Ile Gln Ala Met Lys Thr Pro Leu Arg Pro Phe Ser Asp Asp Ile Asn
                245                 250                 255

His Asn Pro Val Thr Lys Ala Asn Ala Lys Pro Leu Asp Val Phe Glu
            260                 265                 270

Tyr Asn Arg Leu Ser Phe Gln Tyr Asp Asn Leu Ile Phe His Gly Tyr
        275                 280                 285

Ser Ile Pro Glu Leu Asp Arg Val Leu Glu Glu Arg Lys Glu Glu Asp
    290                 295                 300

Arg Ile Phe Ala Ala Phe Leu Leu Ser Gly Ile Lys Arg Ser Ala Asp
305                 310                 315                 320

Val Val Phe Asp Ile Cys Gln Pro Glu His Glu Cys Val Phe Ala Gly
                325                 330                 335

Thr Phe Ala Ile Leu Gly Gly Glu Leu Glu Met Pro Trp Ser Phe Asp
            340                 345                 350

Arg Leu Phe Arg Tyr Asp Ile Thr Lys Val Met Lys Gln Leu His Leu
        355                 360                 365

Arg His Asp Ser Asp Phe Thr Phe Arg Val Lys Ile Val Gly Thr Asp
    370                 375                 380

Asp His Glu Leu Pro Ser Asp Ser Val Lys Ala Pro Thr Ile Glu Phe
385                 390                 395                 400

Glu Pro Gly

<210> SEQ ID NO 186
<211> LENGTH: 511
<212> TYPE: PRT
<213> ORGANISM: Haliotis tuberculata

<400> SEQUENCE: 186

Val His Arg Gly Gly Asn His Glu Asp Glu His His Asp Asp Arg Leu
1               5                   10                  15

Ala Asp Val Leu Ile Arg Lys Glu Val Asp Phe Leu Ser Leu Gln Glu
            20                  25                  30

Ala Asn Ala Ile Lys Asp Ala Leu Tyr Lys Leu Gln Asn Asp Asp Ser
        35                  40                  45

Lys Gly Gly Phe Glu Ala Ile Ala Gly Tyr His Gly Tyr Pro Asn Met
    50                  55                  60

Cys Pro Glu Arg Gly Thr Asp Lys Tyr Pro Cys Cys Val His Gly Met
65                  70                  75                  80

Pro Val Phe Pro His Trp His Arg Leu His Thr Ile Gln Met Glu Arg
```

```
                        85                  90                  95
Ala Leu Lys Asn His Gly Ser Pro Met Gly Ile Pro Tyr Trp Asp Trp
                    100                 105                 110

Thr Lys Lys Met Ser Ser Leu Pro Ser Phe Phe Gly Asp Ser Ser Asn
                    115                 120                 125

Asn Asn Pro Phe Tyr Lys Tyr Tyr Ile Arg Gly Val Gln His Glu Thr
            130                 135                 140

Thr Arg Asp Ile Asn Gln Arg Leu Phe Asn Gln Thr Lys Phe Gly Glu
145                 150                 155                 160

Phe Asp Tyr Leu Tyr Tyr Leu Thr Leu Gln Val Leu Glu Glu Asn Ser
                165                 170                 175

Tyr Cys Asp Phe Glu Val Gln Tyr Glu Ile Leu His Asn Ala Val His
                180                 185                 190

Ser Trp Leu Gly Gly Thr Gly Lys Tyr Ser Met Ser Thr Leu Glu His
            195                 200                 205

Ser Ala Phe Asp Pro Val Phe Met Ile His His Ser Ser Leu Asp Arg
        210                 215                 220

Ile Trp Ile Leu Trp Gln Lys Leu Gln Lys Ile Arg Met Lys Pro Tyr
225                 230                 235                 240

Tyr Ala Leu Asp Cys Ala Gly Asp Arg Leu Met Lys Asp Pro Leu His
                245                 250                 255

Pro Phe Asn Tyr Glu Thr Val Asn Glu Asp Glu Phe Thr Arg Ile Asn
            260                 265                 270

Ser Phe Pro Ser Ile Leu Phe Asp His Tyr Arg Phe Asn Tyr Glu Tyr
                275                 280                 285

Asp Asn Met Arg Ile Arg Gly Gln Asp Ile His Glu Leu Glu Glu Val
            290                 295                 300

Ile Gln Glu Leu Arg Asn Lys Asp Arg Ile Phe Ala Gly Phe Val Leu
305                 310                 315                 320

Ser Gly Leu Arg Ile Ser Ala Thr Val Lys Val Phe Ile His Ser Lys
                325                 330                 335

Asn Asp Thr Ser His Glu Glu Tyr Ala Gly Glu Phe Ala Val Leu Gly
            340                 345                 350

Gly Glu Lys Glu Met Pro Trp Ala Tyr Glu Arg Met Leu Lys Leu Asp
            355                 360                 365

Ile Ser Asp Ala Val His Lys Leu His Val Lys Asp Glu Asp Ile Arg
        370                 375                 380

Phe Arg Val Val Val Thr Ala Tyr Asn Gly Asp Val Val Thr Thr Arg
385                 390                 395                 400

Leu Ser Gln Pro Phe Ile Val His Arg Pro Ala His Val Ala His Asp
                405                 410                 415

Ile Leu Val Ile Pro Val Gly Ala Gly His Asp Leu Pro Pro Lys Val
            420                 425                 430

Val Val Lys Ser Gly Thr Lys Val Glu Phe Thr Pro Ile Asp Ser Ser
        435                 440                 445

Val Asn Lys Ala Met Val Glu Leu Gly Ser Tyr Thr Ala Met Ala Lys
    450                 455                 460

Cys Ile Val Pro Pro Phe Ser Tyr His Gly Phe Glu Leu Asp Lys Val
465                 470                 475                 480

Tyr Ser Val Asp His Gly Asp Tyr Tyr Ile Ala Ala Gly Thr His Ala
                485                 490                 495

Leu Cys Glu Gln Asn Leu Arg Leu His Ile His Val Glu His Glu
            500                 505                 510
```

<210> SEQ ID NO 187
<211> LENGTH: 90
<212> TYPE: DNA
<213> ORGANISM: Haliotis tuberculata

<400> SEQUENCE: 187
ggtcttccgt actgggactg gacgcagcat ctgactcaac tcccagatct ggtgtcagac    60
cccttgtttg tcgacccgga aggaggaaag                                    90

<210> SEQ ID NO 188
<211> LENGTH: 221
<212> TYPE: DNA
<213> ORGANISM: Haliotis tuberculata

<400> SEQUENCE: 188
gcccatgaca acgcatggta tcgtggaaac atcaagtttg agaataagaa gactgcaaga    60
gctgttgacg atcgcctttt cgagaaggtt ggaccaggag agaatacccg actctttgaa   120
ggaattctcg atgctcttga acaggatgaa ttctgcaact tcgagatcca gtttgagttg   180
gctcacaacg ctatccacta cctggttggc ggccgtcaca c                       221

<210> SEQ ID NO 189
<211> LENGTH: 255
<212> TYPE: DNA
<213> ORGANISM: Haliotis tuberculata

<400> SEQUENCE: 189
gtactccatg tctcatctcg agtacacctc ctacgacccc ctcttcttcc tccatcactc    60
caacaccgac cgcatcttcg ccatctggca acgtcttcag gtactcagag gaaaggaccc   120
caacaccgcc gactgcgcac acaacctcat ccatgagccc atggaaccgt tccgtcggga   180
ctcgaaccct cttgacctca ccagggaaaa ctccaaacca attgacagct ttgattatgc   240
ccaccttggc tacca                                                   255

<210> SEQ ID NO 190
<211> LENGTH: 407
<212> TYPE: DNA
<213> ORGANISM: Haliotis tuberculata

<400> SEQUENCE: 190
gtatgatgac ttgaccctga acggtatgac cccagaggaa ttgaactcat atctgcatga    60
acggtcaggc aaggaggggg tgttcgcaag cttccgactc tcaggttttg gcggctctgc   120
taacgttgtt gtctacgcat gccgtcctgc ccacgatgaa atggctgtcg atcagtgcga   180
caaagccggc gacttctttg tgttgggcgg acccaccgag atgccctgga ggttttacag   240
agcattccac ttcgacgtca ccgacagcat cgacaacatc gacaaggacc gccacggcca   300
ctattatgta aaggcggaat tattcagtgt aaatggaagt gcgctaccga atgatctcct   360
gcctcaaccc accatctcac acaggccagc ccgcggacac gttgatg                407

<210> SEQ ID NO 191
<211> LENGTH: 1239
<212> TYPE: DNA
<213> ORGANISM: Haliotis tuberculata

<400> SEQUENCE: 191
aggccccagc tccctcctcg gatgctcacc tcgccgtcag gaaggatatc aaccatctga    60

| | |
|---|---|
| cacgcgagga ggtgtacgag ctgcgcagag ctatggagag attccaggcc gacacatccg | 120 |
| ttgatgggta ccaggctacg gttgagtatc acggcttacc tgctcgatgt ccattccccg | 180 |
| aggccacaaa taggttcgcc tgttgcatcc acggcatggc gacattccct cattggcaca | 240 |
| gactgttcgt tacccaggtg gaagatgcac tgatcaggcg aggatcccct ataggggtcc | 300 |
| cctactggga ctggactcag cctatggcac atctcccagg acttgcagac aacgccacct | 360 |
| atagagatcc catcagcgga gacagcagac acaacccgtt ccacgatgtt gaagttgcct | 420 |
| ttgaaaatgg gcgtacagaa cgtcacccag atagtagatt gtttgaacaa cctctatttg | 480 |
| gcaaacatac gcgtctcttc gacagtatag tctatgcttt tgagcaggag gacttctgcg | 540 |
| attttgaagt tcaatttgag atgacccata ataatattca cgcctggatt ggtggcggcg | 600 |
| ggaagtattc catgtcttct ctacactaca cagccttcga ccctatctcc taccttcatc | 660 |
| actccaacac tgaccgtctc tgggcaattt ggcaagcgtt gcagatacga agaaacaaac | 720 |
| cgtataaggc tcattgtgct tggtctgagg aacgccagcc tctcaaacct ttcgccttca | 780 |
| gttccccact gaacaacaac gaaaaaacct acgaaaactc ggtgcccacc aacgtttacg | 840 |
| actacgaagg agtccttggc tatacttatg atgacctcaa cttcggggc atggacctgg | 900 |
| gtcagcttga ggaatacatc cagaggcaga gacagagaga caggaccttt gctggcttct | 960 |
| ttctgtcaca tattggtaca tcagcgaatg ttgaaatcat tatagaccat gggactcttc | 1020 |
| atacctccgt gggcacgttt gctgttcttg gcggagagaa ggagatgaaa tggggatttg | 1080 |
| accgtttgta caaatatgag attacagatg aactgaggca acttaatctc cgtgctgatg | 1140 |
| atggtttcag catctctgtt aaagtaactg atgttgatgg cagtgagctg tcctctgaac | 1200 |
| tcatcccatc tgctgctatc atcttcgaac gaagccata | 1239 |

<210> SEQ ID NO 192
<211> LENGTH: 1245
<212> TYPE: DNA
<213> ORGANISM: Haliotis tuberculata

<400> SEQUENCE: 192

| | |
|---|---|
| ttgaccatca ggaccctcat caggacacaa tcatcaggaa aaatgttgat aatcttacac | 60 |
| ccgaggaaat taattctctg aggagggcaa tggcagacct tcaatcagac aaaaccgccg | 120 |
| gtggattcca gcaaattgct gcttttcacg gggaacccaa atggtgccca agtcccgatg | 180 |
| ctgagaagaa gttctcctgc tgtgtccatg gaatggctgt cttccctcac tggcacagac | 240 |
| tcctgaccgt gcaaggcgag aatgcccctga aaagcatgat atgtctcgga gctctcccct | 300 |
| actgggactg gactcggccc ctgtctcacc tacctgattt ggtaagtcag cagaactaca | 360 |
| ccgatgccat atccaccgtg gaagcccgaa acccctggta cagcggccat attgatacag | 420 |
| ttggtgttga cacaacaaga agcgtccgtc aagaactgta tgaagctccc ggatttggtc | 480 |
| attatactgg ggtcgctaag caagtgcttc tggctttgga gcaggatgac ttctgtgatt | 540 |
| ttgaagtcca gtttgagata gctcacaatt tcatccacgc tcttgtcggc ggaagcgagc | 600 |
| catatggtat ggcgtcactc cgttacacta cttatgatcc aattttctac ctccatcatt | 660 |
| ctaacactga cagactctgg gctatatggc aggctctaca aaagtacagg ggcaaacctt | 720 |
| acaattccgc caactgtgcc attgcttcta tgagaaaacc cctacagccc tttggtctga | 780 |
| ctgatgagat caacccggat gatgagacaa gacagcatgc tgttcctttc agtgtctttg | 840 |
| attacaagaa caacttcaat tatgaatatg acacccttga cttcaacgga ctatcaatct | 900 |
| cccagctgga ccgtgaactg tcacggagaa agtctcatga cagagtattt gccggatttt | 960 |

```
tgctgcatgg tattcagcag tctgcactag ttaaattctt tgtctgcaaa tcagatgatg    1020
actgtgacca ctatgctggt gaattctaca tccttggtga tgaagctgaa atgccatggg    1080
gctatgatcg tctttacaaa tatgagatca ctgagcagct caatgccctg gatctacaca    1140
tcggagatag attcttcatc agatacgaag cgtttgatct tcatggtaca agtcttggaa    1200
gcaacatctt ccccaaacct tctgtcatac atgacgaagg ggcag                    1245

<210> SEQ ID NO 193
<211> LENGTH: 1242
<212> TYPE: DNA
<213> ORGANISM: Haliotis tuberculata

<400> SEQUENCE: 193
gtcaccatca ggctgacgag tacgacgaag ttgtaactgc tgcaagccac atcagaaaga      60
atttaaaaga tctgtcaaag ggagaagtag agagcctaag gtctgccttc ctgcaacttc     120
agaacgacgg agtctatgag aatattgcca aattccacgg caagcctggg ttgtgtgatg     180
ataacggtcg caaggttgcc tgttgtgtcc atggaatgcc caccttcccc cagtggcaca     240
gactctatgt cctccaggtg gagaatgctt tgctggagag aggatctgcc gtctctgtgc     300
catactggga ctggactgaa acatttacag agctgccatc tttgattgct gaggctacct     360
atttcaattc ccgtcaacaa acgtttgacc ctaatccttt cttcagaggt aaaatcagtt     420
ttgagaatgc tgttacaaca cgtgatcccc agcctgagct gtacgttaac aggtactact     480
accaaaacgt catgttggct tttgaacagg acaactactg cgacttcgag atacagtttg     540
agatggttca caatgttctc catgcttggc ttggtggaag agctacttat tctatttctt     600
ctcttgatta ttctgcattc gaccctgtgt ttttccttca ccatgcgaac acagatagat     660
tgtgggccat ctggcaggag ctgcagaggt acaggaagaa gccatacaat gaagcggatt     720
gtgccattaa cctaatgcgc aaacctctac atcccttcga caacagtgat ctcaatcatg     780
atcctgtaac ctttaaatac tcaaaaccca ctgatggctt tgactaccag aacaactttg     840
gatacaagta tgcaacccct gagttcaatc atttcagtat tcccaggctt gaagaaatca     900
ttcgtattag acaacgtcaa gatcgtgtgt ttgcaggatt cctccttcac aacattggga     960
catccgcaac tgttgagata ttcgtctgtg tccctaccac cagcggtgag caaaactgtg    1020
aaaacaaagc cggaacattt gccgtactcg gaggagaaac agagatggcg tttcattttg    1080
acagactcta caggtttgac atcagtgaaa cactgaggga cctcggcata cagctggaca    1140
gccatgactt tgacctcagc atcaagattc aaggagtaaa tggatcctac cttgatccac    1200
acatcctgcc agagccatcc ttgattttg tgcctggttc aa                        1242

<210> SEQ ID NO 194
<211> LENGTH: 1257
<212> TYPE: DNA
<213> ORGANISM: Haliotis tuberculata

<400> SEQUENCE: 194
gttctttcct gcgtcctgat gggcattcag atgacatcct tgtgagaaaa gaagtgaaca      60
gcctgacaac cagggagact gcatctctga tccatgctct gaaaagtatg caggaagacc     120
attcacctga tgggttccaa gccattgcct ctttccatgc cctgccacca ctctgcccct     180
caccatctgc aactcaccgt tatgcttgct gtgtccacgg catggctaca tttcccccagt    240 ggcacagact gtacactgta cagttccagg atgcactgag gagacatgga gctgcagtag     300
```

```
gtgtaccgta ttgggattgg ctgcgaccgc agtctcacct accagagctt gtcaccatgg      360
agacatacca tgatatttgg agtaacagag atttccccaa tcctttctac caagccaata      420
ttgagtttga aggagaaaac attacaacag agagagaagt cattgcagac aaactttttg      480
tcaaaggtgg acacgttttt gataactggt tcttcaaaca agccatccta gcgcttgagc      540
aggaaaacta ctgtgacttt gagattcagt ttgaaattct tcacaacggc gttcacacgt      600
gggtcggagg cagtcgtacc cactctatcg gacatctcca ttacgcatcc tacgaccctc      660
ttttctacct ccaccattcc cagacagacc gtatttgggc aatctggcaa gaactccagg      720
aacagagagg gctctcaggt gatgaggctc actgtgctct cgagcaaatg agagaaccat      780
tgaagccttt cagcttcggc gctccttata acttgaatca gctaacacag gatttctccc      840 gaccccgagga caccttcgac tacaggaagt ttggttatga atatgacaat ttagaattcc      900
taggaatgtc agttgctgaa ctggatcaat acattattga acatcaagaa aatgatagag      960
tattcgctgg gttcctgttg agtggattcg gaggttccgc atcagttaat ttccaggttt     1020
gtagagctga ttccacatgt caggatgctg ggtacttcac cgttcttggt ggcagtgctg     1080
agatggcgtg ggcatttgac aggctataca aatatgacat tactgaaact ctggagaaaa     1140
tgcaccttcg atatgatgat gacttcacaa tctctgtcag tctgaccgcc aacaacggaa     1200
ctgtcctgag cagcagtcta atcccaacac cgagtgtcat attccagcgg ggacatc       1257

<210> SEQ ID NO 195
<211> LENGTH: 191
<212> TYPE: DNA
<213> ORGANISM: Haliotis tuberculata

<400> SEQUENCE: 195
gtgacataaa taccaagagc atgtcagcga accgtgttcg ccgtgagctg agcgatctgt       60
ctgcgaggga cccgtctagt ctcaagtctg ctctgcgaga cctacaggag gatgatggcc      120
ccaacggata ccaggctctt gcagccttcc atgggctacc agcaggctgc catgatagcc      180
agggaaatga g                                                          191

<210> SEQ ID NO 196
<211> LENGTH: 1057
<212> TYPE: DNA
<213> ORGANISM: Haliotis tuberculata

<400> SEQUENCE: 196
atcgcatgtt gcattcacgg tatgccgacc ttccccagt ggcacagact gtacaccctg       60
cagttggaga tggctctgag gagacatgga tcatctgtcg ccatccccta ctgggactgg      120
acaaagccta tctccgaact ccctcgctc ttcaccagcc ctgagtatta tgacccatgg      180
catgatgctg tggtaaacaa cccattctcc aaaggttttg tcaaatttgc aaatacctac      240
acagtaagag acccacagga gatgctgttc cagctttgtg aacatggaga gtcaatcctc      300
tatgagcaaa ctcttcttgc tctagagcaa accgactact gtgattttga ggtacagttt      360
gaggtcctcc ataacgtgat ccactacctt gttggcggac gtcagaccta cgcattgtct      420
tctctgcatt atgcatccta cgacccattc ttctttatac accattcctt tgtggataag      480
atgtgggtag tatggcaagc tcttcaaaag aggaggaaac ttccatacaa gcgagctgac      540
tgtgctgtca acctaatgac taaaccaatg aggccatttg actccgatat gaatcagaac      600
ccattcacaa agatgcacgc agttcccaac acactctatg actacgagac actgtactac      660
agctacgata atctcgaaat aggtggcagg aatctcgacc agcttcaggc tgaaattgac      720
```

-continued

```
agaagcagaa gccacgatcg cgttttttgct ggattcttgc ttcgtggaat cggaacttct    780
gctgatgtca ggtttttggat ttgtagaaat gaaaatgact gccacagggg tggaataatt    840
ttcatcttag gtggagccaa ggaaatgcca tggtcatttg acagaaactt caagtttgat    900
atcacccatg tactcgagaa agctggcatt agcccagagg acgtgtttga tgctgaggag    960
ccattttata tcaaggttga gatccatgct gttaacaaga ccatgatacc atcgtctgtg    1020
atcccagccc caactatcat ctattctcct ggggaag                              1057
```

<210> SEQ ID NO 197
<211> LENGTH: 219
<212> TYPE: DNA
<213> ORGANISM: Haliotis tuberculata

<400> SEQUENCE: 197

```
gtcgcgctgc tgacagtgca cactcagcca acattgctgg ctctggggtg aggaaggacg     60
tcacgaccct cactgtgtct gagaccgaga acctaagaca ggctcttcaa ggtgtcatcg    120
atgatactgg tcccaatggt taccaagcaa tagcatcctt ccacggaagt cctccaatgt    180
gcgagatgaa cggccgcaag gttgcctgtt gtgctcacg                           219
```

<210> SEQ ID NO 198
<211> LENGTH: 164
<212> TYPE: DNA
<213> ORGANISM: Haliotis tuberculata

<400> SEQUENCE: 198

```
gtatggcctc cttcccacac tggcacagac tgtatgtgaa gcagatggaa gacgccctgg     60
ctgaccacgg atcacatatc ggcatccctt actgggactg gacaactgcc ttcacagagt    120
tacccgccct tgtcacagac tccgagaaca atcccttcca tgag                     164
```

<210> SEQ ID NO 199
<211> LENGTH: 826
<212> TYPE: DNA
<213> ORGANISM: Haliotis tuberculata

<400> SEQUENCE: 199

```
ggtcgcattg atcatctcgg tgtaaccacg tcacgttccc ccagagacat gctgtttaac     60
gacccagagc aaggatcaga gtcgttcttc tatagacaag tcctcctggc tttggagcag    120
actgactact gccagttcga agtccagttt gagctgaccc acaacgccat tcactcctgg    180
acaggtggac gtagccctta cggaatgtcg accctcgagt tcacagccta cgatcctctc    240
ttctggcttc accactccaa caccgacaga atctgggctg tctggcaagc actgcagaaa    300
taccgaggac tcccatacaa cgaagcacac tgtgaaatcc aggttctgaa acagcccttg    360
aggccattca cgatgacat caaccacaat ccaatcacca agactaatgc caggcctatc    420
gattcatttg attatgagag gtttaactat cagtatgaca cccttagctt ccatggtaag    480
agcatccctg aactgaatga cctgctcgag gaaagaaaaa gagaagagag aacatttgct    540
gccttccttc ttcgtggaat cggttgcagt gctgatgtcg tctttgacat ctgccgcccc    600
aatggtgact gtgtctttgc aggaaccttt gctgtgctgg gagggagct agaaatgcct    660 tggtccttcg acagactgtt ccgctatgac atcaccagag tcatgaatca gctccatctc    720
cagtatgatt cagatttcag tttcagggtg aagcttgttg caaccaatgg cactgagctt    780
tcatcagacc tcctcaagtc accaacaatt gaacatgaac ttggag                   826
```

<210> SEQ ID NO 200
<211> LENGTH: 1535
<212> TYPE: DNA
<213> ORGANISM: Haliotis tuberculata

<400> SEQUENCE: 200

| | | | | | |
|---|---|---|---|---|---|
| cccacagagg | accagttgaa | gaaacagaag | tcactcacca | aaatactgac | ggcaatgcac | 60 |
| acttccatcg | taaggaagtt | gattcgctgt | ccctggatga | agcaaacaac | ttgaagaatg | 120 |
| cccctttacaa | gctacagaac | gaccacagtc | taacaggata | cgaagcaatc | tctggttacc | 180 |
| atggataccc | gaatctgtgt | ccggaagaag | gcgatgacaa | ataccctgc | tgcgtccacg | 240 |
| gaatggccat | cttccccac | tggcacagac | tcttgaccat | ccaactggaa | agagctctcg | 300 |
| agcacaatgg | tgcactgctt | ggtgttcctt | actgggactg | gaccaaggac | ctgtcgtcac | 360 |
| tgccggcgtt | cttctccgac | tccagcaaca | acaatcccta | cttcaagtac | cacatcgcag | 420 |
| gtgttggtca | cgacaccgtc | agagagccaa | ctagtcttat | atataaccag | ccccaaatcc | 480 |
| atggttatga | ttatctctat | tacctagcat | tgaccacgct | tgaagaaaac | aattactgtg | 540 |
| actttgaggt | tcagtatgag | atcctccaca | acgccgtcca | ctcctggctt | ggaggatccc | 600 |
| agaagtattc | catgtctacc | ctggagtatt | cggcctttga | ccctgtcttt | atgatccttc | 660 |
| actcgggtct | agacagactt | tggatcatct | ggcaagaact | tcagaagatc | aggagaaagc | 720 |
| cctacaactt | cgctaaatgt | gcttatcata | tgatggaaga | gccactggcg | cccttcagct | 780 |
| atccatctat | caaccaggac | gagttcaccc | gtgccaactc | caagccttct | acagttttg | 840 |
| acagccataa | gttcggctac | cattacgata | acctgaatgt | tagaggtcac | agcatccaag | 900 |
| aactcaacac | aatcatcaat | gacttgagaa | acacagacag | aatctacgca | ggatttgttt | 960 |
| tgtcaggcat | cggtacgtct | gctagtgtca | agatctatct | ccgaacagat | gacaatgacg | 1020 |
| aagaagttgg | aactttcact | gtcctgggag | gagagaggga | aatgccatgg | gcctacgagc | 1080 |
| gagttttcaa | gtatgacatc | acagaggttg | cagatagact | taaactaagt | tatggggaca | 1140 |
| cctttaactt | ccgactagag | atcacatcct | cgatggatc | ggtggtaaac | aagagcctac | 1200 |
| ccaatccttt | catcatctac | agacctgcca | atcatgacta | cgatgttctt | gttatcccag | 1260 |
| taggaagaaa | ccttcacatc | cctcccaaag | ttgtcgtcaa | gagaggcacc | cgcatcgagt | 1320 |
| tccacccagt | cgatgattca | gttacgagac | cagttgttga | tcttggaagc | tacactgcac | 1380 |
| tcttcaactg | tgtggtacca | ccgttcacat | accgcggatt | cgaactgaac | cacgtctatt | 1440 |
| ctgtcaagcc | tggtgactac | tatgttaccg | gaccaacgag | agacctttgc | cagaatgcag | 1500 |
| atgtcaggat | tcatatccat | gttgaggatg | agtaa | | 1535 |

<210> SEQ ID NO 201
<211> LENGTH: 8
<212> TYPE: DNA
<213> ORGANISM: Haliotis tuberculata

<400> SEQUENCE: 201 cgcaacag                                                                 8

<210> SEQ ID NO 202
<211> LENGTH: 211
<212> TYPE: DNA
<213> ORGANISM: Haliotis tuberculata

<400> SEQUENCE: 202
gtttcttggt ctccacatat tcacacatca gcaccaaacg gtttcgaagg acattggcgt    60

```
tcttctctgg caatgcattt caatacaaca ttgaaaatga cttcagcata tcagtgtgct    120
tcgaacgtgt tccggaagta ctcaaatgtg ctatgactga attattgtac atacataact    180
tattgatgtt caataaataa atgttgaaac g                                   211
```

<210> SEQ ID NO 203
<211> LENGTH: 334
<212> TYPE: PRT
<213> ORGANISM: Haliotis tuberculata

<400> SEQUENCE: 203

```
His Arg Leu Phe Val Thr Gln Val Glu Asp Ala Leu Ile Arg Arg Gly
1               5                   10                  15

Ser Pro Ile Gly Val Pro Tyr Trp Asp Trp Thr Gln Pro Met Ala His
            20                  25                  30

Leu Pro Gly Leu Ala Asp Asn Ala Thr Tyr Arg Asp Pro Ile Ser Gly
        35                  40                  45

Asp Ser Arg His Asn Pro Phe His Asp Val Glu Val Ala Phe Glu Asn
    50                  55                  60

Gly Arg Thr Glu Arg His Pro Asp Ser Arg Leu Phe Glu Gln Pro Leu
65                  70                  75                  80

Phe Gly Lys His Thr Arg Leu Phe Asp Ser Ile Val Tyr Ala Phe Glu
                85                  90                  95

Gln Glu Asp Phe Cys Asp Phe Glu Val Gln Phe Glu Met Thr His Asn
            100                 105                 110

Asn Ile His Ala Trp Ile Gly Gly Gly Lys Tyr Ser Met Ser Ser
        115                 120                 125

Leu His Tyr Thr Ala Phe Asp Pro Ile Ser Tyr Leu His His Ser Asn
    130                 135                 140

Thr Asp Arg Leu Trp Ala Ile Trp Gln Ala Leu Gln Ile Arg Arg Asn
145                 150                 155                 160

Lys Pro Tyr Lys Ala His Cys Ala Trp Ser Glu Glu Arg Gln Pro Leu
                165                 170                 175

Lys Pro Phe Ala Phe Ser Ser Pro Leu Asn Asn Asn Glu Lys Thr Tyr
            180                 185                 190

Glu Asn Ser Val Pro Thr Asn Val Tyr Asp Tyr Glu Gly Val Leu Gly
        195                 200                 205

Tyr Thr Tyr Asp Asp Leu Asn Phe Gly Gly Met Asp Leu Gly Gln Leu
    210                 215                 220

Glu Glu Tyr Ile Gln Arg Gln Arg Gln Arg Asp Arg Thr Phe Ala Gly
225                 230                 235                 240

Phe Phe Leu Ser His Ile Gly Thr Ser Ala Asn Val Glu Ile Ile Ile
                245                 250                 255

Asp His Gly Thr Leu His Thr Ser Val Gly Thr Phe Ala Val Leu Gly
            260                 265                 270

Gly Glu Lys Glu Met Lys Trp Gly Phe Asp Arg Leu Tyr Lys Tyr Glu
        275                 280                 285

Ile Thr Asp Glu Leu Arg Gln Leu Asn Leu Arg Ala Asp Asp Gly Phe
    290                 295                 300

Ser Ile Ser Val Lys Val Thr Asp Val Asp Gly Ser Glu Leu Ser Ser
305                 310                 315                 320

Glu Leu Ile Pro Ser Ala Ala Ile Ile Phe Glu Arg Ser His
                325                 330
```

<210> SEQ ID NO 204
<211> LENGTH: 415
<212> TYPE: PRT
<213> ORGANISM: Haliotis tuberculata

<400> SEQUENCE: 204

```
Ile Asp His Gln Asp Pro His Gln Asp Thr Ile Ile Arg Lys Asn Val
1               5                   10                  15

Asp Asn Leu Thr Pro Glu Glu Ile Asn Ser Leu Arg Arg Ala Met Ala
            20                  25                  30

Asp Leu Gln Ser Asp Lys Thr Ala Gly Gly Phe Gln Gln Ile Ala Ala
        35                  40                  45

Phe His Gly Glu Pro Lys Trp Cys Pro Ser Pro Asp Ala Glu Lys Lys
    50                  55                  60

Phe Ser Cys Cys Val His Gly Met Ala Val Phe Pro His Trp His Arg
65                  70                  75                  80

Leu Leu Thr Val Gln Gly Glu Asn Ala Leu Arg Lys His Gly Cys Leu
                85                  90                  95

Gly Ala Leu Pro Tyr Trp Asp Trp Thr Arg Pro Leu Ser His Leu Pro
            100                 105                 110

Asp Leu Val Ser Gln Gln Asn Tyr Thr Asp Ala Ile Ser Thr Val Glu
        115                 120                 125

Ala Arg Asn Pro Trp Tyr Ser Gly His Ile Asp Thr Val Gly Val Asp
    130                 135                 140

Thr Thr Arg Ser Val Arg Gln Glu Leu Tyr Glu Ala Pro Gly Phe Gly
145                 150                 155                 160

His Tyr Thr Gly Val Ala Lys Gln Val Leu Leu Ala Leu Glu Gln Asp
                165                 170                 175

Asp Phe Cys Asp Phe Glu Val Gln Phe Glu Ile Ala His Asn Phe Ile
            180                 185                 190

His Ala Leu Val Gly Gly Ser Glu Pro Tyr Gly Met Ala Ser Leu Arg
        195                 200                 205

Tyr Thr Thr Tyr Asp Pro Ile Phe Tyr Leu His His Ser Asn Thr Asp
    210                 215                 220

Arg Leu Trp Ala Ile Trp Gln Ala Leu Gln Lys Tyr Arg Gly Lys Pro
225                 230                 235                 240

Tyr Asn Ser Ala Asn Cys Ala Ile Ala Ser Met Arg Lys Pro Leu Gln
                245                 250                 255

Pro Phe Gly Leu Thr Asp Glu Ile Asn Pro Asp Asp Glu Thr Arg Gln
            260                 265                 270

His Ala Val Pro Phe Ser Val Phe Asp Tyr Lys Asn Asn Phe Asn Tyr
        275                 280                 285

Glu Tyr Asp Thr Leu Asp Phe Asn Gly Leu Ser Ile Ser Gln Leu Asp
    290                 295                 300

Arg Glu Leu Ser Arg Arg Lys Ser His Asp Arg Val Phe Ala Gly Phe
305                 310                 315                 320

Leu Leu His Gly Ile Gln Gln Ser Ala Leu Val Lys Phe Phe Val Cys
                325                 330                 335

Lys Ser Asp Asp Asp Cys Asp His Tyr Ala Gly Glu Phe Tyr Ile Leu
            340                 345                 350

Gly Asp Glu Ala Glu Met Pro Trp Gly Tyr Asp Arg Leu Tyr Lys Tyr
        355                 360                 365

Glu Ile Thr Glu Gln Leu Asn Ala Leu Asp Leu His Ile Gly Asp Arg
    370                 375                 380
```

```
Phe Phe Ile Arg Tyr Glu Ala Phe Asp Leu His Gly Thr Ser Leu Gly
385                 390                 395                 400

Ser Asn Ile Phe Pro Lys Pro Ser Val Ile His Asp Glu Gly Ala
            405                 410                 415

<210> SEQ ID NO 205
<211> LENGTH: 415
<212> TYPE: PRT
<213> ORGANISM: Haliotis tuberculata

<400> SEQUENCE: 205

Gly His His Gln Ala Asp Glu Tyr Asp Glu Val Val Thr Ala Ala Ser
1               5                   10                  15

His Ile Arg Lys Asn Leu Lys Asp Leu Ser Lys Gly Glu Val Glu Ser
            20                  25                  30

Leu Arg Ser Ala Phe Leu Gln Leu Gln Asn Asp Gly Val Tyr Glu Asn
        35                  40                  45

Ile Ala Lys Phe His Gly Lys Pro Gly Leu Cys Asp Asp Asn Gly Arg
    50                  55                  60

Lys Val Ala Cys Cys Val His Gly Met Pro Thr Phe Pro Gln Trp His
65                  70                  75                  80

Arg Leu Tyr Val Leu Gln Val Glu Asn Ala Leu Leu Glu Arg Gly Ser
                85                  90                  95

Ala Val Ser Val Pro Tyr Trp Asp Trp Thr Glu Thr Phe Thr Glu Leu
            100                 105                 110

Pro Ser Leu Ile Ala Glu Ala Thr Tyr Phe Asn Ser Arg Gln Gln Thr
        115                 120                 125

Phe Asp Pro Asn Pro Phe Phe Arg Gly Lys Ile Ser Phe Glu Asn Ala
    130                 135                 140

Val Thr Thr Arg Asp Pro Gln Pro Glu Leu Tyr Val Asn Arg Tyr Tyr
145                 150                 155                 160

Tyr Gln Asn Val Met Leu Ala Phe Glu Gln Asp Asn Tyr Cys Asp Phe
                165                 170                 175

Glu Ile Gln Phe Glu Met Val His Asn Val Leu His Ala Trp Leu Gly
            180                 185                 190

Gly Arg Ala Thr Tyr Ser Ile Ser Ser Leu Asp Tyr Ser Ala Phe Asp
        195                 200                 205

Pro Val Phe Phe Leu His His Ala Asn Thr Asp Arg Leu Trp Ala Ile
    210                 215                 220

Trp Gln Glu Leu Gln Arg Tyr Arg Lys Pro Tyr Asn Glu Ala Asp
225                 230                 235                 240

Cys Ala Ile Asn Leu Met Arg Lys Pro Leu His Pro Phe Asp Asn Ser
                245                 250                 255

Asp Leu Asn His Asp Pro Val Thr Phe Lys Tyr Ser Lys Pro Thr Asp
            260                 265                 270

Gly Phe Asp Tyr Gln Asn Asn Phe Gly Tyr Lys Tyr Asp Asn Leu Glu
        275                 280                 285

Phe Asn His Phe Ser Ile Pro Arg Leu Glu Glu Ile Ile Arg Ile Arg
    290                 295                 300

Gln Arg Gln Asp Arg Val Phe Ala Gly Phe Leu Leu His Asn Ile Gly
305                 310                 315                 320

Thr Ser Ala Thr Val Glu Ile Phe Val Cys Val Pro Thr Thr Ser Gly
                325                 330                 335

Glu Gln Asn Cys Glu Asn Lys Ala Gly Thr Phe Ala Val Leu Gly Gly
            340                 345                 350
```

Glu Thr Glu Met Ala Phe His Phe Asp Arg Leu Tyr Arg Phe Asp Ile
            355                 360                 365

Ser Glu Thr Leu Arg Asp Leu Gly Ile Gln Leu Asp Ser His Asp Phe
    370                 375                 380

Asp Leu Ser Ile Lys Ile Gln Gly Val Asn Gly Ser Tyr Leu Asp Pro
385                 390                 395                 400

His Ile Leu Pro Glu Pro Ser Leu Ile Phe Val Pro Gly Ser Ser
                405                 410                 415

<210> SEQ ID NO 206
<211> LENGTH: 418
<212> TYPE: PRT
<213> ORGANISM: Haliotis tuberculata

<400> SEQUENCE: 206

Ser Phe Leu Arg Pro Asp Gly His Ser Asp Ile Leu Val Arg Lys
1               5                   10                  15

Glu Val Asn Ser Leu Thr Thr Arg Glu Thr Ala Ser Leu Ile His Ala
                20                  25                  30

Leu Lys Ser Met Gln Glu Asp His Ser Pro Asp Gly Phe Gln Ala Ile
            35                  40                  45

Ala Ser Phe His Ala Leu Pro Pro Leu Cys Pro Ser Pro Ser Ala Thr
50                  55                  60

His Arg Tyr Ala Cys Cys Val His Gly Met Ala Thr Phe Pro Gln Trp
65                  70                  75                  80

His Arg Leu Tyr Thr Val Gln Phe Gln Asp Ala Leu Arg Arg His Gly
                85                  90                  95

Ala Ala Val Gly Val Pro Tyr Trp Asp Trp Leu Arg Pro Gln Ser His
            100                 105                 110

Leu Pro Glu Leu Val Thr Met Glu Thr Tyr His Asp Ile Trp Ser Asn
        115                 120                 125

Arg Asp Phe Pro Asn Pro Phe Tyr Gln Ala Asn Ile Glu Phe Glu Gly
    130                 135                 140

Glu Asn Ile Thr Thr Glu Arg Glu Val Ile Ala Asp Lys Leu Phe Val
145                 150                 155                 160

Lys Gly Gly His Val Phe Asp Asn Trp Phe Phe Lys Gln Ala Ile Leu
                165                 170                 175

Ala Leu Glu Gln Glu Asn Tyr Cys Asp Phe Glu Ile Gln Phe Glu Ile
            180                 185                 190

Leu His Asn Gly Val His Thr Trp Val Gly Gly Ser Arg Thr His Ser
        195                 200                 205

Ile Gly His Leu His Tyr Ala Ser Tyr Asp Pro Leu Phe Tyr Leu His
    210                 215                 220

His Ser Gln Thr Asp Arg Ile Trp Ala Ile Trp Gln Glu Leu Gln Glu
225                 230                 235                 240

Gln Arg Gly Leu Ser Gly Asp Glu Ala His Cys Ala Leu Glu Gln Met
                245                 250                 255

Arg Glu Pro Leu Lys Pro Phe Ser Gly Ala Pro Tyr Asn Leu Asn
            260                 265                 270

Gln Leu Thr Gln Asp Phe Ser Arg Pro Glu Asp Thr Phe Asp Tyr Arg
        275                 280                 285

Lys Phe Gly Tyr Glu Tyr Asp Asn Leu Glu Phe Leu Gly Met Ser Val
    290                 295                 300

Ala Glu Leu Asp Gln Tyr Ile Ile Glu His Gln Glu Asn Asp Arg Val

-continued

```
            305                 310                 315                 320
Phe Ala Gly Phe Leu Leu Ser Gly Phe Gly Ser Ala Ser Val Asn
                    325                 330                 335
Phe Gln Val Cys Arg Ala Asp Ser Thr Cys Gln Asp Ala Gly Tyr Phe
                340                 345                 350
Thr Val Leu Gly Gly Ser Ala Glu Met Ala Trp Ala Phe Asp Arg Leu
                355                 360                 365
Tyr Lys Tyr Asp Ile Thr Glu Thr Leu Glu Lys Met His Leu Arg Tyr
                370                 375                 380
Asp Asp Asp Phe Thr Ile Ser Val Ser Leu Thr Ala Asn Asn Gly Thr
385                 390                 395                 400
Val Leu Ser Ser Ser Leu Ile Pro Thr Pro Ser Val Ile Phe Gln Arg
                    405                 410                 415
Gly His

<210> SEQ ID NO 207
<211> LENGTH: 416
<212> TYPE: PRT
<213> ORGANISM: Haliotis tuberculata

<400> SEQUENCE: 207

Arg Asp Ile Asn Thr Lys Ser Met Ser Ala Asn Arg Val Arg Arg Glu
1               5                   10                  15
Leu Ser Asp Leu Ser Ala Arg Asp Pro Ser Ser Leu Lys Ser Ala Leu
                20                  25                  30
Arg Asp Leu Gln Glu Asp Asp Gly Pro Asn Gly Tyr Gln Ala Leu Ala
                35                  40                  45
Ala Phe His Gly Leu Pro Ala Gly Cys His Asp Ser Gln Gly Asn Glu
            50                  55                  60
Ile Ala Cys Cys Ile His Gly Met Pro Thr Phe Pro Gln Trp His Arg
65              70                  75                  80
Leu Tyr Thr Leu Gln Leu Glu Met Ala Leu Arg Arg His Gly Ser Ser
                85                  90                  95
Val Ala Ile Pro Tyr Trp Asp Trp Thr Lys Pro Ile Ser Glu Leu Pro
                100                 105                 110
Ser Leu Phe Thr Ser Pro Glu Tyr Tyr Asp Pro Trp His Asp Ala Val
                115                 120                 125
Val Asn Asn Pro Phe Ser Lys Gly Phe Val Lys Phe Ala Asn Thr Tyr
130                 135                 140
Thr Val Arg Asp Pro Gln Glu Met Leu Phe Gln Leu Cys Glu His Gly
145                 150                 155                 160
Glu Ser Ile Leu Tyr Glu Gln Thr Leu Leu Ala Leu Glu Gln Thr Asp
                165                 170                 175
Tyr Cys Asp Phe Glu Val Gln Phe Glu Val Leu His Asn Val Ile His
                180                 185                 190
Tyr Leu Val Gly Gly Arg Gln Thr Tyr Ala Leu Ser Ser Leu His Tyr
                195                 200                 205
Ala Ser Tyr Asp Pro Phe Phe Ile His His Ser Phe Val Asp Lys
                210                 215                 220
Met Trp Val Val Trp Gln Ala Leu Gln Lys Arg Lys Leu Pro Tyr
225                 230                 235                 240
Lys Arg Ala Asp Cys Ala Val Asn Leu Met Thr Lys Pro Met Arg Pro
                245                 250                 255
Phe Asp Ser Asp Met Asn Gln Asn Pro Phe Thr Lys Met His Ala Val
```

-continued

```
                260                 265                 270
Pro Asn Thr Leu Tyr Asp Tyr Glu Thr Leu Tyr Tyr Ser Tyr Asp Asn
            275                 280                 285

Leu Glu Ile Gly Gly Arg Asn Leu Asp Gln Leu Gln Ala Glu Ile Asp
        290                 295                 300

Arg Ser Arg Ser His Asp Arg Val Phe Ala Gly Phe Leu Leu Arg Gly
305                 310                 315                 320

Ile Gly Thr Ser Ala Asp Val Arg Phe Trp Ile Cys Arg Asn Glu Asn
                325                 330                 335

Asp Cys His Arg Gly Gly Ile Ile Phe Ile Leu Gly Gly Ala Lys Glu
            340                 345                 350

Met Pro Trp Ser Phe Asp Arg Asn Phe Lys Phe Asp Ile Thr His Val
        355                 360                 365

Leu Glu Lys Ala Gly Ile Ser Pro Glu Asp Val Phe Asp Ala Glu Glu
    370                 375                 380

Pro Phe Tyr Ile Lys Val Glu Ile His Ala Val Asn Lys Thr Met Ile
385                 390                 395                 400

Pro Ser Ser Val Ile Pro Ala Pro Thr Ile Ile Tyr Ser Pro Gly Glu
                405                 410                 415
```

<210> SEQ ID NO 208
<211> LENGTH: 402
<212> TYPE: PRT
<213> ORGANISM: Haliotis tuberculata

<400> SEQUENCE: 208

```
Gly Arg Ala Ala Asp Ser Ala His Ser Ala Asn Ile Ala Gly Ser Gly
1               5                   10                  15

Val Arg Lys Asp Val Thr Thr Leu Thr Val Ser Glu Thr Glu Asn Leu
            20                  25                  30

Arg Gln Ala Leu Gln Gly Val Ile Asp Asp Thr Gly Pro Asn Gly Tyr
        35                  40                  45

Gln Ala Ile Ala Ser Phe His Gly Ser Pro Pro Met Cys Glu Met Asn
    50                  55                  60

Gly Arg Lys Val Ala Cys Cys Ala His Gly Met Ala Ser Phe Pro His
65                  70                  75                  80

Trp His Arg Leu Tyr Val Lys Gln Met Glu Asp Ala Leu Ala Asp His
                85                  90                  95

Gly Ser His Ile Gly Ile Pro Tyr Trp Asp Trp Thr Thr Ala Phe Thr
            100                 105                 110

Glu Leu Pro Ala Leu Val Thr Asp Ser Glu Asn Asn Pro Phe His Glu
        115                 120                 125

Gly Arg Ile Asp His Leu Gly Val Thr Thr Ser Arg Ser Pro Arg Asp
    130                 135                 140

Met Leu Phe Asn Asp Pro Glu Gln Gly Ser Glu Ser Phe Phe Tyr Arg
145                 150                 155                 160

Gln Val Leu Leu Ala Leu Glu Gln Thr Asp Tyr Cys Gln Phe Glu Val
                165                 170                 175

Gln Phe Glu Leu Thr His Asn Ala Ile His Ser Trp Thr Gly Gly Arg
            180                 185                 190

Ser Pro Tyr Gly Met Ser Thr Leu Glu Phe Thr Ala Tyr Asp Pro Leu
        195                 200                 205

Phe Trp Leu His His Ser Asn Thr Asp Arg Ile Trp Ala Val Trp Gln
    210                 215                 220
```

```
Ala Leu Gln Lys Tyr Arg Gly Leu Pro Tyr Asn Glu Ala His Cys Glu
225                 230                 235                 240

Ile Gln Val Leu Lys Gln Pro Leu Arg Pro Phe Asn Asp Ile Asn
        245                 250                 255

His Asn Pro Ile Thr Lys Thr Asn Ala Arg Pro Ile Asp Ser Phe Asp
            260                 265                 270

Tyr Glu Arg Phe Asn Tyr Gln Tyr Asp Thr Leu Ser Phe His Gly Lys
        275                 280                 285

Ser Ile Pro Glu Leu Asn Asp Leu Leu Glu Glu Arg Lys Arg Glu Glu
        290                 295                 300

Arg Thr Phe Ala Ala Phe Leu Leu Arg Gly Ile Gly Cys Ser Ala Asp
305                 310                 315                 320

Val Val Phe Asp Ile Cys Arg Pro Asn Gly Asp Cys Val Phe Ala Gly
                325                 330                 335

Thr Phe Ala Val Leu Gly Gly Glu Leu Glu Met Pro Trp Ser Phe Asp
            340                 345                 350

Arg Leu Phe Arg Tyr Asp Ile Thr Arg Val Met Asn Gln Leu His Leu
        355                 360                 365

Gln Tyr Asp Ser Asp Phe Ser Phe Arg Val Lys Leu Val Ala Thr Asn
        370                 375                 380

Gly Thr Glu Leu Ser Ser Asp Leu Leu Lys Ser Pro Thr Ile Glu His
385                 390                 395                 400

Glu Leu

<210> SEQ ID NO 209
<211> LENGTH: 512
<212> TYPE: PRT
<213> ORGANISM: Haliotis tuberculata

<400> SEQUENCE: 209

Gly Ala His Arg Gly Pro Val Glu Glu Thr Glu Val Thr His Gln Asn
1               5                   10                  15

Thr Asp Gly Asn Ala His Phe His Arg Lys Glu Val Asp Ser Leu Ser
            20                  25                  30

Leu Asp Glu Ala Asn Asn Leu Lys Asn Ala Leu Tyr Lys Leu Gln Asn
        35                  40                  45

Asp His Ser Leu Thr Gly Tyr Glu Ala Ile Ser Gly Tyr His Gly Tyr
    50                  55                  60

Pro Asn Leu Cys Pro Glu Glu Gly Asp Lys Tyr Pro Cys Cys Val
65                  70                  75                  80

His Gly Met Ala Ile Phe Pro His Trp His Arg Leu Leu Thr Ile Gln
                85                  90                  95

Leu Glu Arg Ala Leu Glu His Asn Gly Ala Leu Leu Gly Val Pro Tyr
            100                 105                 110

Trp Asp Trp Thr Lys Asp Leu Ser Ser Leu Pro Ala Phe Phe Ser Asp
        115                 120                 125

Ser Ser Asn Asn Asn Pro Tyr Phe Lys Tyr His Ile Ala Gly Val Gly
    130                 135                 140

His Asp Thr Val Arg Glu Pro Thr Ser Leu Ile Tyr Asn Gln Pro Gln
145                 150                 155                 160

Ile His Gly Tyr Asp Tyr Leu Tyr Tyr Leu Ala Leu Thr Thr Leu Glu
                165                 170                 175

Glu Asn Asn Tyr Cys Asp Phe Gly Val Gln Tyr Glu Ile Leu His Asn
            180                 185                 190
```

Ala Val His Ser Trp Leu Gly Gly Ser Gln Lys Tyr Ser Met Ser Thr
        195                 200                 205

Leu Glu Tyr Ser Ala Phe Asp Pro Val Phe Met Ile Leu His Ser Gly
    210                 215                 220

Leu Asp Arg Leu Trp Ile Ile Trp Gln Glu Leu Gln Lys Ile Arg Arg
225                 230                 235                 240

Lys Pro Tyr Asn Phe Ala Lys Cys Ala Tyr His Met Met Glu Glu Pro
                245                 250                 255

Leu Ala Pro Phe Ser Tyr Pro Ser Ile Asn Gln Asp Glu Phe Thr Arg
            260                 265                 270

Ala Asn Ser Lys Pro Ser Thr Val Phe Asp Ser His Lys Phe Gly Tyr
        275                 280                 285

His Tyr Asp Asn Leu Asn Val Arg Gly His Ser Ile Gln Glu Leu Asn
    290                 295                 300

Thr Ile Ile Asn Asp Leu Arg Asn Thr Asp Arg Ile Tyr Ala Gly Phe
305                 310                 315                 320

Val Leu Ser Gly Ile Gly Thr Ser Ala Ser Val Lys Ile Tyr Leu Arg
                325                 330                 335

Thr Asp Asp Asn Asp Glu Glu Val Gly Thr Phe Thr Val Leu Gly Gly
            340                 345                 350

Glu Arg Glu Met Pro Trp Ala Tyr Glu Arg Val Phe Lys Tyr Asp Ile
        355                 360                 365

Thr Glu Val Ala Asp Arg Leu Lys Leu Ser Tyr Gly Asp Thr Phe Asn
    370                 375                 380

Phe Arg Leu Glu Ile Thr Ser Tyr Asp Gly Ser Val Val Asn Lys Ser
385                 390                 395                 400

Leu Pro Asn Pro Phe Ile Ile Tyr Arg Pro Ala Asn His Asp Tyr Asp
                405                 410                 415

Val Leu Val Ile Pro Val Gly Arg Asn Leu His Ile Pro Pro Lys Val
            420                 425                 430

Val Val Lys Arg Gly Thr Arg Ile Glu Phe His Pro Val Asp Asp Ser
        435                 440                 445

Val Thr Arg Pro Val Val Asp Leu Gly Ser Tyr Thr Ala Leu Phe Asn
    450                 455                 460

Cys Val Pro Pro Phe Thr Tyr Arg Gly Phe Glu Leu Asn His Val
465                 470                 475                 480

Tyr Ser Val Lys Pro Gly Asp Tyr Tyr Val Thr Gly Pro Thr Arg Asp
                485                 490                 495

Leu Cys Gln Asn Ala Asp Val Arg Ile His Ile His Val Glu Asp Glu
            500                 505                 510

<210> SEQ ID NO 210
<211> LENGTH: 967
<212> TYPE: DNA
<213> ORGANISM: Megathura crenulata

<400> SEQUENCE: 210
ggcctaccgt actgggactg gactgaaccc atgacacaca ttccgggtct ggcaggaaac      60
aaaacttatg tggattctca tggtgcatcc cacacaaatc cttttcatag ttcagtgatt     120
gcatttgaag aaaatgctcc ccacaccaaa agacaaatag atcaaagact ctttaaaccc     180
gctacctttg acaccacaca agacctgttc aaccagattt tgtatgcctt tgaacaagaa     240
gattactgtg actttgaagt ccaatttgag attacccata acacgattca cgcttggaca     300
ggaggaagcg aacatttctc aatgtcgtcc ctacattaca cagctttcga tcctttgttt     360

```
tactttcacc attctaacgt tgatcgtctt tgggccgttt ggcaagcctt acagatgaga    420
cggcataaac cctacagggc ccactgcgcc atatctctgg aacatatgca tctgaaacca    480 ttcgccttt catctcccct taacaataac gaaaagactc atgccaatgc catgccaaac    540
aagatctacg actatgaaaa tgtcctccat tacacatacg aagatttaac atttggaggc    600
atctctctgg aaaacataga aaagatgatc cacgaaaacc agcaagaaga cagaatatat    660
gccggttttc tcctggctgg catacgtact tcagcaaatg ttgatatctt cattaaaact    720
accgattccg tgcaacataa ggctggaaca tttgcagtgc tcggtggaag caaggaaatg    780
aagtggggat tgatcgcgt tttcaagttt gacatcacgc acgttttgaa agatctcgat    840
ctcactgctg atggcgattt cgaagttact gttgacatca ctgaagtcga tggaactaaa    900
cttgcatcca gtcttattcc acatgcttct gtcattcgtg agcatgcacg tggtaagctg    960
aatagag                                                               967

<210> SEQ ID NO 211
<211> LENGTH: 1242
<212> TYPE: DNA
<213> ORGANISM: Megathura crenulata

<400> SEQUENCE: 211
ttaaatttga caaagtgcca aggagtcgtc ttattcgaaa aaatgtagac cgtttgagcc     60
ccgaggagat gaatgaactt cgtaaagccc tagccttact gaaagaggac aaaagtgccg    120
gtggatttca gcagcttggt gcattccatg gggagccaaa atggtgtcct agtcccgaag    180
catctaaaaa atttgcctgc tgtgttcacg gcatgtctgt gttccctcac tggcatcgac    240
tgttgacggt tcagagtgaa aatgcttga gacgacatgg ctacgatgga gctttgccgt    300
actgggattg gacctctcct cttaatcacc ttcccgaact ggcagatcat gagaagtacg    360
tcgaccctga agatggggta gagaagcata acccttggtt cgatggtcat atagatacag    420
tcgacaaaac aacaacaaga agtgttcaga ataaactctt cgaacagcct gagtttggtc    480
attatacaag cattgccaaa caagtactgc tagcgttgga acaggacaat ttctgtgact    540
ttgaaatcca atatgagatt gcccataact acatccatgc acttgtagga ggcgctcagc    600
cttatggtat ggcatcgctt cgctacactg cttttgatcc actattctac ttgcatcact    660
ctaatacaga tcgtatatgg gcaatatggc aggctttaca gaagtacaga ggaaaaccgt    720
acaacgttgc taactgtgct gttacatcga tgagagaacc tttgcaacca tttggcctct    780
ctgccaatat caacacagac catgtaacca aggagcattc agtgccattc aacgttttg    840 attacaagac caatttcaat tatgaatatg acactttgga atttaacggt ctctcaatct    900
ctcagttgaa taaaagctc gaagcgataa agagccaaga caggttcttt gcaggcttcc    960
tgttatctgg tttcaagaaa tcatctcttg ttaaattcaa tatttgcacc gatagcagca   1020
actgtcaccc cgctggagag ttttaccttc tgggtgatga aaacgagatg ccatgggcat   1080
acgatagagt cttcaaatat gacataaccg aaaaactcca cgatctaaag ctgcatgcag   1140
aagaccactt ctacattgac tatgaagtat ttgacttaa accagcaagc ctgggaaaag   1200
atttgttcaa gcagccttca gtcattcatg aaccaagaat ag                      1242

<210> SEQ ID NO 212
<211> LENGTH: 1236
<212> TYPE: DNA
<213> ORGANISM: Megathura crenulata
```

<400> SEQUENCE: 212

```
gtcaccatga aggcgaagta tatcaagctg aagtaacttc tgccaaccgt attcgaaaaa    60
acattgaaaa tctgagcctt ggtgaactcg aaagtctgag agctgccttc ctggaaattg   120
aaaacgatgg aacttacgaa tcaatagcta aattccatgg tagccctggt ttgtgccagt   180
taaatggtaa ccccatctct tgttgtgtcc atggcatgcc aactttccct cactggcaca   240
gactgtacgt ggttgtcgtt gagaatgccc tcctgaaaaa aggatcatct gtagctgttc   300
cctattggga ctggacaaaa cgaatcgaac atttacctca cctgatttca gacgccactt   360
actacaattc caggcaacat cactatgaga caaacccatt ccatcatggc aaaatcacac   420
acgagaatga aatcactact agggatccca aggacagcct cttccattca gactactttt   480
acgagcaggt cctttacgcc ttggagcagg ataacttctg tgatttcgag attcagttgg   540
agatattaca caatgcattg cattctttac ttggtggcaa aggtaaatat tccatgtcaa   600
accttgatta cgctgctttt gatcctgtgt tcttccttca tcacgcaacg actgacagaa   660
tctgggcaat ctggcaagac cttcagaggt tccgaaaacg gccataccga aagcgaatt    720
gcgctatcca attgatgcac acgccactcc agccgtttga taagagcgac aacaatgacg   780
aggcaacgaa aacgcatgcc actccacatg atggttttga atatcaaaac agctttggtt   840
atgcttacga taatctggaa ctgaatcact actcgattcc tcagcttgat cacatgctgc   900
aagaaagaaa aaggcatgac agagtattcg ctggcttcct ccttcacaat attggaacat   960
ctgccgatgg ccatgtattt gtatgtctcc caactgggga acacacgaag gactgcagtc  1020
atgaggctgg tatgttctcc atcttaggcg gtcaaacgga gatgtccttt gtatttgaca  1080
gactttacaa acttgacata actaaagcct tgaaaaagaa cggtgtgcac ctgcaagggg  1140
atttcgatct ggaaattgag attacggctg tgaatggatc tcatctagac agtcatgtca  1200
tccactctcc cactatactg tttgaggccg aacag                             1236
```

<210> SEQ ID NO 213
<211> LENGTH: 1257
<212> TYPE: DNA
<213> ORGANISM: Megathura crenulata

<400> SEQUENCE: 213

```
attctgccca cacagatgat ggacacactg aaccagtgat gattcgcaaa gatatcacac    60
aattggacaa gcgtcaacaa ctgtcactgg tgaaagccct cgagtccatg aaagccgacc   120
attcatctga tgggttccag gcaatcgctt ccttccatgc tcttcctcct ctttgtccat   180
caccagctgc ttcaaagagg tttgcgtgct gcgtccatgg catggcaacg ttcccacaat   240
ggcaccgtct gtacacagtc caattccaag attctctcag aaaacatggt gcagtcgttg   300
gacttccgta ctgggactgg accctacctc gttctgaatt accagagctc ctgaccgtct   360
caactattca tgacccggag acaggcagag atataccaaa tccatttatt ggttctaaaa   420
tagagtttga aggagaaaac gtacatacta aagagatat caataggat cgtctcttcc   480
agggatcaac aaaaacacat cataactggt ttattgagca agcactgctt gctcttgaac   540
aaaccaacta ctgcgacttc gaggttcagt ttgaaattat gcataatggt gttcatacct   600
gggttggagg caaggagccc tatggaattg gccatctgca ttatgcttcc tatgatccac   660
ttttctacat ccatcactcc caaactgatc gtatttgggc tatatggcaa tcgttgcagc   720
gtttcagagg actttctgga tctgaggcta actgtgctgt aaatctcatg aaaactcctc   780
tgaagccttt cagctttgga gcaccatata atcttaatga tcacacgcat gatttctcaa   840
```

-continued

```
agcctgaaga tacattcgac taccaaaagt ttggatacat atatgacact ctggaatttg      900
cagggtggtc aattcgtggc attgaccata ttgtccgtaa caggcaggaa cattcaaggg      960
tctttgccgg attcttgctt gaaggatttg gcacctctgc cactgtcgat ttccaggtct     1020
gtcgcacagc gggagactgt gaagatgcag gtacttcac cgtgttggga ggtgaaaaag     1080
aaatgccttg ggcctttgat cggctttaca agtacgacaa aacagaaacc ttagacaaga     1140
tgaaccttcg acatgacgaa atcttccaga ttgaagtaac cattacatcc tacgatggaa     1200
ctgtactcga tagtggcctt attcccacac cgtcaatcat ctatgatcct gctcatc       1257
```

<210> SEQ ID NO 214
<211> LENGTH: 191
<212> TYPE: DNA
<213> ORGANISM: Megathura crenulata

<400> SEQUENCE: 214

```
atgatattag ttcgcaccac ctgtcgctca acaaggttcg tcatgatctg agtacactga       60
gtgagcgaga tattggaagc cttaaatatg ctttgagcag cttgcaggca gatacctcag      120
cagatggttt tgctgccatt gcatccttcc atggtctgcc tgccaaatgt aatgacagcc      180
acaataacga g                                                          191
```

<210> SEQ ID NO 215
<211> LENGTH: 1063
<212> TYPE: DNA
<213> ORGANISM: Megathura crenulata

<400> SEQUENCE: 215

```
gtggcatgct gtatccatgg aatgcctaca ttccccccact ggcacagact ctacaccctc       60
caatttgagc aagctctaag aagacatggc tctagtgtag cagtacccta ctgggactgg      120
acaaagccaa tacataatat tccacatctg ttcacagaca agaatactca cgatgtctgg      180
agaaataaag taatgccaaa tccatttgcc cgagggtatg tcccctcaca cgatacatac      240
acggtaagag acgtccaaga aggcctgttc cacctgacat caacgggtga acactcagcg      300
cttctgaatc aagctctttt ggcgctggaa cagcacgact actgcgattt tgcagtccag      360
tttgaagtca tgcacaacac aatccattac ctagtgggag gacctcaagt ctattctttg      420
tcatcccttc attatgcttc atatgatccg atcttcttca tacaccactc cttttgtagac      480 aaggtttggg ctgtctggca ggctcttcaa gaaaagagag gccttccatc agaccgtgct      540
gactgcgctg ttagtctgat gactcagaac atgaggcctt tccattacga aattaaccat      600
aaccagttca ccaagaaaca tgcagttcca atgatgtttt tcaagtacga actcctgggt      660
tacagatacg acaatctgga atcggtggc atgaatttgc atgaaattga aaaggaaatc      720
aaagacaaac agcaccatgt gagagtgttt gcagggttcc tccttcacgg aattagaacc      780
tcagctgatg tccaattcca gatttgtaaa acatcagaag attgtcacca tggaggccaa      840
atcttcgttc ttgggggggac taaagagatg gcctgggctt ataaccgttt attcaagtac      900
gatattaccc atgctcttca tgacgcacac atcactccag aagacgtatt ccatccctct      960
gaaccattct tcatcaaggt gtcagtgaca gccgtcaacg gaacagttct tccggcttca     1020
atcctgcatg caccaaccat tatctatgaa cctggtctcg gtg                       1063
```

<210> SEQ ID NO 216
<211> LENGTH: 219
<212> TYPE: DNA

<213> ORGANISM: Megathura crenulata

<400> SEQUENCE: 216

```
accatcacga agatcatcat tcttcttcta tggctggaca tggtgtcaga aaggaaatca      60
acacacttac cactgcagag gtggacaatc tcaaagatgc catgagagcc gtcatggcag     120
accacggtcc aaatggatac caggctatag cagcgttcca tggaaaccca ccaatgtgcc     180
ctatgccaga tggaaagaat tactcgtgtt gtacacatg                            219
```

<210> SEQ ID NO 217
<211> LENGTH: 164
<212> TYPE: DNA
<213> ORGANISM: Megathura crenulata

<400> SEQUENCE: 217

```
gcatggctac tttcccccac tggcacagac tgtacacaaa acagatggaa gatgccttga      60
ccgcccatgg tgccagagtc ggccttcctt actgggacgg gacaactgcc tttacagctt     120
tgccaacttt tgtcacagat gaagaggaca tcctttcca tcat                       164
```

<210> SEQ ID NO 218
<211> LENGTH: 126
<212> TYPE: DNA
<213> ORGANISM: Megathura crenulata

<400> SEQUENCE: 218

```
ggtcacatag actatttggg agtggataca actcggtcgc cccgagacaa gttgttcaat      60
gatccagagc gaggatcaga atcgttcttc tacaggcagg ttctcttggc tttggagcag     120
acagat                                                                126
```

<210> SEQ ID NO 219
<211> LENGTH: 322
<212> TYPE: PRT
<213> ORGANISM: Megathura crenulata

<400> SEQUENCE: 219

```
Gly Leu Pro Tyr Trp Asp Trp Thr Glu Pro Met Thr His Ile Pro Gly
1               5                   10                  15

Leu Ala Gly Asn Lys Thr Tyr Val Asp Ser His Gly Ala Ser His Thr
            20                  25                  30

Asn Pro Phe His Ser Ser Val Ile Ala Phe Glu Glu Asn Ala Pro His
        35                  40                  45

Thr Lys Arg Gln Ile Asp Gln Arg Leu Phe Lys Pro Ala Thr Phe Gly
    50                  55                  60

His His Thr Asp Leu Phe Asn Gln Ile Leu Tyr Ala Phe Glu Gln Glu
65                  70                  75                  80

Asp Tyr Cys Asp Phe Glu Val Gln Phe Glu Ile Thr His Asn Thr Ile
                85                  90                  95

His Ala Trp Thr Gly Gly Ser Glu His Phe Ser Met Ser Ser Leu His
            100                 105                 110

Tyr Thr Ala Phe Asp Pro Leu Phe Tyr Phe His His Ser Asn Val Asp
        115                 120                 125

Arg Leu Trp Ala Val Trp Gln Ala Leu Gln Met Arg Arg His Lys Pro
    130                 135                 140

Tyr Arg Ala His Cys Ala Ile Ser Leu Glu His Met His Leu Lys Pro
145                 150                 155                 160

Phe Ala Phe Ser Ser Pro Leu Asn Asn Asn Glu Lys Thr His Ala Asn
```

```
                    165                 170                 175
Ala Met Pro Asn Lys Ile Tyr Asp Tyr Glu Asn Val Leu His Tyr Thr
        180                 185                 190

Tyr Glu Asp Leu Thr Phe Gly Gly Ile Ser Leu Glu Asn Ile Glu Lys
            195                 200                 205

Met Ile His Glu Asn Gln Gln Glu Asp Arg Ile Tyr Ala Gly Phe Leu
    210                 215                 220

Leu Ala Gly Ile Arg Thr Ser Ala Asn Val Asp Ile Phe Ile Lys Thr
225                 230                 235                 240

Thr Asp Ser Val Gln His Lys Ala Gly Thr Phe Ala Val Leu Gly Gly
                245                 250                 255

Ser Lys Glu Met Lys Trp Gly Phe Asp Arg Val Phe Lys Phe Asp Ile
            260                 265                 270

Thr His Val Leu Lys Asp Leu Asp Leu Thr Ala Asp Gly Asp Phe Glu
        275                 280                 285

Val Thr Val Asp Ile Thr Glu Val Asp Gly Thr Lys Leu Ala Ser Ser
    290                 295                 300

Leu Ile Pro His Ala Ser Val Ile Arg Glu His Ala Arg Gly Lys Leu
305                 310                 315                 320

Asn Arg

<210> SEQ ID NO 220
<211> LENGTH: 414
<212> TYPE: PRT
<213> ORGANISM: Megathura crenulata

<400> SEQUENCE: 220

Val Lys Phe Asp Lys Val Pro Arg Ser Arg Leu Ile Arg Lys Asn Val
1               5                   10                  15

Asp Arg Leu Ser Pro Glu Glu Met Asn Glu Leu Arg Lys Ala Leu Ala
            20                  25                  30

Leu Leu Lys Glu Asp Lys Ser Ala Gly Gly Phe Gln Gln Leu Gly Ala
        35                  40                  45

Phe His Gly Glu Pro Lys Trp Cys Pro Ser Pro Glu Ala Ser Lys Lys
    50                  55                  60

Phe Ala Cys Cys Val His Gly Met Ser Val Phe Pro His Trp His Arg
65                  70                  75                  80

Leu Leu Thr Val Gln Ser Glu Asn Ala Leu Arg Arg His Gly Tyr Asp
                85                  90                  95

Gly Ala Leu Pro Tyr Trp Asp Trp Thr Ser Pro Leu Asn His Leu Pro
            100                 105                 110

Glu Leu Ala Asp His Glu Lys Tyr Val Asp Pro Glu Asp Gly Val Glu
        115                 120                 125

Lys His Asn Pro Trp Phe Asp Gly His Ile Asp Thr Val Asp Lys Thr
    130                 135                 140

Thr Thr Arg Ser Val Gln Asn Lys Leu Phe Glu Gln Pro Glu Phe Gly
145                 150                 155                 160

His Tyr Thr Ser Ile Ala Lys Gln Val Leu Ala Leu Glu Gln Asp
                165                 170                 175

Asn Phe Cys Asp Phe Glu Ile Gln Tyr Glu Ile Ala His Asn Tyr Ile
            180                 185                 190

His Ala Leu Val Gly Gly Ala Gln Pro Tyr Gly Met Ala Ser Leu Arg
        195                 200                 205

Tyr Thr Ala Phe Asp Pro Leu Phe Tyr Leu His His Ser Asn Thr Asp
```

```
                210                 215                 220
Arg Ile Trp Ala Ile Trp Gln Ala Leu Gln Lys Tyr Arg Gly Lys Pro
225                 230                 235                 240

Tyr Asn Val Ala Asn Cys Ala Val Thr Ser Met Arg Glu Pro Leu Gln
                245                 250                 255

Pro Phe Gly Leu Ser Ala Asn Ile Asn Thr Asp His Val Thr Lys Glu
                260                 265                 270

His Ser Val Pro Phe Asn Val Phe Asp Tyr Lys Thr Asn Phe Asn Tyr
                275                 280                 285

Glu Tyr Asp Thr Leu Glu Phe Asn Gly Leu Ser Ile Ser Gln Leu Asn
            290                 295                 300

Lys Lys Leu Glu Ala Ile Lys Ser Gln Asp Arg Phe Ala Gly Phe
305                 310                 315                 320

Leu Leu Ser Gly Phe Lys Lys Ser Ser Leu Val Lys Phe Asn Ile Cys
                325                 330                 335

Thr Asp Ser Ser Asn Cys His Pro Ala Gly Glu Phe Tyr Leu Leu Gly
                340                 345                 350

Asp Glu Asn Glu Met Pro Trp Ala Tyr Asp Arg Val Phe Lys Tyr Asp
                355                 360                 365

Ile Thr Glu Lys Leu His Asp Leu Lys Leu His Ala Glu Asp His Phe
            370                 375                 380

Tyr Ile Asp Tyr Glu Val Phe Asp Leu Lys Pro Ala Ser Leu Gly Lys
385                 390                 395                 400

Asp Leu Phe Lys Gln Pro Ser Val Ile His Glu Pro Arg Ile
                405                 410

<210> SEQ ID NO 221
<211> LENGTH: 411
<212> TYPE: PRT
<213> ORGANISM: Megathura crenulata

<400> SEQUENCE: 221

Gly His His Glu Gly Glu Val Tyr Gln Ala Glu Val Thr Ser Ala Asn
1               5                   10                  15

Arg Ile Arg Lys Asn Ile Glu Asn Leu Ser Leu Gly Glu Leu Glu Ser
                20                  25                  30

Leu Arg Ala Ala Phe Leu Glu Ile Glu Asn Asp Gly Thr Tyr Glu Ser
            35                  40                  45

Ile Ala Lys Phe His Gly Ser Pro Gly Leu Cys Gln Leu Asn Gly Asn
        50                  55                  60

Pro Ile Ser Cys Cys Val His Gly Met Pro Thr Phe Pro His Trp His
65                  70                  75                  80

Arg Leu Tyr Val Val Val Glu Asn Ala Leu Leu Lys Lys Gly Ser
                85                  90                  95

Ser Val Ala Val Pro Tyr Trp Asp Trp Thr Lys Arg Ile Glu His Leu
                100                 105                 110

Pro His Leu Ile Ser Asp Ala Thr Tyr Tyr Asn Ser Arg Gln His His
            115                 120                 125

Tyr Glu Thr Asn Pro Phe His His Gly Lys Ile Thr His Glu Asn Glu
        130                 135                 140

Ile Thr Thr Arg Asp Pro Lys Asp Ser Leu Phe His Ser Asp Tyr Phe
145                 150                 155                 160

Tyr Glu Gln Val Leu Tyr Ala Leu Glu Gln Asp Asn Phe Cys Asp Phe
                165                 170                 175
```

```
Glu Ile Gln Leu Glu Ile Leu His Asn Ala Leu His Ser Leu Leu Gly
            180                 185                 190
Gly Lys Gly Lys Tyr Ser Met Ser Asn Leu Asp Tyr Ala Ala Phe Asp
        195                 200                 205
Pro Val Phe Phe Leu His His Ala Thr Thr Asp Arg Ile Trp Ala Ile
    210                 215                 220
Trp Gln Asp Leu Gln Arg Phe Arg Lys Arg Pro Tyr Arg Glu Ala Asn
225                 230                 235                 240
Cys Ala Ile Gln Leu Met His Thr Pro Leu Gln Pro Phe Asp Lys Ser
                245                 250                 255
Asp Asn Asn Asp Glu Ala Thr Lys Thr His Ala Thr Pro His Asp Gly
            260                 265                 270
Phe Glu Tyr Gln Asn Ser Phe Gly Tyr Ala Tyr Asp Asn Leu Glu Leu
        275                 280                 285
Asn His Tyr Ser Ile Pro Gln Leu Asp His Met Leu Gln Glu Arg Lys
    290                 295                 300
Arg His Asp Arg Val Phe Ala Gly Phe Leu Leu His Asn Ile Gly Thr
305                 310                 315                 320
Ser Ala Asp Gly His Val Phe Val Cys Leu Pro Thr Gly Glu His Thr
                325                 330                 335
Lys Asp Cys Ser His Glu Ala Gly Met Phe Ser Ile Leu Gly Gly Gln
            340                 345                 350
Thr Glu Met Ser Phe Val Phe Asp Arg Leu Tyr Lys Leu Asp Ile Thr
        355                 360                 365
Lys Ala Leu Lys Lys Asn Gly Val His Leu Gln Gly Asp Phe Asp Leu
    370                 375                 380
Glu Ile Glu Ile Thr Ala Val Asn Gly Ser His Leu Asp Ser His Val
385                 390                 395                 400
Ile His Ser Pro Thr Ile Leu Phe Glu Ala Gly
                405                 410

<210> SEQ ID NO 222
<211> LENGTH: 420
<212> TYPE: PRT
<213> ORGANISM: Megathura crenulata

<400> SEQUENCE: 222

Thr Asp Ser Ala His Thr Asp Asp Gly His Thr Glu Pro Val Met Ile
1               5                   10                  15
Arg Lys Asp Ile Thr Gln Leu Asp Lys Arg Gln Gln Leu Ser Leu Val
            20                  25                  30
Lys Ala Leu Glu Ser Met Lys Ala Asp His Ser Ser Asp Gly Phe Gln
        35                  40                  45
Ala Ile Ala Ser Phe His Ala Leu Pro Pro Leu Cys Pro Ser Pro Ala
    50                  55                  60
Ala Ser Lys Arg Phe Ala Cys Cys Val His Gly Met Ala Thr Phe Pro
65                  70                  75                  80
Gln Trp His Arg Leu Tyr Thr Val Gln Phe Gln Asp Ser Leu Arg Lys
                85                  90                  95
His Gly Ala Val Val Gly Leu Pro Tyr Trp Asp Trp Thr Leu Pro Arg
            100                 105                 110
Ser Glu Leu Pro Glu Leu Leu Thr Val Ser Thr Ile His Asp Pro Glu
        115                 120                 125
Thr Gly Arg Asp Ile Pro Asn Pro Phe Ile Gly Ser Lys Ile Glu Phe
    130                 135                 140
```

```
Glu Gly Glu Asn Val His Thr Lys Arg Asp Ile Asn Arg Asp Arg Leu
145                 150                 155                 160

Phe Gln Gly Ser Thr Lys Thr His His Asn Trp Phe Ile Glu Gln Ala
            165                 170                 175

Leu Leu Ala Leu Glu Gln Thr Asn Tyr Cys Asp Phe Glu Val Gln Phe
            180                 185                 190

Glu Ile Met His Asn Gly Val His Thr Trp Val Gly Gly Lys Glu Pro
            195                 200                 205

Tyr Gly Ile Gly His Leu His Tyr Ala Ser Tyr Asp Pro Leu Phe Tyr
            210                 215                 220

Ile His His Ser Gln Thr Asp Arg Ile Trp Ala Ile Trp Gln Ser Leu
225                 230                 235                 240

Gln Arg Phe Arg Gly Leu Ser Gly Ser Glu Ala Asn Cys Ala Val Asn
            245                 250                 255

Leu Met Lys Thr Pro Leu Lys Pro Phe Ser Phe Gly Ala Pro Tyr Asn
            260                 265                 270

Leu Asn Asp His Thr His Asp Phe Ser Lys Pro Glu Asp Thr Phe Asp
            275                 280                 285

Tyr Gln Lys Phe Gly Tyr Ile Tyr Asp Thr Leu Glu Phe Ala Gly Trp
            290                 295                 300

Ser Ile Arg Gly Ile Asp His Ile Val Arg Asn Arg Gln Glu His Ser
305                 310                 315                 320

Arg Val Phe Ala Gly Phe Leu Leu Glu Gly Phe Gly Thr Ser Ala Thr
            325                 330                 335

Val Asp Phe Gln Val Cys Arg Thr Ala Gly Asp Cys Glu Asp Ala Gly
            340                 345                 350

Tyr Phe Thr Val Leu Gly Gly Glu Lys Glu Met Pro Trp Ala Phe Asp
            355                 360                 365

Arg Leu Tyr Lys Tyr Asp Ile Thr Glu Thr Leu Asp Lys Met Asn Leu
            370                 375                 380

Arg His Asp Glu Ile Phe Gln Ile Glu Val Thr Ile Thr Ser Tyr Asp
385                 390                 395                 400

Gly Thr Val Leu Asp Ser Gly Leu Ile Pro Thr Pro Ser Ile Ile Tyr
            405                 410                 415

Asp Pro Ala His
            420

<210> SEQ ID NO 223
<211> LENGTH: 418
<212> TYPE: PRT
<213> ORGANISM: Megathura crenulata

<400> SEQUENCE: 223

His Asp Ile Ser Ser His His Leu Ser Leu Asn Lys Val Arg His Asp
1               5                   10                  15

Leu Ser Thr Leu Ser Glu Arg Asp Ile Gly Ser Leu Lys Tyr Ala Leu
            20                  25                  30

Ser Ser Leu Gln Ala Asp Thr Ser Ala Asp Gly Phe Ala Ala Ile Ala
            35                  40                  45

Ser Phe His Gly Leu Pro Ala Lys Cys Asn Asp Ser His Asn Asn Glu
            50                  55                  60

Val Ala Cys Cys Ile His Gly Met Pro Thr Phe Pro His Trp His Arg
65                  70                  75                  80

Leu Tyr Thr Leu Gln Phe Glu Gln Ala Leu Arg Arg His Gly Ser Ser
```

-continued

```
                    85                  90                  95
Val Ala Val Pro Tyr Trp Asp Trp Thr Lys Pro Ile His Asn Ile Pro
                100                 105                 110

His Leu Phe Thr Asp Lys Glu Tyr Tyr Asp Val Trp Arg Asn Lys Val
            115                 120                 125

Met Pro Asn Pro Phe Ala Arg Gly Tyr Val Pro Ser His Asp Thr Tyr
        130                 135                 140

Thr Val Arg Asp Val Gln Glu Gly Leu Phe His Leu Thr Ser Thr Gly
145                 150                 155                 160

Glu His Ser Ala Leu Leu Asn Gln Ala Leu Leu Ala Leu Glu Gln His
                165                 170                 175

Asp Tyr Cys Asp Phe Ala Val Gln Phe Glu Val Met His Asn Thr Ile
            180                 185                 190

His Tyr Leu Val Gly Gly Pro Gln Val Tyr Ser Leu Ser Ser Leu His
        195                 200                 205

Tyr Ala Ser Tyr Asp Pro Ile Phe Phe Ile His His Ser Phe Val Asp
    210                 215                 220

Lys Val Trp Ala Val Trp Gln Ala Leu Gln Glu Lys Arg Gly Leu Pro
225                 230                 235                 240

Ser Asp Arg Ala Asp Cys Ala Val Ser Leu Met Thr Gln Asn Met Arg
                245                 250                 255

Pro Phe His Tyr Glu Ile Asn His Asn Gln Phe Thr Lys Lys His Ala
            260                 265                 270

Val Pro Asn Asp Val Phe Lys Tyr Glu Leu Leu Gly Tyr Arg Tyr Asp
        275                 280                 285

Asn Leu Glu Ile Gly Gly Met Asn Leu His Glu Ile Glu Lys Glu Ile
    290                 295                 300

Lys Asp Lys Gln His His Val Arg Val Phe Ala Gly Phe Leu Leu His
305                 310                 315                 320

Gly Ile Arg Thr Ser Ala Asp Val Gln Phe Gln Ile Cys Lys Thr Ser
                325                 330                 335

Glu Asp Cys His His Gly Gly Gln Ile Phe Val Leu Gly Gly Thr Lys
            340                 345                 350

Glu Met Ala Trp Ala Tyr Asn Arg Leu Phe Lys Tyr Asp Ile Thr His
        355                 360                 365

Ala Leu His Asp Ala His Ile Thr Pro Glu Asp Val Phe His Pro Ser
    370                 375                 380

Glu Pro Phe Phe Ile Lys Val Ser Val Thr Ala Val Asn Gly Thr Val
385                 390                 395                 400

Leu Pro Ala Ser Ile Leu His Ala Pro Thr Ile Ile Tyr Glu Pro Gly
                405                 410                 415

Leu Gly
```

<210> SEQ ID NO 224
<211> LENGTH: 170
<212> TYPE: PRT
<213> ORGANISM: Megathura crenulata

<400> SEQUENCE: 224

```
Asp His His Glu Asp His His Ser Ser Ser Met Ala Gly His Gly Val
1               5                   10                  15

Arg Lys Glu Ile Asn Thr Leu Thr Thr Ala Glu Val Asp Asn Leu Lys
            20                  25                  30

Asp Ala Met Arg Ala Val Met Ala Asp His Gly Pro Asn Gly Tyr Gln
```

```
                35                  40                  45
Ala Ile Ala Ala Phe His Gly Asn Pro Pro Met Cys Pro Met Pro Asp
 50                  55                  60

Gly Lys Asn Tyr Ser Cys Cys Thr His Gly Met Ala Thr Phe Pro His
 65                  70                  75                  80

Trp His Arg Leu Tyr Thr Lys Gln Met Glu Asp Ala Leu Thr Ala His
                 85                  90                  95

Gly Ala Arg Val Gly Leu Pro Tyr Trp Asp Gly Thr Thr Ala Phe Thr
                100                 105                 110

Ala Leu Pro Thr Phe Val Thr Asp Glu Glu Asp Asn Pro Phe His His
                115                 120                 125

Gly His Ile Asp Tyr Leu Gly Val Asp Thr Thr Arg Ser Pro Arg Asp
130                 135                 140

Lys Leu Phe Asn Asp Pro Glu Arg Gly Ser Glu Ser Phe Phe Tyr Arg
145                 150                 155                 160

Gln Val Leu Leu Ala Leu Glu Gln Thr Asp
                165                 170
```

<210> SEQ ID NO 225
<211> LENGTH: 949
<212> TYPE: DNA
<213> ORGANISM: Megathura crenulata

<400> SEQUENCE: 225

```
ggcctgccct actgggattg gaccatgcca atgagtcatt tgccagaact ggctacaagt     60
gagacctacc tcgatccagt tactggggaa actaaaaaca ccctttcca tcacgcccaa    120
gtggcgtttg aaaatggtgt aacaagcagg aatcctgatg ccaaactttt tatgaaacca    180
acttacggag accacactta cctcttcgac agcatgatct acgcatttga gcaggaagac    240
ttctgcgact ttgaagtcca atatgagctc acgcataatg caatacatgc atgggttgga    300
ggcagtgaaa agtattcaat gtcttctctt cactacactg cttttgatcc tatattttac    360
ctccatcact caaatgttga tcgtctctgg gccatttggc aagctcttca aatcaggaga    420
ggcaagtctt acaaggccca ctgcgcctcg tctcaagaaa gagaaccatt aaagcctttt    480
gcattcagtt ccccactgaa caacaacgag aaaacgtacc acaactctgt ccccactaac    540
gtttatgact atgtgggagt tttgcactat cgatatgatg accttcagtt tggcggtatg    600
accatgtcag aacttgagga atatattcac aagcagacac aacatgatag aaccttttgca   660
ggattcttcc tttcatatat tggaacatca gcaagcgtag atatcttcat caatcgagaa    720
ggtcatgata atacaaagt gggaagtttt gtagtacttg gtggatccaa agaaatgaaa     780
tggggctttg atagaatgta caagtatgag atcactgagg ctctgaagac gctgaatgtt    840
gcagtggatg atgggttcag cattactgtt gagatcaccg atgttgatgg atctccccca    900
tctgcagatc tcattccacc tcctgctata atctttgacg tggtcagag                949
```

<210> SEQ ID NO 226
<211> LENGTH: 1248
<212> TYPE: DNA
<213> ORGANISM: Megathura crenulata

<400> SEQUENCE: 226

```
ctgatgccaa agactttggc catagcagaa aaatcaggaa agccgttgat tctctgacag     60
tcgaagaaca aacttcgttg aggcgagcta tggcagatct acaggacgac aaaacatcag    120
gggggtttcca gcagattgca gcattccacg gagaaccaaa atggtgtcca gcccccgaag   180
```

```
cggagaaaaa atttgcatgc tgtgttcatg aatggctgt tttccctcac tggcacagat      240
tgctgacagt tcaaggagaa atgctctga ggaaacatgg atttactggt ggattgccct      300
attgggactg gactcggcca atgagcgccc ttccacattt tgttgctgat cctacttaca      360
atgattctgt ttccagcctc gaagaagata acccatggta tcatggtcac atagattctg      420
ttgggcatga tactacaaga gctgtgcgtg atgatcttta tcaatctcct ggtttcggtc      480
actacacaga tattgcaaaa caagtccttc tggcctttga gcaggacgat ttctgtgatt      540
ttgaggtaca atttgaaatt gcccataatt tcatacatgc tctggttggt ggtaacgaac      600
catacagtat gtcatctttg aggtatacta catacgatcc aatcttcttc ttgcaccgct      660
ccaatacaga ccgactttgg gccatttggc aagctttgca aaataccgg gggaaaccat      720 acaacactgc aaactgtgcc attgcatcca tgagaaaacc acttcagcca tttggtcttg      780
atagtgtcat aaatccagat gacgaaactc gtgaacattc ggttcctttc cgagtcttcg      840
actacaagaa caacttcgac tatgagtatg agagcctggc atttaatggt ctgtctattg      900
cccaactgga ccgagagttg cagagaagaa agtcacatga cagagtcttt gcaggattcc      960
ttcttcatga aattggacag tctgcactcg tgaaattcta cgtttgcaaa cacaatgtat     1020
ctgactgtga ccattatgct ggagaattct acatttttggg agatgaagct gagatgcctt     1080
ggaggtatga ccgtgtgtac aagtacgaga taacacagca gctgcacgat ttagatctac     1140
atgttggaga taatttcttc cttaaatatg aagcctttga tctgaatggc ggaagtcttg     1200
gtggaagtat ctttttctcag ccttcggtga ttttcgagcc agctgcag               1248

<210> SEQ ID NO 227
<211> LENGTH: 1257
<212> TYPE: DNA
<213> ORGANISM: Megathura crenulata

<400> SEQUENCE: 227
gttcacacca ggctgatgaa tatcgtgagg cagtaacaag cgctagccac ataagaaaaa       60
atatccggga cctctcagag ggagaaattg agagcatcga atctgctttc ctccaaattc      120 aaaagaggg tatatatgaa acattgcaa agttccatgg aaaaccagga ctttgtgaac      180
atgatggaca tcctgttgct tgttgtgtcc atggcatgcc cacctttccc cactggcaca      240
gactgtacgt tcttcaggtg gagaatgcgc tcttagaacg agggtctgca gttgctgttc      300
cttactggga ctggaccgag aaagctgact ctctgccatc attaatcaat gatgcaactt      360
atttcaattc acgatcccag accttggatc ctaatccttt cttcagggga catattgcct      420
tcgagaatgc tgtgacgtcc agagatcctc agccagaact atgggacaat aaggacttct      480
acgagaatgt catgctggct cttgagcaag acaacttctg tgactttgag attcagcttg      540
agctgataca caacgccctt cattctagac ttggaggaag gctaaatac tcccttttcgt      600 ctcttgatta taccgcattt gatcctgtat ttttccttca ccatgcaaac gttgacagaa      660
tctgggccat ctggcaggac ttgcagagat atagaaagaa accatacaat gaggctgact      720
gcgcagtcaa cgagatgcgt aaacctcttc aaccatttaa taacccagaa cttaacagtg      780
attccatgac gcttaaacac aacctcccac aagacagttt tgattatcaa aaccgcttca      840
ggtaccaata tgataacctt caatttaacc acttcagcat acaaaagcta gaccaaacta      900
ttcaggctag aaaacaacac gacagagttt tgctggctt tattcttcac aacattggga      960
catctgctgt tgtagatatt tatatttgcg ttgaacaagg aggagaacaa aactgcaaga     1020
```

```
caaaggcggg ttccttcacg attctggggg gagaaacaga aatgccattc cactttgacc    1080
gcttgtacaa atttgacata acgtctgctc tgcataaact tggtgttccc ttggacggac    1140
atggattcga catcaaagtt gacgtcagag ctgtcaatgg atcgcatctt gatcaacaca    1200
tcctcaacga accgagtctg cttttgttc ctggtgaacg taagaatata tattatg       1257
```

<210> SEQ ID NO 228
<211> LENGTH: 1239
<212> TYPE: DNA
<213> ORGANISM: Megathura crenulata

<400> SEQUENCE: 228

```
atgggctttc acaacataat cttgtgcgaa aagaagtaag ctctcttaca acactggaga     60
aacatttttt gaggaaagct ctcaagaaca tgcaagcaga tgattctcca gacggatatc    120
aagctattgc ttctttccac gctttgcctc tctttgtcc aagtccatct gctgcacata    180
gacacgcttg ttgcctccat ggtatggcta ccttccctca gtggcacaga ctctacacag    240
ttcagttcga agattctttg aaacgacatg gttctattgt cggacttcca tattgggatt    300
ggctgaaacc gcagtctgca ctccctgatt tggtgacaca ggagacatac gagcacctgt    360
tttcacacaa aaccttccca aatccgttcc tcaaggcaaa tatagaattt gagggagagg    420
gagtaacaac agagagggat gttgatgctg aacacctctt tgcaaaagga aatctggttt    480
acaacaactg gttttgcaat caggcactat atgcactaga acaagaaaat tactgtgact    540
ttgaaataca gttcgaaatt ttgcataatg gaattcattc atgggttgga ggatcaaaga    600
cccattcaat aggtcatctt cattacgcat catacgatcc actgttctat atccaccatt    660
cgcagacaga tcgcatttgg gctatctggc aagctctcca ggagcacaga ggtctttcag    720
ggaaggaagc acactgcgcc ctggagcaaa tgaaagaccc tctcaaacct ttcagctttg    780
gaagtcccta taatttgaac aaacgcactc aagagttctc caagcctgaa gacacatttg    840
attatcaccg attcgggtat gagtatgatt ccctcgaatt tgttggcatg tctgtttcaa    900
gtttacataa ctatataaaa caacaacagg aagctgatag agtcttcgca ggattccttc    960
ttaaaggatt tggacaatca gcatccgtat cgtttgatat ctgcagacca gaccagagtt   1020
gccaagaagc tggatacttc tcagttctcg gtggaagttc agaaatgccg tggcagtttg   1080
acaggcttta caagtacgac attacaaaaa cgttgaaaga catgaaactg cgatacgatg   1140
acacatttac catcaaggtt cacataaagg atatagctgg agctgagttg gacagcgatc   1200
tgattccaac tccttctgtt ctccttgaag aaggaaagc                         1239
```

<210> SEQ ID NO 229
<211> LENGTH: 191
<212> TYPE: DNA
<213> ORGANISM: Megathura crenulata

<400> SEQUENCE: 229

```
atgggatcaa tgtacgtcac gttggtcgta atcggattcg tatggaacta tctgaactca     60
ccgagagaga tctcgccagc ctgaaatctg caatgaggtc tctacaagct gacgatgggg    120
tgaacggtta tcaagccatt gcatcattcc acggtctccc ggcttcttgt catgatgatg    180
agggacatga g                                                        191
```

<210> SEQ ID NO 230
<211> LENGTH: 1060
<212> TYPE: DNA
<213> ORGANISM: Megathura crenulata

```
<400> SEQUENCE: 230
attgcctgtt gtatccacgg aatgccagta ttcccacact ggcacaggct ttacaccctg    60
caaatggaca tggctctgtt atctcacgga tctgctgttg ctattccata ctgggactgg   120
accaaaccta tcagcaaact gcctgatctc ttcaccagcc ctgaatatta cgatccttgg   180
agggatgcag ttgtcaataa tccatttgct aaaggctaca ttaaatccga ggacgcttac   240
acggttaggg atcctcagga catttttgtac acttgcagg acgaaacggg aacatctgtt    300
ttgttagatc aaactctttt agccttagag cagacagatt tctgtgattt tgaggttcaa   360
tttgaggtcg tccataatgc tattcactac ttggtgggtg gtcgacaagt ttatgctctt   420
tcttctcaac actatgcttc atatgaccca gccttcttta ttcatcactc ctttgttgac   480
aaaatatggg cagtctggca agctctgcaa aagaagagaa agcgtcccta tcataaagcg   540
gattgtgctc ttaacatgat gaccaaacca atgcgaccat ttgcacacga tttcaatcac   600
aatggattca caaaaatgca cgcagtcccc aacactctat ttgactttca ggaccttttc   660
tacacgtatg acaacttaga aattgctggc atgaatgtta atcagttgga agcggaaatc   720
aaccggcgaa aaagccaaac aagagtcttt gccgggttcc ttctacatgg cattggaaga   780
tcagctgatg tacgattttg gatttgcaag acagctgacg actgccacgc atctggcatg   840
atctttatct taggaggttc taaagagatg cactgggcct atgacaggaa ctttaaatac   900
gacatcaccc aagctttgaa ggctcagtcc atacaccctg aagatgtgtt tgacactgat   960
gctcctttct tcattaaagt ggaggtccat ggtgtaaaca agactgctct cccatcttca  1020
gctatcccag cacctactat aatctactca gctggtgaag                         1060

<210> SEQ ID NO 231
<211> LENGTH: 195
<212> TYPE: DNA
<213> ORGANISM: Megathura crenulata

<400> SEQUENCE: 231
atcatattgc tggcagtgga gtcaggaaag acgtgacgtc tcttaccgca tctgagatag    60
agaacctgag gcatgctctg caaagcgtga tggatgatga tggacccaat ggattccagg   120
caattgctgc ttatcacgga agtcctccca tgtgtcacat gcctgatggt agagacgttg   180
catgttgtac tcatg                                                    195

<210> SEQ ID NO 232
<211> LENGTH: 164
<212> TYPE: DNA
<213> ORGANISM: Megathura crenulata

<400> SEQUENCE: 232
gaatggcatc tttccctcac tggcacagac tgtttgtgaa acagatggag gatgcactgg    60
ctgcgcatgg agctcacatt ggcataccat actgggattg acaagtgcg tttagtcatc   120 tgcctgccct agtgactgac cacgagcaca atcccttcca ccac                    164

<210> SEQ ID NO 233
<211> LENGTH: 826
<212> TYPE: DNA
<213> ORGANISM: Megathura crenulata

<400> SEQUENCE: 233
ggacatattg ctcatcggaa tgtggataca tctcgatctc cgagagacat gctgttcaat    60
```

```
gaccccgaac acgggtcaga atcattcttc tatagacagg ttctcttggc tctagaacag    120
acagacttct gccaatttga agttcagttt gaaataacac acaatgcaat ccactcttgg    180
actggaggac atactccata tggaatgtca tcactggaat atacagcata tgatccactc    240
ttttatctcc accattccaa cactgatcgt atctgggcca tctggcaggc actccagaaa    300
tacagaggtt ttcaatacaa cgcagctcat tgcgatatcc aggttctgaa acaacctctt    360
aaaccattca gcgagtccag gaatccaaac ccagtcacca gagccaattc tagggcagtc    420
gattcatttg attatgagag actcaattat caatatgaca cacttacctt ccacggacat    480
tctatctcag aacttgatgc catgcttcaa gagagaaaga aggaagagag aacatttgca    540
gccttcctgt tgcacggatt tggcgccagt gctgatgttt cgtttgatgt ctgcacacct    600
gatggtcatt gtgcctttgc tggaaccttc gcggtacttg gtggggagct tgagatgccc    660
tggtcctttg aaagattgtt ccgttacgat atcacaaagg ttctcaagca gatgaatctt    720
cactatgatt ctgagttcca ctttgagttg aagattgttg gcacagatgg aacagaactg    780
ccatcggatc gtatcaagag ccctaccatt gaacaccatg gaggag               826
```

<210> SEQ ID NO 234
<211> LENGTH: 316
<212> TYPE: PRT
<213> ORGANISM: Megathura crenulata

<400> SEQUENCE: 234

Gly Leu Pro Tyr Trp Asp Trp Thr Met Pro Met Ser His Leu Pro Glu
1               5                   10                  15

Leu Ala Thr Ser Glu Thr Tyr Leu Asp Pro Val Thr Gly Glu Thr Lys
                20                  25                  30

Asn Asn Pro Phe His His Ala Gln Val Ala Phe Glu Asn Gly Val Thr
            35                  40                  45

Ser Arg Asn Pro Asp Ala Lys Leu Phe Met Lys Pro Thr Tyr Gly Asp
        50                  55                  60

His Thr Tyr Leu Phe Asp Ser Met Ile Tyr Ala Phe Glu Gln Glu Asp
65                  70                  75                  80

Phe Cys Asp Phe Glu Val Gln Tyr Glu Leu Thr His Asn Ala Ile His
                85                  90                  95

Ala Trp Val Gly Gly Ser Glu Lys Tyr Ser Met Ser Ser Leu His Tyr
            100                 105                 110

Thr Ala Phe Asp Pro Ile Phe Tyr Leu His His Ser Asn Val Asp Arg
        115                 120                 125

Leu Trp Ala Ile Trp Gln Ala Leu Gln Ile Arg Arg Gly Lys Ser Tyr
    130                 135                 140

Lys Ala His Cys Ala Ser Ser Gln Glu Arg Glu Pro Leu Lys Pro Phe
145                 150                 155                 160

Ala Phe Ser Ser Pro Leu Asn Asn Asn Glu Lys Thr Tyr His Asn Ser
                165                 170                 175

Val Pro Thr Asn Val Tyr Asp Tyr Val Gly Val Leu His Tyr Arg Tyr
            180                 185                 190

Asp Asp Leu Gln Phe Gly Gly Met Thr Met Ser Glu Leu Glu Glu Tyr
        195                 200                 205

Ile His Lys Gln Thr Gln His Asp Arg Thr Phe Ala Gly Phe Phe Leu
    210                 215                 220

Ser Tyr Ile Gly Thr Ser Ala Ser Val Asp Ile Phe Ile Asn Arg Glu
225                 230                 235                 240

```
Gly His Asp Lys Tyr Lys Val Gly Ser Phe Val Leu Gly Gly Ser
                245                 250                 255

Lys Glu Met Lys Trp Gly Phe Asp Arg Met Tyr Lys Tyr Glu Ile Thr
            260                 265                 270

Glu Ala Leu Lys Thr Leu Asn Val Ala Val Asp Asp Gly Phe Ser Ile
            275                 280                 285

Thr Val Glu Ile Thr Asp Val Asp Gly Ser Pro Ser Ala Asp Leu
            290                 295                 300

Ile Pro Pro Pro Ala Ile Ile Phe Asp Val Val Arg
305                 310                 315

<210> SEQ ID NO 235
<211> LENGTH: 416
<212> TYPE: PRT
<213> ORGANISM: Megathura crenulata

<400> SEQUENCE: 235

Ala Asp Ala Lys Asp Phe Gly His Ser Arg Lys Ile Arg Lys Ala Val
1               5                   10                  15

Asp Ser Leu Thr Val Glu Glu Gln Thr Ser Leu Arg Arg Ala Met Ala
            20                  25                  30

Asp Leu Gln Asp Lys Thr Ser Gly Gly Phe Gln Gln Ile Ala Ala
            35                  40                  45

Phe His Gly Glu Pro Lys Trp Cys Pro Ser Pro Glu Ala Glu Lys Lys
    50                  55                  60

Phe Ala Cys Cys Val His Gly Met Ala Val Phe Pro His Trp His Arg
65                  70                  75                  80

Leu Leu Thr Val Gln Gly Glu Asn Ala Leu Arg Lys His Gly Phe Thr
                85                  90                  95

Gly Gly Leu Pro Tyr Trp Asp Trp Thr Arg Pro Met Ser Ala Leu Pro
            100                 105                 110

His Phe Val Ala Asp Pro Thr Tyr Asn Asp Ser Val Ser Ser Leu Glu
            115                 120                 125

Glu Asp Asn Pro Trp Tyr His Gly His Ile Asp Ser Val Gly His Asp
130                 135                 140

Thr Thr Arg Ala Val Arg Asp Asp Leu Tyr Gln Ser Pro Gly Phe Gly
145                 150                 155                 160

His Tyr Thr Asp Ile Ala Lys Gln Val Leu Leu Ala Phe Glu Gln Asp
                165                 170                 175

Asp Phe Cys Asp Phe Glu Val Gln Phe Glu Ile Ala His Asn Phe Ile
            180                 185                 190

His Ala Leu Val Gly Gly Asn Glu Pro Tyr Ser Met Ser Ser Leu Arg
            195                 200                 205

Tyr Thr Thr Tyr Asp Pro Ile Phe Phe Leu His Arg Ser Asn Thr Asp
210                 215                 220

Arg Leu Trp Ala Ile Trp Gln Ala Leu Gln Lys Tyr Arg Gly Lys Pro
225                 230                 235                 240

Tyr Asn Thr Ala Asn Cys Ala Ile Ala Ser Met Arg Lys Pro Leu Gln
                245                 250                 255

Pro Phe Gly Leu Asp Ser Val Ile Asn Pro Asp Asp Glu Thr Arg Glu
            260                 265                 270

His Ser Val Pro Phe Arg Val Phe Asp Tyr Lys Asn Asn Phe Asp Tyr
            275                 280                 285

Glu Tyr Glu Ser Leu Ala Phe Asn Gly Leu Ser Ile Ala Gln Leu Asp
            290                 295                 300
```

-continued

```
Arg Glu Leu Gln Arg Arg Lys Ser His Asp Arg Val Phe Ala Gly Phe
305                 310                 315                 320

Leu Leu His Glu Ile Gly Gln Ser Ala Leu Val Lys Phe Tyr Val Cys
                325                 330                 335

Lys His Asn Val Ser Asp Cys Asp His Tyr Ala Gly Glu Phe Tyr Ile
                340                 345                 350

Leu Gly Asp Glu Ala Glu Met Pro Trp Arg Tyr Asp Arg Val Tyr Lys
                355                 360                 365

Tyr Glu Ile Thr Gln Gln Leu His Asp Leu Asp Leu His Val Gly Asp
                370                 375                 380

Asn Phe Phe Leu Lys Tyr Glu Ala Phe Asp Leu Asn Gly Gly Ser Leu
385                 390                 395                 400

Gly Gly Ser Ile Phe Ser Gln Pro Ser Val Ile Phe Glu Pro Ala Ala
                405                 410                 415

<210> SEQ ID NO 236
<211> LENGTH: 419
<212> TYPE: PRT
<213> ORGANISM: Megathura crenulata

<400> SEQUENCE: 236

Gly Ser His Gln Ala Asp Glu Tyr Arg Glu Ala Val Thr Ser Ala Ser
1               5                   10                  15

His Ile Arg Lys Asn Ile Arg Asp Leu Ser Glu Gly Glu Ile Glu Ser
                20                  25                  30

Ile Arg Ser Ala Phe Leu Gln Ile Gln Lys Glu Gly Ile Tyr Glu Asn
                35                  40                  45

Ile Ala Lys Phe His Gly Lys Pro Gly Leu Cys Glu His Asp Gly His
                50                  55                  60

Pro Val Ala Cys Cys Val His Gly Met Pro Thr Phe Pro His Trp His
65                  70                  75                  80

Arg Leu Tyr Val Leu Gln Val Glu Asn Ala Leu Leu Glu Arg Gly Ser
                85                  90                  95

Ala Val Ala Val Pro Tyr Trp Asp Trp Thr Glu Lys Ala Asp Ser Leu
                100                 105                 110

Pro Ser Leu Ile Asn Asp Ala Thr Tyr Phe Asn Ser Arg Ser Gln Thr
                115                 120                 125

Phe Asp Pro Asn Pro Phe Phe Arg Gly His Ile Ala Phe Glu Asn Ala
130                 135                 140

Val Thr Ser Arg Asp Pro Gln Pro Glu Leu Trp Asp Asn Lys Asp Phe
145                 150                 155                 160

Tyr Glu Asn Val Met Leu Ala Leu Glu Gln Asp Asn Phe Cys Asp Phe
                165                 170                 175

Glu Ile Gln Leu Glu Leu Ile His Asn Ala Leu His Ser Arg Leu Gly
                180                 185                 190

Gly Arg Ala Lys Tyr Ser Leu Ser Ser Leu Asp Tyr Thr Ala Phe Asp
                195                 200                 205

Pro Val Phe Phe Leu His His Ala Asn Val Asp Arg Ile Trp Ala Ile
                210                 215                 220

Trp Gln Asp Leu Gln Arg Tyr Arg Lys Pro Tyr Asn Glu Ala Asp
225                 230                 235                 240

Cys Ala Val Asn Glu Met Arg Lys Pro Leu Gln Pro Phe Asn Asn Pro
                245                 250                 255

Glu Leu Asn Ser Asp Ser Met Thr Leu Lys His Asn Leu Pro Gln Asp
```

-continued

```
                260                 265                 270
Ser Phe Asp Tyr Gln Asn Arg Phe Arg Tyr Gln Tyr Asp Asn Leu Gln
        275                 280                 285
Phe Asn His Phe Ser Ile Gln Lys Leu Asp Gln Thr Ile Gln Ala Arg
        290                 295                 300
Lys Gln His Asp Arg Val Phe Ala Gly Phe Ile Leu His Asn Ile Gly
305                 310                 315                 320
Thr Ser Ala Val Val Asp Ile Tyr Ile Cys Val Glu Gln Gly Gly Glu
                325                 330                 335
Gln Asn Cys Lys Thr Lys Ala Gly Ser Phe Thr Ile Leu Gly Gly Glu
                340                 345                 350
Thr Glu Met Pro Phe His Phe Asp Arg Leu Tyr Lys Phe Asp Ile Thr
                355                 360                 365
Ser Ala Leu His Lys Leu Gly Val Pro Leu Asp Gly His Gly Phe Asp
        370                 375                 380
Ile Lys Val Asp Val Arg Ala Val Asn Gly Ser His Leu Asp Gln His
385                 390                 395                 400
Ile Leu Asn Glu Pro Ser Leu Leu Phe Val Pro Gly Glu Arg Lys Asn
                405                 410                 415
Ile Tyr Tyr

<210> SEQ ID NO 237
<211> LENGTH: 413
<212> TYPE: PRT
<213> ORGANISM: Megathura crenulata

<400> SEQUENCE: 237

Asp Gly Leu Ser Gln His Asn Leu Val Arg Lys Glu Val Ser Ser Leu
1               5                   10                  15
Thr Thr Leu Glu Lys His Phe Leu Arg Lys Ala Leu Lys Asn Met Gln
                20                  25                  30
Ala Asp Asp Ser Pro Asp Gly Tyr Gln Ala Ile Ala Ser Phe His Ala
        35                  40                  45
Leu Pro Pro Leu Cys Pro Ser Pro Ser Ala Ala His Arg His Ala Cys
        50                  55                  60
Cys Leu His Gly Met Ala Thr Phe Pro Gln Trp His Arg Leu Tyr Thr
65                  70                  75                  80
Val Gln Phe Glu Asp Ser Leu Lys Arg His Gly Ser Ile Val Gly Leu
                85                  90                  95
Pro Tyr Trp Asp Trp Leu Lys Pro Gln Ser Ala Leu Pro Asp Leu Val
                100                 105                 110
Thr Gln Glu Thr Tyr Glu His Leu Phe Ser His Lys Thr Phe Pro Asn
        115                 120                 125
Pro Phe Leu Lys Ala Asn Ile Glu Phe Glu Gly Glu Gly Val Thr Thr
130                 135                 140
Glu Arg Asp Val Asp Ala Glu His Leu Phe Ala Lys Gly Asn Leu Val
145                 150                 155                 160
Tyr Asn Asn Trp Phe Cys Asn Gln Ala Leu Tyr Ala Leu Glu Gln Glu
                165                 170                 175
Asn Tyr Cys Asp Phe Glu Ile Gln Phe Glu Ile Leu His Asn Gly Ile
                180                 185                 190
His Ser Trp Val Gly Gly Ser Lys Thr His Ser Ile Gly His Leu His
        195                 200                 205
Tyr Ala Ser Tyr Asp Pro Leu Phe Tyr Ile His His Ser Gln Thr Asp
```

-continued

```
                210                 215                 220
Arg Ile Trp Ala Ile Trp Gln Ala Leu Gln Glu His Arg Gly Leu Ser
225                 230                 235                 240

Gly Lys Glu Ala His Cys Ala Leu Glu Gln Met Lys Asp Pro Leu Lys
                245                 250                 255

Pro Phe Ser Phe Gly Ser Pro Tyr Asn Leu Asn Lys Arg Thr Gln Glu
                260                 265                 270

Phe Ser Lys Pro Glu Asp Thr Phe Asp Tyr His Arg Phe Gly Tyr Glu
                275                 280                 285

Tyr Asp Ser Leu Glu Phe Val Gly Met Ser Val Ser Ser Leu His Asn
                290                 295                 300

Tyr Ile Lys Gln Gln Glu Ala Asp Arg Val Phe Ala Gly Phe Leu
305                 310                 315                 320

Leu Lys Gly Phe Gly Gln Ser Ala Ser Val Ser Phe Asp Ile Cys Arg
                325                 330                 335

Pro Asp Gln Ser Cys Gln Glu Ala Gly Tyr Phe Ser Val Leu Gly Gly
                340                 345                 350

Ser Ser Glu Met Pro Trp Gln Phe Asp Arg Leu Tyr Lys Tyr Asp Ile
                355                 360                 365

Thr Lys Thr Leu Lys Asp Met Lys Leu Arg Tyr Asp Asp Thr Phe Thr
370                 375                 380

Ile Lys Val His Ile Lys Asp Ile Ala Gly Ala Glu Leu Asp Ser Asp
385                 390                 395                 400

Leu Ile Pro Thr Pro Ser Val Leu Leu Glu Glu Gly Lys
                405                 410

<210> SEQ ID NO 238
<211> LENGTH: 417
<212> TYPE: PRT
<213> ORGANISM: Megathura crenulata

<400> SEQUENCE: 238

His Gly Ile Asn Val Arg His Val Gly Arg Asn Arg Ile Arg Met Glu
1               5                   10                  15

Leu Ser Glu Leu Thr Glu Arg Asp Leu Ala Ser Leu Lys Ser Ala Met
                20                  25                  30

Arg Ser Leu Gln Ala Asp Asp Gly Val Asn Gly Tyr Gln Ala Ile Ala
                35                  40                  45

Ser Phe His Gly Leu Pro Ala Ser Cys His Asp Asp Glu Gly His Glu
50                  55                  60

Ile Ala Cys Cys Ile His Gly Met Pro Val Phe Pro His Trp His Arg
65                  70                  75                  80

Leu Tyr Thr Leu Gln Met Asp Met Ala Leu Leu Ser His Gly Ser Ala
                85                  90                  95

Val Ala Ile Pro Tyr Trp Asp Trp Thr Lys Pro Ile Ser Lys Leu Pro
                100                 105                 110

Asp Leu Phe Thr Ser Pro Glu Tyr Tyr Asp Pro Trp Arg Asp Ala Val
                115                 120                 125

Val Asn Asn Pro Phe Ala Lys Gly Tyr Ile Lys Ser Glu Asp Ala Tyr
                130                 135                 140

Thr Val Arg Asp Pro Gln Asp Ile Leu Tyr His Leu Gln Asp Glu Thr
145                 150                 155                 160

Gly Thr Ser Val Leu Leu Asp Gln Thr Leu Leu Ala Leu Glu Gln Thr
                165                 170                 175
```

```
Asp Phe Cys Asp Phe Glu Val Gln Phe Glu Val Val His Asn Ala Ile
            180                 185                 190

His Tyr Leu Val Gly Gly Arg Gln Val Tyr Ala Leu Ser Ser Gln His
        195                 200                 205

Tyr Ala Ser Tyr Asp Pro Ala Phe Phe Ile His Ser Phe Val Asp
    210                 215                 220

Lys Ile Trp Ala Val Trp Gln Ala Leu Gln Lys Arg Lys Arg Pro
225                 230                 235                 240

Tyr His Lys Ala Asp Cys Ala Leu Asn Met Met Thr Lys Pro Met Arg
            245                 250                 255

Pro Phe Ala His Asp Phe Asn His Asn Gly Phe Thr Lys Met His Ala
            260                 265                 270

Val Pro Asn Thr Leu Phe Asp Phe Gln Asp Leu Phe Tyr Thr Tyr Asp
            275                 280                 285

Asn Leu Glu Ile Ala Gly Met Asn Val Asn Gln Leu Glu Ala Glu Ile
            290                 295                 300

Asn Arg Arg Lys Ser Gln Thr Arg Val Phe Ala Gly Phe Leu Leu His
305                 310                 315                 320

Gly Ile Gly Arg Ser Ala Asp Val Arg Phe Trp Ile Cys Lys Thr Ala
            325                 330                 335

Asp Asp Cys His Ala Ser Gly Met Ile Phe Ile Leu Gly Gly Ser Lys
            340                 345                 350

Glu Met His Trp Ala Tyr Asp Arg Asn Phe Lys Tyr Asp Ile Thr Gln
            355                 360                 365

Ala Leu Lys Ala Gln Ser Ile His Pro Glu Asp Val Phe Asp Thr Asp
            370                 375                 380

Ala Pro Phe Phe Ile Lys Val Glu Val His Gly Val Asn Lys Thr Ala
385                 390                 395                 400

Leu Pro Ser Ser Ala Ile Pro Ala Pro Thr Ile Ile Tyr Ser Ala Gly
                    405                 410                 415

Glu

<210> SEQ ID NO 239
<211> LENGTH: 395
<212> TYPE: PRT
<213> ORGANISM: Megathura crenulata

<400> SEQUENCE: 239

Asp His Ile Ala Gly Ser Gly Val Arg Lys Asp Val Thr Ser Leu Thr
1               5                   10                  15

Ala Ser Glu Ile Glu Asn Leu Arg His Ala Leu Gln Ser Val Met Asp
            20                  25                  30

Asp Asp Gly Pro Asn Gly Phe Gln Ala Ile Ala Ala Tyr His Gly Ser
        35                  40                  45

Pro Pro Met Cys His Met Pro Asp Gly Arg Asp Val Ala Cys Cys Thr
    50                  55                  60

His Gly Met Ala Ser Phe Pro His Trp His Arg Leu Phe Val Lys Gln
65                  70                  75                  80

Met Glu Asp Ala Leu Ala Ala His Gly Ala His Ile Gly Ile Pro Tyr
            85                  90                  95

Trp Asp Trp Thr Ser Ala Phe Ser His Leu Pro Ala Leu Val Thr Asp
        100                 105                 110

His Glu His Asn Pro Phe His His Gly His Ile Ala His Arg Asn Val
    115                 120                 125
```

-continued

```
Asp Thr Ser Arg Ser Pro Arg Asp Met Leu Phe Asn Asp Pro Glu His
        130                 135                 140
Gly Ser Glu Ser Phe Phe Tyr Arg Gln Val Leu Leu Ala Leu Glu Gln
145                 150                 155                 160
Thr Asp Phe Cys Gln Phe Glu Val Gln Phe Glu Ile Thr His Asn Ala
                165                 170                 175
Ile His Ser Trp Thr Gly Gly His Thr Pro Tyr Gly Met Ser Ser Leu
                180                 185                 190
Glu Tyr Thr Ala Tyr Asp Pro Leu Phe Tyr Leu His His Ser Asn Thr
            195                 200                 205
Asp Arg Ile Trp Ala Ile Trp Gln Ala Leu Gln Lys Tyr Arg Gly Phe
        210                 215                 220
Gln Tyr Asn Ala Ala His Cys Asp Ile Gln Val Leu Lys Gln Pro Leu
225                 230                 235                 240
Lys Pro Phe Ser Glu Ser Arg Asn Pro Asn Pro Val Thr Arg Ala Asn
                245                 250                 255
Ser Arg Ala Val Asp Ser Phe Asp Tyr Glu Arg Leu Asn Tyr Gln Tyr
                260                 265                 270
Asp Thr Leu Thr Phe His Gly His Ser Ile Ser Glu Leu Asp Ala Met
            275                 280                 285
Leu Gln Glu Arg Lys Lys Glu Glu Arg Thr Phe Ala Ala Phe Leu Leu
        290                 295                 300
His Gly Phe Gly Ala Ser Ala Asp Val Ser Phe Asp Val Cys Thr Pro
305                 310                 315                 320
Asp Gly His Cys Ala Phe Ala Gly Thr Phe Ala Val Leu Gly Gly Glu
                325                 330                 335
Leu Glu Met Pro Trp Ser Phe Glu Arg Leu Phe Arg Tyr Asp Ile Thr
                340                 345                 350
Lys Val Leu Lys Gln Met Asn Leu His Tyr Asp Ser Glu Phe His Phe
            355                 360                 365
Glu Leu Lys Ile Val Gly Thr Asp Gly Thr Glu Leu Pro Ser Asp Arg
        370                 375                 380
Ile Lys Ser Pro Thr Ile Glu His His Gly Gly
385                 390                 395
```

NUCLEIC ACID MOLECULE COMPRISING A NUCLEIC ACID SEQUENCE CODING FOR A HAEMOCYANIN

CROSS-REFERENCE TO RELATED APPLICATIONS

This is a division of application Ser. No. 10/049,988 filed Jul. 15, 2002 which issued as U.S. Pat. No. 7,125,557 on Oct. 24, 2006, which application claims benefit of PCT application PCT/EP00/08129 filed 21 Aug. 2000 which claims benefit of German application No. 199 39 578.0 filed 20 Aug. 1999, the contents of which are all incorporated herein by reference.

BACKGROUND OF THE INVENTION

The present invention relates to a nucleic acid molecule comprising a nucleic acid sequence which codes for a haemocyanin, a haemocyanin domain or a fragment with the immunological properties of at least one domain of haemocyanin, and comprising at least one intron sequence, constructs which comprise such molecules, host cells which comprise the nucleic acid sequences or the constructs, processes for the preparation of haemocyanin polypeptides, and recombinant haemocyanin polypeptides.

Haemocyanin is a blue copper protein which occurs in a freely dissolved form in the blood of numerous molluscs and arthropods and transports oxygen. Of the molluscs, the cephalopods, chitons, most gastropods and some bivalves contain haemocyanin. Among the arthropods, haemocyanin is typical of arachnids, xiphosurans, malacostracan crustaceans and *Scutigera*. Numerous species of insects contain proteins which are derived from haemocyanin. Haemocyanins are present in the extracellular medium and float in the haemolymph.

While arthropod haemocyanin has a maximum diameter of 25 nm under an electron microscope and a subunit has a molecular weight of 75,000 Da, mollusc cyanins are much larger. Thus e.g. the haemocyanin of *Megathura* has a diameter of 35 nm and is composed of 2 subunits. Each subunit has a molecular weight of approx. 400,000 Da and is divided into eight oxygen-binding domains, each of which has a molecular weight of approx. 50,000. The domains differ immunologically. These domains can be liberated from the subunit by limited proteolysis.

The haemocyanin of gastropods visible under an electron microscope has a molecular weight of approx. 8 million Da and is a di-decamer. In contrast to this, the haemocyanin of cephalopods is arranged as an isolated decamer, which also differs significantly from the haemocyanin of gastropods in the quaternary structure.

The haemocyanin of the Californian keyhole limpet *Megathura crenulata* is of particular immunological interest. The haemocyanin is therefore also called keyhole limpet haemocyanin (KLH). Haemocyanins are very potent antigens. Immunization of a vertebrate leads to a non-specific activation of the immune system which to date is not very well understood. By the general activation of the immune system, it is then possible also to achieve an immune reaction to other foreign structures which have previously been tolerated. KLH is used above all as a hapten carrier in order thus to achieve the formation of antibodies against the hapten.

In addition to *Megathura crenulata*, the abalone *Haliotis tuberculata* also belongs to the Archaegastropoda group, which is relatively old in respect of evolution. It is known that *Haliotis* also produces haemocyanin.

KLH is a mixture of two different haemocyanins, which are called KLH1 and KLH2. The subunit of KLH1 is a 390 kDa polypeptide which consists of eight globular domains called 1 a to 1 h according to their sequence in the subunit. On the other hand, KLH2 has a molecular weight of 350 kDa and according to the most recent data also contains 8 domains, called 2 a to 2 h. In vivo every type of subunit forms homo-oligomers, while no hetero-oligomers have been observed.

Amino-terminal, internal and carboxy-terminal domains have been obtained by limited proteolysis and crossed immunoelectrophoresis of the subunit of KLH1 and KLH2, and their amino-terminal sequences has been determined (Sbhngen et al., Eur. J. Biochem. 248 (1997), 602-614; Gebauer et al., Zoology 98 (1994), 51-68). However, the resulting sequences do not allow designing of sequence-specific primers and/or probes which promise success for hybridization with genomic DNA. Although both KLH types have been known since 1991 and 1994 respectively, it has so far not been possible to clarify the primary structure.

At the DNA level, in respect of molluscs only the cDNA sequence of the haemocyanin subunit from the cephalopod *Octopus dofleini* is so far known (Miller et al., J. Mol. Biol. 278 (1998), 827-842). *Octopus dofleini* is phylogenetically very far removed from the archaegastropods. A haemocyanin gene sequence from molluscs is so far not known at all.

As described by Miller at al. supra, it is difficult both to isolate a single functional domain (functional unit=domain; also called functional domain) and to obtain tissue which is suitable for purification of mRNA for cDNA sequencing.

There is a further difficulty in the analysis of the haemocyanin from *Megathura crenulata* in that the test animals must have reached an age of 4 to 8 years for haemolymph to be taken from them in the first place. After the haemolymph has been taken, haemocyanin is not subsequently produced in these animals. It is not yet known how haemocyanin synthesis could be stimulated. Furthermore, culture of *Megathura* is extremely expensive, since special flow basins are required for this.

BRIEF SUMMARY OF THE INVENTION

It is therefore an object of the present invention to provide means and ways in order to be able to produce haemocyanin and/or domains thereof in a sufficient amount and inexpensively. This includes the further object of providing a process with which this haemocyanin can be prepared.

This object is achieved according to the invention by a nucleic acid molecule comprising a nucleic acid sequence which codes for a haemocyanin, a haemocyanin domain or a functional fragment thereof with the immunological properties of at least one domain of a haemocyanin, the nucleic acid sequence being selected from (a) nucleic acid sequences which are selected from the group consisting of the DNA sequences shown below or the corresponding RNA sequences or which contain these:

SEQ ID NO:1 (HtH1 domain a+signal peptide),
SEQ ID NO:2 (HtH1 domain b),
SEQ ID NO:3 (HtH1 domain c),
SEQ ID NO:4 (HtH1 domain d),
SEQ ID NO:5 (HtH1 domain e),
SEQ ID NO:6 (HtH1 domain f),
SEQ ID NO:7 (HtH1 domain g),
SEQ ID NO:8 (HtH1 domain h),
SEQ ID NO:9 (partial HtH2 domain b), SEQ ID NO:10 (HtH2 domain c),
SEQ ID NO:11 (HtH2 domain d),
SEQ ID NO:12 (HtH2 domain e),
SEQ ID NO:13 (HtH2 domain f),
SEQ ID NO:14 (HtH2 domain g),
SEQ ID NO:15 (HtH2 domain h),
SEQ ID NO:16 (partial KLH1 domain b),
SEQ ID NO:17 (KLH1 domain c),
SEQ ID NO:18 (KLH1 domain d),
SEQ ID NO:19 (partial KLH1 domain e),
SEQ ID NO:20 (KLH2 domain b),
SEQ ID NO:21 (KLH2 domain c),
SEQ ID NO:22 (partial KLH2 domain d),
SEQ ID NO:23 (KLH2 domain g),
SEQ ID NO:24 (partial KLH2 domain h),
SEQ ID NO:49 (HtH1 domain a'+signal peptide),
SEQ ID NO:50 (partial HtH2 domain a),
SEQ ID NO:51 (HtH2 domain b'),
SEQ ID NO:52 (HtH2 domain d'),
SEQ ID NO:53 (HtH2 domain e'),
SEQ ID NO:54 (KLH1 domain e'),
SEQ ID NO:55 (KLH1 domain f),
SEQ ID NO:56 (KLH1 domain g),
SEQ ID NO:57 (KLH2 domain b'),
SEQ ID NO:58 (KLH2 domain c'),
SEQ ID NO:59 (KLH2 domain d'),
SEQ ID NO:60 (KLH1 domain e),
SEQ ID NO:61 (KLH2 domain f),
SEQ ID NO:62 (KLH2 domain g'),
SEQ ID NO:80 (HtH1 domain a"+signal peptide),
SEQ ID NO:81 (HtH1 domain b"),
SEQ ID NO:82 (HtH1 domain c"),
SEQ ID NO:83 (HtH1 domain d"),
SEQ ID NO:84 (HtH1 domain e"),
SEQ ID NO:85 (HtH1 domain f"),
SEQ ID NO:86 (HtH1 domain g"),
SEQ ID NO:87 (HtH1 domain h"),
SEQ ID NO:88 (partial HtH2 domain a"),
SEQ ID NO:89 (HtH2 domain b"),
SEQ ID NO:90 (HtH2 domain c"),
SEQ ID NO:91 (HtH2 domain d"),
SEQ ID NO:92 (HtH2 domain e"),
SEQ ID NO:93 (HtH2 domain f"),
SEQ ID NO:94 (HtH2 domain g"),
SEQ ID NO:95 (HtH2 domain h"),
SEQ ID NO:96 (partial KLH1 domain b"),
SEQ ID NO:97 (KLH1 domain c"),
SEQ ID NO:98 (KLH1 domain d"),
SEQ ID NO:99 (KLH1 domain e"),
SEQ ID NO:100 (KLH1 domain f"),
SEQ ID NO:101 (KLH1 domain g"),
SEQ ID NO:102 (KLH2 domain b"),
SEQ ID NO:103 (KLH2 domain c"),
SEQ ID NO:104 (KLH2 domain d"),
SEQ ID NO:105 (KLH2 domain e"),
SEQ ID NO:106 (KLH2 domain f"),
SEQ ID NO:107 (KLH2 domain g"),
SEQ ID NO:108 (partial KLH2 domain h"),
SEQ ID NO:157 (complete HtH2 domain a),
b) nucleic acid sequences which hybridize with the counter-strand of a nucleic acid sequence according to (a) and code for a polypeptide which has the immunological properties of at least one domain of a haemocyanin;
c) nucleic acid sequences which on the basis of the genetic code are degenerated to the DNA sequences defined under (a) and (b) and code for a polypeptide which has the immunological properties of at least one domain of a haemocyanin;
(d) nucleic acid sequences which hybridize with one of the nucleic acid sequences described under (a) to (c) and the counter-strand of which codes for a polypeptide which has the immunological properties of at least one domain of a haemocyanin;
(e) nucleic acid sequences which are at least 60% homologous to one of the nucleic acid sequences described under (a);
(f) variants of the sequences described under (a) to (e), the variants containing additions, deletions, insertions or inversions and coding for a polypeptide which has the immunological properties of at least one domain of haemocyanin; and
(g) combinations of several of the DNA sequences described under (a) to (f).

Preferably, the intron sequence is selected from the following sequences:
(i) nucleic acid sequences which are selected from the group consisting of the DNA sequences shown below or the corresponding RNA sequences or which contain these:
SEQ ID NO:109 (HtH1 intron 1S-1/1S-2),
SEQ ID NO:110 (HtH1 intron 1S-2/1A-1),
SEQ ID NO:111 (HtH1 intron 1A-1/1A-2),
SEQ ID NO:112 (HtH1 intron 1A-2/1A-3),
SEQ ID NO:113 (HtH1 intron 1A-3/1A-4),
SEQ ID NO:114 (HtH1 intron 1A-4/1B),
SEQ ID NO:115 (HtH1 intron 1B/1C),
SEQ ID NO:116 (HtH1 intron 1C/1D),
SEQ ID NO:117 (HtH1 intron 1D/1E),
SEQ ID NO:118 (HtH1 intron 1E/1F-1),
SEQ ID NO:119 (HtH1 intron 1F-1/1F-2),
SEQ ID NO:120 (HtH1 intron 1F-2/1G-1),
SEQ ID NO:121 (HtH1 intron 1F-1/1G-2),
SEQ ID NO:122 (HtH1 intron 1G-2/1G-3),
SEQ ID NO:123 (HtH1 intron 1G-3/1H),
SEQ ID NO:124 (HtH1 intron in the 3'UTR of HtH1;
SEQ ID NO:125 (HtH2 intron 2A-1/2A-2);
SEQ ID NO:126 (HtH2 intron 2A-1/2A-3),
SEQ ID NO:127 (HtH1 intron 2A-1/2A-4),
SEQ ID NO:128 (HtH1 intron 2A-4/2B),
SEQ ID NO:129 (HtH1 intron 2B/2C),
SEQ ID NO:130 (HtH1 intron 2C/2D),
SEQ ID NO:131 (HtH1 intron 2D/2E),
SEQ ID NO:132 (HtH1 intron 2F-1/2F-2),
SEQ ID NO:133 (HtH1 intron 2F-2/2GF-1),
SEQ ID NO:134 (HtH1 intron 2F-2/2GF-1),
SEQ ID NO:135 (HtH1 intron 2G-1/2G-2),
SEQ ID NO:136 (HtH1 intron 2G-2/2G-3),
SEQ ID NO:137 (HtH1 intron 2G-3/2H),
SEQ ID NO:138 (HtH1 intron in the 3'UTR of HtH2),
SEQ ID NO:139 (KLH1 intron 1B/1C),
SEQ ID NO:140 (KLH1 intron 1C/1D),
SEQ ID NO:141 (KLH1 intron 1D/1E),
SEQ ID NO:142 (KLH1 intron 1E/1F),
SEQ ID NO:143 (KLH1 intron 1F-1/2F-2),
SEQ ID NO:144 (KLH1 intron 1F-2/1G-1),
SEQ ID NO:145 (KLH1 intron 1G-1/1G-2),
SEQ ID NO:146 (KLH1 intron 1G-2/1G-3),
SEQ ID NO:147 (KLH1 intron 2B/2C),
SEQ ID NO:148 (KLH2 intron 2C/2D),
SEQ ID NO:149 (KLH2 intron 2D/2E),
SEQ ID NO:150 (KLH2 intron 2E/2F),
SEQ ID NO:151 (KLH2 intron 2F), SEQ ID NO:152 (KLH2 intron 2F-2/2G),
SEQ ID NO:153 (KLH2 intron 2G-2/2G-2),
SEQ ID NO:154 (KLH2 intron 2G-2/2G-3),
SEQ ID NO:155 (KLH2 intron 2G/2H);

(ii) nucleic acid sequences which hybridize with the counter-strand of a nucleic acid sequence according to (1);

(iii) nucleic acid sequences which are at least 60% homologous to one of the nucleic acid sequences described under (i);

(vi) variants of the sequences described under (i) to (iii), the variants containing additions, deletions, insertions or inversions with respect to the sequences described under (i) to (iii); and (v) combinations of several of the DNA sequences described under (i) to (iv).

Some terms are explained in more detail below in order to clarify how they are to be understood in connection with the present application.

The term "haemocyanin" as used below in the description includes complete haemocyanin, haemocyanin domains and/or fragments, haemocyanin mutants and fusion proteins. In respect of fusion proteins, these include, in particular, those in which the fusion comprises haemocyanin and antigens.

"Domains" are understood as meaning functional partial sequences of the haemocyanin subunits which can be separated from one another, for example, by limited proteolysis. They can furthermore have different immunological properties.

The "immunological properties of at least one domain of haemocyanin" means the property of a polypeptide of inducing, in the same manner as at least one domain of haemocyanin, an immunological response of the recipient immunized with the polypeptide. "Immunological response" here is understood as meaning T and/or B cell responses to haemocyanin epitopes, such as, for example, an antibody production. The immunological reaction can be observed, for example, by immunization of a mammal, such as e.g. a mouse, a rat or a rabbit, with the corresponding polypeptide and comparison of the immune response to the polypeptide used for the immunization with the immune response to natural haemocyanins.

The term "intron sequence" refers either to a sequence interrupting an eukaryotic gene or to the corresponding sequence in the RNA transcript. The intron sequence(s) and the coding sequence(s) are transcribed together; the intron transcript or transcripts are then deleted to obtain the functional RNA.

According to the invention, the term "antigen" includes both haptens and weak and potent antigens. Haptens are characterized in that they are substances of low molecular weight (less than 4,000 Da), but without being coupled to a carrier molecule are not capable of inducing an immunological reaction. Weak antigens are substances which can themselves already induce an immunological reaction and of which the potential to be able to induce an immunological reaction can be increased further by coupling with a carrier molecule at the protein and/or DNA level.

"H is tag" means a sequence of at least 6 histidine amino acids which, by corresponding cloning and fusion with an expressible sequence, leads to a fusion protein which has at least 6 H is residues on the $NH_2$ terminus and can easily be purified by complexing with an $Ni^{2+}$ column.

"Cloning" is intended to include all cloning methods known in the prior art which could be employed here but which are not all described in detail because they belong to the obvious hand tools of the skilled person.

"Variants" of a nucleic acid sequences include additions, deletions, insertions or inversions and code for a polypeptide which has the immunological properties of at least one domain of a haemocyanin. Variants can be synthetic or natural. Allelic variants are an example of natural variants.

"Recombinant expression in a suitable host cell" is to be understood as meaning all the expression methods known in the prior art in known expression systems which could be employed here but which are not all described in detail because they belong to the obvious hand tools of the skilled person.

The nucleic acid sequence contained in the nucleic acid molecule according to the invention can be genomic DNA, cDNA or synthetic DNA, synthetic DNA sequences also being understood as meaning those which comprise modified internucleoside bonds. The nucleic acid sequences can furthermore be RNA sequences, which may be necessary e.g. for expression by means of recombinant vector systems. The nucleic acid sequences according to (b) are obtainable, for example, by using a detectably marked probe which corresponds to one of the sequences described under (a) or a fragment, or a counter-strand thereof for screening cDNA/genomic DNA libraries from molluscs or arthropods. The mRNA on which the cDNA library is based is preferably to be obtained from mollusc tissues which express haemocyanin to a particularly high degree, such as e.g. mantle tissue from gastropods and branchial gland tissue from cephalopods.

Positive cDNA/genomic DNA clones are identified by standard methods. Cf. Maniatis et al., Molecular Cloning (1989) Cold Spring Harbor Laboratory Press.

In a preferred embodiment, the hybridization described under (b) or (d) is carried out under stringent conditions. Stringent hybridization conditions are e.g. 68° C. overnight in 0.5×SSC; 1% blocking reagent (Boehringer Mannheim); 0.1% sodium lauryl sarcosinate and subsequent washing with 2×SSC; 0.1% SDS.

In a preferred embodiment, nucleic acid sequences which are at least 60% homologous to one of the nucleic acid sequences described under (a) are provided. The nucleic acid sequences are preferably at least 80% homologous to one of the nucleic acid sequences described under (a). The nucleic acid sequences are particularly preferably at least 90% homologous to one of the nucleic acid sequences described under (a). In particular, the nucleic acid sequences are at least 95% homologous to one of the nucleic acid sequences described under (a).

In a further preferred embodiment, nucleic acid sequences comprising at least one intron sequence which is at least 60% homologous to one of the nucleic acid sequences described under (i) are provided. Intron sequence(s) which are at least 80% homologous to one of the nucleic acid sequences described under (i) are preferred. Intron sequence(s) which are at least 90% homologous to one of the nucleic acid sequences described under (i) are particularly preferred. In particular, the intron sequence(s) are at least 95% to one of the nucleic acid sequences described under (i).

According to the invention, the term "homology" means homology at the DNA level, which can be determined by known methods, e.g. computer-assisted sequence comparisons (Basic local alignment search tool, S. F. Altschul et al., J. Mol. Biol. 215 (1990), 403-410).

The term "homology" known to the skilled person describes the degree to which two or more nucleic acid molecules are related, this being determined by the concordance between the sequences. The percentage of "homology" is obtained from the percentage of identical regions in two or more sequences, taking into account gaps or other sequence peculiarities.

The homology of nucleic acid molecules which are related to one another can be determined with the aid of known methods. As a rule, special computer programs with algorithms which take account of the particular requirements are employed.

Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (WI)); BLASTP, BLASTN and FASTA (Altschul, S. et al., J. Mol. Biol. 215:403-410 (1990)). The BLASTX program can be obtained from the National Centre for Biotechnology Information (NCBI) and from other sources (BLAST Handbook, Altschul S., et al., NCB NLM NIH Bethesda Md. 20894; Altschul, S., et al., J. Mol. Biol. 215:403-410 (1990)). The known Smith Waterman algorithm can also be used for determining homologies.

Preferred parameters for the comparison of nucleic acid sequences include the following:

Algorithm: Needeman and Wunsch, J. Mol. Biol. 48:443-453 (1970)

| Comparison matrix: | Concordance (matches) = +10 |
| --- | --- |
|  | Non-concordance (mismatch) = 0 |
| Gap penalty: | 50 |
| Gap length penalty: | 3 |

The GAP program is also suitable for use with the above parameters. The above parameters are the default parameters for nucleic acid sequence comparisons.

Further algorithms, gap opening penalties, gap extension penalties and comparison matrices by way of example, including those mentioned in the Program Handbook, Wisconsin Package, version 9, September 1997, can be used. The choice depends on the comparison to be made and furthermore on whether the comparison is to be made between sequence pairs, in which case GAP or Best Fit are preferred, or between a sequence and a comprehensive sequence databank, in which case FASTA or BLAST are preferred.

A concordance of 60% determined with the abovementioned algorithm is designated 60% homology in the context of this application. The same applies accordingly to higher degrees of homology.

In a preferred embodiment, the DNA sequence according to the invention is a combination of several of the DNA sequences described under (a) to (f), which can be obtain by fusion and optionally cloning, which are known to the skilled person. These combinations are of particular interest, since they are particularly immunogenic. Combinations which contain several or all of the domains in the sequence (a to h) which occurs naturally in the subunit are particularly preferred. Embodiments in which the nucleic acid sequences which code for the domains are coupled to one another directly in frame are particularly preferred.

Constructs which comprise the nucleic acid molecules according to the invention are furthermore provided. In a preferred embodiment, the construct according to the invention comprises a promoter which is suitable for expression, the nucleic acid sequence being under the control of the promoter. The choice of promoter depends on the expression system used for expression. Generally, constitutive promoters are preferred, but inducible promoters, such as e.g. the metallothionein promoter, are also possible.

In a further preferred embodiment, the construct furthermore comprises an antigen-coding nucleic acid sequence which is bonded directly to the haemocyanin nucleic acid according to the invention. The antigen-coding sequence can be located both 5' and 3' relative to the haemocyanin sequence or also on both ends. It either follows the haemocyanin sequence directly in the same reading frame, or is coupled to it by a nucleic acid linker, the reading frame being preserved. By fusion of the antigen-coding sequence with the haemocyanin sequence the formation of a fusion protein in which the antigen-coding sequence is bonded covalently to the haemocyanin sequence is intended. The antigen according to the invention is a medically relevant antigen, which is selected, for example, from: tumour antigens, virus antigens and antigens of bacterial or parasitic pathogens. Tumour antigens can be, for example, Rb and p53. The virus antigens preferably originate from immunologically relevant viruses, such as e.g. influenza virus, hepatitis virus and HIV. Pathogen antigens are, inter alia, those from mammalian pathogens, in particular organisms which are pathogenic to humans, such as e.g. *Plasmodium*. Bacterial antigens can originate e.g. from *Klebsiella, Pseudomonas, E. coli, Vibrio cholerae, Chlamydia*, Streptococci or Staphylococci.

In another preferred embodiment, the construct furthermore comprises at least a part of a vector, in particular regulatory regions, the vector being selected from: bacteriophages, such as □ derivatives, adenoviruses, vaccinia viruses, baculoviruses, SV40 viruses and retroviruses, preferably MoMuLV (Moloney murine leukaemia virus).

A construct which additionally comprises a H is tag-coding DNA sequence, which, when expressed, leads to the formation of a fusion protein with a H is tag on the $NH_2$ terminus of the haemocyanin, facilitating purification of the protein on a nickel column by chelate formation, is furthermore preferred.

The invention furthermore provides host cells which contain the construct and which are suitable for expression of the construct. Numerous prokaryotic and eukaryotic expression systems are known in the prior art, the host cells being selected, for example, from prokaryotic cells, such as *E. coli* or *B. subtilis*, from eukaryotic cells, such as yeast cells, plant cells, insect cells and mammalian cells, e.g. CHO cells, COS cells or HeLa cells, and derivatives thereof. For example certain CHO production lines of which the glycosylation patterns are altered compared with CHO cells are known in the prior art. The haemocyanins obtained using glycosylation-deficient or glycosylation-reduced host cells possibly have additional epitopes which are otherwise not accessible to the immune system of the recipient in the case of complete glycosylation, so that haemocyanins with a reduced glycosylation under certain circumstances have an increased immunogenicity. From plant cells transformed with the construct according to the invention it is possible to produce transgenic plants or plant cell cultures which produce haemocyanin polypeptides, for example tobacco, potato, tomato, sugar beet, soya bean, coffee, pea, bean, rape, cotton, rice or maize plants or plant cell cultures.

The present invention also relates to a process for the preparation of a haemocyanin polypeptide. For this, the nucleic acid molecule according to the invention and/or the construct is expressed in a suitable host cell and the protein is isolated from the host cell or the medium by means of conventional processes.

Numerous processes for expression of DNA sequences are known to the skilled person; compare Recombinant Gene Expression Protocols in Methods in Molecular Biology, volume 62, Humana Press Totowa N.J. (1995). The expression can be both constitutive and inducible, inducers such as, for example, IPTG and $Zn^{2+}$ being known to the skilled person. If a H is tag has been fused on to the $NH_2$ terminus of the haemocyanin, the haemocyanin prepared can be purified by chelate formation on a nickel column. Processes for the purification of haemocyanin, in particular KLH, are to be found in Harris et al., Micron 26 (1995), 201-212. The haemocyanin is preferably purified by ion exchange chromatography and/or gel filtration chromatography. The procedure for these measures is known to the skilled person.

In another preferred embodiment, the haemocyanin prepared according to the invention is modified. The modifications include di-, oligo- and polymerization of the monomeric starting substance, for example by crosslinking, e.g. by means of dicyclohexylcarbodiimide or pegylation or association (self assembly). The di-, oligo- and polymers prepared in this way can be separated from one another by gel filtration. The formation of decamers, didecamers or multidecamers is intended in particular. Further modifications include side chain modifications, for example of ε-amino-lysine residues of the haemocyanin, or amino- or carboxy-terminal modifications. Modification of the haemocyanin by covalent bonding to an antigen is particularly preferred, it being possible for the antigen to be reacted stoichiometrically or non-stoichiometrically with the haemocyanin. The antigen is preferably selected from tumour antigens, virus antigens and pathogen antigens, as mentioned above. Further modifications include post-translational events, e.g. glycosylation or partial or complete deglycosylation of the protein.

In a preferred embodiment, the haemocyanin obtained by recombinant expression in prokaryotes or glycosylation-deficient eukaryotes is non-glycosylated. Haemocyanin which is glycosylated by recombinant expression in eukaryotes which are capable of glycosylation, such as yeast cells, plant cells, insect cells or mammalian cells, such as CHO cells or HeLa cells, is also possible according to the invention.

Haemocyanin polypeptides which comprise an amino acid sequence, the amino acid sequence being coded by one or more of the nucleic acid molecules according to the invention, are provided in another embodiment, Haemocyanin polypeptides which comprise at least one amino acid sequence selected from the following group:

SEQ ID NO:25 (HtH1 domain a+signal peptide),
SEQ ID NO:26 (HtH1 domain b),
SEQ ID NO:27 (HtH1 domain c),
SEQ ID NO:28 (HtH1 domain d),
SEQ ID NO:29 (HtH1 domain e),
SEQ ID NO:30 (HtH1 domain f),
SEQ ID NO:31 (HtH1 domain g),
SEQ ID NO:32 (HtH1 domain h),
SEQ ID NO:33 (partial HtH2 domain b),
SEQ ID NO:34 (HtH2 domain c),
SEQ ID NO:35 (HtH2 domain d),
SEQ ID NO:36 (HtH2 domain e),
SEQ ID NO:37 (HtH2 domain f),
SEQ ID NO:38 (HtH2 domain g),
SEQ ID NO:39 (HtH2 domain h),
SEQ ID NO:40 (partial KLH1 domain b),
SEQ ID NO:41 (KLH1 domain c),
SEQ ID NO:42 (partial KLH1 domain d),
SEQ ID NO:43 (partial KLH1 domain e),
SEQ ID NO:44 (KLH2 domain b),
SEQ ID NO:45 (KLH2 domain c),
SEQ ID NO:46 (partial KLH2 domain d),
SEQ ID NO:47 (KLH2 domain g),
SEQ ID NO:48 (partial KLH2 domain h),
SEQ ID NO:63 (HtH1 domain a'+signal peptide),
SEQ ID NO:64 (HtH1 domain h'),
SEQ ID NO:65 (partial HtH2 domain a),
SEQ ID NO:66 (HtH2 domain b'),
SEQ ID NO:67 (HtH2 domain d'),
SEQ ID NO:68 (HtH2 domain e'),
SEQ ID NO:69 (partial KLH1 domain b'),
SEQ ID NO:70 (KLH1 domain e'),
SEQ ID NO:71 (KLH1 domain f),
SEQ ID NO:72 (KLH1 domain g),
SEQ ID NO:73 (KLH1 domain h),
SEQ ID NO:74 (KLH2 domain b'),
SEQ ID NO:75 (KLH2 domain c'),
SEQ ID NO:76 (KLH2 domain d'),
SEQ ID NO:77 (KLH2 domain e),
SEQ ID NO:78 (KLH2 domain f),
SEQ ID NO:79 (KLH2 domain g'),
SEQ ID NO.:158 (partial KLH2 domain h), or a fragment of one of these sequences which has the immunological properties of at least one domain of haemocyanin are preferred.

The invention also includes haemocyanin polypeptides of which the sequence shows at least 60% or 70%, preferably at least 80%, particularly preferably at least 90% or 95% homology to one of the amino acid sequences according to SEQ ID NO:25 to 48 and SEQ ID NO:63 to 79 over a partial region of at least 90 amino acids.

In this connection, the expression "at least 70%, preferably at least 80%, particularly preferably at least 90% homology" relates to concordance at the amino acid sequence level, which can be determined by known methods, e.g. computer-assisted sequence comparisons (Basic local alignment search tool, S. F. Altschul et al., J. Mol. Biol. 215 (1990), 403-410).

The term "homology" known to the skilled person describes here the degree to which two or more polypeptide molecules are related, this being determined by the concordance between the sequences, concordance being understood as meaning both identical concordance and conservative amino acid exchange. The percentage of "homology" is obtained from the percentage of regions in concordance in two or more sequences, taking into account gaps or other sequence peculiarities.

The expression "conservative amino acid exchange" relates to an exchange of an amino acid residue for another amino acid residue, where the exchange does not lead to a change in polarity or charge. An example of a conservative amino acid exchange is the exchange of a non-polar amino acid residue for another non-polar amino acid residue.

The homology of polypeptide molecules which are related to one another can be determined with the aid of known methods. As a rule, special computer programs with algorithms which take account of the particular requirements are employed. Preferred methods for the determination of homology initially produce the greatest concordance between the sequences analysed. Computer programs for determination of the homology between two sequences include, but are not limited to, the GCG program package, including GAP (Devereux, J., et al., Nucleic Acids Research 12 (12): 387 (1984); Genetics Computer Group University of Wisconsin, Madison, (WI)); BLASTP, BLASTN and FASTA (Altschul, S. et al., J. Molec. Biol. 215:403/410 (1990)). The BLAST X program can be obtained from the National Centre for Biotechnology Information (NCBI) and from other sources (BLAST Handbook, Altschul S., et al., NCB NLM NIH Bethesda Md. 20894; Altschul, S., et al., J. Mol. 215:403/410 (1990)). The known Smith Waterman algorithm can also be used for determining homology.

Preferred parameters for the sequence comparison include the following:

| Algorithm: | Needleman and Wunsch, J. Mol. Biol 48:443-453 (1970) |
|---|---|
| Comparison matrix: | BLOSUM 62 of Henikoff and Henikoff, Proc. Natl. Acad. Sci. USA 89:10915-10919 (1992) |
| Gap penalty: | 12 |
| Gap length penalty: | 4 |
| Similarity threshold: | 0 |

The GAP program is also suitable for use with the above parameters. The above parameters are the standard parameters (default parameters) for amino acid sequence comparisons where gaps at the ends do not reduce the homology value. If sequences are very short compared with the reference sequence, it may furthermore be necessary to increase the expected value to up to 100,000 and where appropriate to reduce the word size down to 2.

Further algorithms, gap opening penalties, gap extension penalties and comparison matrices by way of example, including those mentioned in the Programm-Handbuch, Wisconsin-Paket [Program Handbook, Wisconsin Package], version 9, September 1997, can be used. The choice depends on the comparison to be made and furthermore on whether the comparison is to be made between sequence pairs, in which case GAP or best fit are preferred, or between a sequence and a comprehensive sequence database, in which case FASTA or BLAST are preferred.

A concordance of 60% determined with the above mentioned algorithm is designated 60% homology in the context of this Application. The same applies accordingly to higher degrees of homology.

In another embodiment, the invention provides haemocyanin polypeptides which are obtainable by the recombinant preparation method or modifications thereof.

Preferred haemocyanin polypeptides are those which comprise each of the sequences SEQ ID NO: 25 to 32, it being possible for the sequence with SEQ ID NO:25 to be replaced by SEQ ID NO:63 and/or SEQ ID NO:32 to be replaced by SEQ ID NO:64. Haemocyanin polypeptides which are also preferred are those which comprise either the sequences SEQ. ID NO: 33 to 39 or the sequences SEQ ID NO:65, 66, 34-39, it being possible for SEQ ID NO:35 to be replaced by SEQ ID NO:67 and/or SEQ ID NO:36 to be replaced by SEQ ID NO:68. These haemocyanin polypeptides are particularly preferably haemocyanin 1 or 2 from *Haliotis tuberculata*.

Haemocyanin 1 from *Haliotis tuberculata*, which has an apparent molecular weight of 370 kDa in SDS-PAGE under reducing conditions, is particularly preferred. Haemocyanin 2 from *Haliotis tuberculata*, which has an apparent molecular weight of 370 kDa in SDS-PAGE under reducing conditions, is furthermore particularly preferred. The haemocyanins are obtainable from whole haemocyanin from *Haliotis tuberculata* by the selective dissociation process described in the examples.

Haemocyanin polypeptides which are furthermore preferred are those which comprise each of the sequences SEQ ID NO: 40 to 43 or the sequences SEQ ID NO:40 to 43 and SEQ ID NO:71 to 73, it being possible in each case for the sequence with SEQ ID NO:40 to be replaced by SEQ ID NO:66 and/or SEQ ID NO:43 to be replaced by SEQ ID NO:70. Haemocyanin polypeptides which are also preferred are those which comprise either each of the sequences SEQ ID NO: 44 to 48 or the sequences SEQ ID NO:44 to 46, 77, 78, 47, 48, it being possible in each case for the sequence with SEQ ID NO:44 to be replaced by SEQ ID NO:74, SEQ ID NO:45 to be replaced by SEQ ID NO:75, SEQ ID NO:46 to be replaced by SEQ ID NO:76 and/or SEQ ID NO:47 to be replaced by SEQ ID NO:79.

These haemocyanin polypeptides are particularly preferably complete haemocyanin 1 (KLH1) or 2 (KLH2) from *Megathura crenulata*.

Non-glycosylated and glycosylated haemocyanin polypeptide obtainable by expression in host cells which are capable or incapable of glycosylation is furthermore provided. Depending on the envisaged use of the haemocyanin polypeptide, the glycosylation pattern of yeast, in particular methylotrophic yeast, of plant cells or of COS or HeLa cells can be preferred.

The invention furthermore relates to pharmaceutical compositions which comprise the nucleic acid molecules according to the invention and physiologically tolerated additives known in the prior art. The pharmaceutical compositions are preferably employed for non-specific immunostimulation in the form of a gene therapy, haemocyanin polypeptides being expressed after transformation with a suitable vector and serving to antigenize the tissue.

In particular, the invention provides the use of a nucleic acid molecule according to the invention which is bonded to an antigen-coding DNA sequence for specific immunization against this antigen. Without being bound to this theory, the immunization here is based on non-specific stimulation of the immune system by haemocyanin polypeptide epitopes and more extensive specific immunization by recognition of antigen epitopes by the immune system.

Such an immunization is particularly valuable in respect of pathogen antigens, and especially in respect of tumour antigens. The usability of the pharmaceutical composition according to the invention for treatment of tumour diseases also results from the cross-reactivity of the haemocyanin-specific antibodies with carbohydrate residues, which occur on the surface of tumours, such as e.g. the Thomsen-Friedenreich antigen, which occurs in the majority of human tumours, such as epithelial carcinomas, ovarian carcinoma, colorectal carcinoma, mammary carcinoma, bronchial carcinoma and bladder carcinoma.

The pharmaceutical compositions according to the invention can furthermore be employed for treatment of parasitic diseases, such as schistosomiasis, and for prevention of cocaine abuse.

Pharmaceutical compositions which comprise a haemocyanin polypeptide according to the invention in combination with one or more physiologically tolerated additives are provided as a further embodiment of the present invention. As already mentioned above, such a haemocyanin polypeptide can consist of a complete haemocyanin subunit, of one or more domains and of one or more fragments of such domains, provided that these fragments still have the immunological properties of at least one domain of a haemocyanin. Such a pharmaceutical composition is suitable e.g. as an antiparasitic composition, antivirus composition or antitumour composition due to either the non-specific immunostimulation, which is to be attributed solely to the haemocyanin, or due to the specific immune reaction to antigens associated with the haemocyanin. It can thus be employed e.g. for treatment of schistosomiasis, epithelial carcinomas, ovarian carcinoma, colorectal carcinoma, mammary carcinoma, bronchial carcinoma and bladder carcinomas, but is also suitable for treatment of high blood pressure. The treatment of high blood pressure is achieved by carrying out an immunization with the aid of haemocyanin-β-adrenergic receptor peptide constructs and/or fusion proteins.

In another embodiment, the pharmaceutical compositions according to the invention are used as vaccines. They can thus make a valuable contribution to the prophylaxis of diseases caused by known pathogens. This applies in particular to pharmaceutical compositions in which a haemocyanin polypeptide is coupled to a virus, virus constituent, killed bacteria, bacteria constituents, in particular surface proteins from virus or bacteria envelopes, DNA, DNA constituents, inorganic or organic molecules, e.g. carbohydrates, peptides and/or glycoproteins.

According to another preferred embodiment, the pharmaceutical composition according to the invention is used for prevention of cocaine abuse.

Liposomes are particularly suitable for administration both of the nucleic acid molecules according to the invention and of the haemocyanin polypeptides. The present invention accordingly relates to liposomes which comprise a nucleic acid molecule according to the invention, a construct according to the invention or a haemocyanin polypeptide according to the invention.

Various methods for the preparation of liposomes which can be used for pharmaceutical purposes are known to the skilled person. The selectivity of the liposomes comprising the nucleic acid molecules or haemocyanin polypeptides according to the invention can be increased by the additional incorporation into the liposome of cell recognition molecules, which bind selectively to target cells. Receptor ligands which bind to receptors of the target cells or, especially in the case of tumours, antibodies directed against surface antigens of the particular target cells envisaged are particularly suitable for this.

The haemocyanin polypeptides according to the invention are furthermore envisaged as carrier molecules for medicaments, such as e.g. cytostatics. The increase in the molecular weight prolongs the physiological half-life of the medicaments considerably since the loss due to ultrafiltration in the kidneys is significantly reduced.

The vaccines are formulated by methods known to the skilled person; in some embodiments the additional use of adjuvants, such as e.g. Freund's adjuvant or polysaccharides, is envisaged.

The invention furthermore provides antibodies which react specifically with the haemocyanin polypeptide according to the invention and are obtainable by immunization of a test animal with a haemocyanin polypeptide. Polyclonal antibodies can be obtained by immunization, for example, of rabbits and subsequent isolation of antisera. Monoclonal antibodies can be obtained by standard methods by immunization of e.g. mice, isolation and immortalization of the spleen cells and cloning of the hybridomas which produce antibodies specific for haemocyanin.

A screening method for identification of tumour-specific DNA in a cell is furthermore provided, this comprising the steps:

a) bringing cell DNA and/or cell protein into contact with a probe comprising the nucleic acid molecule according to the invention and/or the antibody according to the invention and b) detecting the specific binding.

The tumour to be detected is preferably a bladder carcinoma, epithelial carcinoma, ovarian carcinoma, mammary carcinoma, bronchial carcinoma or colorectal carcinoma.

It is intended to illustrate the invention with the following figures and examples, but not to limit this in any way. Further embodiments, which are also included, are accessible to the skilled person on the basis of the description and the examples.

BRIEF DESCRIPTION OF THE SEVERAL VIEWS OF THE DRAWINGS

FIG. 1 shows the characterization and purification of *Haliotis tuberculata* haemocyanin (HtH):

Figure 2L:
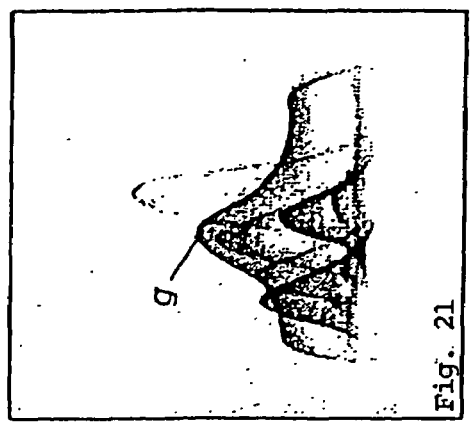
Figure 2P:
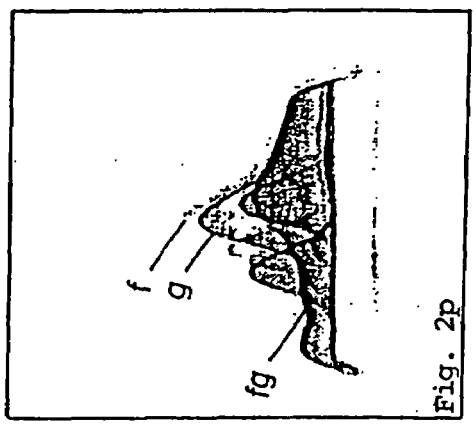

(a) Electron microscopy of negatively stained whole HtH, which has been purified by ultracentrifugation of cell-free haemolymph;

(b) SDS polyacrylamide gel electrophoresis (7.5% polyacrylamide) of HtH1 compared with KLH (MW 370 kDa);

(c) Native polyacrylamide gel electrophoresis (5% polyacrylamide) of the HtH subunit preparation, the anode being at the lower edge;

(d) Crossed immunoelectrophoresis of the two HtH subunits using anti-HtH antibodies from the rabbit;

(e) Electron microscopy of the remaining HtH1 didecamers (white arrows) after selective dissociation of HtH2 (black arrows);

(f) Elution profile of the gel filtration chromatography (Biogel A15m) in the presence of ammonium molybdate/polyethylene glycol solution (pH 5.9) after selective dissociation of HtH2 into its subunit and subsequent concentration of HtH1 by ultracentrifugation;

(g) Native polyacrylamide gel electrophoresis (6.5% polyacrylamide) of HtH1 and HtH2 subunits purified by gel chromatography compared with the starting material;

(h,i) Crossed immunoelectrophoresis of chromatographically purified HtH subunits; and (j,m) Crossed immunoelectrophoresis of the purified HtH subunits using anti-KLH antibodies from the rabbit which are specific for KLH1 and KLH2.

FIG. 2 shows the analysis of the subunit organization of HtH1, anti-HtH1 antibodies from the rabbit having been used for the immunoelectrophoresis and the anode being on the left-hand side;

(a) Crossed immunoelectrophoresis after limited proteolysis of HtH1 with the aid of elastase;

(b) SDS polyacrylamide gel electrophoresis (7.5% polyacrylamide) of the elastase-cleaved HtH1 subunit;

(c,d,g-j,l,n,p) Crossed immunoelectrophoresis of the elastase cleavage products of the HtH1 subunit;

(e) Crossed immunoelectrophoresis after limited proteolysis of HtH1 with the aid of V8 protease;

(f) SDS polyacrylamide gel electrophoresis (7.5% polyacrylamide) of the V8 protease-cleaved HtH1 subunit;

(k,m,o) Crossed immunoelectrophoresis after limited proteolysis of HtH1 with the aid of the three stated proteases.

FIG. 3 shows the separation of proteolytic cleavage products of the subunit HtH1 with the aid of HPLC.

FIG. 4 shows the genomic sequence of the HtH1 gene.

FIG. 5 shows the primary structure deduced for the HtH1 protein.

FIG. 6 shows the genomic sequence of the HtH2 gene.

FIG. 7 shows the primary structure deduced for the HtH2 protein.

FIG. 8 shows the genomic sequence of the KLH1 gene.

FIG. 9 shows the primary structure deduced for the KLH1 protein.

FIG. 10 shows the genomic sequence of the KLH2 gene.

FIG. 11 shows the primary structure deduced for the KLH2 protein.

DETAILED DESCRIPTION OF THE INVENTION

Examples

Material and Methods

1. Preparation of the Haemolymph and Isolation of Haemocyanin

Individuals of the European abalone *Haliotis tuberculata* from the French Atlantic coast region were provided by S. M. E. L (Blainville sur Mer, France) and Biosyn (Fellbach, Germany). The animals were kept in a 300 l sea-water aquarium at 17° C. and fed with brown algae. For removal of the haemolymph, the abalones were placed on ice in a closed plastic bag. After one hour, large volumes of haemolymph had been secreted through their skin. It emerged that the haemocyanin obtained by this process is identical to the haemocyanin which could be collected by cutting a hollow in the foot of cooled-down sea snails using a scalpel blade. The blood cells were separated from the haemolymph by centrifugation at 800 g for 30 min at 4° C. The whole haemocyanin was then immediately sedimented by preparative ultracentrifugation at 30,000 g for 4 hours at 4° C. The supernatant was discarded and the blue haemocyanin pellet was suspended overnight in "stabilization buffer" (0.05 M Tris, 5 mM $CaCl_2$, 5 mM $MgCl_2$, 0.15 M NaCl, 1 mM PMSF, pH 7.4) and stored at 4° C.

Using the process described by Harris et al., 1995, supra, intact HtH1 was obtained from the whole HtH by selective dissociation of HtH2 in ammonium molybdate/polyethylene glycol (1%/0.2%) solution, pH 5.9 and subsequent ultracentrifugation. The partly purified HtH1 pellet formed was dissolved and purified to homogeneity by gel filtration on a Biogel A15m device. The last step resulted in small amounts of purified HtH2. Native HtH1 and HtH2 was dissociated quantitatively into the subunits by dialysis against "dissociation buffer" (0.13 M glycine/NaOH, pH 9.6) at 4° C. overnight; the presence of EDTA was not necessary. 1 mM PMSF was added at each stage of the purification to inhibit proteolysis.

2. Electron Microscopy

Conventional "negative staining" was carried out by the individual drop method (Harris and Horne in Harris, J. R. (editors) Electron microscopy in biology, (1991), IRL Press Oxford, p. 203-228). Carbon carrier films were initially subjected to glow discharge for 20 seconds to render them hydrophilic and adsorptive for the protein. The protein samples are allowed to adsorb on to the carbon films for 60 seconds. The buffer salts are then removed by sequential washing with four successive 20 µl drops of water. Finally, the gratings are negatively stained with a 20 µl drop of 5% aqueous ammonium molybdate containing 1% trehalose (pH 7.0) and left to dry at room temperature. A Zeiss EM 900 transmission electron microscope is used for the electron microscopy analysis.

3. Polyacrylamide Gel Electrophoresis and Immunoelectrophoresis

SDS polyacrylamide gel electrophoresis (SDS-PAGE) was carried out by the method of Laemmli (Nature 227 (1970), 670-685). An alkaline system according to Markl et al. (1979) J. Comp. Physiol. 133 B, 167-175 with a 0.33 M Tris/borate, pH 9.6 as the gel buffer and 0.065 M Tris/borate, pH 9.6 as the electrode buffer was used for the native PAGE. Crossed and "crossed-line" immunoelectrophoresis (1E) were carried out in accordance with Weeke (Scand. J. Immunol. 2 (1973), Suppl. 1, 47-56) or Kroll (Scand. J. Immunol. 2, Suppl. 1 (1973), 79-81). Rabbit antibodies against dissociated whole HtH and purified HtH1 were produced by Charles River Deutschland (Kisslegg, Germany). The immunization process was carried out in accordance with Markl and Winter (J. Comp. Physiol. 159B (1989), 139-151).

4. Limited Proteolysis and Isolation of the Fragments

The limited proteolysis was carried out at 37° C. in 0.13 M glycine/NaOH, pH 9.6 by addition of one of the following enzymes (Sigma, Deisenhofen, Germany), which were dissolved in 0.1 M $NH_4HCO_3$, pH 8.0: *Staphylococcus aureus* V8 protease type XVII (8400), papain type II from papaya milk (P-3125), bovine pancreas elastase type IV (E-0258), chymotrypsin and trypsin. The haemocyanin concentration was between 1 and 10 mg/ml. The final concentration of the enzyme was 2% (weight/weight). The proteolysis was ended after 5 hours by freezing to −20° C. The HPLC process was carried out on a device from Applied Biosystems (BAI, Bensheim, Germany) equipped with a model 1000S Diode Array detector. The proteolytic fragments were introduced on to a small Mono-Q anion exchanger column (Pharmacia, Freiburg, Germany), which had been equilibrated with 0.02 M Tris/HCl, pH 8.0, and were eluted with a linear sodium chloride gradient (0.0 M -0.5 M CaCl) in the same buffer at a flow rate of 1 ml/min. Alternatively, the proteolytic fragments were isolated by cutting out the bands from native PAGE gels (Markl et al., 1979) J. Comp. Physiol. 133 B, 167-175, after they had first been inversely stained with the Roti-White system (Roth, Karlsruhe, Germany) in accordance with Fernandez-Patron et al. (1995) Anal. Biochem. 224, 203-211. For subsequent cleavage with a second enzyme, the fragments isolated were first dialysed overnight against 0.13 M glycine/NaOH, pH 9.6 to remove NaCl.

5. Amino Acid Sequence Analysis

The proteins obtained by the HPLC process were denatured in SDS-containing sample buffer and separated by SDS-PAGE (Laemmli, 1970, supra; 7.5% polyacrylamide). To prevent blocking of the $NH_2$ terminus, 0.6% (weight/weight) thioglycollic acid was added to the cathode buffer (Walsh et al., Biochemistry 27 (1988), 6867-6876). The protein bands were transferred by electro-transfer to ProBlot membranes (Applied Biosystems, Germany) in a vertical blotting chamber (25 mM borate buffer, pH 8.8, containing 2 mM EDTA; 10 min/100 mA, 15 min/200 mA, 12 h/300 mA). Detection of the individual polypeptides on the membranes was carried out with Ponceau S stain. The polypeptide bands of interest were cut out and sequenced in a 477A protein sequencing device from Applied Biosystems. The amounts of polypeptides applied to the sequencing device were in the lower pmol range.

6. cDNA Cloning and Sequence Analysis

A lambda-cDNA expression library was established from poly(A$^+$)—RNA from Haliotis mantle tissue using the vector Lambda ZAP Express® in accordance with the manufacturer's instructions (Stratagene, Heidelberg, Germany). The clones were isolated using HtH-specific rabbit antibodies. The nucleotide sequencing was carried out on both strands using the Taq Dye deoxy Terminator® system. The sequences were arranged with the software CLUSTAL W (1.7)® and TREEVIEW® (Thompson et al., Nucl. Acids Res. 22 (1994), 4673-4680).

Example 1

Isolation of HtH and Separation of Two Different Types (HtH1 and HtH2)

The haemolymph was obtained from adult abalones. The blood cells were removed by centrifugation and the haemocyanin was then sedimented by ultracentrifugation. The blue haemocyanin pellet was dissolved again in "stabilization buffer" (pH 7.4) and examined by electron microscopy (FIG. 1a). It comprised mainly typical di-decamers, accompanied by a small content of decamers and tridecamers. Denaturing in 2% SDS in the presence of reducing substances and subsequent SDS-PAGE separation resulted in a single band, which corresponded to the polypeptide with an apparent molecular weight of 370 kDa, which is only slightly below the apparent subunit weight of KLH (FIG. 1b). Complete dissociation of the oligomers and of the di-decamers into the native polypeptides (subunits) was achieved by overnight dialysis of HtH against "dissociation buffer" (pH 9.6). The native PAGE method, which was used on these samples, showed a main and a secondary component (FIG. 1c). Crossed immunoelectrophoresis (crossed IE) using polyclonal rabbit antibodies generated against purified whole HtH showed two components which are immunologically different but show the classical reaction of being partly immunologically identical (FIG. 1d). Their preparative isolation (FIG. 1e-i) showed that they are subunits of two different HtH types, called HtH1 and HtH2, and the patterns of the native PAGE and crossed IE methods could be assigned to each individually (FIG. 1c, d).

The separation of HtH1 and HtH2 was carried out by the method of selective dissociation according to Harris et al., 1995, supra. In ammonium molybdate/polyethylene glycol, HtH1 in the oligomer state (di-decamer) was completely stable, while HtH2 dissociated completely into the subunits (FIG. 1e). This allowed quantitative sedimentation of HtH1 in an ultracentrifuge, while the majority of the HtH2 remained in the supernatant. Large amounts of HtH1 were purified to homogeneity from the redissolved pellet by gel filtration chromatography, which also resulted in small amounts of pure HtH2 (FIG. 1f). The fractions were investigated by native PAGE (FIG. 1g) and crossed IE (FIG. 1h, i). The process of selective dissociation of HtH2 removed all the tri-decamer from the samples, which suggests that the latter are built up from HtH2, but not from HtH1 (FIG. 1e). The selective dissociation behaviour of HtH2 and also the ability to form aggregates which are larger than in vivo di-decamers correspond to the properties of KLH2. Conversely, the stability of HtH1 under these conditions and its inability to assemble into aggregates larger than di-decamers resemble the behaviour of KLH1. This feature of being related is demonstrated further by the reaction of anti-KLH1 and anti-KLH2 antibodies against the two HtH types (FIG. 1j-m).

Example 2

Analysis of the Organization of the HtH1 Subunit

The eight functional units (FUs, often called "functional domains") which form a mollusc haemocyanin subunit differ in primary structure and show no immunological cross-reactivity, as emerged from crossed IE. In the case of the purified HtH1 subunit (FIG. 1g, h), small concentrations of five different proteases (elastase, V8 protease, papain, trypsin and chymotrypsin) which had cleaved the peptide bonds between adjacent FUs of KLH1 and KLH2 were used (Gebauer et al., 1994, supra, Söhngen et al., 1997, supra). The cleavage products were investigated by crossed IE and SDS-PAGE (FIG. 2). Elastase treatment produces eight individual FUs, deduced from the number of different immunoprecipitation peaks in the crossed IE (FIG. 2a) and with the apparent molecular weight of approx. 50 kDa of the main portion of the cleavage products in SDS-PAGE (FIG. 2b). A further precipitation peak was recognized as FU dimer, which was formed by incomplete cleavage of the segment ab (FIG. 2a). By an HPLC process with a Mono-Q column (FIG. 3a), two of the elastase cleavage products were obtained in a sufficient purity to allow their clear assignment to two of the eight precipitation peaks (FIG. 2c, d) by "crossed-line IE". The other four proteases had different cleavage patterns, which comprised mixtures of individual FUs and larger fragments containing two, three or more FUs (e.g. FIG. 2e, f). Many of them were concentrated to a sufficient amount by the HPLC process (FIGS. 3b-e) to allow their identification in their corresponding SDS-PAGE and crossed IE patterns. A number of these components were sequenced N-terminally by blot transfer of SDS gels on ProBlot® membranes (Table 1). The results were compared with the N-terminal sequences which had been obtained from the apparently orthologous protein in Megathura crenulata, KLH1 (Table I), the complete FU arrangement of which is available (Söhngen et al., 1997, supra; cf. FIG. 5b). The result of the entire batch led to the determination of the complete FU arrangement within the HtH1 subunit (FIG. 2a).

Figure 2K:
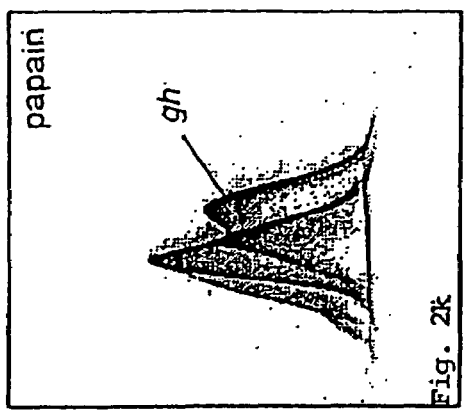
Figure 2O:
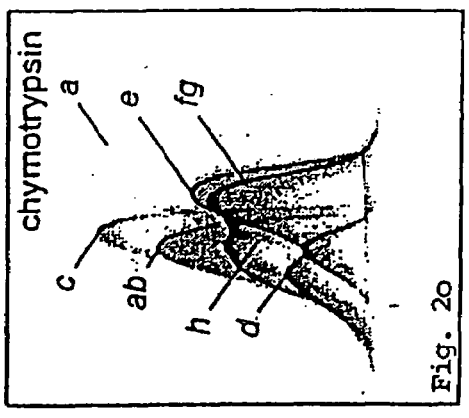
Figure 2J:
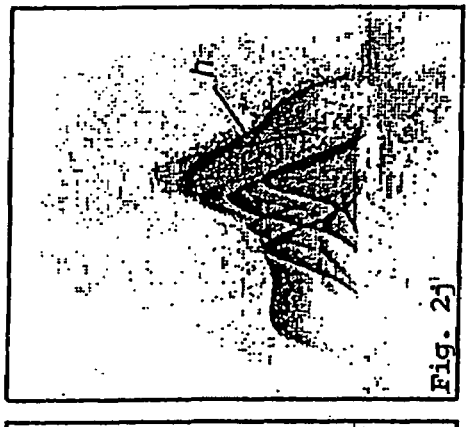
Figure 3A:
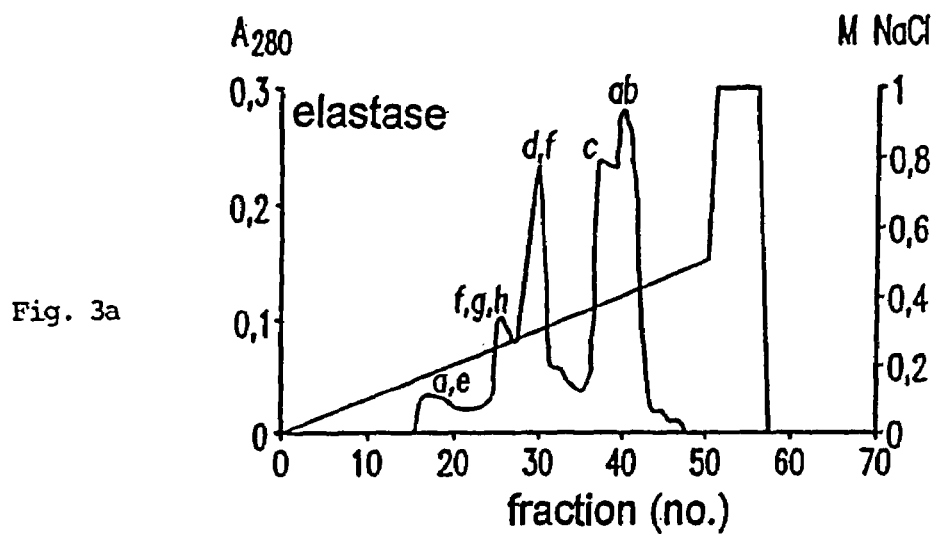
Figure 3B:
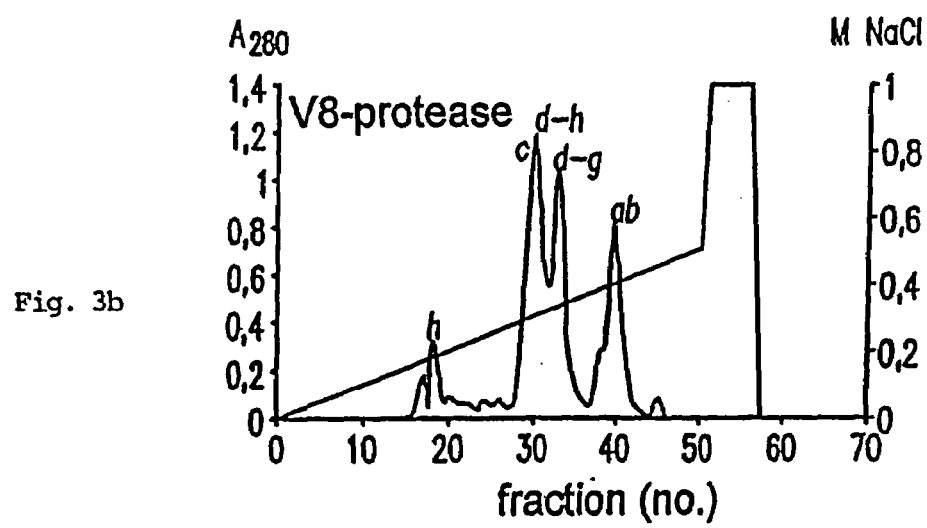
Figure 3C:
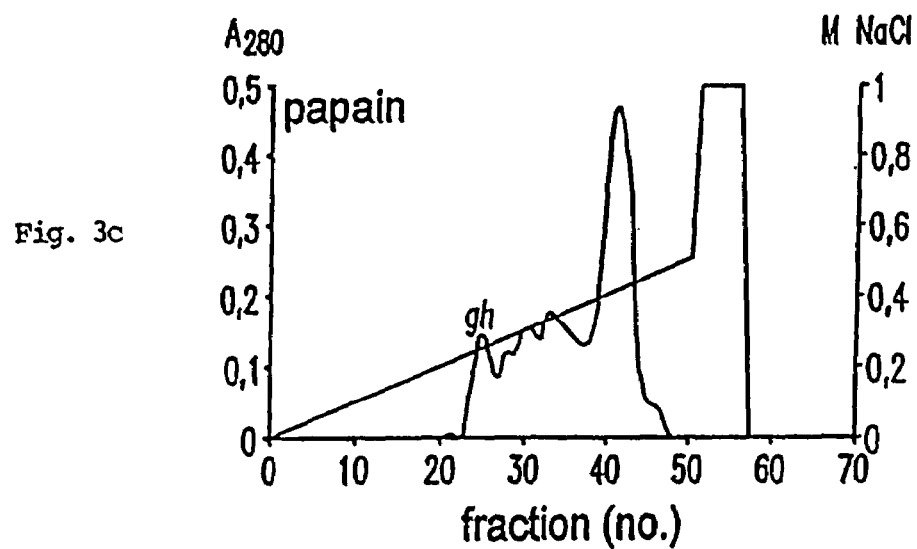

In particular, cleavage of the HtH1 subunit (1-abcdefgh) with V8 protease resulted in four precipitation peaks in the crossed IE (FIG. 2e). The SDS-PAGE showed five different fragments (FIG. 2f): 220 kDa (5 FUs), 185 kDa (4 FUs), 100 kDa (2 FUs), 55 kDa (1 FU) and 46 kDa (1 FU). The 100 kDa fragment was isolated by the HPLC method (FIG. 3b) and identified by N-terminal sequencing as 1-ab, since the sequence was identical to that of the intact subunit (Table I). In the "crossed-line" IE process, 1-ab fused with three precipitation peaks of the elastase cleavage pattern. On the basis of the evaluation, they represent fragments 1-ab, 1-a and 1-b (FIG. 2g). However, it remained unclear which peak represents 1-a and which 1-b. In a second step, the 1-ab purified by HPLC was cleaved by elastase into its component FUs, from which one could be eluted by the native PAGE gel strip method and was assigned to the elastase pattern by the "crossed-line" IE method (FIG. 2h) and sequenced N-terminally. This component had the same N-terminal sequence as the whole subunit and was therefore identical to 1-a. The second FU of the 100 kDa fragment is thus 1-b (FIG. 2a; Table I). HPLC-purified 1-c and 1-h were also obtained (FIG. 3b), identified by N-terminal sequence similarities with the corresponding FUs in KLH1 (Table I) and assigned by the "crossed-line" IE method to their corresponding precipitation peaks in the elastase pattern (FIG. 2i, j). 1-a, 1-b, 1-c and 1-h were furthermore identified (FIG. 2a). Using papain for subunit cleavage, five different peaks were obtained in the crossed IE method (FIG. 2k). A 100 kDa fragment (2 FUs) was purified from such a sample by the HPLC method (FIG. 3c), and, according to the "crossed-line" IE method, contained the FU 1-h already identified and one of the four FUs still not identified and therefore must be 1-gh (FIG. 2k, 3c). In fact, this fragment had an N-terminal sequence which showed similarities with KLH1-g (Table I). For further confirmation, the HPLC-purified fragment 1-gh was cleaved into its constituent FUs with elastase, from which 1-g was purified and identified by N-terminal sequencing. It was assigned to its peak in the elastase cleavage patter by the "crossed-line" IE method (FIG. 2l).

Figure 2N:
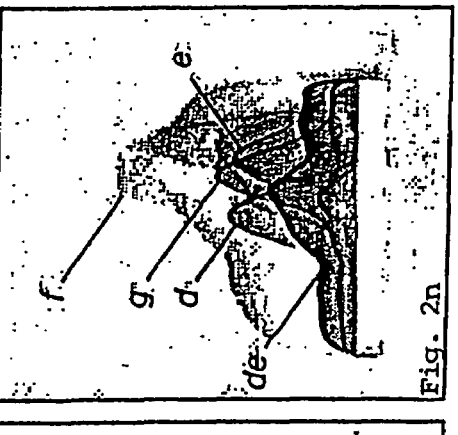
Figure 2I:
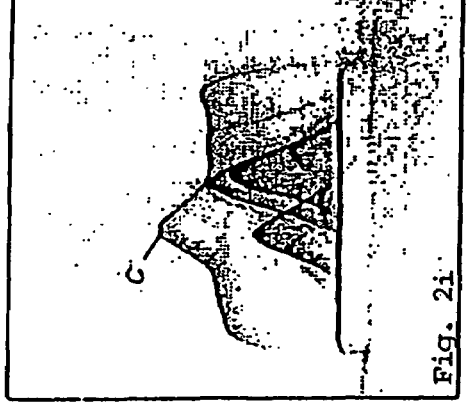
Figure 2M:
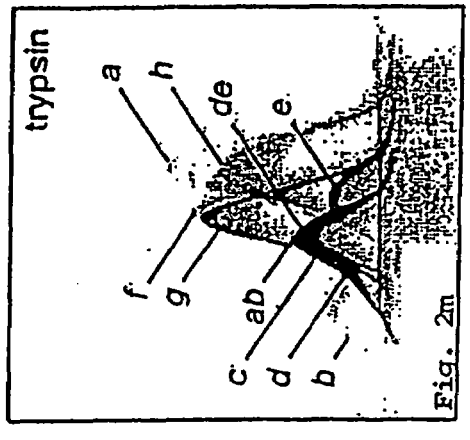
Figure 3D:
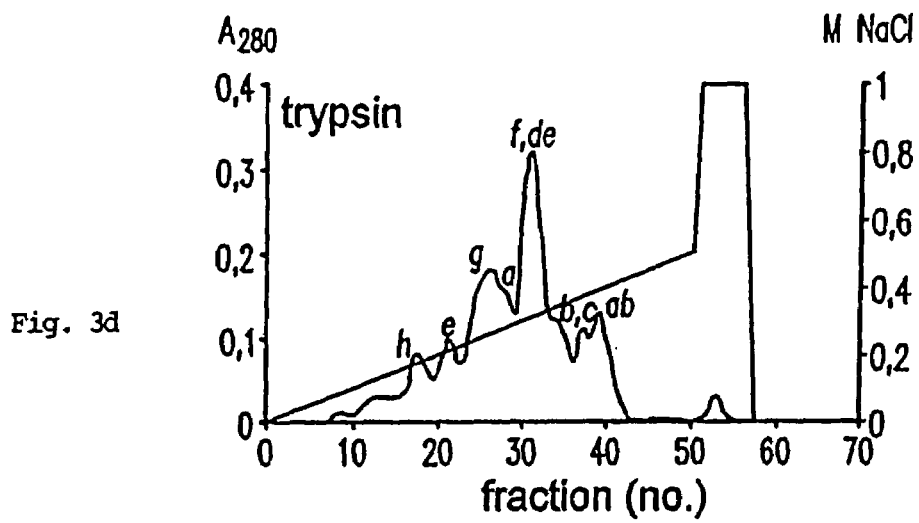
Figure 3E:
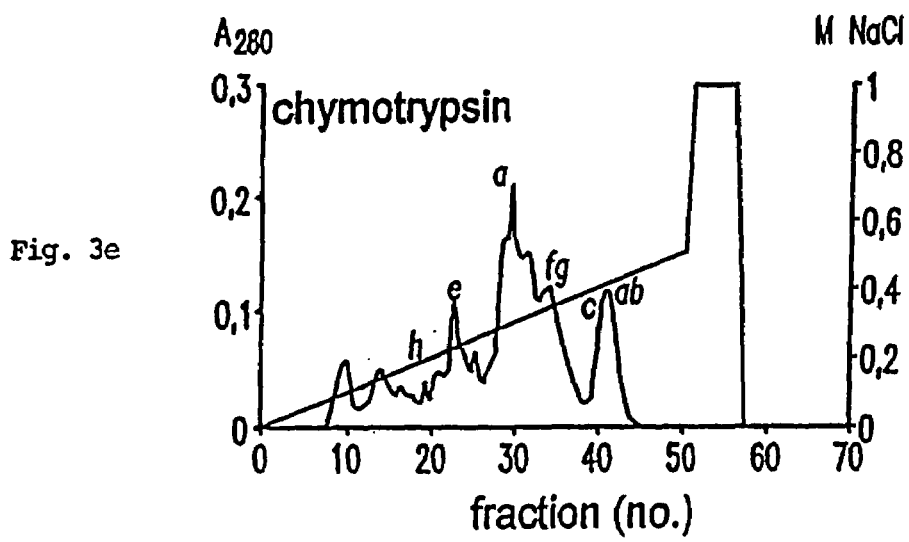

The 220 kDa fragment from the V8 protease cleavage (FIG. 2e, f) was purified by HPLC (FIG. 3b) and in the "crossed-line" IE method fused with 1-h, 1-g and three peaks of the elastase cleavage pattern which have not yet been identified. The 185 kDa fragment was furthermore obtained in a sufficient purity (FIG. 2e, f; 3b), and it was shown that it comprised the same components with the exception of 1-h. This suggested that the 22 kDa and the 185 kDa fragment are 1-defgh and 1-defg respectively. In fact, the N-terminal sequence was practically identical and furthermore showed similarity with KLH1-d (Table I). Cleavage of the HtH1 subunit with trypsin resulted in a large number of components in the molecular weight range of one or two FUs (FIG. 2m). Several of the components were concentrated in HPLC fractions (FIG. 3d). A 100 kDa fragment proved to be particularly useful since it had the same N-terminal sequence as the fragment 1-defg from the v8 protease cleavage (Table I); the 100 kDa fragment should therefore be 1-de. In the "crossed-line" IE method, this component fused with two of the three FU peaks of the elastase cleavage pattern not yet identified (FIG. 2n), which should therefore be 1-d and 1-e, and thus left a single possibility for 1-f. The "crossed-line" IE method also showed that FU 1-f was furthermore present in the 1-de fraction (FIG. 2n). The identification of 1-f was confirmed by cleavage of the subunit with chymotrypsin (FIG. 2o) and a subsequent HPLC process (FIG. 3e). This cleavage gave, inter alia, a 95 kDa fragment (2 FUs) which fused with 1-g and a second peak (FIG. 2p) in the "crossed-line" IE method and could therefore be either 1-gh (which could be ruled out since 1-h had already been identified) or 1-fg (which seems appropriate on the basis of the further peak in question, which was identical to the remaining candidate). In fact, this fragment showed a new N-terminal sequence which is similar to KLH1-f in a certain manner. The last problem was now to assign the two remaining FU peaks to 1-d and 1-e. This was achieved using HPLC-isolated FUs from samples in which the subunit had been cleaved with elastase. (FIGS. 2c, d; 3a). The more acidic component in the crossed IE method was deduced as 1-d from its N-terminal sequence, which is identical to that of 1-defgh (FIG. 2c, Table I), while the more basic component of the 1-d/1-g pair had a new N-terminal sequence (Table I) and therefore had to be 1-e (FIG. 2a). The structure of the functional units of subunit HtH1 was thus clarified.

Example 3

Comparison of the molecular weights and N-terminal sequences of the biochemically isolated functional units (FUs) from HtH1 and KLH1. The various FUs, each with an intact binuclear copper-binding site, were liberated from their larger unit as globular segments by limited proteolysis; cf. the section "Isolation and analysis of the units from HtH1". The KLH1 data were obtained from Söhngen et al., supra. The assignment as an actual unit was done on the basis of the molecular weight and the immunological properties (cf. FIG. 2). The unusually low molecular weight of isolated HtH1-d could means that a large peptide was split off C-terminally.

TABLE 1

| Functional unit | Weight (kDa) | N-terminal sequence |
| --- | --- | --- |
| HtH1-a | 53 | DNVVRKDVSHLTDDEVQ |
| KLH1-a | 50 | ENLVRKDVERL |
| HtH1-b | 48 | ? |
| KLH1-b | 45 | ? |
| HtH1-c | 46 | FEDEKHSLRIRKNVDSLTPEENTNERLR |
| KLH1-c | 45 | KVPRSRLIRKNVDRLTPSE |
| HtH1-d | 40 | VEEVTGASHIRKNLNDLNTGEM |
| KLH1-d | 50 | EVTSANRIRKNIENLS |
| HtH1-e | 49 | ILDHDHEEETLVRKNIIDLSP |
| KLH1-e | 50 | ? |
| HtH1-f | 50 | KLNSRKHTPNRVRHELSSLSSRDIASLKA |
| KLH1-f | 45 | HHLSXNKVRHDLSTL |
| HtH1-g | 45 | DHQSGSIAGSGVRKDVNTLTKAETDNLRE |
| KLH1-g | 45 | SSMAGHFVRKDINTLTP |
| HtH1-h | 55 | DEHHDDRLADVLIRKEVDFLSLQEANAIKD |
| KLH1-h | 60 | HEDHHEDILVRKNTHSL |

Example 4

Cloning of Haemocyanin cDNA

1. For cloning the cDNA of haemocyanin, mRNA was isolated from the mantle tissue of the particular mollusc. The first cDNA strand was obtained by reverse transcription with Oligo(dT) as a primer. The second strand was obtained conventional synthesis with random primers. The cDNA obtained in this way was cloned in a lambda expression vector to form a cDNA expression library. Using an anti-haemocyanin antibody, the library was searched under suitable conditions, positive clones being obtained. These positive clones were isolated, sequenced and characterized.

2. A cDNA probe was prepared from the N-terminal region of a positive clone obtained, and the cDNA library was searched with this. The positive clones obtained were in turn isolated, sequenced and characterized.

3. To obtain sequences arranged still further to 5', another expression library was established from cDNA, this being obtained with the aid of a combination of haemocyanin-specific and "random" primers. This cDNA library was searched with cDNA probes which correspond to the "N-terminal" regions of the positive clones obtained under (2.). The positive clones obtained were isolated, sequenced and characterized.

Example 5

Cloning of Haemocyanin Genes

Genomic DNA was isolated by standard methods. The PCR reaction was carried out with the aid of haemocyanin-specific primers in order to amplify the gene sections of the haemocyanins of interest. The amplification products obtained were cloned in a suitable vector (for example pgem T or pGem T easy (Promega, Mannheim) sequenced and characterized.

Example 6

Recombinant Expression of Haemocyanin

A PCR reaction was carried out with a cDNA clone which contains the coding sequence for HtH-1d in order to amplify specifically the coding sequence of the domain 1d. Synthetically prepared oligonucleotides were used as primers.

Primer 1 (upstream) comprises six nucleotides of the end of the domain HtH-1c, an SacI cleavage site and 12 nucleotides of the end of the domain HtH-1d. Primer 2 (downstream) comprises six nucleotides of the start of the domain HtH-1e, an SalI cleavage site and an HtH1-d-specific sequence.

| PCR conditions: | 2 min 95° C. |
| --- | --- |
| | 30 sec 95° C. |
| | 30 sec 55° C. |
| | 1 min 72° C. |
| | 35 cycles |
| | 10 min 72° C. |

The amplification product was cloned in the pGEM T easy PCR cloning vector (Promega) in XL-1 Blue (Stratagene). After isolation of the recombinant plasmid and restriction with SacI and SalI, the cDNA of domain 1d could be isolated. The expression vector pQE30 (Qiagen) was also restricted with the corresponding enzymes.

The ligation was then carried out between the HtH-1d-cDNA (restricted with SacI and SalI) and pQE (restricted with SacI and SalI). Directed cloning of the cDNA which codes for HtH-1d in an expression vector is thus possible. The expression of HtH1-d in pQE in XL-1 Blue is carried out in accordance with the manufacturer's instructions. The expression of further HtH1, HtH2 or KLH1 or KLH2 domains can be carried out analogously.

The invention claimed is:

1. An isolated nucleic acid molecule comprising a nucleic acid sequence that codes for a Keyhole Limpit Hemocyanin 2 (KLH2) polypeptide and comprises at least one intron sequence, wherein said nucleic acid sequence is selected from the group consisting of, (a) a DNA sequence or the corresponding RNA sequence selected from the group consisting of:
SEQ ID NO:20 (KLH2 domain b),
SEQ ID NO:21 (KLH2 domain c),
SEQ ID NO:22 (partial KLH2 domain d),
SEQ ID NO:23 (KLH2 domain g),
SEQ ID NO:24 (partial KLH2 domain h),
SEQ ID NO:57 (KLH2 domain b'),
SEQ ID NO:58 (KLH2 domain c'),
SEQ ID NO:59 (KLH2 domain d'),
SEQ ID NO:60 (KLH2 domain e),
SEQ ID NO:61 (KLH2 domain f),
SEQ ID NO:62 (KLH2 domain g'),
SEQ ID NO:102 (KLH2 domain b"),
SEQ ID NO:103 (KLH2 domain c"),
SEQ ID NO:104 (KLH2 domain d"),
SEQ ID NO:105 (KLH2 domain e"),
SEQ ID NO:106 (KLH2 domain f"),
SEQ ID NO:107 (KLH2 domain g"); and,
SEQ ID NO:108 (partial KLH2 domain h"), (b) a nucleic acid sequence that hybridizes under stringent hybridization conditions of 0.55×SSC; 1% blocking reagent; 0.1% sodium dodecyl sulfate (SDS) at about 68° C. overnight, to a counter-strand of a nucleic acid sequence according to (a); and (c) a nucleic-acid sequence that has at least 90% sequence identity to one of the nucleic acid sequences described under (a).

2. The isolated nucleic acid molecule according to claim 1, wherein the intron sequence is selected from:

(i) a DNA sequencer the corresponding RNA sequence selected from the group consisting of:
SEQ ID NO:147 (KLH2 intron 2B/2C),
SEQ ID NO:148 (KLH2 intron 2C/2D),
SEQ ID NO:149 (KLH2 intron 2D/2E),
SEQ ID NO:150 (KLH2 intron 2E/2F), SEQ ID NO:151 (KLH2 intron 2F),
SEQ ID NO:152 (KLH2 intron 2F-2/2G),
SEQ ID NO:153 (KLH2 intron 2G-1/2G-2),
SEQ ID NO:154 (KLH2 intron 2G-2/2G-3), and
SEQ ID NO:155 (KLH2 intron 2G/2H);
(ii) a nucleic acid sequence that hybridizes under stringent conditions with the counter-strand of a nucleic acid sequence according to (i);
(iii) a nucleic acid sequence that has at least 90% sequence identity to one of the nucleic acid sequences described under (i); and
(iv) combinations of several of the DNA sequences described under (i) to (iii).

3. The isolated nucleic acid molecule according to claim 1, wherein the nucleic acid molecule described under (b) has at least 95% identity to a nucleic acid sequence described under (a).

4. The isolated nucleic acid molecule according to claim 2, wherein the nucleic acid molecule described under (iii) has at least 95% identity to one of the nucleic acid sequence described under (i).

5. The isolated nucleic acid molecule according to claim 1 that is a deoxyribonucleic acid molecule.

6. A process for the preparation of a KLH2 haemocyanin polypeptide, wherein the nucleic acid molecule according to claim 1 is expressed in a suitable host cell and the protein is isolated.

7. The process according to claim 6, wherein the KLH2 haemocyanin polypeptide prepared is modified naturally or chemically.

8. The process according to claim 7, wherein the modification is cross-linking or covalent bonding to an antigen.

9. The process according to claim 6, wherein the expression is carried out in a host cell is a prokaryotic or eukaryotic cell suitable for expression of the construct.

10. A composition comprising a nucleic acid molecule having a sequence according to claim 1.

11. A construct comprising a nucleic acid molecule sequence that codes for a Keyhole Limpit Hemocyanin 2 (KLH2) polypeptide and comprises at least one intron sequence wherein said nucleic acid sequence is selected from the group consisting of:
(a) a DNA sequence or the corresponding RNA sequence selected from the group consisting of:
SEQ ID NO:20 (KLH2 domain b),
SEQ ID NO:21 (KLH2 domain c),
SEQ ID NO:22 (partial KLH2 domain d),
SEQ ID NO:23 (KLH2 domain g),
SEQ ID NO:24 (partial KLH2 domain h),
SEQ ID NO:57 (KLH2 domain b'),
SEQ ID NO:58 (KLH2 domain c'),
SEQ ID NO:59 (KLH2 domain d'),
SEQ ID NO:60 (KLH2 domain e),
SEQ ID NO:61 (KLH2 domain f),
SEQ ID NO:62 (KLH2 domain g'),
SEQ ID NO:102 (KLH2 domain b"),
SEQ ID NO:103 (KLH2 domain c"),
SEQ ID NO:104 (KLH2 domain d"),
SEQ ID NO:105 (KLH2 domain e"),
SEQ ID NO:106 (KLH2 domain f"),
SEQ ID NO:107 (KLH2 domain g"), and
SEQ ID NO:108 (partial KLH2 domain h");
(b) a nucleic acid sequence that hybridizes under stringent hybridization conditions of 0.55×SSC; 1% blocking reagent; 0.1% sodium dodecyl sulfate (SDS) at about 68° C. overnight, to a counter-strand of a nucleic acid sequence according to (a); and
(c) a nucleic-acid sequence that has at least 90% sequence identity to one of the nucleic acid sequences described under (a)
(d) a combination of the DNA sequences described under (a) to (c).

12. The construct according to claim 11, further comprising a promoter suitable for expression control, the nucleic acid sequence that codes for a KLH2 polypeptide being under the control of the promoter.

13. The construct according to claim 11, further comprising a nucleic acid sequence that codes for an antigen and is coupled directly to the nucleic acid sequence that codes for a KLH2 polypeptide.

14. The construct according to claim 13, wherein the antigen is selected from the group consisting of: a tumour antigens, a virus antigens and an antigens of a bacterial or parasitic pathogen.

15. The construct according to claim 11, wherein the construct comprises at least a part of a vector, the vector being selected from the group consisting of: a bacteriophag, an adenovirus, a vaccinia virus, a baculovirus, SV40 virus and a retrovirus.

16. The construct according to claim 11, wherein the construct further comprises a H is tag-coding nucleic acid sequence and the expression of the construct forms a fusion protein with a H is tag.

17. A isolated host cell containing a construct according to claim 11, wherein the host cell is a prokaryotic or eukaryotic cell suitable for expression of the construct.

18. The host cell according to claim 17, wherein the prokaryotic host cell is selected from *E. coli* and *Bacillus subtilis*.

19. The host cell according to claim 17, wherein the eukaryotic host cell is selected from the group consisting of a yeast cell, a plant cell, an insect cell and a mammalian cell.

20. The host cell according to claim 19, wherein the host cell is a CHO cell, a COS cell or a HeLa cell.

21. A process for the preparation of a KLH2 haemocyanin polypeptide, wherein the construct-according to claim 11 is expressed in a suitable host cell and the protein is isolated.

* * * * *